United States Patent
Anderson et al.

(10) Patent No.: US 12,109,266 B2
(45) Date of Patent: Oct. 8, 2024

(54) MODULATING GABARAP TO MODULATE IMMUNOGENIC CELL DEATH

(71) Applicant: Dana-Farber Cancer Institute, Inc., Boston, MA (US)

(72) Inventors: Kenneth C. Anderson, Wellesley, MA (US); Annamaria Gullà, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 17/518,272

(22) Filed: Nov. 3, 2021

(65) Prior Publication Data

US 2022/0211848 A1      Jul. 7, 2022

Related U.S. Application Data

(60) Provisional application No. 63/113,284, filed on Nov. 13, 2020.

(51) Int. Cl.
| | |
|---|---|
| A61K 39/395 | (2006.01) |
| A61K 39/00 | (2006.01) |
| A61P 35/04 | (2006.01) |
| C07K 16/28 | (2006.01) |

(52) U.S. Cl.
CPC ........ *A61K 39/39558* (2013.01); *A61P 35/04* (2018.01); *C07K 16/2818* (2013.01); *A61K 2039/505* (2013.01); *A61K 2039/572* (2013.01); *C07K 2317/21* (2013.01); *C07K 2317/52* (2013.01); *C07K 2317/732* (2013.01); *C07K 2317/76* (2013.01)

(58) Field of Classification Search
CPC ........ A61K 39/39558; A61K 2039/505; A61P 35/04; C07K 16/2818
See application file for complete search history.

(56) References Cited

U.S. PATENT DOCUMENTS

2022/0211848 A1    7/2022   Anderson et al.

OTHER PUBLICATIONS

Bowie et al., Deciphering the Message in Protein Sequences: Tolerance to Amino Acid Substitutions, Science, 1990, 247:1306-1310 (Year: 1990) (Year: 1990).*
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biol. 111:2129-2138, 1990 (Year: 1990).*
Lazar et al., Transforming Growth Factor ox: Mutation of Aspartic Acid 47 and Leucine 48 Results in Different Biological Activities, Mol. Cell. Biol., 8:1247-1252, 1988 (Year: 1988).*
Lin et al., Stanniocalcin 1 is a phagocytosis checkpoint driving tumor immune resistance, Cancer Cell 39, 480-493 (Year: 2021).*
Bocian et al., Development of a Novel Calreticulin Reporter for Determination of ImmunogenicCell Death, The FASEB Journal, vol. 33, Issue S1, p. 782.6-782.6, Publication Date: Apr. 1, 2019 (Year: 2019).*
Zhao et al., Expression, function and clinical application of stanniocalcin-1 in cancer, J Cell Mol Med. 24 (14): 7686-7696, Publication Date: May 29, 2020 (Year: 2020).*
Gulla et al., "Loss-of-Function of Gabarap Impairs Bortezomib-Induced Anti-Tumor Immunity in Multiple Myeloma: Clinical Application", ASH Oral Presentation, Dec. 7, 2019.
Gulla et al., "Loss-of-Function of Gabarap Impairs Bortezomib-Induced Anti-Tumor Immunity in Multiple Myeloma: Clinical Application", Blood 134:134 (Nov. 13, 2019).
Attal et al., Lenalidomide, Bortezomib, and Dexamethasone with Transplantation for Myeloma, Apr. 6, 2017, *N Engl J Med.*, 376(14):1311-1320. doi: 10.1056/NEJMoa1611750.
Gulla et al., "Bortezomib induces anti-multiple myeloma immune response mediated by cGAS/STING pathway activation," Sep. 2021, *Blood Cancer Discov.*, 2(5):468-483. doi: 10.1158/2643-3230. BCD-21-0047. Epub Apr. 23, 2021.
Kroemer et al., "Immunogenic cell death in cancer therapy," 2013, *Annu Rev Immunol.*, 31:51-72. doi: 10.1146/annurev-immunol-032712-100008. Epub Nov. 12, 2012.
Kumar et al., "Immune Therapies in Multiple Myeloma," 2016, *Clin Cancer Res*, 22(22):5453-460.
Legrand et al., "The Diversification of Cell Death and Immunity: Memento Mori," Oct. 2019, *Molecular Cell Review*, 76(2):232-242. doi: 10.1016/j.molcel.2019.09.006. Epub Oct. 2, 2019.
Nagarsheth et al., "Chemokines in the cancer microenvironment and their relevance in cancer immunotherapy," Sep. 2017, *Nat Rev Immunol.*, 17(9):559-72. doi: 10.1038/nri.2017.49. Epub May 30, 2017.
Thielmann et al., "Structural framework of the GABARAP-calreticulin interface—implications for substrate binding to endoplasmic reticulum chaperones," Feb. 2009, *Febs J.*, 276(4): 1140-52. doi: 10.1111/j.1742-4658.2008.06857.x. Epub Jan. 16, 2009.

* cited by examiner

*Primary Examiner* — Peter J Reddig
*Assistant Examiner* — Cheng Lu
(74) *Attorney, Agent, or Firm* — Mueting Raasch Group

(57) ABSTRACT

The present invention relates, in part, to methods of inducing immunogenic cell death to treat a cancer in a subject comprising administering to the subject a therapeutically effective amount of an agent that increases one or more biomarkers listed in Table 1 in combination with an inducer of immunogenic cell death (ICD).

10 Claims, 98 Drawing Sheets

Specification includes a Sequence Listing.

*In vitro* studies     *In vivo* studies     MM patients transcriptomic profiling

Calreticulin binding partner

Calreticulin

KMS11 cells carry mono allelic deletion of GABARAP and undetectable level of protein

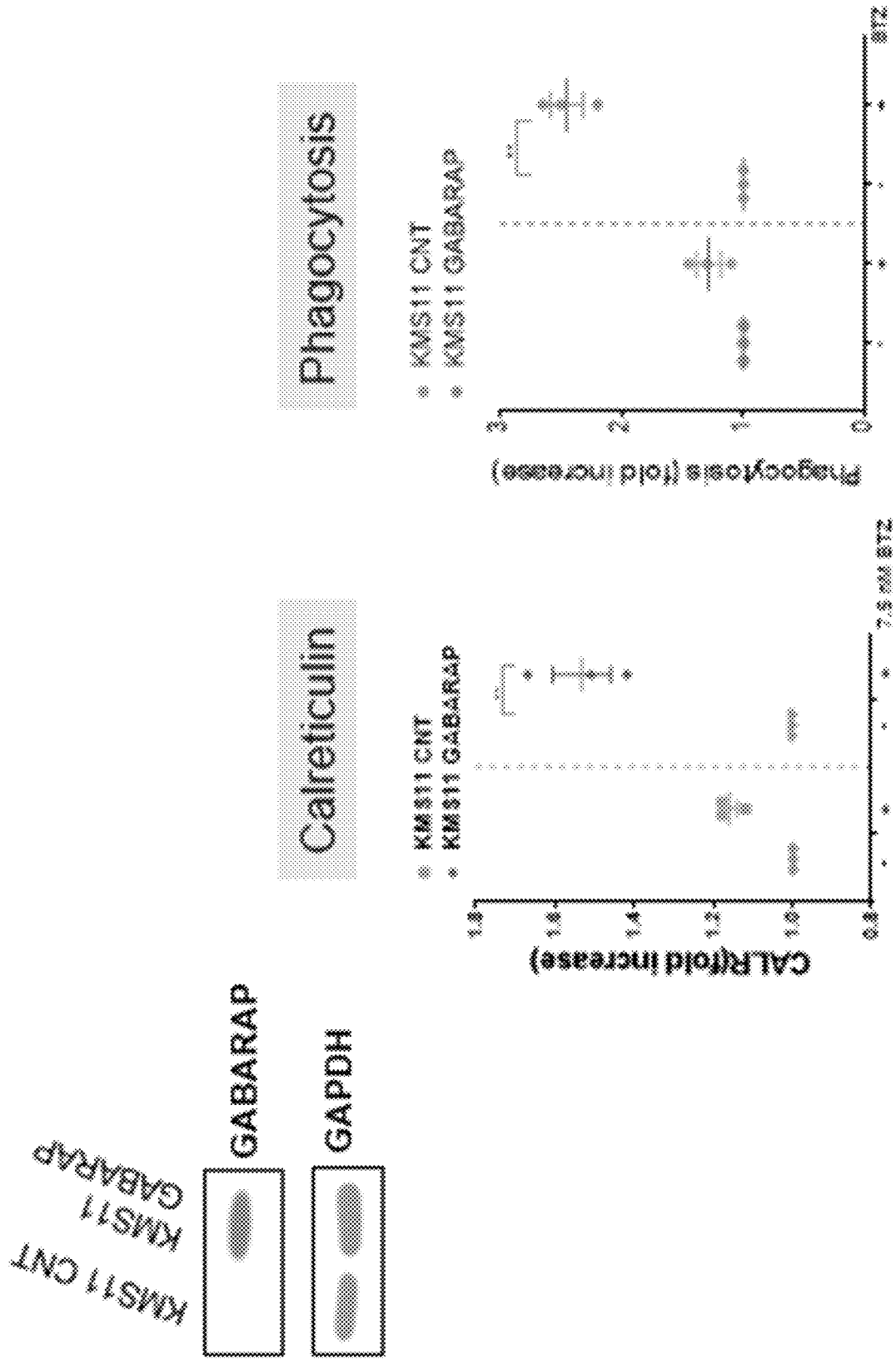

H929

AMO1 STING^(KO)-BTZ vs WT-BTZ

SEQUENCE LISTING

```
<160> NUMBER OF SEQ ID NOS: 39

<210> SEQ ID NO 1
<211> LENGTH: 117
<212> TYPE: PRT
<213> ORGANISM: Homo sapiens

<400> SEQUENCE: 1

Met Lys Phe Val Tyr Lys Glu Glu His Pro Phe Glu Lys Arg Arg Ser
1               5                   10                  15

Glu Gly Glu Lys Ile Arg Lys Lys Tyr Pro Asp Arg Val Pro Val Ile
            20                  25                  30

Val Glu Lys Ala Pro Lys Ala Arg Ile Gly Asp Leu Asp Lys Lys Lys
        35                  40                  45

Tyr Leu Val Pro Ser Asp Leu Thr Val Gly Gln Phe Tyr Phe Leu Ile
    50                  55                  60

Arg Lys Arg Ile His Leu Arg Ala Glu Asp Ala Leu Phe Phe Phe Val
65                  70                  75                  80

Asn Asn Val Ile Pro Pro Thr Ser Ala Thr Met Gly Gln Leu Tyr Gln
                85                  90                  95

Glu His His Glu Glu Asp Phe Phe Leu Tyr Ile Ala Tyr Ser Asp Glu
            100                 105                 110

Ser Val Tyr Gly Leu
        115

<210> SEQ ID NO 2
<211> LENGTH: 1319
<212> TYPE: DNA
<213> ORGANISM: Homo sapiens

<400> SEQUENCE: 2
gcaaattcgt ggatcgctcc gctgaatccg cccgcgcgtc gccgccgtcg tcgccgcccc        60
ccgtcccggc cccctgggt tccctcagcc cagccctgtc cagcccggtt cccgggagga       120
tgaagttcgt gtacaaagaa gagcatccgt tcgagaagcg ccgctctgag ggcgagaaga       180
tccgaaagaa atacccggac cgggtgccgg tgatagtaga aaaggctccc aaagctcgga       240
taggagacct ggacaaaaag aaatacctgg tgccttctga tctcacagtt ggtcagttct       300
acttcttgat ccggaagcga attcatctcc gagctgagga tgccttgttt ttctttgtca       360
```

```
acaatgtcat tccacccacc agtgccacaa tgggtcagct gtaccaggaa caccatgaag    420
aagacttctt tctctacatt gcctacagtg acgaaagtgt ctacggtctg tgaagctgct    480
gcccctgagc tggagggggg tctcattcta caaagagaga ggtggccccc ctttcttgac    540
ctcctcctcc ttcaagctca acaccacct cccttattca ggaccggcac ttcttaatgt     600
ttgtggcttt ctctccagcc tctcttagga ggggtaatgg tggagttggc atcttgtaac    660
tctcctttct cctttcttcc cctttctctg cccgcctttc ccatcctgct gtagacttct    720
tgattgtcag tctgtgtcac atccagtgat tgttttggtt tctgttccct ttctgactgc    780
ccaaggggct cagaacccca gcaatcccct cctttcacta ccttctttt tggggggtagt   840 tggaagggac tgaaattgtg ggggaaggt aggaggcaca tcaataaaga ggaaaccacc    900
aagctgaact gaattttgcc ttgtgttgct ccctcgtcc cgctgatttt aagtctttcc    960
aaggtgtcag tgggtttcag tggtggggaa agaagagtac tgggtacaag ctggagggat   1020
agaagtatat tttggtttat tctgttcatg ttgggctttt ccctgtctgc aaaaagaggg   1080
tgcttttgtt gtgatggaat ggaatactga ggattatttc ttgaaacttt agttttataa   1140
cacgcatgtg aaactaaatg ttaaaaatgc tcatgtaaaa aaaatttttt ttttactgtg   1200
ggttcctgtg agaaagttc cgaagtacct gctttaggtg aacatccaca tttgctagaa    1260
cattctaact aagatatttt catgtgtgca agctagtaaa acggctgttc tcagttgca    1319

<210> SEQ ID NO 3
<211> LENGTH: 117
<212> TYPE: PRT
<213> ORGANISM: Mus musculus

<400> SEQUENCE: 3

Met Lys Phe Val Tyr Lys Glu Glu His Pro Phe Glu Lys Arg Arg Ser
1               5                   10                  15

Glu Gly Glu Lys Ile Arg Lys Lys Tyr Pro Asp Arg Val Pro Val Ile
            20                  25                  30

Val Glu Lys Ala Pro Lys Ala Arg Ile Gly Asp Leu Asp Lys Lys Lys
        35                  40                  45

Tyr Leu Val Pro Ser Asp Leu Thr Val Gly Gln Phe Tyr Phe Leu Ile
    50                  55                  60

Arg Lys Arg Ile His Leu Arg Ala Glu Asp Ala Leu Phe Phe Phe Val
65                  70                  75                  80

Asn Asn Val Ile Pro Pro Thr Ser Ala Thr Met Gly Gln Leu Tyr Gln
                85                  90                  95

Glu His His Glu Glu Asp Phe Phe Leu Tyr Ile Ala Tyr Ser Asp Glu
            100                 105                 110

Ser Val Tyr Gly Leu
        115

<210> SEQ ID NO 4
<211> LENGTH: 1122
<212> TYPE: DNA
<213> ORGANISM: Mus musculus

<400> SEQUENCE: 4
caactttgta ctgtgggaaa gggttttca gttcactcga acaacagca accttatctg       60 cgatgtcata tgtgtaaccc acaagttgat tccaaagcag ttacgctgaa ggcgtaagag    120
gaccaggcta cgggttgcgc tagcaagctg agctagtggc gtatgttagc aggcggggcc    180
```

```
ggtccgatgg tcggggcgg ggttgatgaa tagggaagtg gcgcaaattc gtggatcgct    240
ccgccaagtc tgttcgtcga agccgcctcc gccgccgccc cctgtcccgg cccccccct    300 gggttccctc agcccagctc ggtccagccc ggttctcggg agaatgaagt tcgtgtacaa    360
agaggagcat ccgttcgaga agcgccgctc tgagggcgag aaaatccgaa agaaataccc    420
agaccgggtc ccggtgatag tggaaaaagc ccccaaagct cggataggag acctggacaa    480
aaagaaatac ctggtgcctt ctgatcttac agttggtcaa ttctacttct tgatccggaa    540
gcgaattcat ctccgtgctg aagatgcctt gttttctttt gtcaacaatg tcattccacc    600
caccagtgcc acgatgggtc agctgtacca ggaacaccat gaagaagact ctttctata    660 cattgcctac agtgatgaaa gcgtctatgg tctgtgaagc tgctgtacct gaggtggggg    720
gttccattct acgaagagag gtggcgctcc ttccttgaca tccagttcct ccttcaggct    780
caaacaccac ctcctttctt caggacctgc acttaatgtt tgaggctgtc tctccagtcc    840
ctctcagcag gagggtaat ggtagataca gcctccatac atctcttttct ccccttgttt    900 accctccatt cccactctga tttagacttc ttgattgtcg atctctgtca catccgatga    960
ttgttttggt ttctattccc tttctaactg cccatcgggc tcagaacccc aataatccct    1020
tcctttcact atcttctttt tggggggtag gtggaaggga ttgacattgg atgggggagg    1080
taggaggcac atcaataaaa aggaaaccac cgagctgaat tg    1122
```

```
<210> SEQ ID NO 5
<211> LENGTH: 117
<212> TYPE: PRT
<213> ORGANISM: Rattus norvegicus

<400> SEQUENCE: 5

Met Lys Phe Val Tyr Lys Glu Glu His Pro Phe Glu Lys Arg Arg Ser
1               5                   10                  15

Glu Gly Glu Lys Ile Arg Lys Lys Tyr Pro Asp Arg Val Pro Val Ile
            20                  25                  30

Val Glu Lys Ala Pro Lys Ala Arg Ile Gly Asp Leu Asp Lys Lys Lys
        35                  40                  45

Tyr Leu Val Pro Ser Asp Leu Thr Val Gly Gln Phe Tyr Phe Leu Ile
    50                  55                  60

Arg Lys Arg Ile His Leu Arg Ala Glu Asp Ala Leu Phe Phe Val
65                  70                  75                  80

Asn Asn Val Ile Pro Pro Thr Ser Ala Thr Met Gly Gln Leu Tyr Gln
                85                  90                  95

Glu His His Glu Glu Asp Phe Phe Leu Tyr Ile Ala Tyr Ser Asp Glu
            100                 105                 110

Ser Val Tyr Gly Leu
        115

<210> SEQ ID NO 6
<211> LENGTH: 853
<212> TYPE: DNA
<213> ORGANISM: Rattus norvegicus

<400> SEQUENCE: 6 cccctgggt tccctcagcc cagctcggtc cagcccggtt ctcgggagaa tgaagttcgt    60
gtacaaagag gagcatccgt tcgagaagcg ccgctctgag ggcgagaaaa tccgaaagaa    120
atacccagac cgggtcccgg tgatagtgga aaaagctccc aaagctcgga taggggacct    180
ggacaaaaag aaatacttgg tgccttctga tcttacagtt ggtcaattct acttcttgat    240
```

-continued

```
ccggaagcga attcatctcc gtgctgaaga tgccttgttt ttctttgtca acaatgtcat      300
tccacccacc agtgccacga tgggtcagct gtaccaggaa caccatgaag aagacttctt      360
tctatacatt gcctacagtg atgaaagcgt ctacggtctg tgaagttgct gtcccggagg      420
tgggggttcc attctacaaa gagaggtggc gctccttcct tggcatccag ttcctccttc      480
aggctcaaac accatctcct ttcttcagga cctgcactta atgtttgagg ctgtctctcc      540
agtccctctg agcaggaggg gtaatggtag atgcagccgc tgtacatctc tctttcccct      600
tgtttaccct ccattcccac tctgctttag acttctggat tgtcgatctc tgtcacatcg      660
gatgattgtt ttggtttcta ttcccttct aactgcccac tgggctcaga accccaataa       720
acccttcctt tcactacctt ctttttgggg ggtagatgga aggggttgac attgggtggg      780
ggaggtagga ggcacatcaa taaagaggaa accaccgagc tgaaataaaa aaaaaaaaa      840 aaaaaaaaaa aaa                                                         853
```

<210> SEQ ID NO 7
<211> LENGTH: 417
<212> TYPE: PRT
<213> ORGANISM: Homo sapiens

<400> SEQUENCE: 7

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
                35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                    85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255
```

```
Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Asp Lys Lys Arg Lys Glu Glu Glu Ala Glu Asp
        370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 8
<211> LENGTH: 1901
<212> TYPE: DNA
<213> ORGANISM: Homo sapiens

<400> SEQUENCE: 8
gtccgtactg cagagccgct gccggagggt cgttttaaag ggcccgcgcg ttgccgcccc      60
ctcggcccgc catgctgcta ccgtgccgc tgctgctcgg cctcctcggc ctggccgtcg     120
ccgagcctgc cgtctacttc aaggagcagt tctggacgg agacgggtgg acttcccgct     180
ggatcgaatc caaacacaag tcagattttg caaattcgt tctcagttcc ggcaagttct     240
acggtgacga ggagaaagat aaaggtttgc agacaagcca ggatgcacgc ttttatgctc     300
tgtcggccag tttcgagcct ttcagcaaca aggccagac gctggtggtg cagttcacgg     360
tgaaacatga gcagaacatc gactgtgggg gcggctatgt gaagctgttt cctaatagtt     420
tggaccagac agacatgcac ggagactcag aatacaacat catgtttggt cccgacatct     480
gtggccctgg caccaagaag gttcatgtca tcttcaacta caagggcaag aacgtgctga     540
tcaacaagga catccgttgc aaggatgatg agtttacaca cctgtacaca ctgattgtgc     600
ggccagacaa cacctatgag gtgaagattg acaacagcca ggtggagtcc ggctccttgg     660
aagacgattg ggacttcctg ccacccaaga gataaaagga tcctgatgct tcaaaaccgg     720
aagactggga tgagcgggcc aagatcgatg atcccacaga ctccaagcct gaggactggg     780
acaagcccga gcatatccct gaccctgatg ctaagaagcc cgaggactgg gatgaagaga     840
tggacggaga gtgggaaccc ccagtgattc agaaccctga gtacaagggt gagtggaagc     900
cccggcagat cgacaaccca gattacaagg gcacttggat ccacccagaa attgacaacc     960
ccgagtattc tcccgatccc agtatctatg cctatgataa ctttggcgtg ctgggcctgg    1020
acctctggca ggtcaagtct ggcaccatct tgacaacttt cctcatcacc aacgatgagg    1080
catacgctga ggagtttggc aacgagacgt ggggcgtaac aaaggcagca gagaaacaaa    1140
tgaaggacaa acaggacgag gagcagaggc ttaaggagga ggaagaagac aagaaacgca    1200
```

-continued

```
aagaggagga ggaggcagag gacaaggagg atgatgagga caaagatgag gatgaggagg    1260
atgaggagga caaggaggaa gatgaggagg aagatgtccc cggccaggcc aaggacgagc    1320
tgtagagagg cctgcctcca gggctggact gaggcctgag cgctcctgcc gcagagctgg    1380
ccgcgccaaa taatgtctct gtgagactcg agaactttca tttttttcca ggctggttcg    1440
gatttggggt ggattttggt tttgttcccc tcctccactc tccccaccc cctcccgcc     1500 cttttttttt tttttttta aactggtatt ttatctttga ttctccttca gccctcaccc    1560
ctggttctca tctttcttga tcaacatctt ttcttgcctc tgtccccttc tctcatctct    1620
tagctcccct ccaacctggg gggcagtggt gtggagaagc cacaggcctg agatttcatc    1680
tgctctcctt cctggagccc agaggagggc agcagaaggg ggtggtgtct ccaaccccc    1740 agcactgagg aagaacgggg ctcttctcat ttcacccctc cctttctccc ctgccccag    1800 gactgggcca cttctgggtg gggcagtggg tcccagattg gctcacactg agaatgtaag    1860
aactacaaac aaaatttcta ttaaattaaa ttttgtgtct c                        1901
```

<210> SEQ ID NO 9
<211> LENGTH: 416
<212> TYPE: PRT
<213> ORGANISM: Mus musculus

<400> SEQUENCE: 9

```
Met Leu Leu Ser Val Pro Leu Leu Gly Leu Gly Leu Ala Ala
1               5                   10                  15

Ala Asp Pro Ala Ile Tyr Phe Lys Glu Gln Phe Leu Asp Gly Asp Ala
            20                  25                  30

Trp Thr Asn Arg Trp Val Glu Ser Lys His Lys Ser Asp Phe Gly Lys
        35                  40                  45

Phe Val Leu Ser Ser Gly Lys Phe Tyr Gly Asp Leu Glu Lys Asp Lys
    50                  55                  60

Gly Leu Gln Thr Ser Gln Asp Ala Arg Phe Tyr Ala Leu Ser Ala Lys
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Ser Gly Leu Asp Gln Lys Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ala Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
```

```
                245                 250                 255
Met Asp Gly Glu Trp Glu Pro Pro Val Ile Gln Asn Pro Glu Tyr Lys
                    260                 265                 270

Gly Glu Trp Lys Pro Arg Gln Ile Asp Asn Pro Asp Tyr Lys Gly Thr
                275                 280                 285

Trp Ile His Pro Glu Ile Asp Asn Pro Glu Tyr Ser Pro Asp Ala Asn
        290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                    325                 330                 335

Ala Tyr Ala Glu Glu Phe Gly Asn Glu Thr Trp Gly Val Thr Lys Ala
                340                 345                 350

Ala Glu Lys Gln Met Lys Asp Lys Gln Asp Glu Gln Arg Leu Lys
                355                 360                 365

Glu Glu Glu Glu Asp Lys Lys Arg Lys Glu Glu Glu Ala Glu Asp
            370                 375                 380

Lys Glu Asp Asp Asp Arg Asp Glu Asp Glu Asp Glu Glu Asp Glu
385                 390                 395                 400

Lys Glu Glu Asp Glu Glu Ser Pro Gly Gln Ala Lys Asp Glu Leu
                    405                 410                 415
```

<210> SEQ ID NO 10
<211> LENGTH: 1943
<212> TYPE: DNA
<213> ORGANISM: Mus musculus

<400> SEQUENCE: 10

```
ggctgtgtca ggttcgggtg agaggtaggt gaatataaat tgaagcggcg gtggccgcgt      60
ccgtcaatac cgcagagccg ctgcctgaag atcgtcttaa aaggcctgtg tgccgccgcc     120
ccctcggccc gccatgctcc tttcggtgcc gctcctgctt ggcctcctcg gcctggccgc     180
cgcagaccct gccatctatt tcaaagagca gttcttggac ggagatgcct ggaccaaccg     240
ctgggtcgaa tccaaacata agtccgattt tggcaaattt gtcctcagtt ctggcaaatt     300
ttacggggac ctggagaagg ataaagggct gcagacaagc caagatgccc gattttacgc     360
actgtccgcc aaattcgaac ccttcagcaa taagggccag acactggtgg tacagttcac     420
ggtgaagcat gagcagaata tcgactgtgg gggcggctac gtgaagctgt tccgagtgg      480
tttggaccag aaggacatgc atggagactc agaatataac atcatgtttg gtccggacat     540
ctgcggtcct ggcaccaaga aggttcatgt catctttaac tacaagggca agaatgtgct     600
gatcaacaag gatatccggt gtaaggatga tgaattcaca cacctataca cactgattgt     660
gcggccagac aacacctatg aggtgaaaat tgacaacagc caggtggagt caggctcctt     720
ggaggatgat tgggactttc tgccacccaa gaagataaag gaccctgatg ctgccaagcc     780
ggaagactgg gatgaacgag ccaagatcga tgaccccaca gattccaagc tgaggactg      840
ggacaagcca gagcacatcc ctgaccctga tgctaagaag cctgaggact gggatgaaga     900
gatggatgga gagtgggaac accagtgat tcaaatcct gaatacaagg gcgagtggaa      960
accacgtcaa attgacaacc cagattacaa gggtacctgg atacacccag aaattgacaa    1020
ccctgaatac tccccgatg caaatatcta tgcctatgat agtttgctg tactgggcct     1080
agatctctgg caggtcaagt ccgggacaat ctttgacaat ttcctcatca ccaatgatga    1140
ggcctatgca gaggagtttg gcaatgagac gtggggtgtt accaaggctg cagagaagca    1200
```

-continued

```
gatgaaggac aagcaggatg aggagcagag gcttaaggaa gaagaagagg acaagaagcg      1260
taaagaggaa gaagaagctg aggataaaga ggatgatgat gacagagatg aagatgagga      1320
cgaagaagat gagaaggagg aagatgagga agaatcccct ggccaagcca aggatgagct      1380
gtagaggcca caccacctgc cttcagggct ggactgaggc ctgaacaccc tgccgcagag      1440
ctggctgctc ccaataatgt ctctatgaga ctcaagaact tttcattttt tccaggcagg      1500
ttcagatctg gggtagattc tgattttgtt ccctgcctc ccccattacc cccccccctt      1560 tttttttta ctggtgtttg tctttaattc tccttcagcc ctcatctggt ttctcatttt      1620
tgaatcaaca tcttttcctt ctgtccctcc ctttctccat cttttggtca ctaccctcca      1680
actctaggaa cagggtgta gaggagaagc ctaggcttg agatttcatc tgctctcctt       1740
cctgcatctc agaggagggc aggagaaggg ggtggtgttt tccctccccc cgcactgagg      1800
aagaatgggg ctcttctcat cccctttctc ccttgcccccc aggactgggc cacttgtggg     1860
gcagccagtt ctagcacagc tcacactgag agtgtaagaa ctacaaacaa aatttctatt      1920
aaattaagtt ttgtgtcttc cct                                              1943
```

<210> SEQ ID NO 11
<211> LENGTH: 416
<212> TYPE: PRT
<213> ORGANISM: Rattus norvegicus

<400> SEQUENCE: 11

```
Met Leu Leu Ser Val Pro Leu Leu Gly Leu Leu Gly Leu Ala Ala
1               5                  10                  15

Ala Asp Pro Ala Ile Tyr Phe Lys Glu Gln Phe Leu Asp Gly Asp Ala
                20                  25                  30

Trp Thr Asn Arg Trp Val Glu Ser Lys His Lys Ser Asp Phe Gly Lys
            35                  40                  45

Phe Val Leu Ser Ser Gly Lys Phe Tyr Gly Asp Gln Glu Lys Asp Lys
        50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Gly Gly Leu Asp Gln Lys Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Trp Asp Phe Leu Pro Pro Lys Lys Ile
        195                 200                 205

Lys Asp Pro Asp Ala Ala Lys Pro Glu Asp Trp Glu Arg Ala Lys
    210                 215                 220

Ile Asp Asp Pro Thr Asp Ser Lys Pro Glu Asp Trp Asp Lys Pro Glu
225                 230                 235                 240
```

```
His Ile Pro Asp Pro Asp Ala Lys Lys Pro Glu Asp Trp Asp Glu Glu
                245                 250                 255
Met Asp Gly Glu Trp Glu Pro Pro Val Ile Gln Asn Pro Glu Tyr Lys
            260                 265                 270
Gly Glu Trp Lys Pro Arg Gln Ile Asp Asn Pro Asp Tyr Lys Gly Thr
        275                 280                 285
Trp Ile His Pro Glu Ile Asp Asn Pro Glu Tyr Ser Pro Asp Ala Asn
    290                 295                 300
Ile Tyr Ala Tyr Asp Ser Phe Ala Val Leu Gly Leu Asp Leu Trp Gln
305                 310                 315                 320
Val Lys Ser Gly Thr Ile Phe Asp Asn Phe Leu Ile Thr Asn Asp Glu
                325                 330                 335
Ala Tyr Ala Glu Glu Phe Gly Asn Glu Thr Trp Gly Val Thr Lys Ala
            340                 345                 350
Ala Glu Lys Gln Met Lys Asp Lys Gln Asp Glu Glu Gln Arg Leu Lys
        355                 360                 365
Glu Glu Glu Asp Lys Lys Arg Lys Glu Glu Glu Glu Ala Glu Asp
    370                 375                 380
Lys Glu Asp Glu Asp Asp Arg Asp Glu Asp Glu Asp Glu Glu Asp Glu
385                 390                 395                 400
Lys Glu Glu Asp Glu Glu Asp Ala Thr Gly Gln Ala Lys Asp Glu Leu
                405                 410                 415

<210> SEQ ID NO 12
<211> LENGTH: 1865
<212> TYPE: DNA
<213> ORGANISM: Rattus norvegicus

<400> SEQUENCE: 12
cgcagagccg ctgcttgaag atcgttttaa agggccagtg tgccgccgcc ccctcggccc      60
gccatgctcc tttcggtgcc gctcctgctt ggcctcctcg gcctggctgc cgcagaccct     120
gccatctatt tcaaagagca gttcttggac ggagatgcct ggaccaaccg ctgggtcgaa     180
tccaaacata agtctgattt tggcaaattc gtcctcagtt ctggcaaatt ctacggggac     240
caggagaagg ataaagggtt gcagacaagc caagatgccc gattttacgc gctgtccgcc     300
agattcgaac ccttcagcaa caagggccag acactggtgg tacagttcac cgtgaagcat     360
gagcagaata tcgactgtgg gggcggctac gtgaagctgt tccgggtgg cttggaccag     420 aaggacatgc atggagactc agaatataac atcatgtttg gtccggacat ctgcggtcct     480
ggcaccaaga aggttcatgt catctttaac tacaagggca agaacgtgct gatcaacaag     540
gatatccggt gtaaggatga tgaattcaca catctcatac cgctgattgt gcggccagac     600
aacacctacg aggtgaaaat tgacaacagc caggtggagt cgggctcctt ggaggatgat     660
tgggactttc tgccgcccaa gaagattaag gatcctgacg ctgccaagcc agaagactgg     720
gatgaacgag ccaagattga tgacccaca gattccaagc tgaggactg ggacaagcca     780 gagcacatcc ctgaccctga tgctaagaag cctgaggact gggacgaaga gatggatgga     840
gagtgggaac caccagtgat tcaaaatcct gaatacaagg gcgaatggaa gccacgtcaa     900
attgacaacc cagattacaa gggtacctgg atacacccag agattgacaa tcctgaatac     960
tcccccgatg cgaatatcta tgcctatgat agttttgctg tactgggctt agacctctgg    1020
caggtcaagt ctggcacaat ttttgacaac ttcctcatca ccaatgatga ggcctatgca    1080
gaggagtttg gcaatgagac ctggggtgtc accaaggctg cagagaagca gatgaaggac    1140
```

```
aagcaggatg aggagcagag gcttaaggaa gaagaagaag acaagaagcg taaagaggaa    1200
gaggaggccg aggataaaga ggatgaggat gacagagatg aagatgaaga tgaagaggat    1260
gagaaggaag aagatgagga ggatgccact ggccaagcca aggatgagct gtagaggcca    1320
caccacctgc ctccagggct ggactgaggc ctgaacaccc cgccacagag ctggctgctc    1380
ccaataatgt ctctatgaga ctcaagaact tttcattttt tttccaggca ggttcaggtc    1440
tggggtggat tctgattttt gttcccctgc ctccccatcc tccccacccc ccttttttt    1500 ttactggtgt ttgtctttaa ttcttcagcc ctcacctcct ggcctctcat ttttgaatca    1560 acatttttc tttctgtccc tttctccatc tcttggtcac tatcctccaa ctctaggaac    1620
aggtatggag gaaaagccct aggcttgaga tttcatctgc tctcctttct gaatctcaga    1680
ggagggtagg agaaggggt ggtatcttcc ctcccccag cactgaggaa gaatgggct    1740 cttccctttt ctcccttgcc cccaggactg ggccatttgt ggggcagcca gttctagcac    1800
agctcacact gagagtgtaa gaactacaaa caaaatttct attaaattaa gttttgtgtc    1860
ttccc                                                                1865

<210> SEQ ID NO 13
<211> LENGTH: 3868
<212> TYPE: DNA
<213> ORGANISM: Homo sapiens

<400> SEQUENCE: 13
agtttgcaaa agccagaggt gcaagaagca gcgactgcag cagcagcagc agcagcggcg      60
gtggcagcag cagcagcagc ggcggcagca gcagcagcag cggaggcacc ggtggcagca     120
gcagcatcac cagcaacaac aacaaaaaaa aatcctcatc aaatcctcac ctaagctttc     180
agtgtatcca gatccacatc ttcactcaag ccaggagagg gaaagaggaa aggggggcag     240
gaaaaaaaaa aaacccaaca acttagcgga aacttctcag agaatgctcc aaaactcagc     300
agtgcttctg gtgctggtga tcagtgcttc tgcaacccat gaggcggagc agaatgactc     360
tgtgagcccc aggaaatccc gagtggcggc tcaaaactca gctgaagtgg ttcgttgcct     420
caacagtgct ctacaggtcg gctgcggggc ttttgcatgc ctggaaaact ccacctgtga     480
cacagatggg atgtatgaca tctgtaaatc cttcttgtac agcgctgcta aatttgacac     540
tcagggaaaa gcattcgtca agagagcttt aaaatgcatc gccaacgggg tcacctccaa     600
ggtcttcctc gccattcgga ggtgctccac tttccaaagg atgattgctg aggtgcagga     660
agagtgctac agcaagctga atgtgtgcag catcgccaag cggaaccctg aagccatcac     720
tgaggtcgtc cagctgccca atcacttctc caacagatac tataacagac ttgtccgaag     780
cctgctggaa tgtgatgaag acacagtcag cacaatcaga gacagcctga tggagaaaat     840
tgggcctaac atggccagcc tcttccacat cctgcagaca gaccactgtg cccaaacaca     900
cccacgagct gacttcaaca ggagacgcac caatgagccg cagaagctga agtcctcct     960 caggaacctc cgaggtgagg aggactctcc ctcccacatc aaacgcacat cccatgagag    1020
tgcataacca gggagaggtt attcacaacc tcaccaaact agtatcattt tagggtgtt     1080 gacacaccag ttttgagtgt actgtgcctg gtttgatttt tttaaagtag ttcctatttt    1140
ctatccccct taaagaaaat tgcatgaaac taggcttctg taatcaatat cccaacattc    1200
tgcaatggca gcattccac caacaaaatc catgtgacca ttctgcctct cctcaggaga    1260
aagtaccctc ttttaccaac ttcctctgcc atgtttttcc cctgctcccc tgagaccacc    1320
```

```
cccaaacaca aaacattcat gtaactctcc agccattgta atttgaagat gtggatccct    1380
ttagaacggt tgccccagta gagttagctg ataaggaaac tttatttaaa tgcatgtctt    1440
aaatgctcat aaagatgtta aatggaattc gtgttatgaa tctgtgctgg ccatggacga    1500
atatgaatgt cacatttgaa ttcttgatct ctaatgagct agtgtcttat ggtcttgatc    1560
ctccaatgtc taattttctt tccgacacat ttaccaaatt gcttgagcct ggctgtccaa    1620
ccagactttg agcctgcatc ttcttgcatc taatgaaaaa caaaaagcta acatctttac    1680
gtactgtaac tgctcagagc tttaaaagta tctttaacaa ttgtcttaaa accagagaat    1740
cttaaggtct aactgtggaa tataaatagc tgaaaactaa tgtactgtac ataaattcca    1800
gaggactctg cttaaacaaa gcagtatata ataactttat tgcatataga tttagttttg    1860
taacttagct ttattttct tttcctggga atggaataac tatctcactt ccagatatcc    1920
acataaatgc tccttgtggc cttttttata actaaggggg tagaagtagt tttaattcaa    1980
catcaaaact taagatgggc ctgtatgaga caggaaaaac caacaggttt atctgaagga    2040
ccccaggtaa gatgttaatc tcccagccca cctcaaccca gaggctactc ttgacttaga    2100
cctatactga agatctctg tcacatccaa ctggaaattc caggaaccaa aaagagcatc     2160
cctatgggct tggaccactt acagtgtgat aaggcctact atacattagg aagtggcagt    2220
tctttactcg tccccttca tcggtgcctg gtactctggc aaatgatgat ggggtgggag     2280
actttccatt aaatcaatca ggaatgagtc aatcagcctt taggtcttta gtccggggga    2340
cttggggctg agagagtata aataaccctg ggctgtccag ccttaataga cttctcttac    2400
atttcgtcc tgtagcacgc tgcctgccaa agtagtcctg gcagctggac catctctgta     2460
ggatcgtaaa aaatagaaa aaagaaaaa aaaagaaag aaagagggaa aaagagctgg       2520
tggtttgatc atttctgcca tgatgtttac aagatggcga ccaccaaagt caaacgacta    2580
acctatctat gaacaacagt agtttctcag ggtcactgtc cttgaaccca acagtccctt    2640
atgagcgtca ctgcccacca aaggtcaatg tcaagagagg aagagaggga ggaggggtag    2700
gactgcaggg gccactccaa actcgcttag gtagaaacta ttggtgcttg actctcacta    2760
ggctaaactc aagatttgac caaatcgagt gatagggatc ctggtgggag gagagagggc    2820
acatctccag aaaaatgaaa agcaatacaa ctttaccata aagcctttaa aaccagtaac    2880
gtgctgctca aggaccaaga gcaattgcag cagacccagc agcagcagca gcagcacaaa    2940
cattgctgcc tttgtcccca cacagcctct aagcgtgctg acatcagatt gttaagggca    3000
ttttatact cagaactgtc ccatcccag gtccccaaac ttatggacac tgccttagcc      3060
tcttggaaat caggtagacc atattctaag ttagactctt cccctccctc ccacacttcc    3120
cacccccagg caaggctgac ttctctgaat cagaaaagct attaaagttt gtgtgttgtg    3180
tccattttgc aaacccaact aagccaggac cccaatgcga caagtagttc atgagtattc    3240
ctagcaaatt tctctctttc ttcagttcag tagatttcct tttttctttt ctttttttt    3300
tttttttttt ttggctgtga cctcttcaaa ccgtggtacc ccccctttc tccccacgat     3360
gatatctata tatgtatcta caatacatat atctacacat acagaaagaa gcagttctca    3420
caatgttgct agttttttgc ttctctttcc cccaccctac tccctccaat tccccccttaa   3480
acttccaaag cttcgtcttg tgtttgctgc agagtgattc ggggggctgac ctagaccagt   3540
ttgcatgatt cttctcttgt gatttggttg cactttagac attttttgtgc cattatattt   3600
gcattatgta tttataattt aaatgatatt taggtttttg gctgagtact ggaataaaca    3660
gtgagcatat ctggtatatg tcattattta ttgttaaatt acattttaa gctccatgtg     3720
```

```
catataaagg ttatgaaaca tatcatggta atgacagatg caagttattt tatttgctta    3780
tttttataat taaagatgcc atagcataat atgaagcctt tggtgaattc cttctaagat    3840
aaaaataata ataaagtgtt acgtttta                                       3868
```

<210> SEQ ID NO 14
<211> LENGTH: 178
<212> TYPE: PRT
<213> ORGANISM: Homo sapiens

<400> SEQUENCE: 14

```
Met Tyr Asp Ile Cys Lys Ser Phe Leu Tyr Ser Ala Ala Lys Phe Asp
1               5                   10                  15

Thr Gln Gly Lys Ala Phe Val Lys Glu Ser Leu Lys Cys Ile Ala Asn
            20                  25                  30

Gly Val Thr Ser Lys Val Phe Leu Ala Ile Arg Arg Cys Ser Thr Phe
        35                  40                  45

Gln Arg Met Ile Ala Glu Val Gln Glu Cys Tyr Ser Lys Leu Asn
    50                  55                  60

Val Cys Ser Ile Ala Lys Arg Asn Pro Glu Ala Ile Thr Glu Val Val
65                  70                  75                  80

Gln Leu Pro Asn His Phe Ser Asn Arg Tyr Tyr Asn Arg Leu Val Arg
                85                  90                  95

Ser Leu Leu Glu Cys Asp Glu Asp Thr Val Ser Thr Ile Arg Asp Ser
            100                 105                 110

Leu Met Glu Lys Ile Gly Pro Asn Met Ala Ser Leu Phe His Ile Leu
        115                 120                 125

Gln Thr Asp His Cys Ala Gln Thr His Pro Arg Ala Asp Phe Asn Arg
    130                 135                 140

Arg Arg Thr Asn Glu Pro Gln Lys Leu Lys Val Leu Leu Arg Asn Leu
145                 150                 155                 160

Arg Gly Glu Glu Asp Ser Pro Ser His Ile Lys Arg Thr Ser His Glu
                165                 170                 175

Ser Ala
```

<210> SEQ ID NO 15
<211> LENGTH: 2463
<212> TYPE: DNA
<213> ORGANISM: Rattus norvegicus

<400> SEQUENCE: 15

```
gaagcagcag cagcagcagc agcaacaaca acagcagcag tagcagcagc agcagcagca     60
gcagcagcag cagcagcagc agcagccacc gccgccgctt gccagccagc cacacagcca    120
cacaaaaatt cctcctcaaa tcctcaccta agctttcagt atatccagat ccacatcttc    180
actcaagccg ggagagggaa agaggaaagg gggggaggaa aaaaaaagcc aacaacttag    240
cggaaacttc tcagagaatg ctccaaaact cagcagtgat tctggcgctg gtcatcagtg    300
ctgctgcagc tcacgaggcg aacagaatg attctgtgag ccccagaaaa tcccgggtgg    360
cggctcaaaa ttcagctgaa gtggtccgct gcctcaacag tgccctacag gttggctgtg    420
gggcttttgc atgcctggaa aactccacat gtgacacaga tgggatgtac gacatttgta    480
aatccttctt gtacagtgct gctaaatttg acactcaggg aaaagcattt gtcaaagaga    540
gcttaaagtg catcgccaat gggatcacct ccaaggtctt ccttgccatt cggaggtgtt    600
ctactttcca gaggatgatc gccgaggtgc aggaggactg ctacagcaag ctcaatgttt    660
```

```
gcagcattgc caagcgcaac ccggaagcca tcactgaagt catacagctg cccaatcact    720
tctccaacag atactacaac agacttgtcc gaagccttct ggaatgtgat gaagatacgg    780
tcagcacaat cagagacagc ctgatggaga agatcgggcc caacatggcc agcctcttcc    840
atatcctgca gacagaccac tgtgcccaga cacaccccag agctgacttc aataggaggc    900
gcacaaatga gccacagaag ctgaaagtcc tcctcaggaa cctccgaggt gaggggatt     960 ctccctcaca catcaaacgc acctcccaag agaatgcgta agcagggaga ggtattcaca   1020
gcctcaccaa actaatagcg ttttaggggt gtttacacac caactttgag tgtactgtgc   1080
ctggtttgat ttttttttaa gtagtaccta ttttctatcc cccttaaag aaaactgcat    1140 gaaactaagc ttccatgatc aatatcccaa tattctgcaa tgacagcatt cttagcaata   1200
gaatacatgt ggtcattctg cctcttctgg agagagaatg taccctcttc catcccccct   1260
ctctctcaat tcttttcaa gatccccatc tactctctgc aaacacaaaa cattcatgta    1320
actgcccagt cattgtaatc tgaagatgta ggtcccttta gaatggtcac ccagtagagt   1380
tagccaatac aaaacaactt tatttaaatg catgtcttaa atgctcataa atatgttaaa   1440
tggaattcgt gttatgaatc tgtgctggcc atggacgaat atgaatgtca tgtttgaatt   1500
cttgatctct aatgagtctt atggtctcaa tcctccaatg tctaacttcc tttctgacat   1560
atttaccaaa ttgctcaaac ctggttctcc aaccagattt tgagccagca tcttcttgca   1620
tctaatgaaa acaaaaagc taacatcttt atgtactgta actgctcaga gctttaaaag    1680
tatctttaac aattgtctta aaacagaga atcttaaggt ctaactgtgg aatataaata    1740
gctgaaaact attgtactgt acataaattc cagaggactc tgcttaacag agcagtctat   1800 ataacttta ttgcatatag atttagtttt gtaccttagc tttattttcc ttttcctggg    1860
aatggaataa ctatctcact tccagatatc cgcgttcatg ctccttgtgg ccttttttat   1920
aactaagggg gtagaagtag ttttaactca acatcagaac ttaagatggg cctatacttg   1980
ataggaaaac ccaacaggtt atctgaagga ccccaggtga gatatcaatc tcccagccca   2040
gctcaaccca gaggctacat ttgacttaga tgtatcctga acagctctg tcacagccaa    2100 ctgggaatta caggaatcaa agagatcatc cctctgggct tgatcactt agtgtgacaa    2160 ggcctactat ccccttggaa gtggcagttc ttggctcatt gccttccatc aatgcctggc   2220
actctggtaa atgatggaat gggatattgt tccactaagc caatcaggaa tgagtcaatc   2280
agcctttggg tctttagtcc tgggaacttg ggcttaaggg ggtataaata accctgggct   2340
gtccagcctt aatagactcc tcttacatct tttgtcctgt aacacgctgc ctgccaaagt   2400
agtcctggca gctggaccat ctctgtagga tcttaaaaaa aaaaaaaaaa aaaaaaaaa    2460 aaa                                                                2463
```

<210> SEQ ID NO 16
<211> LENGTH: 247
<212> TYPE: PRT
<213> ORGANISM: Rattus norvegicus

<400> SEQUENCE: 16

Met Leu Gln Asn Ser Ala Val Ile Leu Ala Leu Val Ile Ser Ala Ala
 1               5                  10                  15

Ala Ala His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

```
Ala Leu Gln Val Gly Cys Gly Ala Phe Ala Cys Leu Glu Asn Ser Thr
 50                  55                  60

Cys Asp Thr Asp Gly Met Tyr Asp Ile Cys Lys Ser Phe Leu Tyr Ser
 65                  70                  75                  80

Ala Ala Lys Phe Asp Thr Gln Gly Lys Ala Phe Val Lys Glu Ser Leu
                 85                  90                  95

Lys Cys Ile Ala Asn Gly Ile Thr Ser Lys Val Phe Leu Ala Ile Arg
            100                 105                 110

Arg Cys Ser Thr Phe Gln Arg Met Ile Ala Glu Val Gln Glu Asp Cys
            115                 120                 125

Tyr Ser Lys Leu Asn Val Cys Ser Ile Ala Lys Arg Asn Pro Glu Ala
        130                 135                 140

Ile Thr Glu Val Ile Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
210                 215                 220

Leu Leu Arg Asn Leu Arg Gly Glu Gly Asp Ser Pro Ser His Ile Lys
225                 230                 235                 240

Arg Thr Ser Gln Glu Asn Ala
                245

<210> SEQ ID NO 17
<211> LENGTH: 3743
<212> TYPE: DNA
<213> ORGANISM: Mus musculus

<400> SEQUENCE: 17
agtatatcca gatccacatc ttcactcaag ccgggagagg gaaagaggaa agggggggag      60
gaaaaaaaaa agccaacaac ttagcggaaa cttctcagag aatgctccaa aactcagcag     120
tgattctggc gctggtcatc agtgcagctg cagcgcacga ggcggaacaa aatgattctg     180
tgagccccag aaaatcccgg gtggcggctc aaaattcagc tgaagtggtt cgctgcctca     240
acagtgccct gcaggttggc tgcggggctt ttgcatgcct ggaaaactcc acatgtgaca     300
cagatgggat gtacgacatt tgtaaatcct tcttgtacag tgctgctaaa tttgacactc     360
agggaaaagc atttgtcaaa gagagcttaa agtgcatcgc caatgggatc acctccaagg     420
tattccttgc cattcggagg tgttcgactt ccagaggat gatcgccgag gtgcaggagg     480
actgctacag caagcttaac gtttgcagca tcgccaagcg caacccggaa gccatcactg     540
aagtcataca gctgcccaat cacttctcca acagatacta caacagactt gtccgaagcc     600
ttctggaatg tgatgaagac acggtcagta caatcagaga cagcctgatg gagaagatcg     660
ggcccaacat ggccagcctc ttccacatcc tgcagacaga ccactgtgcc cagacacacc     720
ccagagctga cttcaatagg aggcgcacaa atgagccaca gaagctgaaa gtcctcctca     780
ggaacctccg aggtgagggg gactctcct cacacatcaa acgcacctcc caagagagtg     840
cgtaagcagg gagaggtatt cacagcctca ccaaactaat agcatttag gggtgttgac     900 acccaacctt tgagtgtact gtgcctggtt tgatttttttt taagtagtac ctattttcta     960
```

-continued

```
tcccccgtt aaagaaaaat tgcatgaaac taggcttcca taatcaatat cccaacattc   1020
tgcaatgaca gcattcttac caacagaata catgtgtggt cattctgcct ctcctcaaga   1080
gagaatgtac cctcttccat ccccctctc tctgaattct tttcccagat ccctatctac    1140
tctccgcaaa cacaaaccat tcatgtaact acccagtcat tgtaatctga aaatgtagat   1200 cccttagaa tggtcacctg gtagagttag ccaatacaaa acaactttat ttaaatgcat    1260
gtcttaaatg ctcataaata tgttaaatgg aattcgtgtt atgaatctgt gctggccatg   1320
gacgaatatg aatgtcatgt ttgaattctt gatctctaac gagtcttatg gtctctatcc   1380
tccaatgtct aatttccttt ctgacatatt taccaaattg ctcaaacctg gttctccaac   1440
cagactttga gctagcatct tcttgcatct aatgaaaaac aaaaaagcta acatctttat   1500
gtactgtaac tgctcagagc tttaaaagta tctttaacaa ttgtcttaaa aaacggagaa   1560
tcttaaggtc taactgtgga atataaatag ctgaaaacta ttgtactgta cataaattcc   1620
agaggactct gcttaacaga gcagtctata ataactttat tgcatataga tttagttttg   1680
taccttagct ttatttcct tttcctggga atggaataac tatctcactt ccagatatcc     1740
acattcatgc tccttgtggc cttttttata actaagggg tagaagtagt tttaactcaa     1800
catcagaact taagatgggc ctatacttga caggaaaacc caacaggtta tctgaaggac   1860
cccaggtaag acgttaatct cccagcccac ctcaacccgg aggctacgtt tgacttagat   1920
gtatcctgaa acagctctgt cacatccaac tgggaataac aagaatcaaa aagaccatcc   1980
ctttgggctt ggaccacttg gtgtgacaag gcctactatc cccttggaag tggcagttct   2040
tggctcatcg ccttccatca gtgcctggca ctctggtaaa tgatggagtg ggatattgtt   2100
ccactaagcc aatcaggaat gagtcaatca gcctttgggt cttagtccg ggaaacttgg     2160 gcttaagggg gtatgaataa ccctgggctg tccagcctta atagactcct cttacatctt   2220
ttgtcctgta acatgctgcc tgccaaagta gtcctggcag ctggaccatc tctgtaggat   2280
ctttaaaaaa aaagaaaaaa agaaaaaaaa aagaaaaaat atagagagaa tgaaggaggg   2340
cataagcgct ggtggtttga tcatttctgc tgtgatgttt acaggatggt agccaccaaa   2400
gccaaatgat taacctgtct acgaacaaca gtagtttctc agggtcattg tccttgaacc   2460
caacagcccc aattatgagt gtcactgctc accaaaggtc aatgctgaga gaggaagagg   2520
gaggggctgc tccaaactca tttgggtaga aactatcggt gcttgactct cactaggcta   2580 cacccccagag ttgaccaaat tgagtgatag ggaccctggt gggaggaggg agggcacctc  2640
tccagggaaa tcaaaagcaa tacaacttta ccacaaagcc tttaaaacca gtaacatagt   2700
gctcaaggac caagatcaag cgtagcagct gcagctgcag cagcggcccc aaggctgcag   2760
cctctgtccc cacacagcct cgaagcgcgc tgacatcaga ttgttaaggg cattttcata   2820
cttagaactg tcccatcccc aggtcccaaa caaatggaca ctgccttagc ctcttggaaa   2880
tcaggtagca catattctaa gctagattca cccctctccc ccacccccaa cttcccaccc   2940
caggcaaggc tgacttcttt gaaccagaaa agctagtcaa gtgtgtgtgt gttgtgcatt   3000
gttgcaaacc cactaagcca gaagcccaaa gtggcaaata gcttatgaga attcctagta   3060
caattctctt aagttcagta aactttcttt ctctcttttc tctttttttt tatttttttt   3120
atttttgctg tgacctttc aatctgtgat ataccctcct ttctcccac agtgacattg      3180 gtatatgtac caacaatgca catatctaca catatgaaaa gaagcagttc tcacaacgtt   3240
gctgggtttt tgttttgttt tgttttttgg ttttgttttt tgttttttg cttcttttt      3300
```

```
cccctcccc ctgcccctct ccacctcctt cttgaacttc caaagctttg tctcgtgttt    3360
gctgcagagc gattcgggga ctgacctaga cctgtttgca tgatctcctc tcttgtgatt    3420
tggttgcact ttagaacatt tttgtgccgt attatttgca ttatgtattt ataatttaaa    3480
tgatatttag ttttttggct gagtactgga ataaacagtg agcatatctg gtatatgtca    3540
ttatttattg ttaaattaca tttttaagct ccatgtgcat ataaaagtta tgaaacatat    3600
catggtaatg acagatgcaa gttatttat ttgcttattt ttataattaa agatgccata    3660
gcataatttg aagcctttgg tgaattcctt ctacgataat aataataata ataaagtgtt    3720
aacgttttat ttgttcccccc tcc                                          3743
```

<210> SEQ ID NO 18
<211> LENGTH: 247
<212> TYPE: PRT
<213> ORGANISM: Mus musculus

<400> SEQUENCE: 18

Met Leu Gln Asn Ser Ala Val Ile Leu Ala Leu Val Ile Ser Ala Ala
1               5                   10                  15

Ala Ala His Glu Ala Glu Gln Asn Asp Ser Val Ser Pro Arg Lys Ser
                20                  25                  30

Arg Val Ala Ala Gln Asn Ser Ala Glu Val Val Arg Cys Leu Asn Ser
            35                  40                  45

Ala Leu Gln Val Gly Cys Gly Ala Phe Ala Cys Leu Glu Asn Ser Thr
        50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Ile Thr Ser Lys Val Phe Leu Ala Ile Arg
            100                 105                 110

Arg Cys Ser Thr Phe Gln Arg Met Ile Ala Glu Val Gln Glu Asp Cys
        115                 120                 125

Tyr Ser Lys Leu Asn Val Cys Ser Ile Ala Lys Arg Asn Pro Glu Ala
    130                 135                 140

Ile Thr Glu Val Ile Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
    210                 215                 220

Leu Leu Arg Asn Leu Arg Gly Glu Gly Asp Ser Pro Ser His Ile Lys
225                 230                 235                 240

Arg Thr Ser Gln Glu Ser Ala
                245

<210> SEQ ID NO 19
<211> LENGTH: 379
<212> TYPE: PRT
<213> ORGANISM: Homo sapiens

<400> SEQUENCE: 19

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Asn Gly Val Cys
50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Gly Leu Lys Gly Leu Ala Pro Ala Glu Ile
130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
                180                 185                 190

Ala Val Ser Gln Arg Leu Tyr Ile Leu Leu Pro Leu Asp Cys Gly Val
                195                 200                 205

Pro Asp Asn Leu Ser Met Ala Asp Pro Asn Ile Arg Phe Leu Asp Lys
210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
                260                 265                 270

Gln Tyr Ser Gln Ala Gly Phe Ser Arg Glu Asp Arg Leu Glu Gln Ala
                275                 280                 285

Lys Leu Phe Cys Arg Thr Leu Glu Asp Ile Leu Ala Asp Ala Pro Glu
                290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
                340                 345                 350

Ser Thr Ser Thr Met Ser Gln Glu Pro Glu Leu Leu Ile Ser Gly Met
                355                 360                 365

Glu Lys Pro Leu Pro Leu Arg Thr Asp Phe Ser
370                 375
```

<210> SEQ ID NO 20
<211> LENGTH: 1140
<212> TYPE: DNA
<213> ORGANISM: Homo sapiens

<400> SEQUENCE: 20

```
atgccccact ccagcctgca tccatccatc ccgtgtccca ggggtcacgg ggcccagaag      60
gcagccttgg ttctgctgag tgcctgcctg gtgacccttt gggggctagg agagccacca     120
gagcacactc tccggtacct ggtcctccac ctagcctccc tgcagctggg actgctgtta     180
aacgggtct gcagcctggc tgaggagctg cgccacatcc actccaggta ccggggcagc     240
tactggagga ctgtgcgggc ctgcctgggc tgccccctcc gccgtggggc cctgttgctg     300
ctgtccatct atttctacta ctccctccca aatgcggtcg gcccgcccct cacttggatg     360
cttgccctcc tgggcctctc gcaggcactg aacatcctcc tgggcctcaa gggcctggcc     420
ccagctgaga tctctgcagt gtgtgaaaaa gggaatttca acgtggccca tgggctggca     480
tggtcatatt acatcggata tctgcggctg atcctgccag agctccaggc ccggattcga     540
acttacaatc agcattacaa caacctgcta cggggtgcag tgagccagcg gctgtatatt     600
ctcctcccat ggactgtgg ggtgcctgat aacctgagta tggctgaccc caacattcgc     660
ttcctggata aactgcccca gcagaccggt gaccgtgctg gcatcaagga tcgggtttac     720
agcaacagca tctatgagct tctggagaac gggcagcggg cgggcaccty tgtcctggag     780
tacgccaccc ccttgcagac tttgtttgcc atgtcacaat acagtcaagc tggctttagc     840
cgggaggata ggcttgagca ggccaaactc ttctgccgga cacttgagga catcctggca     900
gatgccctg agtctcagaa caactgccgc tcattgcct accaggaacc tgcagatgac     960
agcagcttct cgctgtccca ggaggttctc cggcacctgc ggcaggagga aaaggaagag    1020
gttactgtgg gcagcttgaa gacctcagcg gtgcccagta cctccacgat gtcccaagag    1080
cctgagctcc tcatcagtgg aatggaaaag ccctccctc tccgcacgga tttctcttga    1140
```

<210> SEQ ID NO 21
<211> LENGTH: 372
<212> TYPE: PRT
<213> ORGANISM: Mus musculus

<400> SEQUENCE: 21

```
Met Pro Tyr Ser Asn Leu His Pro Ala Ile Pro Arg Pro Arg Gly His
1               5                   10                  15

Arg Ser Lys Tyr Val Ala Leu Ile Phe Leu Val Ala Ser Leu Met Ile
                20                  25                  30

Leu Trp Val Ala Lys Asp Pro Pro Asn His Thr Leu Lys Tyr Val Gly
            35                  40                  45

Leu His Leu Ala Leu His Glu Leu Gly Leu Leu Leu Lys Asn Leu Cys
        50                  55                  60

Cys Leu Ala Glu Glu Leu Cys His Val Gln Ser Arg Tyr Gln Gly Ser
65                  70                  75                  80

Tyr Trp Lys Ala Val Arg Ala Cys Leu Gly Cys Pro Ile His Cys Met
                85                  90                  95

Ala Met Ile Leu Leu Ser Phe Tyr Phe Tyr Phe Leu Gln Asn Thr Ala
                100                 105                 110

Asp Met Cys Leu Leu Val Leu Ser Lys Ser Leu Ser Met Leu Leu Gly
            115                 120                 125

Leu Gln Ser Leu Thr Pro Ala Glu Val Ser Ala Val Cys Glu Glu Lys
        130                 135                 140

Lys Leu Asn Val Ala His Gly Leu Ala Trp Ser Tyr Tyr Ile Gly Tyr
145                 150                 155                 160

Leu Arg Leu Ile Leu Pro Gly Leu Gln Ala Arg Ile Arg Met Phe Asn
```

```
            165                 170                 175
Gln Leu His Asn Asn Met Leu Ser Gly Ala Gly Ser Arg Arg Leu Tyr
            180                 185                 190

Ile Leu Phe Pro Leu Asp Cys Gly Val Pro Asp Asp Leu Ser Val Val
            195                 200                 205

Asp Pro Asn Ile Arg Phe Arg Asp Met Leu Pro Gln Gln Asn Ile Asp
        210                 215                 220

Arg Ala Gly Ile Lys Asn Arg Val Tyr Ser Asn Ser Val Tyr Glu Ile
225                 230                 235                 240

Leu Glu Asn Gly Gln Pro Ala Gly Val Cys Ile Leu Glu Tyr Ala Thr
            245                 250                 255

Pro Leu Gln Thr Leu Phe Ala Met Ser Gln Asp Ala Lys Ala Gly Phe
            260                 265                 270

Ser Arg Glu Asp Arg Leu Glu Gln Ala Lys Leu Phe Cys Arg Thr Leu
            275                 280                 285

Glu Glu Ile Leu Glu Asp Val Pro Glu Ser Arg Asn Asn Cys Arg Leu
            290                 295                 300

Ile Val Tyr Gln Glu Pro Thr Asp Gly Asn Ser Phe Ser Leu Ser Gln
305                 310                 315                 320

Glu Val Leu Arg His Ile Arg Gln Glu Glu Lys Glu Glu Val Thr Met
            325                 330                 335

Asn Ala Pro Met Thr Ser Val Ala Pro Pro Ser Val Leu Ser Gln
            340                 345                 350

Glu Pro Arg Leu Leu Ile Ser Gly Met Asp Gln Pro Leu Pro Leu Arg
            355                 360                 365

Thr Asp Leu Ile
    370

<210> SEQ ID NO 22
<211> LENGTH: 1119
<212> TYPE: DNA
<213> ORGANISM: Mus musculus

<400> SEQUENCE: 22
atgccatact ccaacctgca tccagccatc ccacggccca gaggtcaccg ctccaaatat    60
gtagccctca tctttctggt ggccagcctg atgatccttt gggtggcaaa ggatccacca   120
aatcacactc tgaagtacgt aggacttcac ctagccttgc acgaacttgg actactgttg   180
aaaaacctct gctgtctggc tgaagagctg tgccatgtcc agtccaggta ccagggaagc   240
tactggaagg ctgtgcgcgc ctgcctggga tgccccatcc actgtatggc tatgattcta   300
ctatcgtttt atttctattt cctccaaaac actgctgaca tgtgccttct ggtcctctct   360
aagtccctaa gcatgctcct gggccttcag agcttgactc cagcggaagt ctctgcagtc   420
tgtgaagaaa agaagttaaa tgttgcccac gggctggcct ggtcatacta cattgggtac   480
ttgcggttga tcttaccagg gctccaggcc cggatccgaa tgttcaatca gctacataac   540
aacatgctca gtggtgcagg gagccgaaga ctgtacatcc tctttccatt ggactgtggg   600
gtgcctgacg acctgagtgt ggttgacccc aacattcgat tccgagatat gctgccccag   660
caaaacatcg accgtgctgg catcaagaat cgggtttatt ccaacagcgt ctacgagatt   720
ctggagaacg gacagccagc aggcgtctgt atcctggagt acgccacccc cttgcagacc   780
ctgtttgcca tgtcacagga tgccaaagct ggcttcagtc gggaggatcg gcttgagcag   840
gctaaactct tctgccggac acttgaggaa atcctggaag atgtccccga gtctcgaaat   900
```

-continued

```
aactgccgcc tcattgtcta ccaagaaccc acagatggaa acagtttctc actgtctcag    960
gaggtgctcc ggcacattcg tcaggaagaa aaggaggagg ttaccatgaa tgccccatg    1020 acctcagtgg cacctcctcc ctccgtactg tcccaagagc caagactcct catcagtggt   1080
atggatcagc ctctcccact ccgcactgac ctcatctga                          1119
```

<210> SEQ ID NO 23
<211> LENGTH: 379
<212> TYPE: PRT
<213> ORGANISM: Rattus norvegicus

<400> SEQUENCE: 23

```
Met Pro Tyr Ser Asn Leu His Pro Ser Ile Pro Arg Pro Arg Ser Tyr
1               5                   10                  15

Arg Phe Lys Leu Ala Ala Phe Val Leu Leu Val Gly Ser Leu Met Ser
            20                  25                  30

Leu Trp Met Thr Gly Glu Pro Pro Ser His Thr Leu His Tyr Leu Ala
        35                  40                  45

Leu His Val Ala Ser Gln Gln Leu Gly Leu Leu Leu Lys Lys Leu Cys
    50                  55                  60

Cys Leu Ala Glu Glu Leu Cys His Val Gln Ser Arg Tyr Gln Gly Ser
65                  70                  75                  80

Tyr Trp Lys Ala Val Arg Ala Cys Val Gly Ser Pro Ile Cys Phe Met
                85                  90                  95

Ala Leu Ile Leu Leu Ser Phe Tyr Phe Tyr Cys Ser Leu Glu Asn Thr
            100                 105                 110

Ser Asp Leu Arg Leu Ala Trp His Leu Gly Ile Leu Val Leu Ser Lys
        115                 120                 125

Ser Leu Ser Met Thr Leu Asp Leu Gln Ser Leu Ala Pro Ala Glu Val
    130                 135                 140

Ser Ala Val Cys Glu Glu Lys Asn Phe Asn Val Ala His Gly Leu Ala
145                 150                 155                 160

Trp Ser Tyr Tyr Ile Gly Tyr Leu Lys Leu Ile Leu Pro Gly Leu Gln
                165                 170                 175

Ala Arg Ile Arg Met Phe Asn Gln Leu His Asn Asn Met Leu Ser Gly
            180                 185                 190

Ala Gly Ser Arg Arg Leu Tyr Ile Leu Phe Pro Leu Asp Cys Gly Val
        195                 200                 205

Pro Asp Asp Leu Ser Val Ala Asp Pro Asn Ile Arg Phe Arg Asp Met
    210                 215                 220

Leu Pro Gln Gln Asn Thr Asp Arg Ala Gly Val Lys Asn Arg Ala Tyr
225                 230                 235                 240

Ser Asn Ser Val Tyr Glu Leu Leu Glu Asn Gly Gln Pro Ala Gly Ala
                245                 250                 255

Cys Ile Leu Glu Tyr Ala Thr Pro Leu Gln Thr Leu Phe Ala Met Ser
            260                 265                 270

Gln Asp Gly Lys Ala Gly Phe Ser Arg Glu Asp Arg Leu Glu Gln Ala
        275                 280                 285

Lys Leu Phe Cys Arg Thr Leu Glu Glu Ile Leu Ala Asp Val Pro Glu
    290                 295                 300

Ser Arg Asn His Cys Arg Leu Ile Val Tyr Gln Glu Ser Glu Glu Gly
305                 310                 315                 320

Asn Ser Phe Ser Leu Ser Gln Glu Val Leu Arg His Ile Arg Gln Glu
                325                 330                 335
```

```
Glu Lys Glu Glu Val Thr Met Ser Gly Pro Pro Thr Ser Val Ala Pro
            340                 345                 350

Arg Pro Ser Leu Leu Ser Gln Glu Pro Arg Leu Leu Ile Ser Gly Met
        355                 360                 365

Glu Gln Pro Leu Pro Leu Arg Thr Asp Leu Ile
    370                 375
```

<210> SEQ ID NO 24
<211> LENGTH: 2040
<212> TYPE: DNA
<213> ORGANISM: Rattus norvegicus

<400> SEQUENCE: 24

```
ctctcctggg cttctactaa attcttagct tagagcccga gatttcagga agtagagtgt    60
gctgtttacc ctctcaatct ctcctgtgca atcctccctc ctgatgtcct agggatagat   120
agtggagggt ttgggggcat cttgaaatcc tgtgggggc cctgtcactt tgggtccttg    180
tgtgagtcct gcctggtgtc tactgcagcg tgttgcatcc cacggacctt tagaggaatc   240
cggagtgcgg ggctgtgact gctgtctgcc ctttgagagg ccacttgccg gtcgctacgg   300
aagggttctt catagtctct ccagttccag gaacacttcg gtctaggaag cagaagatgc   360
catactccaa cctgcatcca tccatcccac ggcccagaag ttaccgcttc aaactggcag   420
ccttcgtctt gctggtgggc agcctgatga gcctttggat gacaggggaa ccaccaagtc   480
acactctgca ttacctagca cttcacgtag cctcgcagca acttggatta ctgttgaaaa   540
agctctgctg tctggctgaa gagttgtgcc atgtccagtc caggtaccag ggcagctact   600
ggaaggctgt gcgcgcctgc gtggggagtc ccatctgctt tatggccctg atcctactgt   660
cattttattt ctactgctcc ctcgaaaata cttctgacct cgcgccttgct tggcatcttg   720
gcatcctggt cctttcaaag tccctaagca tgaccctgga cctcagagc ttggcccag   780
cagaagtctc tgcggtctgt gaagaaaaga acttcaatgt tgcccatgga ctggcctggt   840
cgtactacat tgggtacctg aagctgatct tgccaggact gcaggcccgg atccggatgt   900
tcaatcagct acacaacaac atgctctcgg gtgcggggag ccggcggctg tatatcctct   960
tcccattgga ctgtggggtg cctgatgatc tgagtgtggc tgaccccaat attcgattcc  1020
gagatatgct gccccagcaa acacagacc gtgctggcgt caagaatcgg gcttattcca  1080
acagtgtcta tgaacttctg gagaatgggc agccggcagg tgcctgtatc ctggagtacg  1140
ccaccccctt gcagaccttg tttgccatgt cacaggatgg caaagctggc ttcagtcggg  1200
aggaccggct tgagcaggcc aaactcttct gtcggacact tgaggaaatt ctggctgatg  1260
tccctgagtc tcgaaaccac tgccgcctca ttgtctacca agaatccgaa gagggaaaca  1320
gtttctcgct gtctcaggag gtgctccggc acattcggca agaagaaaag gaggaagtta  1380
ccatgagtgg ccccccgacc tcagtggcac ctcgtccctc cctactgtcc caagagccga  1440
gacttctcat cagtggcatg gagcagcctc tcccactccg cacggacctc atctgaggca  1500
tgagacagcc ttgcctgggt cccagtgacc cttcagcctc ttgactgggc tcccctttaa  1560
tggctggggg cctcatagag acttcacatc tccagatgag tcccacattc ccgggcaagc  1620
cacttcacct ctctgagcct cagcctgccc cactccaaag gccatcataa ggtattccct  1680
gcccactcag ggttttttgtg aagacaatac atgtagaagt ttggtgtcaa tgcctggtaa  1740
acttgagaga taggccaagt atttcccatg atgatcagca ttctccactc tctgttgact  1800
tgtgtgggtt gttccagcag acctctgacc cagcttctgg tcatgtgtgt tcaacgggag  1860
```

-continued

```
cctcagtaga tggagagagg gagaaggaac atgtgttctg taggcagtca cagtgggccg    1920
ccctgccagg ctgtcttctc agtaaacata tttattctca ggtttctaga atggtctctt    1980
ctccttgccc cagcactggt atttgtgtga cactggagta cttactgtct gtggtctctt    2040
```

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tatgtttgga ttcgacccag                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atagatggca gggtctgcgg                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cgtaaaattt gccagaactg                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggagcgcacc atcttcttca                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggatcttctc gccctcagag                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 30
gcgaattcat ctccgagctg                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gttcgagaag cgccgctctg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aaagccccca aagctcggat                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccgaaagaaa tacccagacc                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tatctcggaa tcgaatgttg                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gaaggccaaa catccaactg                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 36
ctacataaca acatgctcag                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
acagcagcaa cagggcccca                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atagatggac agcagcaaca                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcagcaacag ggccccacgg                                              20
```

MODULATING GABARAP TO MODULATE IMMUNOGENIC CELL DEATH

RELATED APPLICATIONS

This application claims the priority of U.S. Patent Application No. 63/113,284, filed Nov. 13, 2020; the entire contents of said application is incorporated herein in its entirety by this reference.

SEQUENCE LISTING

The instant application contains a Sequence Listing which has been submitted electronically in ASCII format and is hereby incorporated by reference in its entirety. Said ASCII copy, created on Mar. 18, 2022, is named DFS-30701_SL.txt and is 65,196 bytes in size.

STATEMENT OF RIGHTS

This invention was made with government support under grant number P50 CA100707 awarded by The National Institutes of Health. The government has certain rights in the invention.

BACKGROUND OF THE INVENTION

Carcinogenesis and cell death are two biologic processes defined by a specific sequence of molecular events. First, cancer arising from the carcinogenesis process was initially defined as a cell autonomous disease with an imbalance between proto-oncogene activation and/or inactivation of oncosuppressor genes, leading to uncontrolled cell proliferation and resistance to cell death. In this way, cytotoxic chemotherapy was developed with the major aim of killing proliferative cells. However, this strategy only aims to disrupt the cell death/proliferation balance and does not take into account physiological strategies for defense against carcinogenesis. This view of therapeutics in oncology has been revolutionized by new discoveries related to the antitumor immune response and the mechanisms associated with its inhibition by immune checkpoints. Indeed, carcinogenesis is no longer defined solely as genetic disturbances of the malignant cell that give it enhanced proliferation properties, but rather, its definition now also includes an alteration of the immune system that becomes permissive to tumor proliferation. Thus, the last decade has been characterized by the emergence of immunotherapy, with the development of a new strategy to fight cancer cells.

The aim of immunotherapy is not to destroy proliferating cells per se, but to improve the adaptive immune response to recognize and eliminate cancer cells. This major discovery pertains to immune checkpoints, which consist of membranous molecules physiologically expressed during T-cell activation and in inflammatory conditions. Immune checkpoint inhibitors drastically improve immune response, leading to improvement of antitumor immune response. Since the early 2010's, many immunotherapies based on the inhibition of immune-response control points have been developed and shown to be therapeutically superior to conventional chemotherapy. This is notably the case for antibodies targeting the CTLA4 or the PD-1/PD-L1 pathways, which have revolutionized the treatment of melanoma or lung cancer. For example, use of anti-PD-1 antibodies as monotherapy in metastatic non-small cell lung cancer (NSCLC), in second line or more, provides 20-30% lasting control of the disease.

Despite this revolutionary efficacy, many patients present an intrinsic resistance to immunotherapy, which may be explained by many biologic phenomena. Most of these tumors present an absence of lymphocyte infiltration (for example, NK, CD8, Th1, and the like). It is now established that the presence of a cytotoxic response is a prerequisite for the effectiveness of immunotherapy. Biologic phenomena related to this lack of immune response include: (i) loss of antigenicity in tumor cells, which may be linked to a restricted neoantigen level, the disappearance of antigenic presentation systems, the inability of cells to respond to interferons, and/or powerful inducers of antigenic presentation; (ii) absence or inhibition of danger signals linked to inflammatory and immune response in the tumor microenvironment; and (iii) enrichment of regulatory immune cells blocking infiltration and cytotoxic functions of antitumor lymphocytes.

To modulate these phenomena, a combination of immunotherapy with chemotherapy has been proposed and clinically tested. In NSCLC, a significant survival benefit was shown in a Phase III study comparing the combination of pembrolizumab (anti-PD-1) and platinum/pemetrexed chemotherapy versus chemotherapy alone. The observed therapeutic effect was independent of the expression of PD-L1 by tumor cells. The biologic and immunological rationale to explain the efficacy of this combination is based on the ability of chemotherapy to restore an immune response through several complementary mechanisms in non-infiltrated tumors. Indeed, there is an increasing body of evidence showing that chemotherapies can cause so-called "immunogenic" cell death (ICD) of cells like cancer cells, which can stimulate host antitumor immunity. These immunological properties enable chemotherapy to transform a non-inflammatory tumor, known as "cold", into a tumor enriched with cytotoxic cells, known as "hot." This change in phenotype makes it possible to sensitize the tumor to checkpoint blockade, which requires a pre-existing immune response. Currently, some clinically approved therapies and clinical trials are using associations of chemotherapies and immunotherapies. However, it is still not understood how ICD is induced, and why a significant number of patients do not respond to the combination of chemotherapy and immunotherapy. Accordingly, there is a great need in the art for therapeutic strategies to efficiently induce ICD in patients.

SUMMARY OF THE INVENTION

Induction of immunogenic cell death (ICD) represents a promising immunotherapeutic strategy in cancer. ICD inducers can boost a specific immune response against cancer antigens and drive long-term therapeutic success. The present invention is based, at least in part, on the discovery that the deletion of the GABARAP gene impairs induction of ICD upon treatment with an ICD inducer, such as a proteasome inhibitor like bortezomib (BTZ), in cancer, such as in a hematological cancer like multiple myeloma (MM). Thus, increasing the copy number, expression level, and/or activity of GABARAP and/or its binding partner calreticulin (CRT) (such as by increasing the exposure of CRT on a cell surface like a cancer cell surface), in combination with an ICD inducer (e.g., a proteasome inhibitor, a chemotherapeutic agent, radiation therapy, and the like) provides a new strategy for treating cancer. In addition, the discovery that a lower copy number, expression level, and/or activity of GABARAP indicates a poor prognosis in cancer patients, e.g., in MM patients, provides novel diagnostic and prognostic methods for cancer patients.

The present invention is also based, in part, on the discovery that treatment with BTZ increases the binding of CALR to mitochondrial proteins in AMO1 GABARAP$^{KO}$ cells and not WT cells, indicating preferential mitochondrial localization of CALR in the GABARAP$^{KO}$ cells upon induction of ICD. Moreover, it was found that stanniocalcin 1 (STC1) protein levels decrease in WT cells after BTZ treatment, in contrast to GABARAP$^{KO}$ cells, in which intracellular levels of STC1 are even higher after BTZ treatment. These findings identify a molecular mechanism whereby GABARAP prevents STC1 binding to CALR; conversely, in low-GABARAP cells STC1 binding to CALR induces trapping of CALR in the mitochondria. Thus, decreasing the copy number, expression level, and/or activity of STC1, in combination with an ICD inducer (e.g., a proteasome inhibitor, a chemotherapeutic agent, radiation therapy, and the like) provides a new strategy for treating cancer. In addition, a higher copy number, expression level, and/or activity of STC1 indicates a poor prognosis in cancer patients, e.g., in multiple myeloma patients, and may provide novel diagnostic and prognostic methods for cancer patients.

Additionally, the present invention is also based, in part, on the discovery that BTZ induces anti-multiple myeloma immune response mediated by cGAS/STING pathway activation. Provided herein are validation of STING signaling mediating BTZ-induced anti-tumor immunity, providing the rationale for clinical trials evaluating BTZ-STING agonist combination therapy to improve patient outcome in cancer (e.g., multiple myeloma). Thus, increasing the copy number, expression level, and/or activity of STING in combination with an ICD inducer (e.g., a proteasome inhibitor, a chemotherapeutic agent, radiation therapy, and the like) provides a new strategy for treating cancer. In addition, a lower copy number, expression level, and/or activity of STING indicates a poor prognosis in cancer patients, e.g., in MM patients, and provides novel diagnostic and prognostic methods for cancer patients.

In certain aspects, a method of preventing or treating a subject afflicted with a cancer comprising administering to the subject a therapeutically effective amount of an agent that i) increases the copy number, the expression level, and/or the activity of one or more biomarkers listed in Table 1 or a fragment thereof, and/or ii) decreases the copy number, the expression level, and/or the activity of one or more biomarkers listed in Table 2, and an inducer of immunogenic cell death (ICD), is provided.

In certain aspects, a method of inducing an immunogenic cell death of a cancer cell, the method comprising contacting the cancer cell with an agent that i) increases the copy number, the expression level, and/or the activity of one or more biomarkers listed in Table 1 or a fragment thereof, and/or ii) decreases the copy number, the expression level, and/or the activity of one or more biomarkers listed in Table 2 or a fragment thereof, and an inducer of immunogenic cell death (ICD), is provided.

Numerous embodiments are further provided that can be applied to any aspect of the present invention and/or combined with any other embodiment described herein. For example, in some embodiments, the method comprises an agent that increases the copy number, the expression level, and/or the activity of gamma-aminobutyric acid receptor-associated protein (GABARAP), calreticulin (CRT) and/or stimulator of interferon genes protein (STING). In some embodiments, the agent is a STING agonist (e.g., ADUS-100, MK-1454, macrocycle-bridged STING agonist E7766, BMS-986301, GSK3745417, IMSA101, MK-2118, SB 11285, SNX281, TAK-676, or STING agonist-containing PTGFRN-expressing exosomes CDK002). In some embodiments, the agent increases the biological activity of GABARAP, CRT, and/or STING. In some embodiments, the agent increases the biological activity selected from the group consisting of (a) a chloride-gating activity, (b) a calcium (Ca2+)-binding activity, (c) a charaperone activity, (d) a substrate-binding activity (e.g., GABARAP's CRT-binding activity, CRT's GABARAP-binding activity) and/or (e) type I interferon production. In another example, the method comprises an agent that decreases the copy number, the expression level, and/or the activity of stanniocalcin 1 (STC1). In some embodiments, the agent decreases the biological activity of STC1. In some embodiments, the agent decreases the biological activity selected from the group consisting of SUMO E3 ubiquitin ligase activity, localization of CALR to the mitochondria, and/or a substrate-binding activity (e.g. binding of STC1 to CALR or SUMO1).

In certain aspects, the biomarker comprises a nucleic acid sequence having at least about 80% identity to a nucleic acid sequence listed in Table 1 and/or encodes an amino acid sequence having at least about 80% identity to an amino acid sequence listed in Table 1 or wherein the biomarker comprises a nucleic acid sequence having at least about 80% identity to a nucleic acid sequence listed in Table 2 and/or encodes an amino acid sequence having at least about 80% identity to an amino acid sequence listed in Table 2. In some embodiments, the one or more biomarkers are human, mouse, chimeric, or a fusion. In some embodiments, the GABARAP comprises an amino acid sequence listed in Table 1, optionally wherein the amino acid sequence is selected from the group consisting of SEQ ID NOs: 1, 3, and 5. In some embodiments, the GABARAP is encoded by a nucleic acid comprising a sequence listed in Table 1, optionally wherein the nucleic acid sequence is selected from the group consisting of SEQ ID NOs: 2, 4, and 6. In some embodiments, the CRT comprises an amino acid sequence listed in Table 1, optionally wherein the amino acid sequence is selected from the group consisting of SEQ ID NOs: 7, 9, and 11. In some embodiments, the CRT is encoded by a nucleic acid comprising sequence listed in Table 1, optionally wherein the nucleic acid sequence is selected from the group consisting of SEQ ID NOs: 8, 10, and 12. In some embodiments, the STING comprises an amino acid sequence listed in Table 1, optionally wherein the amino acid sequence is selected from the group consisting of SEQ ID NOs: 19, 21, or 23. In some embodiments, the STING is encoded by a nucleic acid comprising sequence listed in Table 1, optionally wherein the nucleic acid sequence is selected from the group consisting of SEQ ID NOs: 20, 22, or 24.

In some embodiments, the STC1 comprises an amino acid sequence listed in Table 2, optionally wherein the amino acid sequence is selected from the group consisting of SEQ ID NOs: 13, 15, and 17. In some embodiments, the STC1 is encoded by a nucleic acid comprising a sequence listed in Table 2, optionally wherein the nucleic acid sequence is selected from the group consisting of SEQ ID NOs: 14, 16, and 18.

In certain aspects, the inducer of ICD is selected from the group consisting of chemotherapeutic agents, radiation therapy, oxazophorines, platinum-based compounds, anthracyclines, anthracenediones, and proteasome inhibitors. In some embodiments, the inducer of ICD is selected from the group consisting of bortezomib, carfilzomib, cyclophosphamide, idarubicin, doxorubicin, mitoxantrone, epirubicin, and oxaliplatin. In some embodiments, the inducer of ICD further comprises a lipid (e.g., a liposome) or a targeting polypeptide (e.g., a ligand or an antibody). In some embodiments, the inducer of ICD is administered before, after, or concurrently with the agent.

In certain aspects, the agent comprises a small molecule, a peptide, a polypeptide, an aptamer, an antibody or a binding fragment thereof, an intrabody or a binding fragment thereof, and/or a nucleic acid. In some embodiments, the nucleic acid comprises a sequence encoding one or more biomarkers listed in Table 1 or fragment thereof and/or the nucleic acid comprises a sequence encoding one or more biomarkers listed in Table 2 or a fragment thereof. In some embodiments, (i) the nucleic acid is operably linked to a promoter, and/or (ii) the nucleic acid comprises a sequence having at least about 80% identity to a genomic sequence of the cancer cell that facilitates homologous recombination into the genome of the cancer cell. In some embodiments, the nucleic acid is in a viral particle. In some embodiments, the viral particle is a lentivirus particle, an adenovirus, or an adeno-associated virus particle.

In certain aspects, the agent is cell-based. In some embodiments, the agent comprises i) a cancer cell that is modified to comprise an increased copy number, expression level, and/or activity of one or more biomarkers listed in Table 1 or a fragment thereof and/or ii) a cancer cell that is modified to comprise a decrease in copy number, expression level, and/or activity of one or more biomarkers listed in Table 2 or a fragment thereof, optionally further comprising an inducer of ICD. In some embodiments, the cancer cell is non-replicative. In some embodiments, the cancer cell is non-replicative due to an inducer of ICD (e.g., irradiation, heat treatment, a chemotherapeutic compound). In some embodiments, the cell of the cancer cell is autologous or allogeneic.

In certain aspects, the agent increases the exposure of CRT by the cancer cell. In some embodiments, the agent induces extracellular release of adenosine-5'-triphosphate (ATP) and/or high mobility group box 1 protein (HMGB1). In some embodiments, the agent reduces the T cell exhaustion and/or the number of CD4+ T cells, optionally wherein the T cells are intratumoral T cells. In some embodiments, the agent increases the cell surface expression of CD86/CD83 on an intratumoral dendritic cell (DC), and/or induces differentiation of a DC. In some embodiments, the agent increases phagocytosis of the cancer cell, optionally wherein the agent increases the phagocytosis of the cancer cell by a DC. In some embodiments, the agent increases the immune response against the cancer cell. In some embodiments, the agent reduces the number of proliferating cancer cells and/or reduces the volume or size of a tumor comprising the cancer cells. In some embodiments, the agent decreases the binding of STC1 to CALR and/or decreases levels of CALR in the mitochondria.

In some embodiments, the method further comprises administering to the subject, or contacting the cancer cell with, an additional cancer therapy. In some embodiments, the additional cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, and/or an interferon-inducing agent. In some embodiments, the immunotherapy and/or a cancer therapy is administered before, after, or concurrently with the agent. In some embodiments, the immunotherapy comprises an anti-cancer vaccine or virus. In some embodiments, the immunotherapy is cell-based. In some embodiments, the immunotherapy inhibits an immune checkpoint. In some embodiments, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD48, 2B4 (CD244), B7.1, B7.2, ILT-2, ILT-4, TIGIT, HHLA2, butyrophilins, IDO, CD39, CD73 and A2aR. In some embodiments, the immune checkpoint is selected from the group consisting of CTLA-4, PD-1, PD-L1, and PD-L2.

In some embodiments, the cancer is a relapsed cancer. In some embodiments, the cancer is selected from the group consisting of melanoma, sporadic cutaneous melanoma, breast cancer, nasopharyngeal carcinoma, acute myeloid leukemia, hepatocellular carcinoma, colorectal cancer, lung cancer, colon adenocarcinoma, prostate cancer, mesothelioma, non-small cell lung cancer, urothelial carcinoma, glioblastoma, glioma, neuroblastoma, Wilms tumor, cervical cancer, prometastatic cervical cancer, gastric cancer, ovarian cancer, thyroid cancer, Burkitt lymphoma, chronic lymphocytic leukemia, Kaposi sarcoma, cutaneous T-cell lymphoma, liver cancer, liver adenoma, pancreatic cancer, pancreatic adenocarcinoma, squamous cell carcinoma, head and neck cancer, biliary tract cancer, non-Hodgkin lymphoma, leukemia, bladder cancer, endometrial cancer, chronic myeloid leukemia, promyelocytic leukemia, neuroblastoma, esophageal squamous cell carcinoma, oligodendroglioma, astrocytoma, lymphoma, myeloma, multiple myeloma, plasma cell myeloma, osteosarcoma, renal medullary carcinoma, small cell lung cancer, gastric cancer, esophageal cancer, gastroesophageal cancer, and astrocytic glioma, optionally wherein the cancer is multiple myeloma. In some embodiments, the cancer is selected from the group consisting of myeloma, multiple myeloma, plasma cell myeloma, bladder cancer, breast cancer, lymphoma, neuroblastoma, osteosarcoma, ovarian cancer, renal medullary carcinoma, small cell lung cancer, colorectal cancer, gastric cancer, esophageal cancer, gastroesophageal cancer, pancreatic cancer, and acute myeloid leukemia. In some embodiments, the subject is an animal model of the cancer, preferably a mouse model, or a human, optionally wherein the human has a del(17p). In some embodiments, the agent is in a pharmaceutically acceptable formulation.

In certain aspects, a method of determining whether a subject afflicted with a cancer or at risk for developing a cancer would benefit from i) increasing the copy number, amount, and/or activity of at least one biomarker listed in Table 1 and/or ii) decreasing the copy number, amount, and/or activity of at least one biomarker listed in Table 2, optionally in combination with an inducer of ICD, the method comprising: a) obtaining a biological sample from the subject; b) determining the copy number, amount, and/or activity of at least one biomarker listed in Table 1 or Table 2; c) determining the copy number, amount, and/or activity of the at least one biomarker in a control; and d) comparing the copy number, amount, and/or activity of the at least one biomarker detected in steps b) and c); wherein either a significant decrease in, the copy number, amount, and/or activity of, the at least one biomarker listed in Table 1 in the subject sample relative to the control copy number, amount, and/or activity of, the at least one biomarker indicates that the subject afflicted with the cancer or at risk for developing the cancer would benefit from increasing the copy number, amount, and/or activity of the at least one biomarker listed in Table 1, or a significant increase in, the copy number, amount, and/or activity of, the at least one biomarker listed in Table 2 in the subject sample relative to the control copy number, amount, and/or activity of, the at least one biomarker indicates that the subject afflicted with the cancer or at risk for developing the cancer would benefit from decreasing the copy number, amount, and/or activity of the at least one biomarker listed in Table 2.

In some embodiments, the method further comprises recommending, prescribing, or administering an agent that i) increases the copy number, amount, and/or activity of the at least one biomarker listed in Table 1 increases the copy number, amount, and/or activity of the at least one biomarker listed in Table 1 or ii) decreases the copy number, amount, and/or activity of the at least one biomarker listed in Table 2 if the cancer is determined to benefit from the agent, optionally further administering at least one additional cancer therapy. In some embodiments, the method further comprises recommending, prescribing, or administering cancer therapy other than an agent that increases the copy number, amount, and/or activity of the at least one biomarker listed in Table 1 if the cancer is determined to not benefit from the agent. In some embodiments, the method further comprises recommending, prescribing, or administering cancer therapy other than an agent that decreases the copy number, amount, and/or activity of the at least one biomarker listed in Table 2 if the cancer is determined to not benefit from the agent. In some embodiments, the cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy, interferon, and/or an interferon-inducing agent. In some embodiments, the control sample is determined from a cancerous or non-cancerous sample from either the patient or a member of the same species to which the patient belongs. In some embodiments, the control sample comprises cells.

In certain aspects, a method of determining whether a subject afflicted with a cancer would likely respond to an inducer of ICD, the method comprising: a) determining a copy number, amount, and/or activity of at least one biomarker listed in Table 1 and/or Table 2 in a subject sample; b) determining the copy number, amount, and/or activity of the at least one biomarker in a control (e.g., having a good response to an inducer of ICD); and c) comparing the copy number, amount, and/or activity of the at least one biomarker in the subject sample and in the control; wherein a significant decrease in, the copy number, amount, and/or activity of, the at least one biomarker listed in Table 1 and/or a significant increase in, the copy number, amount, and/or activity of the at least one biomarker listed in Table 2 in the subject sample as compared to the copy number, amount and/or activity in the control, is an indication that the subject is not likely to respond to an inducer of ICD.

In certain aspects, a method for predicting the clinical outcome of a subject afflicted with a cancer, in response to an inducer of ICD, the method comprising: a) determining the copy number, amount, and/or activity of at least one biomarker listed in Table 1 and/or Table 2 in a subject sample; b) determining the copy number, amount, and/or activity of the at least one biomarker in a control having a good clinical outcome; and c) comparing the copy number, amount, and/or activity of the at least one biomarker in the subject sample and in the control; wherein a significant decrease in the copy number, amount, and/or activity of, the at least one biomarker listed in Table 1 in the subject sample as compared to the copy number, amount and/or activity in the control or a significant increase in the copy number, amount, and/or activity of, the at least one biomarker listed in Table 2 in the subject sample as compared to the copy number, amount and/or activity in the control, is an indication that the subject has a poor clinical outcome. In some embodiments, the subject has undergone cancer treatment, completed cancer treatment, concurrently under cancer treatment, and/or is in remission for the cancer.

As described above, numerous embodiments are further provided that can be applied to any aspect of the present invention and/or combined with any other embodiment described herein. For example, in some embodiments, the inducer of ICD is selected from the group consisting of chemotherapeutic agents, radiation therapy, oxazophorines, platinum-based compounds, anthracyclines, anthracenediones, and proteasome inhibitors. In some embodiments, the inducer of ICD is selected from the group consisting of bortezomib, carfilzomib, cyclophosphamide, idarubicin, doxorubicin, mitoxantrone, epirubicin, and oxaliplatin. In some embodiments, the sample is selected from the group consisting of ex vivo and in vivo samples. In some embodiments, the sample is a portion of a single sample or pooled samples obtained from the subject.

As described above, in some embodiments, the sample comprises cells, serum, peritumoral tissue, and/or intratumoral tissue obtained from the subject. In some embodiments, the at least one biomarker listed in Table 1 comprises GABARAP, CRT, and/or STING. In some embodiments, the at least one biomarker comprises a nucleic acid sequence having at least about 80% identity to a nucleic acid sequence listed in Table 1 and/or encode an amino acid sequence having at least about 80% identity to an amino acid sequence listed in Table 1. In some embodiments, the GABARAP comprises an amino acid sequence listed in Table 1, optionally wherein the amino acid sequence is selected from the group consisting of SEQ ID NOs: 1, 3, and 5. In some embodiments, the GABARAP is encoded by a nucleic acid comprising a sequence listed in Table 1, optionally wherein the nucleic acid sequence is selected from the group consisting of SEQ ID NOs: 2, 4, and 6. In some embodiments, the CRT comprises an amino acid sequence listed in Table 1, optionally wherein the amino acid sequence is selected from the group consisting of SEQ ID NOs: 7, 9, and 11. In some embodiments, the CRT is encoded by a nucleic acid comprising a sequence listed in Table 1, optionally wherein the nucleic acid sequence is selected from the group consisting of SEQ ID NOs: 8, 10, and 12. In some embodiments, the STING comprises an amino acid sequence listed in Table 1, optionally wherein the amino acid sequence is selected from the group consisting of SEQ ID NOs: 19, 21, or 23. In some embodiments, the STING is encoded by a nucleic acid comprising sequence listed in Table 1, optionally wherein the nucleic acid sequence is selected from the group consisting of SEQ ID NOs: 20, 22, or 24.

In some embodiments, the at least one biomarker listed in Table 2 comprises STC1. In some embodiments, the at least one biomarker comprises a nucleic acid sequence having at least about 80% identity to a nucleic acid sequence listed in Table 2 and/or encode an amino acid sequence having at least about 80% identity to an amino acid sequence listed in Table 2. In some embodiments, the STC1 comprises an amino acid sequence listed in Table 2, optionally wherein the amino acid sequence is selected from the group consisting of SEQ ID NOs: 13, 15, and 17. In some embodiments, the STC1 is encoded by a nucleic acid comprising a sequence listed in Table 2, optionally wherein the nucleic acid sequence is selected from the group consisting of SEQ ID NOs: 14, 16, and 18.

In some embodiments, the cancer is a relapsed cancer. In some embodiments, the cancer is selected from the group consisting of melanoma, sporadic cutaneous melanoma, breast cancer, nasopharyngeal carcinoma, acute myeloid leukemia, hepatocellular carcinoma, colorectal cancer, lung cancer, colon adenocarcinoma, prostate cancer, mesothelioma, non-small cell lung cancer, urothelial carcinoma, glioblastoma, glioma, neuroblastoma, Wilms tumor, cervical cancer, prometastatic cervical cancer, gastric cancer, ovarian cancer, thyroid cancer, Burkitt lymphoma, chronic lymphocytic leukemia, Kaposi sarcoma, cutaneous T-cell lymphoma, liver cancer, liver adenoma, pancreatic cancer, pancreatic adenocarcinoma, squamous cell carcinoma, head and neck cancer, biliary tract cancer, non-Hodgkin lymphoma, leukemia, bladder cancer, endometrial cancer, chronic myeloid leukemia, promyelocytic leukemia, neuroblastoma, esophageal squamous cell carcinoma, oligodendroglioma, astrocytoma, lymphoma, myeloma, multiple myeloma, plasma cell myeloma, osteosarcoma, renal medullary carcinoma, small cell lung cancer, gastric cancer, esophageal cancer, gastroesophageal cancer, and astrocytic glioma, optionally wherein the cancer is multiple myeloma. In some embodiments, the cancer is selected from myeloma, multiple myeloma, plasma cell myeloma, bladder cancer, breast cancer, lymphoma, neuroblastoma, osteosarcoma, ovarian cancer, renal medullary carcinoma, small cell lung cancer, colorectal cancer, gastric cancer, esophageal cancer, gastroesophageal cancer, pancreatic cancer, or acute myeloid leukemia. In some embodiments, the cancer is in a subject and the subject is a mammal. In some embodiments, the mammal is a mouse or a human. In some embodiments, the mammal is a human, optionally wherein the human has a del(17p).

In certain aspects, a method of identifying a compound that induces immunogenic cell death (ICD) of a cancer cell comprising a decrease in a copy number, amount, and/or activity of at least one biomarker listed in Table 1, the method comprising: a) contacting a cancer cell comprising a decrease in the copy number, amount, and/or activity of at least one biomarker listed in Table 1, relative to a control, with (i) a test compound and (ii) an inducer of ICD; b) co-culturing the said cancer cell with a dendritic cell; and c) assaying the phagocytosis of the cancer cell by the co-cultured dendritic cell to determine the functional maturation of the co-cultured dendritic cell, wherein the increase in the level of phagocytosis of the cancer cell in the presence of the test compound as compared to the level of phagocytosis of the cancer cell in the absence of the test compound, indicates that the test compound induces ICD of the cancer cell comprising a decrease in the copy number, amount, and/or activity of at least one biomarker listed in Table 1, is provided.

In certain aspects, a method of identifying a compound that induces immunogenic cell death (ICD) of a cancer cell comprising an increase in a copy number, amount, and/or activity of at least one biomarker listed in Table 2, the method comprising: a) contacting a cancer cell comprising an increase in the copy number, amount, and/or activity of at least one biomarker listed in Table 2, relative to a control, with (i) a test compound and (ii) an inducer of ICD; b) co-culturing the said cancer cell with a dendritic cell; and c) assaying the phagocytosis of the cancer cell by the co-cultured dendritic cell to determine the functional maturation of the co-cultured dendritic cell, wherein the increase in the level of phagocytosis of the cancer cell in the presence of the test compound as compared to the level of phagocytosis of the cancer cell in the absence of the test compound, indicates that the test compound induces ICD of the cancer cell comprising an increase in the copy number, amount, and/or activity of at least one biomarker listed in Table 2, is provided.

In certain aspects, a method of identifying a compound that induces immunogenic cell death (ICD) of a cancer cell comprising a decrease in a copy number, amount, and/or activity of GABARAP, the method comprising: a) contacting a cancer cell comprising a decrease in the copy number, amount, and/or activity of GABARAP, relative to the copy number, amount, and/or activity of GABARAP in a non-cancerous cell, with (i) a test compound and (ii) an inducer of ICD; and b) determining the level of calreticulin exposed by the cancer cell, wherein the increase in the level of calreticulin exposed by the cancer cell in the presence of the test compound as compared to the level of calreticulin exposed by the cancer cell in the absence of the test compound indicates that the test compound induces ICD of the cancer cell comprising a decrease in the copy number, amount, and/or activity of GABARAP.

In certain aspects, a method of identifying a compound that induces immunogenic cell death (ICD) of a cancer cell comprising an increase in a copy number, amount, and/or activity of STC1, the method comprising: a) contacting a cancer cell comprising an increase in the copy number, amount, and/or activity of STC1, relative to the copy number, amount, and/or activity of STC1 in a non-cancerous cell, with (i) a test compound and (ii) an inducer of ICD; and b) determining the level of calreticulin trapped in the mitochondria of the cancer cell, wherein the decrease in the level of calreticulin in the mitochondria of the cancer cell in the presence of the test compound as compared to the level of calreticulin exposed by the cancer cell in the absence of the test compound indicates that the test compound induces ICD of the cancer cell comprising an increase in the copy number, amount, and/or activity of STC1.

In some embodiments, the at least one biomarker listed in Table 1 comprises GABARAP, CRT, and/or STING. In some embodiments, the at least one biomarker listed in Table 2 comprises STC1. In some embodiments, the at least one biomarker comprises a nucleic acid sequence having at least about 80% identity to a nucleic acid sequence listed in Table 1 and/or encode an amino acid sequence having at least about 80% identity to an amino acid sequence listed in Table 1. In some embodiments, the GABARAP comprises an amino acid sequence listed in Table 1, optionally wherein the amino acid sequence is selected from the group consisting of SEQ ID NOs: 1, 3, and 5. In some embodiments, the GABARAP is encoded by a nucleic acid comprising a sequence listed in Table 1, optionally wherein the nucleic acid sequence is selected from the group consisting of SEQ ID NOs: 2, 4, and 6. In some embodiments, the CRT comprises an amino acid sequence listed in Table 1, optionally wherein the amino acid sequence is selected from the group consisting of SEQ ID NOs: 7, 9, and 11. In some embodiments, the CRT is encoded by a nucleic acid comprising a sequence listed in Table 1, optionally wherein the nucleic acid sequence is selected from the group consisting of SEQ ID NOs: 8, 10, and 12. In some embodiments, the STING comprises an amino acid sequence listed in Table 1, optionally wherein the amino acid sequence is selected from the group consisting of SEQ ID NOs: 19, 21, or 23. In some embodiments, the STING is encoded by a nucleic acid comprising sequence listed in Table 1, optionally wherein the nucleic acid sequence is selected from the group consisting of SEQ ID NOs: 20, 22, or 24.

In some embodiments, the at least one biomarker listed in Table 2 comprises STC1. In some embodiments, the at least one biomarker comprises a nucleic acid sequence having at least about 80% identity to a nucleic acid sequence listed in Table 2 and/or encodes an amino acid sequence having at least about 80% identity to an amino acid sequence listed in Table 2. In some embodiments, the STC1 comprises an amino acid sequence listed in Table 2, optionally wherein the amino acid sequence is selected from the group consisting of SEQ ID NOs: 13, 15, and 17. In some embodiments, the STC1 is encoded by a nucleic acid comprising a sequence listed in Table 2, optionally wherein the nucleic acid sequence is selected from the group consisting of SEQ ID NOs: 14, 16, and 18.

In some embodiments, the cancer cell is from a relapsed cancer. In some embodiments, the cancer is selected from the group consisting of melanoma, sporadic cutaneous melanoma, breast cancer, nasopharyngeal carcinoma, acute myeloid leukemia, hepatocellular carcinoma, colorectal cancer, lung cancer, colon adenocarcinoma, prostate cancer, mesothelioma, non-small cell lung cancer, urothelial carcinoma, glioblastoma, glioma, neuroblastoma, Wilms tumor, cervical cancer, prometastatic cervical cancer, gastric cancer, ovarian cancer, thyroid cancer, Burkitt lymphoma, chronic lymphocytic leukemia, Kaposi sarcoma, cutaneous T-cell lymphoma, liver cancer, liver adenoma, pancreatic cancer, pancreatic adenocarcinoma, squamous cell carcinoma, head and neck cancer, biliary tract cancer, non-Hodgkin lymphoma, leukemia, bladder cancer, endometrial cancer, chronic myeloid leukemia, promyelocytic leukemia, neuroblastoma, esophageal squamous cell carcinoma, oligodendroglioma, astrocytoma, lymphoma, myeloma, multiple myeloma, plasma cell myeloma, osteosarcoma, renal medullary carcinoma, small cell lung cancer, gastric cancer, esophageal cancer, gastroesophageal cancer, and astrocytic glioma, optionally wherein the cancer cell is from multiple myeloma. In some embodiments, the cancer is selected from myeloma, multiple myeloma, plasma cell myeloma, bladder cancer, breast cancer, lymphoma, neuroblastoma, osteosarcoma, ovarian cancer, renal medullary carcinoma, small cell lung cancer, colorectal cancer, gastric cancer, esophageal cancer, gastroesophageal cancer, pancreatic cancer, or acute myeloid leukemia.

In some embodiments, the method comprises an inducer of ICD that is selected from the group consisting of chemotherapeutic agents, radiation therapy, oxazophorines, platinum-based compounds, anthracyclines, anthracenediones, and proteasome inhibitors. In some embodiments, the inducer of ICD is selected from the group consisting of bortezomib, carfilzomib, cyclophosphamide, idarubicin, doxorubicin, mitoxantrone, epirubicin, and oxaliplatin.

In certain aspects, a cell, such as a cancer cell, that is modified to comprise an increased copy number, expression level, and/or activity of one or more biomarkers listed in Table 1 or a fragment thereof, is provided. In certain aspects, a cell, such as a cancer cell, that is modified to comprise a decreased copy number, expression level, and/or activity of one or more biomarkers listed in Table 2 or a fragment thereof, is provided. In some embodiments, the cell is non-replicative. In some embodiments, the cell is non-replicative due to an inducer of ICD (e.g., irradiation, heat treatment, a chemotherapeutic compound, and the like). In some embodiments, the biomarker comprises a nucleic acid sequence having at least about 80% identity to a nucleic acid sequence listed in Table 1 and/or encodes an amino acid sequence having at least about 80% identity to an amino acid sequence listed in Table 1. In some embodiments, the biomarker comprises a nucleic acid sequence having at least about 80% identity to a nucleic acid sequence listed in Table 2 and/or encodes an amino acid sequence having at least about 80% identity to an amino acid sequence listed in Table 2. In some embodiments, the one or more biomarkers are human, mouse, chimeric, or a fusion. In some embodiments, the biomarker comprise gamma-aminobutyric acid receptor-associated protein (GABARAP), calreticulin (CRT), stimulator of interferon genes protein (STING), and/or Stanniocalcin 1 (STC1). In some embodiments, the GABARAP comprises an amino acid sequence listed in Table 1, optionally wherein the amino acid sequence is selected from the group consisting of SEQ ID NOs: 1, 3, and 5. In some embodiments, the GABARAP is encoded by a nucleic acid comprising a sequence listed in Table 1, optionally wherein the nucleic acid sequence is selected from the group consisting of SEQ ID NOs: 2, 4, and 6. In some embodiments, the CRT comprises an amino acid sequence listed in Table 1, optionally wherein the amino acid sequence is selected from the group consisting of SEQ ID NOs: 7, 9, and 11. In some embodiments, the CRT is encoded by a nucleic acid comprising sequence listed in Table 1, optionally wherein the nucleic acid sequence is selected from the group consisting of SEQ ID NOs: 8, 10, and 12. In some embodiments, the STING comprises an amino acid sequence listed in Table 1, optionally wherein the amino acid sequence is selected from the group consisting of SEQ ID NOs: 19, 21, or 23. In some embodiments, the STING is encoded by a nucleic acid comprising sequence listed in Table 1, optionally wherein the nucleic acid sequence is selected from the group consisting of SEQ ID NOs: 20, 22, or 24.In some embodiments, the STC1 comprises an amino acid sequence listed in Table 2, optionally wherein the amino acid sequence is selected from the group consisting of SEQ ID NOs: 13, 15, and 17. In some embodiments, the STC1 is encoded by a nucleic acid comprising a sequence listed in Table 2, optionally wherein the nucleic acid sequence is selected from the group consisting of SEQ ID NOs: 14, 16, and 18.

In certain aspects, a cancer vaccine comprising the cell of the present disclosure (e.g., the cancer cell that is modified to comprise an increased copy number, expression level, and/or activity of one or more biomarkers listed in Table 1 or a fragment thereof), is provided. In some embodiments, the cancer vaccine further comprises an inducer of ICD. In some embodiments, the inducer of ICD is selected from the group consisting of chemotherapeutic agents, radiation therapy, oxazophorines, platinum-based compounds, anthracyclines, anthracenediones, and proteasome inhibitors. In some embodiments, the inducer of ICD is selected from the group consisting of bortezomib, carfilzomib, cyclophosphamide, idarubicin, doxorubicin, mitoxantrone, epirubicin, and oxaliplatin. In some embodiments, the cancer vaccine further comprises an additional cancer therapy. In some such embodiments, the additional cancer therapy is an immunotherapy, chemotherapy, radiation therapy, and/or hormone therapy. In some embodiments, the immunotherapy inhibits an immune checkpoint. In some embodiments, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD48, 2B4 (CD244), B7.1, B7.2, ILT-2, ILT-4, TIGIT, HHLA2, butyrophilins, IDO, CD39, CD73 and A2aR. In some embodiments, the immune checkpoint is selected from the group consisting of CTLA-4, PD-1, PD-L1, and PD-L2. In some embodiments, the cell is a cancer cell, such as a cancer cell from a relapsed cancer.

In some embodiments, the cancer cell is selected from the group consisting of melanoma, sporadic cutaneous melanoma, breast cancer, nasopharyngeal carcinoma, acute myeloid leukemia, hepatocellular carcinoma, colorectal cancer, lung cancer, colon adenocarcinoma, prostate cancer, mesothelioma, non-small cell lung cancer, urothelial carcinoma, glioblastoma, glioma, neuroblastoma, Wilms tumor, cervical cancer, prometastatic cervical cancer, gastric cancer, ovarian cancer, thyroid cancer, Burkitt lymphoma, chronic lymphocytic leukemia, Kaposi sarcoma, cutaneous T-cell lymphoma, liver cancer, liver adenoma, pancreatic cancer, pancreatic adenocarcinoma, squamous cell carcinoma, head and neck cancer, biliary tract cancer, non-Hodgkin lymphoma, leukemia, bladder cancer, endometrial cancer, chronic myeloid leukemia, promyelocytic leukemia, neuroblastoma, esophageal squamous cell carcinoma, oligodendroglioma, astrocytoma, lymphoma, myeloma, multiple myeloma, plasma cell myeloma, osteosarcoma, renal medullary carcinoma, small cell lung cancer, gastric cancer, esophageal cancer, gastroesophageal cancer, and astrocytic glioma, optionally wherein the cancer is multiple myeloma.

Further provided herein is a method of preventing or treating a subject afflicted with a cancer comprising administering to the subject a therapeutically effective amount of the cell, such as a cancer cell, or vaccine, such as a cancer vaccine, described herein.

BRIEF DESCRIPTION OF THE DRAWINGS

FIG. 12A has been generated by using the The Human Reference Interactome Atlas (available on the World Wide Web at interactome-atlas.org/) and FIG. 12B is adapted from Thielmann et al. (2008) *FEBS J.* 276:1140-1152.

FIG. 13A-FIG. 13E show that low GABARAP correlates with poor prognosis and blocks ICD induction by BTZ in MM. FIG. 13A provides Kaplan-Meier curves demonstrating association of EFS (p=0.018) with GABARAP expression, as analyzed by log-rank test in a dataset of 400 newly diagnosed MM patients enrolled in the IFM/DFCI clinical study (Attal et al. (2017) *New Engl. J. Med.* 376:1311-1320). This analysis does not include patients carrying del(17p). FIG. 13B shows the level of calreticulin exposed by KMS11 cells upon treatment with various concentrations of BTZ. FIG. 13C shows Western blot analysis results illustrating that KMS11 cells that carry a monoallelic deletion of GABARAP has an undetectable level of the GABARAP protein. FIG. 13D shows results of a phagocytosis assay: DCs and BTZ-treated AMO1, H929, 5TGM1 or KMS11 cells were co-cultured for 4 hours. Percentage of double positive DCs assessed by flow cytometry, is represented. Bortezomib does not induce ICD in GABARAP-null cells. FIG. 13E provides Western blot analysis results showing GABARAP and GAPDH levels after overexpression in KMS11 cells. Calreticulin expression and phagocytosis assay in KMS11 control (CNT) and in KMS11 overexpressing GABARAP after treatment with BTZ.

FIG. 14A shows AMO1 and H929 clones positive for GABARAP knock out (KO). GAPDH was used as loading control. FIG. 14B shows quantification of CALR exposure in AMO1 and H929 WT (red) and GABARAP$^{KO}$ clones (blue) after treatment with BTZ as assessed by flow cytometry: geometric mean normalized to untreated cells. FIG. 14C shows results of a phagocytosis assay in AMO1 WT and GABARAP$^{KO}$ after treatment with BTZ. FIG. 14D shows results of a phagocytosis assay in AMO1 GABARAP$^{KO}$ in presence or absence of recombinant calreticulin (rCALR). GABARAP$^{KO}$ abrogates phagocytosis by DCs by inhibiting CALR exposure. FIG. 14E shows quantification of CALR exposure by flow cytometry in AMO1 GABARAP$^{KO}$ control (CNT) or after GABARAP overexpression after BTZ treatment. The upper panel of FIG. 14E shows Western Blot results of GABARAP confirming gene overexpression in AMO1 KO clones.

(FIG. 15C). GABARAP$^{KO}$ antagonizes BTZ induced anti-tumor T cell response.

FIG. 16A shows tumor incidence in mice vaccinated with BTZ-treated WT or calr KO or gabarap KO 5TGM1 or PBS and re-challenged with living 5TGM1 1 week later is reported for n=8 animals per group, according to the Kaplan-Meier method. FIG. 16B shows spots of IFN-gamma (IFN-y) secreting T cells as detected by ELISpot assay using mice splenocytes. Splenocytes were culture alone, with a tumor control cell line (B16/F10) or MM 5TGM1 experimental cells. Reactive T cells against 5TGM1 induced the formation of the spots. As demonstrated in FIG. 12-FIG. 16, loss of function of GABARAP impairs the induction of ICD after BTZ treatment in myeloma. Resistance to ICD induction contributes to the poor clinical outcome in high risk patients with del (17p).

FIG. 17A shows human AMO1, H929, and murine 5TGM1 MM cell lines were treated with BTZ (1-10 nM) or media (CNT) for 16 h. CALR exposure was quantified by flow cytometry: analysis of fluorescence intensity was assessed on viable (7-AAD negative) cells. Floating bars show fold increase of the geometric mean normalized to CNT cells. Internal panels: percentage of apoptotic cells (annexin-V-positive) after BTZ treatment. Error bars are s.d. of three independent experiments for CALR analysis, and two experiments for apoptosis assays. P values were calculated by using two-tailed unpaired t test. FIG. 17B and FIG. 17C shows phagocytosis assays. FAR-RED stained human AMO1, H929 and murine 5TGM1 were left untreated or treated with BTZ for 16 hours. Then, they were co-cultured with CFSE stained heterologous human DCs (hDCs) or murine DCs (mDCs), respectively. JAWSII cell line was used as source of immature mDCs. Analysis was performed after 4 hours. FIG. 17B depicts representative confocal images showing interaction of mDCs and 5TGM1 MM cells, either untreated (CNT) or BTZ treated, after 4 hours co-culture. Scale bars, 20 m. In FIG. 17C, it is shown that the fold increase in percentage of double positive DCs compared to CNT, as assessed by flow cytometry. Error bars are s.e.m. of three independent experiments. Two-tailed unpaired t test. FIG. 17D shows CFSE-mDCs and 16 hours BTZ-treated or untreated FAR-RED-5TGM1 WT or CalrKO (#1, #2, #3) MM cells were co-cultured for 4 hours; fold increase in percentage of double positive mDCs compared to CNT is shown. Error bars are s.e.m. of four independent experiments. Unpaired t test to analyze the effect on each CalrKO clone compared to WT cells. FIG. 17E shows a phagocytosis assay of BTZ-treated or untreated FAR-RED-5TGM1 WT, CalrKO #3 or CalrKO #3 re-overexpressing Calr (#3 Calr add-back) co-cultured with CFSE-mDCs. Fold increase of percentage of double positive mDCs compared to CNT is shown. Error bars are s.e.m. of three independent experiments. Unpaired two-tailed t test. In the right panel, western blot of CALR protein in 5TGM1 WT, CalrKO #3, and CalrKO #3-Calr add-back is shown, with GAPDH as loading control. In the add-back clones, molecular weight of full-length Calr is larger than endogenous because its cDNA is in-frame with the cDNA of the 5' end of decay accelerating factor (DAF), which encodes a signal sequence for attachment of a glycophosphatidylinositol (GPI) anchor to the C-terminus of the resulting CALR-DAF fusion protein to facilitate CALR anchoring in the plasma membrane. FIG. 17F shows 16 hours BTZ-treated or untreated AMO1 and H929 cells were co-cultured for 5 days with human DCs and T cells derived from the same healthy donors. CD4+ and CD8+ T cells were identified based on semi-unsupervised bioinformatic analysis, and are represented in a uniform manifold approximation and projection (UMAP) merging independent experiments for each cell line (left panel, arrows represent differentiation pattern). On the right panels, boxplots show absolute percentage of T cell subsets which are significantly increased in the BTZ condition (according to ANOVA pairwise comparisons): CD4_EMCD69het (p=0.024), CD8_TEMRA_CD69dim (p=0.029), CD8_EM_CD69het (p=0.067), and total CD8 (p=0.05). Data include n=8 independent experiments for AMO1 and n=4 for H929 cell line. Defining features T cell subset clusters are detailed in FIG. 24A. FIG. 17G shows 16 hours BTZ-treated or untreated U266 cells were co-cultured with HLA-matched hDCs and T cells from the same healthy donors. After 5 days, T cells were negatively selected from both co-culture conditions (CNT and BTZ) and then cultured for 24 h with new U266 cells pre-stained with CFSE at 1:0, 1:1, and 1:2 target:effector (T:E) ratio, followed by 7-AAD staining and quantification of MM cell lysis by flow cytometry. Graph shows absolute percentage of dead MM cells. ns=not significant, *P<0.05, P<0.01, *P<0.005, ****P<0.0001.

FIG. 18A shows a flow-cytometry based phagocytosis assay: CFSE-human DCs (hDCs) from healthy donors were co-cultured for 4 hours with BTZ-treated (5 and 10 nM) or untreated FAR-RED-patient-derived MM cells (pdMM). Shown is the fold increase in percentage of double positive DCs compared to CNT. Error bars are s.e.m. of two independent experiments. *P<0.001, **P<0.0001 compared to CNT; two-tailed unpaired t test. FIG. 18B shows total autologous BMMCs from MM patients were cultured in the presence or absence of BTZ (5 nM). After 5 days, flow cytometry analysis on CD4+(n=4) and CD8+ T (n=6) cells was performed. On the top panel, Automatic Population Separator (APS) showing cells clustered based on their immunophenotypes. On the bottom panels, boxplots show absolute percentage of T cell subsets which are significantly increased in the BTZ condition (according to paired Student's t test): CD4_EM_CD69het (p=0.07), CD8_TEMRA_CD69dim (p=0.04), and total CD8 (p=0.005).

FIG. 19A-D) In vivo growth of subcutaneous xenografts of 5TGM1WT (FIG. 19A-B) or 5TGM1 CalrKO (c,d) MM cells in immunocompetent C57BL/KaLwRjj (a,c) or immunodeficient SCID/NOD (FIG. 19B and FIG. 19D) mice treated with either PBS (CNT) or BTZ (0.5 mg/kg twice/week for 2 weeks) when tumors became measurable by electronic caliper. Fold increase of tumor growth from day 1 (start of treatment) to day 8±s.d. (n=5 animals per group in FIG. 19A-C and n=4 in FIG. 19D). One representative experiment of two yielding similar results is shown for each condition. P values were calculated using unpaired Student's t test. FIG. 19E shows an immunocompetent C57BL/KaLwRjj (n=5) bearing 5TGM1WT tumors were treated with BTZ as in FIG. 19A. Two weeks after tumor regression, BTZ-treated mice (n=5) were rechallenged with viable 5TGM1 cells, along with naïve mice (n=5) and percentage of mice remaining tumor free in the two cohorts is shown according to the Kaplan-Meier method. P value was calculated by using log-rank test. Schema of the experimental design is shown in upper panel.

FIG. 19F shows ex vivo enzyme-linked immunospot (ELISPOT) was performed on splenocytes harvested from mice treated as in FIG. 19E. Splenocytes were left unstimulated or stimulated with: B16 tumor cells as negative control; 5TGM1; or anti-CD3 as positive control to test T-cell avidity in an IFN-γ Elispot assay. Spot forming colonies (SFC) per million are represented for n=3 naïve and n=5 BTZ treated mice±s.d. ELISPOT experiments were performed in triplicate wells per sample; unpaired Student's t test for statistical analysis. ELISPOT images are shown in FIG. 26. FIG. 19G shows in vitro BTZ-treated 5TGM1WT or CalrKO cells were injected into naïve mice; control mice (no-vax) received PBS as a negative control. Mice (n=8 animals per group) were rechallenged with viable 5TGM1 cells 1 week later, and percentage of mice remaining tumor free in the three cohorts is shown according to the Kaplan-Meier method. Log-rank test was used for statistical significance. Schema of the experimental design is shown in upper panel. *P<0.05; P<0.01; *P<0.001; ****P<0.0001.

FIG. 20A shows a log 2 fold-change (log 2FC) values for 90 genes, as determined by RNA-seq analysis, in 5TGM1WT or 5TGM1 CalrKO tumors growing in immunocompetent C57BL/KaLwRjj mice after two BTZ treatments (0.5 mg/kg). Columns represent the conditions, and rows are those differentially expressed genes (DEGs) in BTZ-treated compared to CNT cohort (n=3 mice per group). FC>1.5 and FDR<0.05. FIG. 20B-D shows an analysis of the human orthologs of this 90 gene murine ICD signature was performed in CD138+MM cells from two independent Bort-treated MM patient cohorts: FIG. 20B shows IFM/DFCI 2009 dataset n=327; and FIG. 20D shows GSE9782, n=152. Heatmaps identified three clusters of MM patients showing high, medium, and low expression of these signature genes. FIG. 20C-E) Kaplan-Meier plots show overall survival (OS) for the 3 patient clusters identified by expression of the 90 ICD gene signature. Curves represent OS of patients with high, medium, and low ICD-signature expression, respectively. Log-rank test p-values for IFM/DFCI 2009 dataset is p=0.01 and GSE9782 dataset is p=0.047.

FIG. 21A shows AMO1 cells were treated with BTZ (0 to 7.5 nM) for 16 hours. Viable cells were separated using Ficoll gradient centrifugation. Dot plots show micronuclei quantification as a percentage of diploid nuclei, as detected by flow cytometry. In the analysis, remaining apoptotic cells were gated out by using ethidium monoazide dye that crosses the compromised outer membrane of apoptotic and necrotic cells. One of two experiments yielding similar results is shown. FIG. 21B shows a heatmap showing the correlation analysis of 57 ISGs included in the ICD signature with STING/TMEM173 gene expression across the three subsets of MM patients (IFM/DFCI 2009 dataset) expressing high, medium, and low levels of the ICD-signature (as in FIG. 20). FIG. 21C shows a western blot (WB) analysis of STING pathway in AMO1 cells treated with increasing doses of BTZ (5 to 10 nM) for 16 h. GAPDH was used as a loading control to quantify cGAS, TBK1, phosphor-TBK1 (pTBK1), and pIRF3 expression. FIG. 21D shows a WB analysis of cGAS, pTBK1, and STING in AMOWT and STINGKO cells treated with BTZ (5 nM). FIG. 21E shows a qRT-PCR analysis of IFNA1 and IFNB1 messenger RNAs (mRNAs) in AMOWT and STINGKO cells either untreated or after BTZ (5 nM). Raw Ct values were normalized to GAPDH housekeeping gene and expressed as ΔΔCt values. Data are the average of three independent experiments performed in triplicate. *P<0.05, ns=not significant; unpaired t test. FIG. 21F shows analysis of modulation of CXCL9 in AMOWT and STINGKO cells after treatment with BTZ (5 nM) for 16 h by qRT-PCR analysis of CXCL9 mRNA (left) and ELISA quantification of extracellular CXCL9 (right). Data are means of two independent experiments±s.e.m. *P<0.1 (unpaired Student's t test) compared to untreated cells. FIG. 21G shows BTZ-treated or untreated AMOWT and STINGKO cells were co-cultured with hDCs and T cells from the same healthy donors for 5 days. Cells were analyzed using a bioinformatic pipeline, and results reported in a uniform manifold approximation and projection (UMAP) including n=8 independent experiments for AMO1WT and n=4 for AMO1 STINGKO cell line (upper panel). Bottom panels show absolute percentage of t cell subsets and increase in BTZ treated compared to CNT in both cell lines: CD4_EM_CD69het (AMOWT p=0.027; STINGKO: p=ns), CD8_TEMRA_CD69het (AMOWT p=0.1; STINGKO: p=0.09), CD8_EM_CD69het (AMOWT p=0.064; STINGKO: p=ns) and total CD8 (AMOWT p=0.09; STINGKO: p=ns); *P<0.1; ANOVA pairwise. Defining features T cell subset clusters are detailed in FIG. 30H.

FIG. 22A shows tumor volume changes of subcutaneous 5TGM1WT xenografts in C57BL/KaLwRjj mice treated with PBS (CNT), BTZ (0.375 mg/kg twice/week for 2 weeks), intra-tumor administration of ADU-S100 (100 ug day 1 and 2), or the combination of BTZ and ADU-S100. Average tumor growth±s.e.m. for each group (n=5) is reported. P values were calculated using unpaired Student t test. FIG. 22B shows the percentage of positive cells for CD3 staining. Graph depicts the mean±s.d. of tumor xenograft sections 100 m apart from representative CNT, BTZ, ADU-S100 and COMBO treated mice. Welch's t test was used for statistical analysis. On the right, representative images of IHC CD3 staining on tumors retrieved from each group. Scale bars, 100 m. FIG. 22C shows tumor volume changes of subcutaneous 5TGM1WT xenografts in SCID/NOD mice treated as in a). Average tumor growth±s.e.m. for each group (n=6) is reported. Unpaired Student t test. FIG. 22D shows tumor volume analysis of subcutaneous 5TGM1 StingKO xenografts in C57BL/KaLwRjj mice treated as in FIG. 22A. Average tumor growth±s.e.m. for each group (n=5) is reported. Unpaired Student t test. FIG. 22E shows a schematic model. Combination of BTZ (which augments anti-MM immune response by stimulating the STING pathway by increasing genomic instability) and STING agonist (which activates intratumor and tumor microenvironment STING downstream signaling) potentiates the type I IFN response, and increases T cell recruitment and activation. *P<0.05, *P<0.005, **P<0.001, ns=not significant.

FIG. 23A shows a western blot analysis of EIF2A, phospho-EIF2A (pEIF2A), ATF4, and CHOP in AMO1 and 5TGM1 cells. Beta-actin was used as loading control in AMO1 cells, and pEIF2A was normalized to expression of total EIF2A in 5TGM1 cells. FIG. 23B shows confocal images showing 5TGM1 cells co-cultured with murine DCs (JAWSII) for 4 hours, treated (right panel) or untreated (left panel) with BTZ (5 nM). Scale bars, 20 m. FIG. 23C shows representative dot plot of phagocytosis assay using flow cytometry. X axis shows CFSE+ DCs and y axis FAR-RED+ AMO1 cells. Red arrow indicates double positive DCs. FIG. 23D shows surface expression of CD80 and CD83 on CD11c+ DCs was measured in human DCs (hDCs) before and after treatment with BTZ (5 nM), TNF-α (50 ng/ml) or control media (left panel); or after 24 h of co-culture of hDCs with BTZ-treated or untreated AMO1 MM cells (right panel). FIG. 23E shows a western blot of CALR in monoclonal 5TGM1 Calr$^{KO}$ lines expanded from 2 different single guide RNAs (sgRNA). GAPDH was used as loading control. FIG. 23F shows a percentage of apoptotic cells (annexin-V-positive) after BTZ treatment (7.5 nM) in 5TGM1 WT (red bars) and Calr$^{KO}$ clones (#1 and #3, blue bars). Error bars are s.d. two experiments. P<0.01, *P<0.005 compared to CNT; two-tailed unpaired t test.

FIG. 24A shows a heatmap shows distribution of cluster of differentiation (CD) markers in T cell subsets related to analysis in FIG. 18F. FIG. 24B shows a representative dotplots showing CD8 (top) and CD4 (bottom) subpopulations distribution according to CCR7 and CD45RO markers which demonstrate the classification performed through bioinformatic clustering. FIG. 24C shows DCs and T cells (DCT) derived from the same healthy donors were co-cultured for 5 days in the presence or absence of BTZ (5 nM). Unbiased monitoring of CD4+ and CD8+ T cell populations was performed in 4 independent experiments. Boxplots show absolute percentage of T cell subsets in CNT and BTZ cultures (means+standard error, ns=not significant in paired Student t test).

FIG. 25A shows representative overlay histograms showing the proliferation of CellTrace Violet (CTV) positive CD4+ and CD8+ naïve T cell subsets after 5 day co-culture with DCs derived from the same healthy donors and AMO1 cells, either untreated or pre-treated with BTZ (5 nM). Each histogram represents the count of alive CTV stained CD4+ or CD8+ population. Median MFI is depicted within the panel. FIG. 25B shows analysis of naïve T cells proliferation as described above performed in n=6 independent experiments for AMO1 and n=5 for H929 cells (i). Naïve T cells were also cultured in the absence of MM cells, and in the presence of phytohemagglutinin (PHA) as positive control; results are shown in (ii). P values were calculated using paired Student t test.

FIG. 29A shows GSEA analysis of signatures included in the Hallmark "IFNγ response" collection. Shown are pathways significantly upregulated in AMO1 cells after in vitro treatment with BTZ (5 nM for 16 h). FRD<25%. FIG. 29B shows qRT-PCR analysis of IFNA1, IFNB1, and CXCL9 mRNAs in AMO1 and H929 cells treated with BTZ (5 nM for 16 h). Raw Ct values were normalized to GAPDH housekeeping gene and expressed as ΔΔCt values. Data are the average of two independent experiments performed in triplicate. *P<0.1, P<0.05; *PC 0.005; unpaired t test. FIG. 29C shows a fold increase in tumor volume of 5TGM1 cells growing in C57BL/KaLwRjj mice treated with PBS or BTZ (0.5 mg/kg twice/week for 2 weeks) in combination with IFNAR1 blocking antibody (MAR1-5A3) (500 ug i.p. on day 0 and 250 ug i.p. on days 2,4,6) or isotype control MoAb. Fold increase±s.e.m. of tumor growth at day 8 compared to day 0 is shown. ns=not significant, *P<0.05, unpaired Student's t test. FIG. 29D shows a qRT-PCR of Cxcl9 mRNA in tumors harvested from mice treated with CNT, BTZ plus Isotype control MoAb, and BTZ plus MAR1-5A3 Ab. Raw Ct values were normalized to Gapdh housekeeping gene and expressed as ΔΔCt values. *P<0.05, ns=not significant, unpaired t test. FIG. 29E shows survival analysis showing the correlation between the expression of CXCL9 gene and overall survival in uniformly treated MM patients enrolled in the IFM/DFCI 2009 clinical trial. (n=327, P=0.037).

FIG. 30A show dot plots showing gating strategy performed to remove residual apoptotic cells (ethidium monoazide positive cells) after BTZ treatment in AMO1 and H929 cells, before micronuclei analysis. FIG. 30B shows dot plots show the percentage of cells with micronuclei, as detected by flow cytometry, after treatment of H929 cells with BTZ (0 to 5 nM). One of two experiments yielding similar results is shown. FIG. 30C shows western blot analysis of cGAS, TBK1, and pTBK1 in H929 MM cells after treatment with BTZ (0-4 nM). GAPDH was used as a loading control. FIG. 30D shows western blot to detect STING and confirm knock-out among monoclonal 5TGM1 (left) and AMO1 (right) cell lines growing from different sgRNAs. GAPDH was used as a loading control. FIG. 30E shows human AMO1 and murine 5TGM1 MM cell either WT or STING$^{KO}$ lines were treated with BTZ (5 nM and 7.5 nM, respectively) or left untreated for 16 h. CALR exposure was quantified by flow cytometry, and fluorescence intensity was assessed on viable (7-AAD negative) cells. Dot plots show fold increase of the geometric mean normalized to CNT cells (horizontal dotted bar). Error bars are s.d. of three independent experiments for 5TGM1 and two experiments for AMO1 cells. FIG. 30F shows GSEA enrichment plot of hallmark "Interferon alpha response" signature, which is downregulated in AMO1 STING$^{KO}$ cells compared to WT cells after treatment with BTZ (upper panel). Bars show negative enrichment scores of the signature (bottom panel). FIG. 30G shows a heatmap shows cluster of differentiation (CD) markers in T cell subsets. Analysis was carried out as described in FIG. 21G. FIG. 30H shows qRT-PCR analysis of Ifna1 and Ifnb1 messenger RNAs (mRNAs) in 5TGM1$^{WT}$ and Sting$^{KO}$ cells treated with BTZ (7.5 nM). Raw Ct values were normalized to Gapdh housekeeping gene and expressed as ΔΔCt values. Data are the average of three independent experiments performed in triplicate. *P<0.05, **P<0.01, ns=not significant; unpaired t test.

FIG. 31A shows WB analysis of pTBK1 in AMO cells treated with BTZ (5 nM), STING agonist ADUS-100 (10 uM), or the combination. GAPDH was used as a loading control. FIG. 31B qRT-PCR analysis of IFNA1 and IFNB1 mRNAs in H929 cells treated with BTZ (5 nM), STING agonist (10 uM), or the combination (COMBO). Raw Ct values are normalized to GAPDH housekeeping gene and expressed as ΔΔCt values. Data are the average of two independent experiments performed in triplicate. *P<0.05, PC 0.01, *P<0.005, ***PC 0.001; unpaired Student t test. FIG. 31C shows cell counting kit 8 (CCK8) proliferation assay of 5TGM1 MM cells after 72 hr treatment with ADUS-100 (0-5 uM). Data are presented as percentage of ADUS-100 treated live cells (absorbance) compared with untreated cells. Data from 1 of 3 independent experiments is shown. *P<0.05; **P<0.005.

FIG. 32A shows a western blot analysis of CALR expression in AMO1 WT and GABARAP$^{KO}$ in absence or presence of BTZ. GAPDH was used as loading control. FIG. 32B shows a heatmap of absolute number of unique peptides identified by MS analysis of proteins bound to CALR or IgG in both AMO1 WT and GABARAP$^{KO}$ in absence or presence of BTZ. Color key indicates unique peptide number value: dark blue: lowest; dark red: highest.

FIG. 33A shows a western blot analysis of STC1 and GABARAP in a panel of 8 MM cell lines. B-actin was used as loading control. FIG. 33B shows a WB analysis of 293T cells stably expressing 3×FLAG-tagged GABARAP. STC1 and CALR levels were detected in FLAG- and IgG-immunoprecipitated proteins. FLAG antibody was used to confirm immunoprecipitation. FIG. 33C shows a WB analysis of STC1 and CALR levels in CALR- and IgG-immunoprecipitated proteins in both AMO1 WT and GABARAP$^{KO}$ cells. GAPDH was used as loading control. FIG. 33D shows that a western blot analysis of STC1 in 5TGM1 (left) and AMO1 (right) WT and GABARAP$^{KO}$ in presence or absence of BTZ. B-actin was used as loading control.

DETAILED DESCRIPTION OF THE INVENTION

Figure 1A:
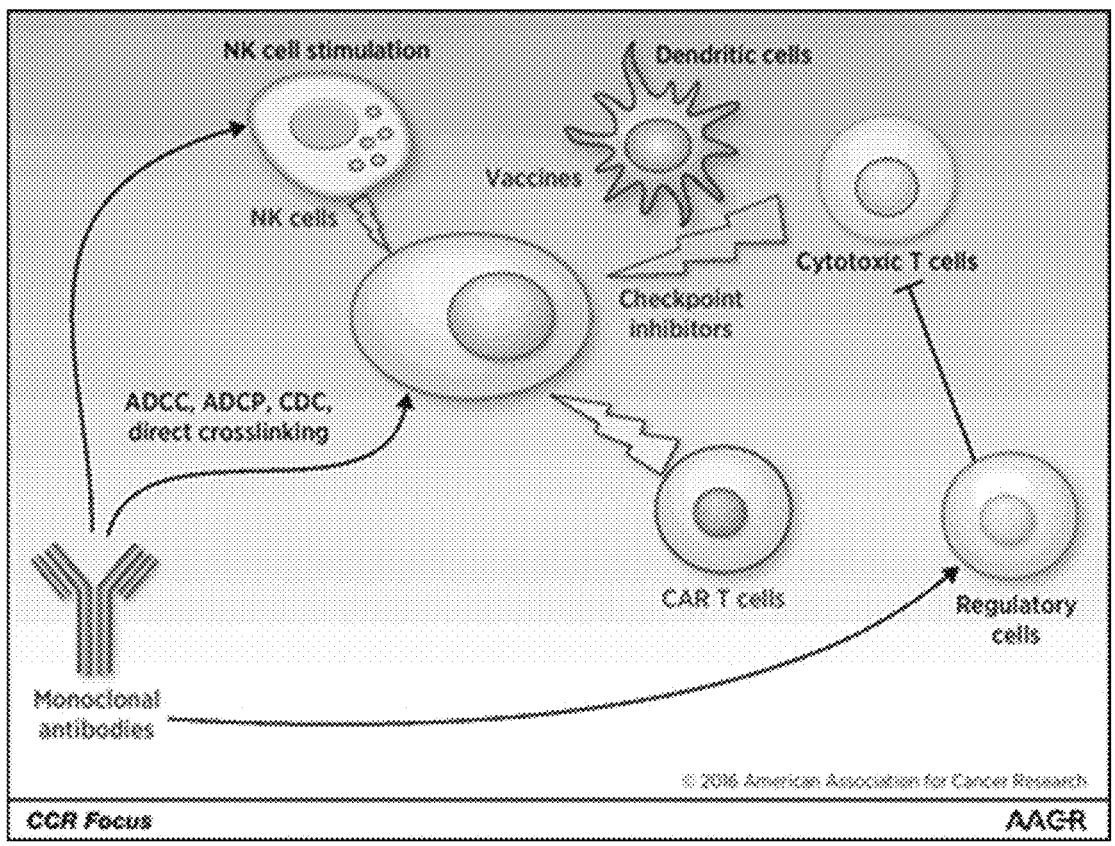
FIG. 1A-FIG. 1C show schematic diagrams that illustrate restoration of immunosurveillance in myeloma via induction of immunogenic cell death (ICD). The schematic diagrams have been adapted from Nagarsheth et al. (2017) *Nat. Rev. Immunol.* 17:559-572, Kumar and Anderson (2016) *Clin Cancer Res.* 22:5453-5460, and Legrand et al. (2019) Mol. Cell 76:232-242.
Figure 1B:
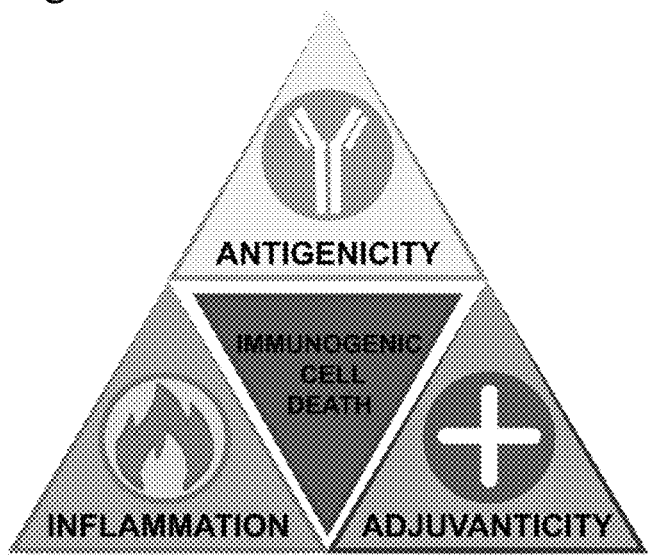
Figure 1C:
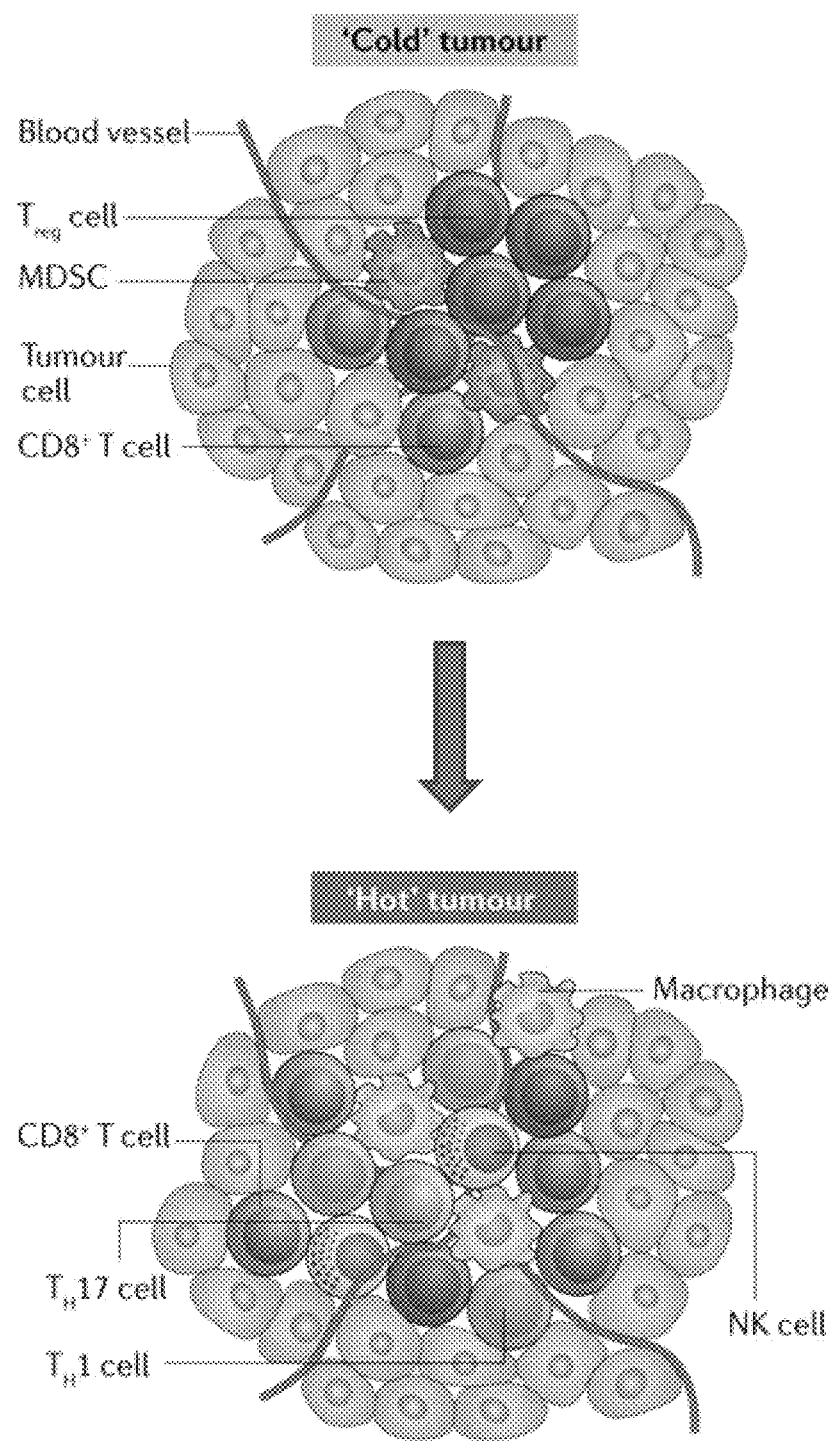
Figure 2A:
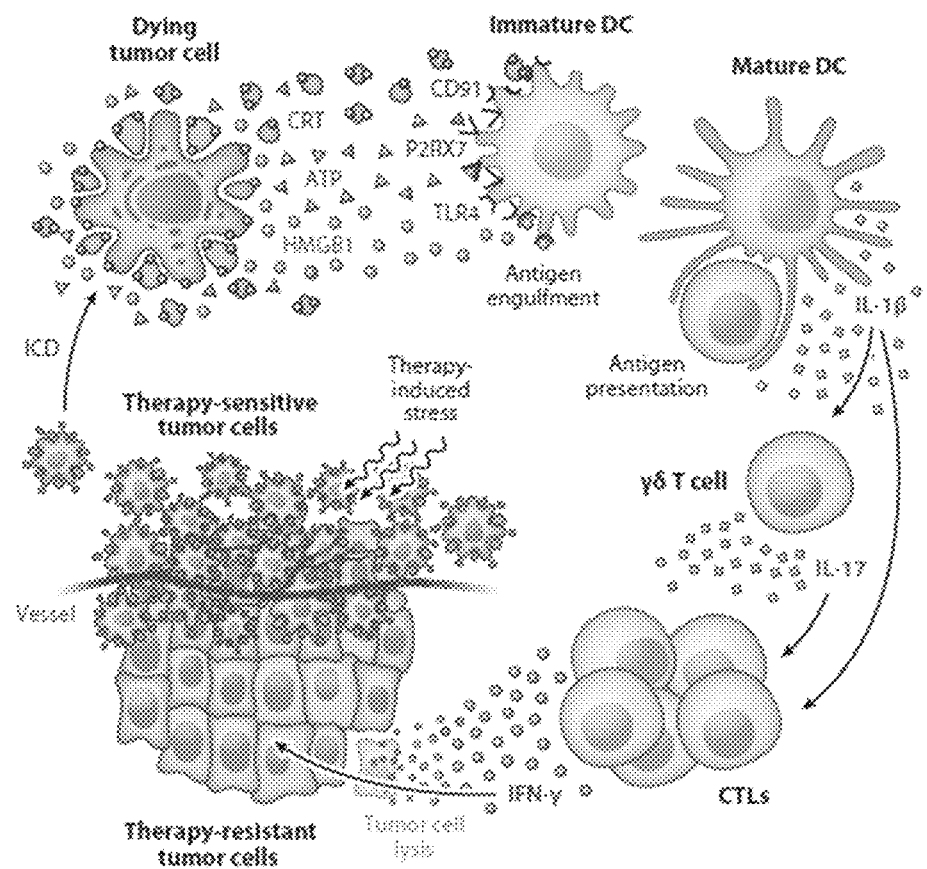
FIG. 2A and FIG. 2B show schematic diagrams that illustrate how cell death triggers an immune response, and the approaches used herein to address the role of ICD inducers like bortezomib (BTZ) as an ICD inducer in cancers such as MM. The schematic diagrams have been adapted from Kroemer et al. (2013) *Annu. Rev. Immunol.* 31:51-72.
Figure 2B:
Figure 2B:
Figure 2B:
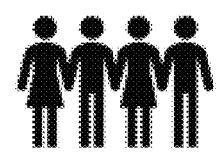
Figure 3A:
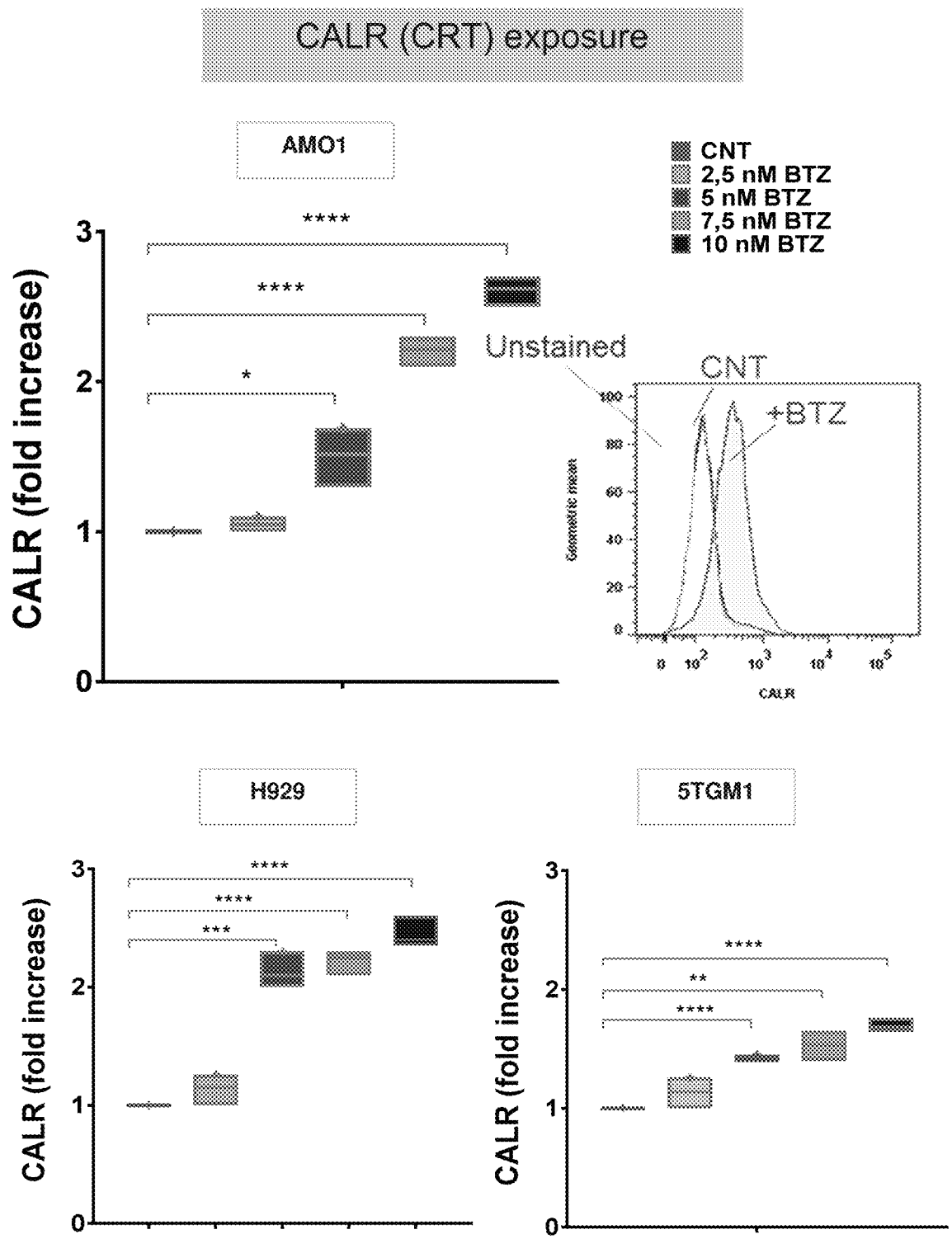
FIG. 3A and FIG. 3B show that BTZ triggers calreticulin (CALR; also referred to as CRT) exposure by cancer cells, and induces functional maturation of dendritic cells (DCs) in vitro.
Figure 3B:
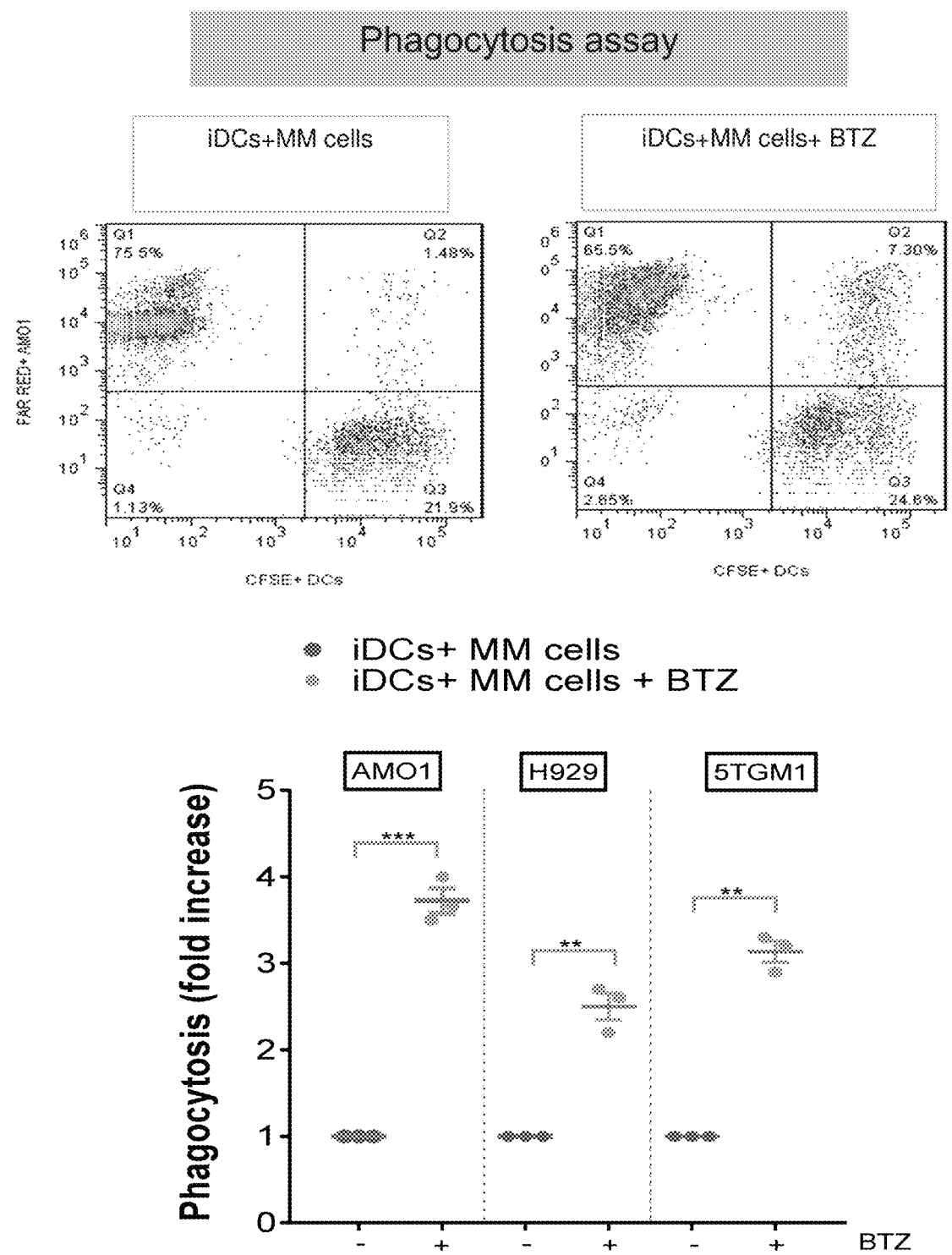
Figure 4:
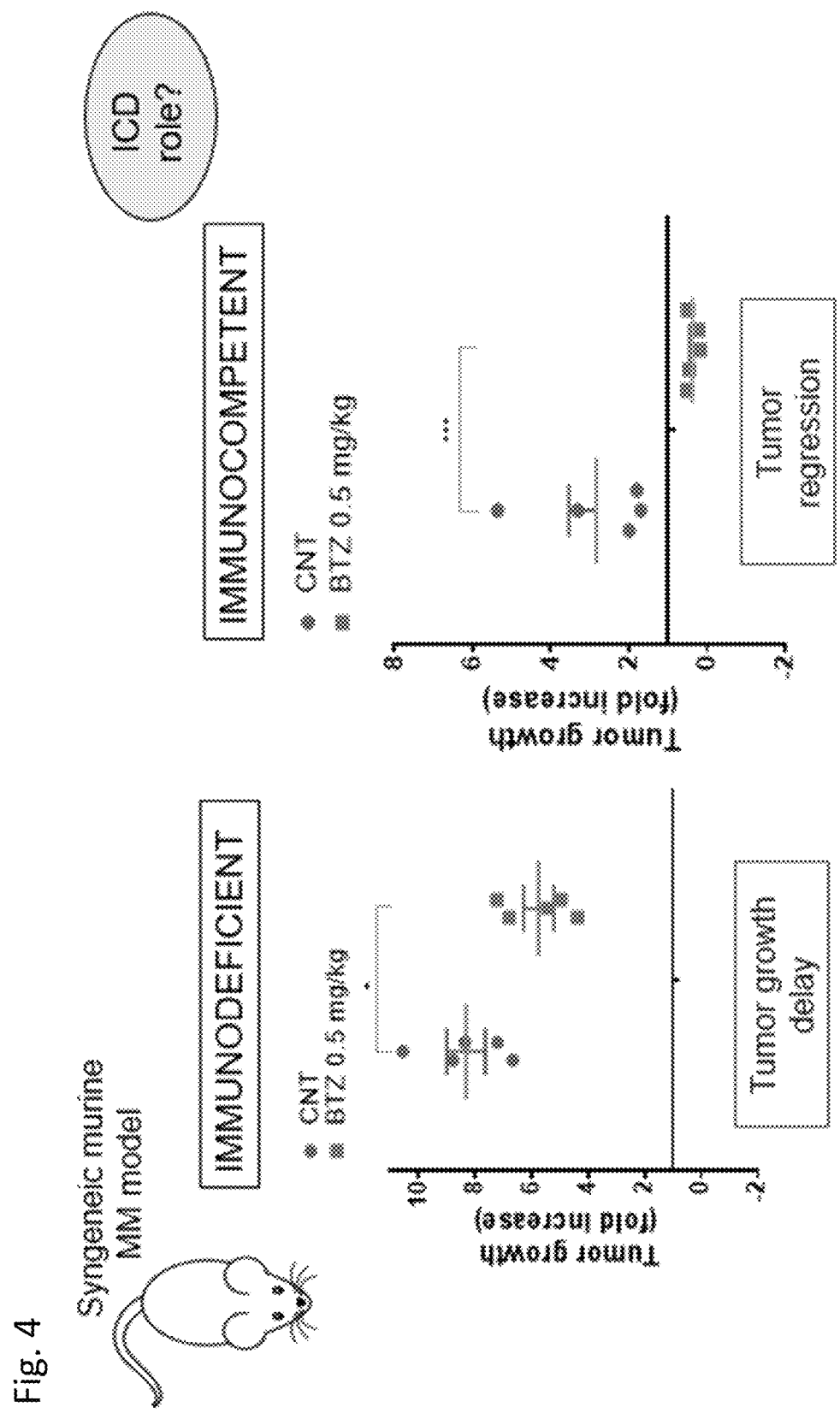
FIG. 4 shows that low dose of BTZ induces tumor regression in the presence of the immune system in vivo.
Figure 5A:
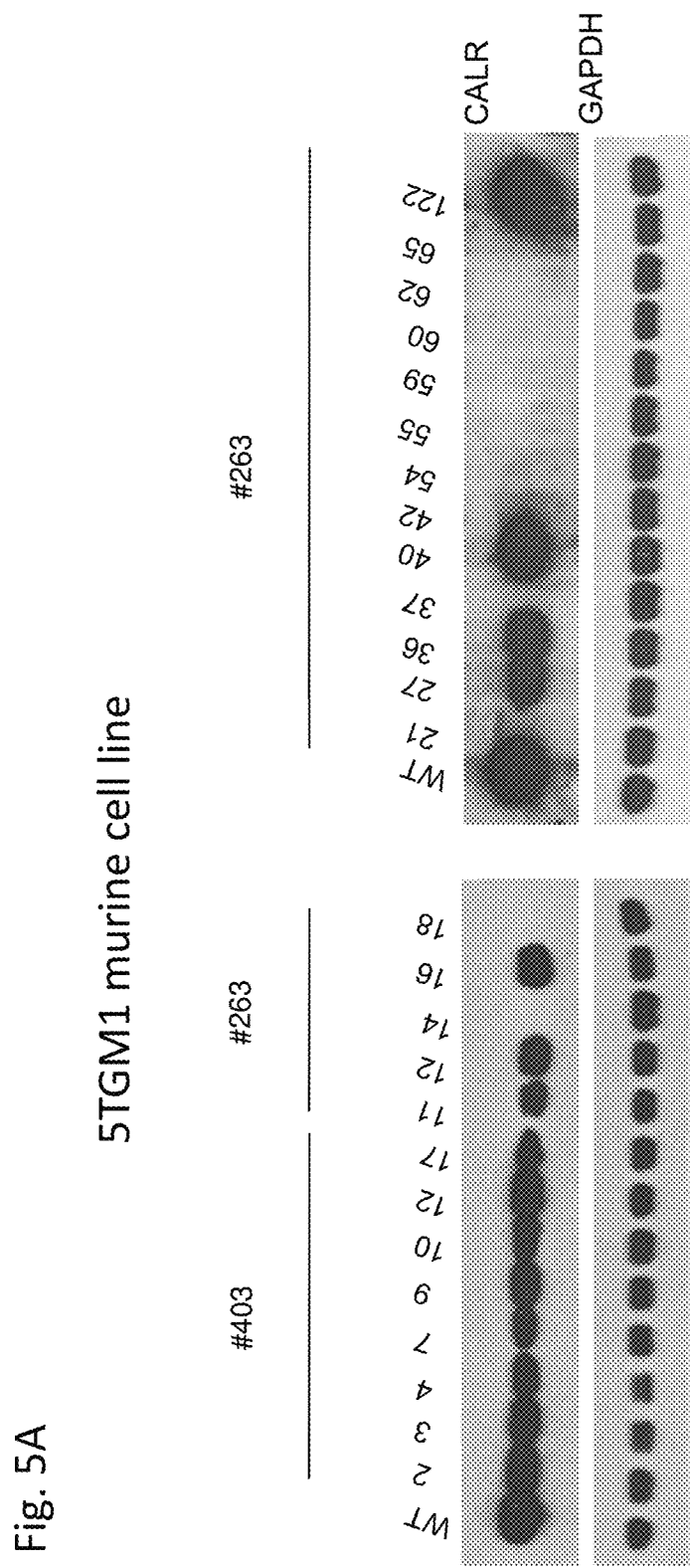
FIG. 5A and FIG. 5B show that calreticulin is necessary for induction of ICD by BTZ in vitro.
Figure 5B:
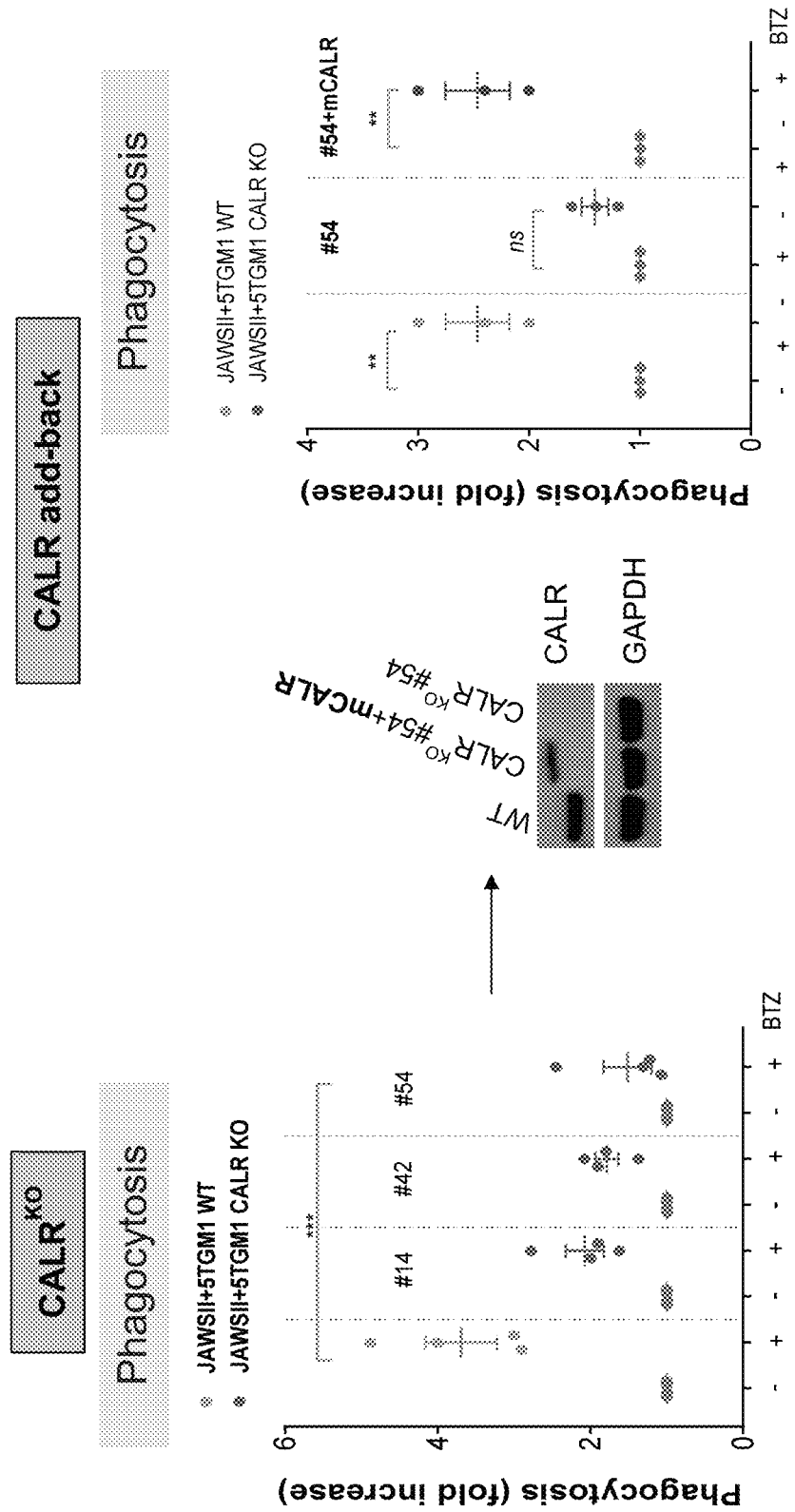
Figure 6:
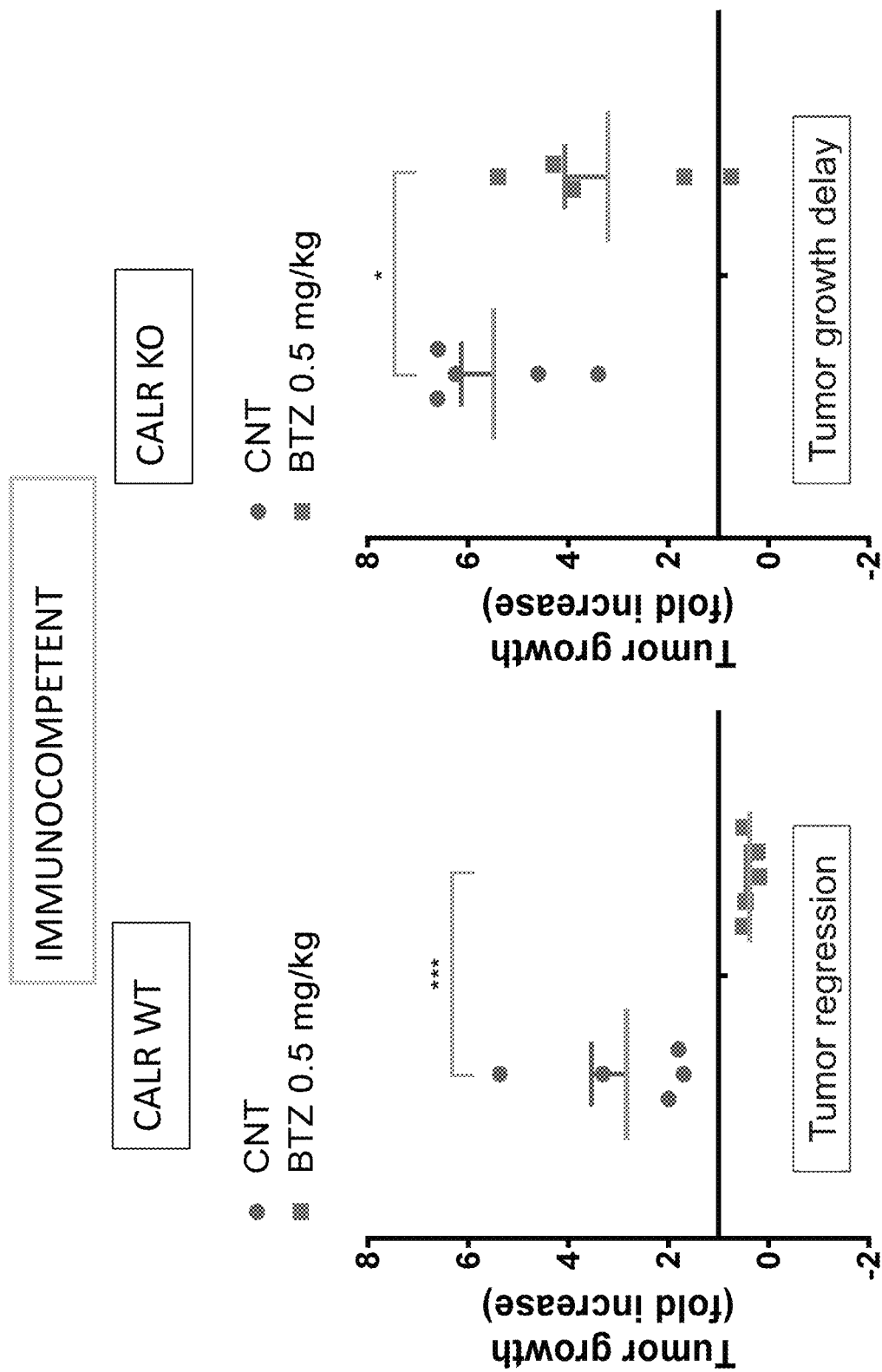
FIG. 6 shows that the in vivo immunogenic effect of BTZ is antagonized in CALR$^{KO}$ tumors.
Figure 7A:
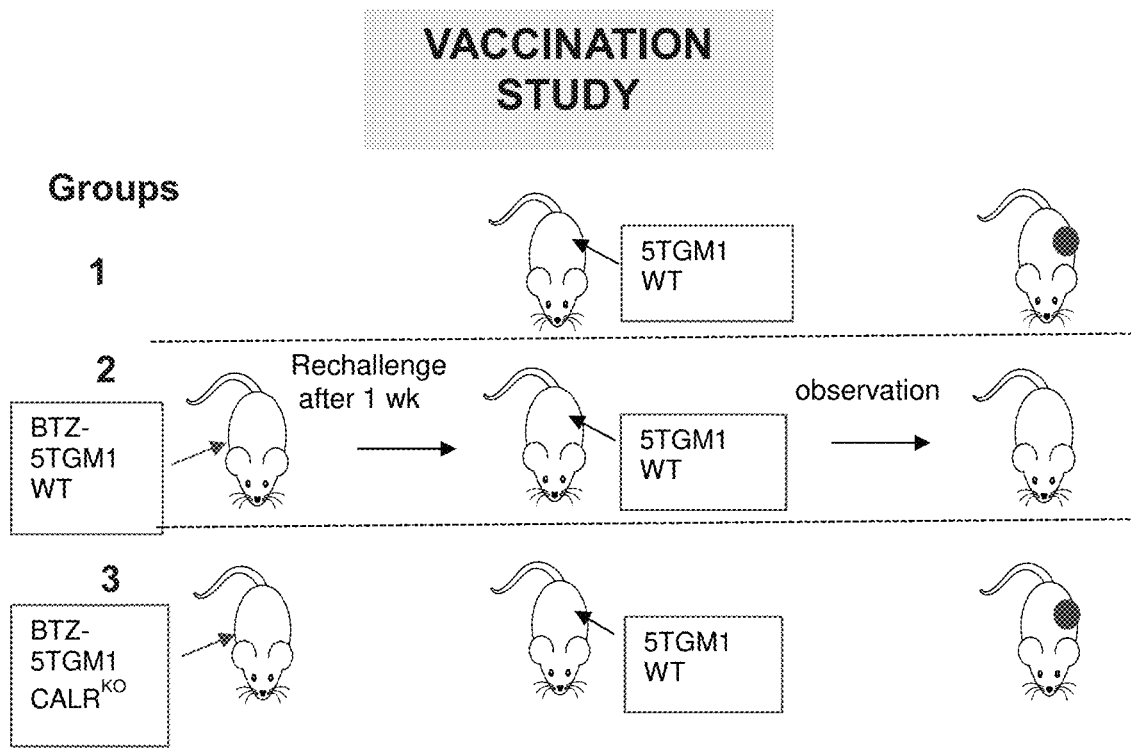
FIG. 7A-FIG. 7C show that mice vaccinated with BTZ-treated WT cells, but not CALR$^{KO}$ cells, were protected against tumor rechallenge.
Figure 7B:
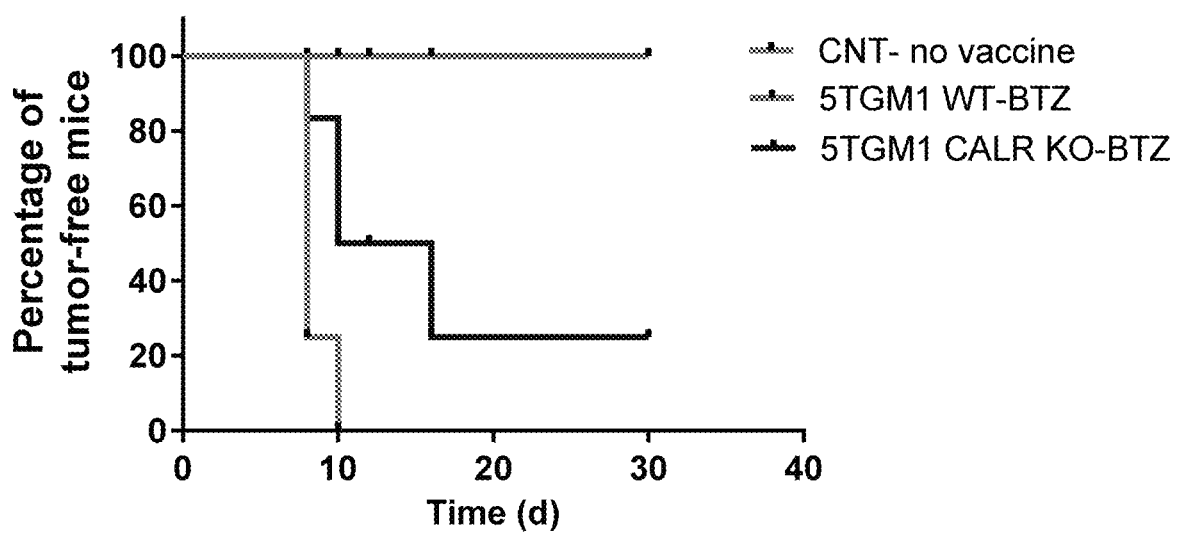
Figure 7C:
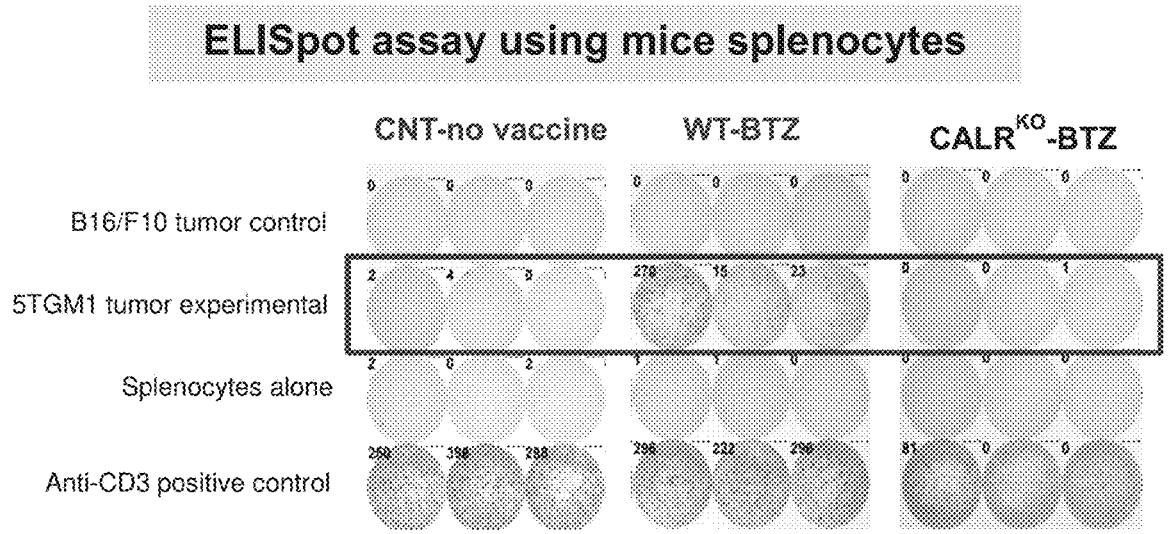
Figure 8:
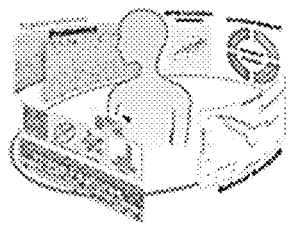
FIG. 8 shows a schematic diagram of the studies undertaken herein to understand whether ICD induction correlates with clinical outcome in MM patients.
Figure 8:
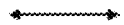
Figure 9:
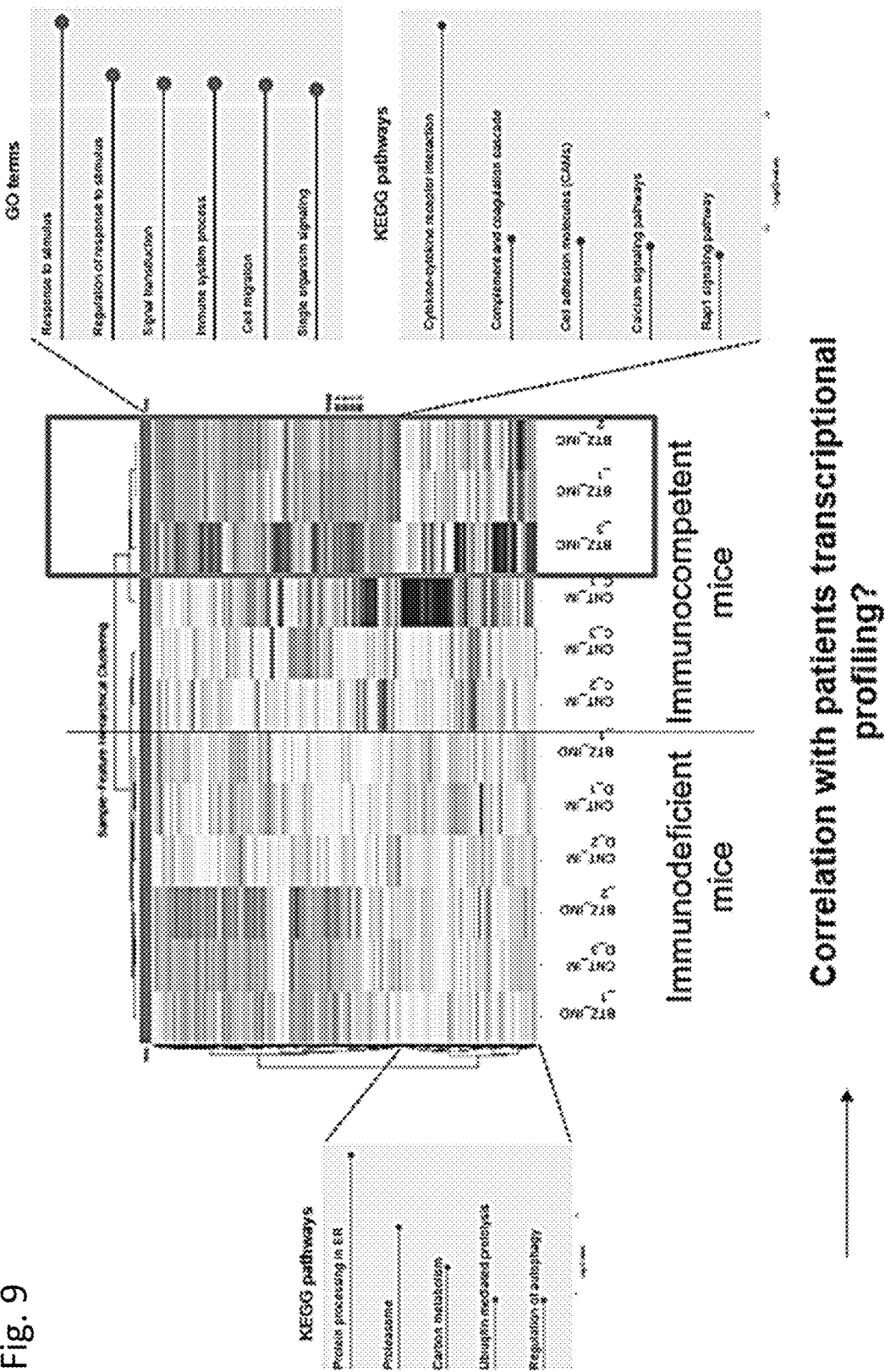
FIG. 9 shows that in vivo BTZ treatment in immunocompetent mice switched on a transcriptional program that is linked to the activation of an immune response.
Figure 10A:
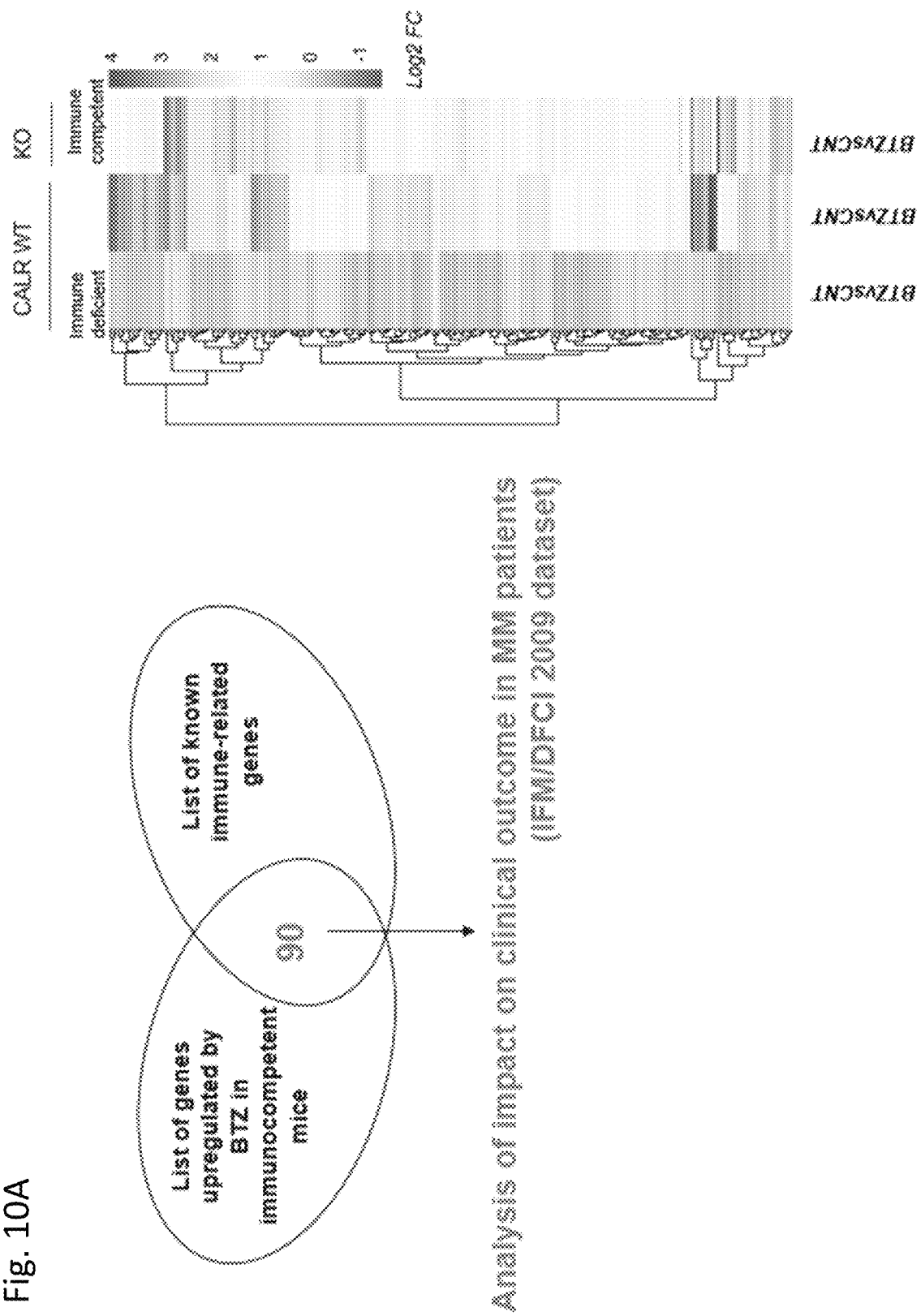
FIG. 10A and FIG. 10B show that an ICD-signature predicts clinical outcome in MM patients after BTZ treatment.
Figure 10B:
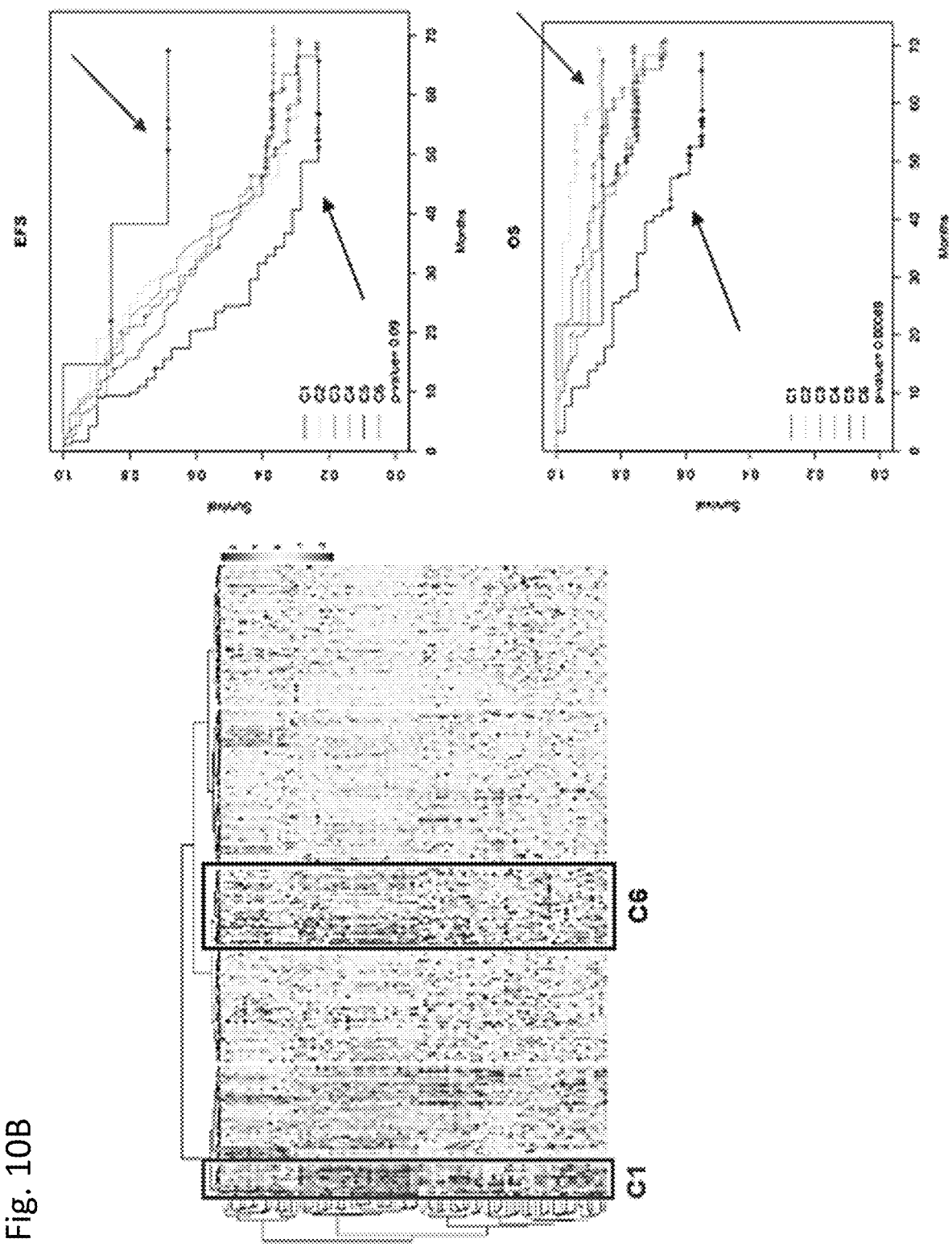
Figure 11:
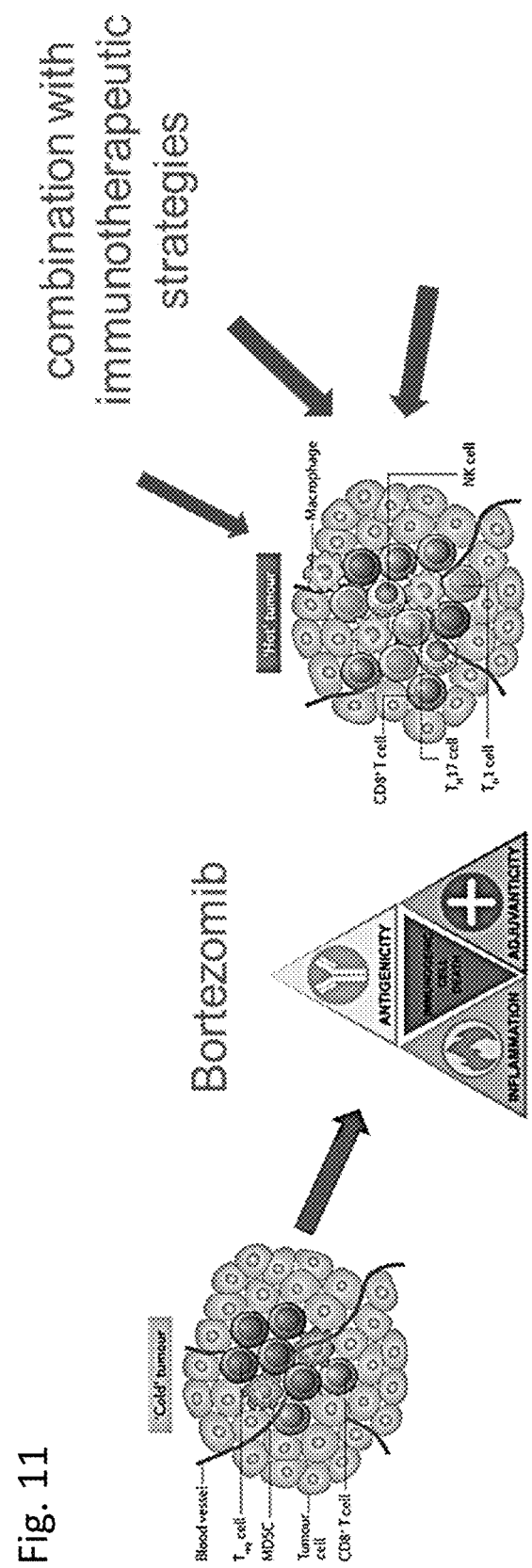
FIG. 11 shows a schematic diagram summarizing certain findings presented in FIG. 1-FIG. 10. Briefly, ICD induction occurs in myeloma and correlates with long-term clinical benefit in patients. Bortezomib is an ICD inducer, and CALR is necessary for induction of ICD in myeloma. CALR is exposed on MM cell surface upon ICD induction.
Figure 12A:
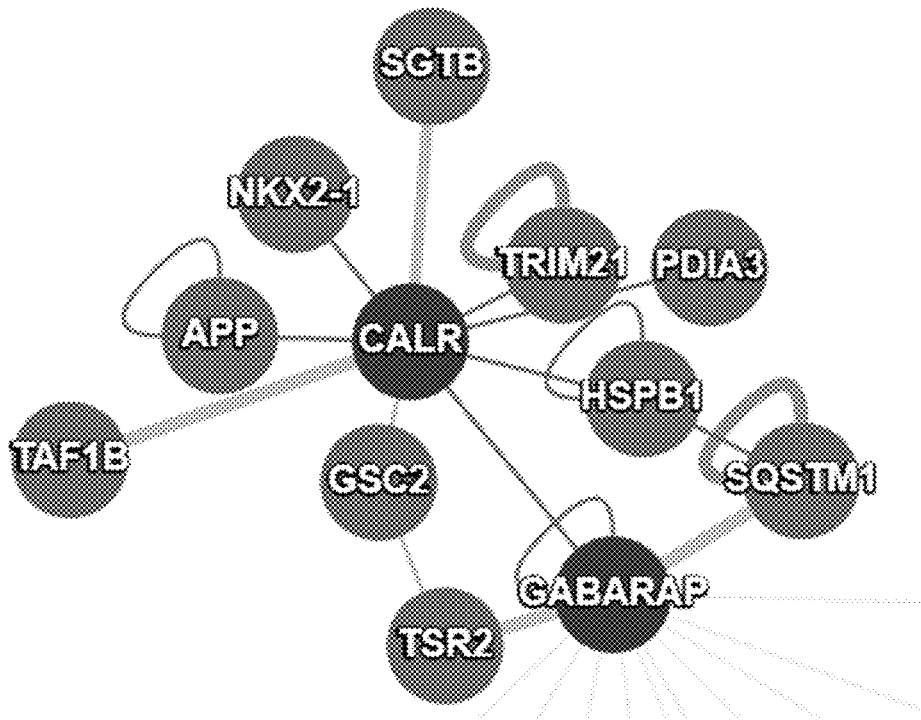
FIG. 12A-12B show that GABARAP and CALR are binding partners.
Figure 12B:
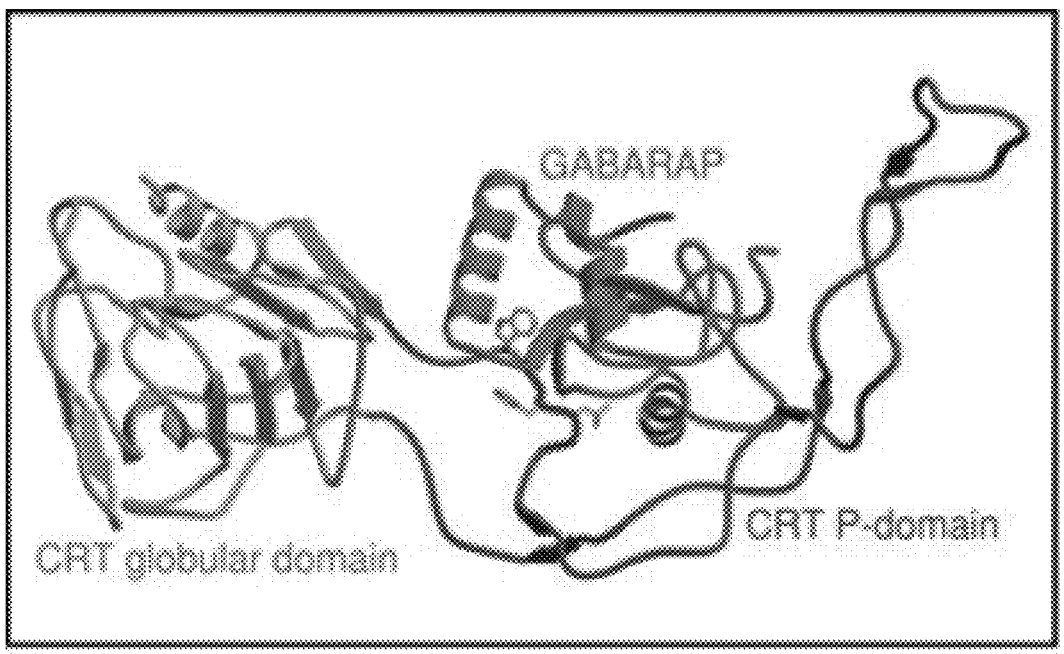
Figure 12C:
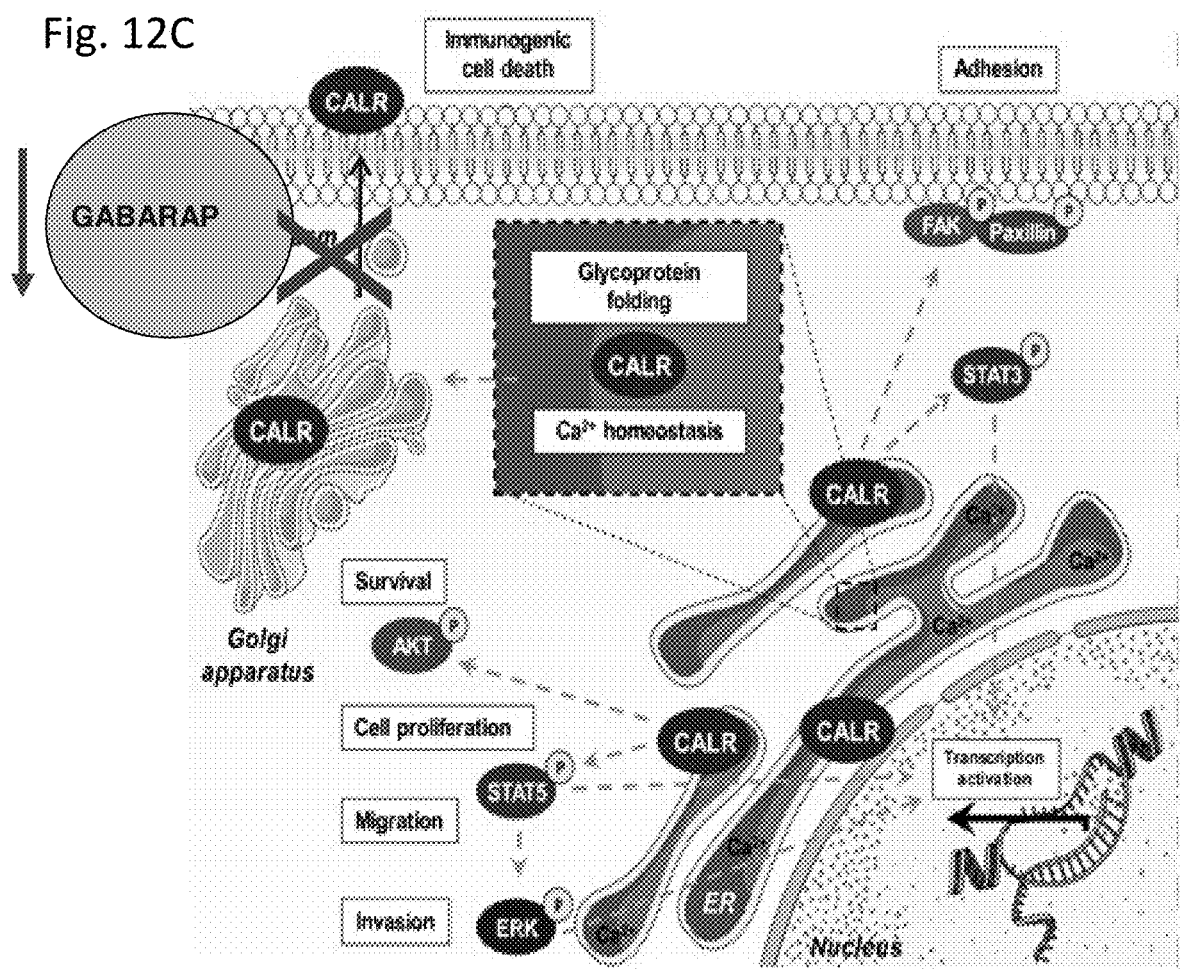
FIG. 12C has been adapted from the Atlas of Genetics and Cytogenetics in Oncology and Haematology (available on the World Wide Web at atlasgeneticsoncology.org//Genes/CALRID904ch19p13.html and shows a schematic diagram of the hypothesis illustrating that GABARAP mediates CALR exposure during ICD.

It has been determined herein that a decrease in the copy number, expression level, and/or activity of GABARAP gene impairs induction of ICD upon treatment with the ICD inducer such as proteasome inhibitor bortezomib (BTZ) in cancer, e.g., multiple myeloma (MM). Indeed, even a mono-allelic deletion of GABARAP leads to impaired ICD induction and poor prognosis in cancer patients. Similarly, a decrease in the copy number, expression level, and/or activity of calreticulin (CRT or CALR) impairs induction of ICD. It has also been determined herein that an increase in the copy number, expression level, and/or activity of STC1 gene impairs induction of ICD upon treatment with the ICD inducer such as proteasome inhibitor bortezomib (BTZ) in cancer, e.g., multiple myeloma (MM). By contrast, an increase in the copy number, expression level, and/or activity of GABARAP, CRT, or STING restore the impaired ICD. A decrease in the copy number, expression level, and/or activity of STC1 may restore impaired ICD. Accordingly, the modulation of the level of GABARAP, CRT, and/or STC1 provide an important treatment strategy for cancer patients being treated with an ICD inducer, e.g., chemotherapeutic agents, radiation therapy, oxazophorines, platinum-based compounds, anthracyclines, anthracenediones, or proteasome inhibitors. Furthermore, the level of GABARAP, CRT, STING and STC1 serve as an indication for various diagnostic and prognostic methods described herein.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as glycosylation, ubiquitylation, phosphorylation, and/or proteolytic cleavage of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, immune response (e.g., differentiation of a dendritic cell, T cell exhaustion, phagocytosis, etc.), cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" refers to antigen-binding portions adaptable to be expressed within cells as "intracellular antibodies" or intrabodies (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of effects of combinatorial therapies comprising one or more agents that modulate the copy number, expression level, and/or activity of one or more biomarkers listed in Table 1 and 2, such GABARAP, CRT, STING and/or STC1, and an ICD inducer (e.g., chemotherapeutic agents, radiation therapy, oxazophorines, platinum-based compounds, anthracyclines, anthracenediones, or proteasome inhibitors) on a cancer. Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the expression and activity of cellular pathways regulated by one or more biomarkers listed in Table 1 and/or Table 2. In some embodiments, the cancer cells described herein are not receptive to induction of ICD. Such lack of responsiveness to induction of ICD, without limitation, may be related to the inactivation or decreased level and activity, compared to control cells (e.g., normal and/or wild-type non-cancer cells, and/or cancer cells that are responsive to induction of ICD), of one or more biomarkers listed in Table 1. In some embodiments, such lack of responsiveness to induction of ICD, without limitation, may be related to the activation or increased level and activity, compared to control cells (e.g., normal and/or wild-type non-cancer cells, and/or cancer cells that are responsive to induction of ICD), of one or more biomarkers listed in Table 2.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., myelomas like multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), myeloma, multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the present disclosure encompasses myelomas, such as multiple myeloma. Multiple myeloma (MM) is characterized by malignant plasma cells (PC) in the BM associated in most cases with monoclonal protein in serum and or urine; PC can also be detected in extramedullary sites and/or peripheral blood during progression of disease. Examination for MM-defining events allows for the discrimination between MM and its precursor stages, namely monoclonal gammopathy of undetermined significance (MGUS) and smoldering MM (SMM). Specifically, diagnosis of MM requires 10% or more PC in the BM plus one or more signs of end-organ damage including hypercalcemia, renal dysfunction, anemia, or bone disease (CRAB criteria). Even without CRAB features, patients who manifest MM-defining events including clonal BM PC>60%, serum:ratio>100 fold, and/or more than one bone focal lesion on magnetic resonance imaging (MRI) or positron emission tomography (PET)/computed tomography (CT) scan are also treated, as their risk of progression to symptomatic disease is approximately 80% at 2 years. Clinical manifestations of MM result from excessive production of monoclonal immunoglobulin protein by malignant PC in blood and/or urine, infiltration of BM by neoplastic clone, and aberrant cytokine secretion.4 MGUS patients are monitored for progression off all therapy, as their risk of progression overall is 1% yearly. The standard of practice is also to follow SMM patients expectantly off treatment, as the risk of progression is 10% per year in the first 5 years, dropping to 3% per year thereafter. Recently, the new "20-20-20" Mayo Clinic criteria have identified a high-risk (HR)-SMM subgroup (patients with two or more features including: BM PC infiltration>20%, monoclonal protein>20 g/L and FLC ratio>20) with a median time to progression of 29 months. The QuiRedex study showed that lenalidomide+dexamethasone treatment prolonged time to progression and overall survival (OS) in HR-SMM. More recently lenalidomide alone has been shown to delay progressions of HR-SMM; however, there was a high rate of treatment discontinuation and secondary cancers in the lenalidomide cohort. Ongoing clinical trials are also evaluating alternative treatment strategies to delay progression of HR-SMM.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; dendritic cells; myeloid cells, such as monocytes, macrophages, eosinophils, mast cells, basophils, and granulocytes.

Macrophages (and their precursors, monocytes) are the 'big eaters' of the immune system. These cells reside in every tissue of the body, albeit in different guises, such as microglia, Kupffer cells and osteoclasts, where they engulf apoptotic cells and pathogens and produce immune effector molecules. Upon tissue damage or infection, monocytes are rapidly recruited to the tissue, where they differentiate into tissue macrophages. Macrophages are remarkably plastic and can change their functional phenotype depending on the environmental cues they receive. Through their ability to clear pathogens and instruct other immune cells, these cells have a central role in protecting the host but also contribute to the pathogenesis of inflammatory and degenerative diseases. Macrophages that encourage inflammation are called M1 macrophages, whereas those that decrease inflammation and encourage tissue repair are called M2 macrophages. M1 macrophages are activated by LPS and IFN-gamma, and secrete high levels of IL-12 and low levels of IL-10. M2 is the phenotype of resident tissue macrophages, and can be further elevated by IL-4. M2 macrophages produce high levels of IL-10, TGFβ and low levels of IL-12. Tumor-associated macrophages are mainly of the M2 phenotype, and seem to actively promote tumor growth.

Myeloid derived suppressor cells (MDSCs) are an intrinsic part of the myeloid cell lineage and are a heterogeneous population comprised of myeloid cell progenitors and precursors of granulocytes, macrophages and dendritic cells. MDSCs are defined by their myeloid origin, immature state and ability to potently suppress T cell responses. They regulate immune responses and tissue repair in healthy individuals and the population rapidly expands during inflammation, infection and cancer. MDSC are one of the major components of the tumor microenvironment. The main feature of these cells is their potent immune suppressive activity. MDSC are generated in the bone marrow and, in tumor-bearing hosts, migrate to peripheral lymphoid organs and the tumor to contribute to the formation of the tumor microenvironment. This process is controlled by a set of defined chemokines, many of which are upregulated in cancer. Hypoxia appears to have a critical role in the regulation of MDSC differentiation and function in tumors. Therapeutic strategies are now being developed to target MDSCs to promote antitumour immune responses or to inhibit immune responses in the setting of autoimmune disease or transplant rejection.

Dendritic cells (DCs) are professional antigen-presenting cells located in the skin, mucosa and lymphoid tissues. Their main function is to process antigens and present them to T cells to promote immunity to foreign antigens and tolerance to self antigens. They also secrete cytokines to regulate immune responses.

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naïve T cells, activated T cells, memory T cells, resting Tcons, or Tcons that have differentiated toward, for example, the Th1 or Th2 lineages. In some embodiments, Teffs are a subset of non-Treg T cells. In some embodiments, Teffs are CD4+ Teffs or CD8+ Teffs, such as CD4+ helper T lymphocytes (e.g., Th0, Th1, Tfh, or Th17) and CD8+ cytotoxic T lymphocytes. As described further herein, cytotoxic T cells are CD8+ T lymphocytes. "Naïve Tcons" are CD4+ T cells that have differentiated in bone marrow, and successfully underwent a positive and negative processes of central selection in a thymus, but have not yet been activated by exposure to an antigen. Naïve Tcons are commonly characterized by surface expression of L-selectin (CD62L), absence of activation markers such as CD25, CD44 or CD69, and absence of memory markers such as CD45RO. Naïve Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) Philos. Trans. R. Soc. Lond. Biol. Sci. 356: 625-637). In tumors, exhausted cells can present hallmarks of anergy.

The term "immunotherapy" or "immunotherapies" refer to any treatment that uses certain parts of a subject's immune system to fight diseases such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. A cancer vaccine may also comprise neoantigens that are specifically expressed on cancer cell surface. Similarly, a cancer vaccine may comprise partially inactivated cancer cells, e.g., heat-treated, or cancer cells treated with a chemotherapeutic agent, an ICD inducer, or radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "immunogenic chemotherapy" refers to any chemotherapy that has been demonstrated to induce immunogenic cell death, a state that is detectable by the release of one or more damage-associated molecular pattern (DAMP) molecules, including, but not limited to, calreticulin, ATP and HMGB1 (Kroemer et al. (2013), Annu. Rev. Immunol., 31:51-72). In addition, the term "immunogenic chemotherapy" further refers to any chemotherapy that results in priming the immune system such that it leads to enhanced immune activity towards cancer. Specific representative examples of consensus immunogenic chemotherapies include 5'-fluorouracil, anthracyclines, such as doxorubicin, and the platinum drug, oxaliplatin, among others.

In some embodiments, immunotherapy comprises inhibitors of one or more immune checkpoints. The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD48, 2B4 (CD244), B7.1, B7.2, ILT-2, ILT-4, TIGIT, HHLA2, butyrophilins, IDO, CD39, CD73 and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein. In some embodiments, the immune checkpoint is PD-1.

Immune checkpoints and their sequences are well-known in the art and representative embodiments are described below. For example, the term "PD-i" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM_005018.2 and NP_005009.2 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well-known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027-1034) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two R sheets, each consisting of anti-parallel R strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of R strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of PD-LiS is shown from about amino acid 1 to about amino acid 18. The signal sequence of PD-L1M is shown: from about amino acid 1 to about amino acid 18. The IgV domain of PD-LiS is shown from about amino acid 19 to about amino acid 134 and the IgV domain of PD-L1M is shown from about amino acid 19 to about amino acid 134. The IgC domain of PD-LiS is shown from about amino acid 135 to about amino acid 227 and the IgC domain of PD-L1M is shown from about amino acid 135 to about amino acid 227. The hydrophilic tail of the PD-L1 exemplified in PD-LiS comprises a hydrophilic tail shown from about amino acid 228 to about amino acid 245. The PD-L1 polypeptide exemplified in PD-L1M comprises a transmembrane domain shown from about amino acids 239 to about amino acid 259 and a cytoplasmic domain shown from about 30 amino acid 260 to about amino acid 290. In addition, nucleic acid and polypeptide sequences of PD-L1 orthologs in organisms other than humans are well-known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) *Eur. J. Immunol.* 37:2405). APC-expressed PD-L2 is able to both inhibit T cell activation through ligation of PD-1 and costimulate T cell activation, through a PD-1 independent mechanism (Shin et al. (2005) *J. Exp. Med.* 201:1531). In addition, ligation of dendritic cell-expressed PD-L2 results in enhanced dendritic cell cytokine expression and survival (Radhakrishnan et al. (2003) *J. Immunol.* 37:1827; Nguyen et al. (2002) *J. Exp. Med.* 196:1393). The nucleic acid and amino acid sequences of representative human PD-L2 biomarkers are well-known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of PD-L2 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) *Annu. Rev. Neurosci.* 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two B sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the Cl set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well-known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2

(XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "GABARAP," also known as Gamma-Aminobutyric Acid Receptor-Associated Protein, GABA Type A Receptor-Associated Protein, GABA(A) Receptor-Associated Protein, MM46, ATG8A, Epididymis Secretory Sperm Binding Protein, GABARAP-A, or FLC3B, refers to a ligand-gated chloride channel that mediates inhibitory neurotransmission. GABARAP is highly positively charged in its N-terminus and shares sequence similarity with light chain-3 of microtubule-associated proteins 1A and 1B. This protein clusters neurotransmitter receptors by mediating interaction with the cytoskeleton. GABARAP is a ubiquitin-like modifier that plays a role in intracellular transport of GABA(A) receptors and its interaction with the cytoskeleton. It is involved in apoptosis and in autophagy. While LC3s are involved in elongation of the phagophore membrane, the GABARAP/GATE-16 subfamily is essential for a later stage in autophagosome maturation. Through its interaction with the reticulophagy receptor TEX264, GABARAP participates in the remodeling of subdomains of the endoplasmic reticulum into autophagosomes upon nutrient stress, which then fuse with lysosomes for endoplasmic reticulum turnover. Diseases associated with GABARAP include Stiff-Person Syndrome; Hyperoxaluria, Primary, Type II; Hereditary Sensory And Autonomic Neuropathy Type 1; Amyotrophic Lateral Sclerosis 1. Among its related pathways are TBC/RABGAPs and Macroautophagy.

The term "GABARAP" is intended to include fragments, variants (e.g., allelic variants) and derivatives thereof. GABARAP encompasses few domains for its function, including ubiquitin-like domain and Atg8-like domain. Post-translational modifications for GABARAP includes a cleavage by ATG4B to form the cytosolic form, GABARAP-I. This is activated by APG7L/ATG7, transferred to ATG3 and conjugated to phospholipid to form the membrane-bound form, GABARAP-II. The nucleic acid and amino acid sequences of a representative human GABARAP is available to the public at the GenBank database (Gene ID 11337) and is shown in Table 1. The nucleic acid encoding GABARAP has been annotated in multiple NCBI Reference Sequences: NM_007278.2, AB030711.1, AF044671.1, AF067171.1, AF161586.1, AF183425.1, AK098634.1, AK312205.1, AL050182.1, BC106748.1, BC106749.1, CR457043.1, CR542235.1, GQ891383.1, JN663880.1, and U65413.1.

Nucleic acid and polypeptide sequences of GABARAP orthologs in organisms other than humans are well known and include, for example, chimpanzee GABARAP (XM_003315344.2 and XP_003315392.1), dog GABARAP (XM_536616.4 and XP_536616.2), rat GABARAP (NM_172036.3 and NP_742033.1), mouse GABARAP (NM_019749.4 and NP_062723.1), cow GABARAP (NM_001034048.1 and NP_001029220.1), Cow (*Bos Taurus*) GABARAP (NM_001034048.1 and NP_001029220.1), Oppossum (*Monodelphis domestica*) GABARAP (Primary_assembly 4: 112,857,750-112,858,181), Lizard (*Anolis carolinensis*) GABARAP (Scaffold GL343198.1: 4,793, 321-4,804,105), zebrafish GABARAP (NM_001013260.1 and NP_001013278.1), fly (*Drosophila melanogaster*) GABARAP (Chromosome X: 10,658,911-10,662,368), worm (*Caenorhabditis elegans*) GABARAP (Chromosome II: 6,346,957-6,347,719), and baker's yeast (*Saccharomyces cerevisiae*) GABARAP (Chromosome II: 80,378-80,731).

The term "GABARAP activity" includes the ability of a GABARAP polypeptide (and its fragments, domains, and/or motifs thereof, discussed herein) to bind its substrate and/or function as a chloride channel (e.g., chloride-gating activity), mediate inhibitory neurotransmission, and facilitate remodeling of subdomains of the endoplasmic reticulum into autophagosomes. As discovered herein, the GABARAP activity also include facilitation of immunogenic cell death (ICD) and the activity to promote cell surface exposure of calreticulin. GABARAP activity further includes regulation of immune response, e.g., maturation of a dendritic cell, and/or increasing phagocytosis of cancer cells. GABARAP may be proteolytically modified, glycosylated, phosphorylated, ubiquitinylated, citrullinated, sumoylated, or otherwise disclosed herein, for it functions.

The term "GABARAP substrate(s)" includes binding partners of a GABARAP polypeptide (and its fragments, domains, and/or motifs thereof, discussed herein), e.g., the proteins and compounds listed herein, including GPHN, NSF, ATG3, ATG7, ATG13, alpha-tubulin, beta-tubulin, GABRG2, RB1CC1, ULK1, CALR, DDX47, TP53INP1, TP53INP2, TBC1D5, TBC1D25, SQSTM1, MAPK15, TECPR2, PCM1, TRIM5, TRIM21, MEFV, KIF21B, WDFY3, TEX264, UBA5, and FLCN. Furthermore, GABARAP substrates may refer to downstream members in the pathways where GABARAP has a functional role.

The term "GABARAP-regulated pathway(s)" includes pathways in which GABARAP (and its fragments, domains, and/or motifs thereof, discussed herein) binds to at least one of its substrate, through which at least one cellular function and/or activity and/or cellular protein profiles is changed (e.g., immune response, immunogenic cell death). In some embodiments, CRT-regulated pathways include regulating immune response to cancer cells.

An agent that increases the copy number, expression level, amount, and/or activity of GABARAP includes any natural or non-natural agent prepared, synthesized, manufactured, and/or purified by human that is capable of increasing, improving, and/or enhancing the ability of a GABARAP polypeptide (and its fragments, domains, and/or motifs thereof, discussed herein). In some embodiments, the agent is a nucleic acid encoding GABARAP or a fragment thereof (e.g., a biologically active fragment thereof). Importantly, the nucleic acid or a fragment thereof may encode a wild-type protein, or may comprise one or more mutations that enhances its activity. The mutation may be deletion, substation, addition, or other chemical modifications. Such mutation may lack a negative regulatory domain, or confer increased interaction with one of its substrates. The nucleic acid may be transiently expressed in the target cell (e.g., cancer cell), or it may be integrated into the target cell genome. Such nucleic acid may be DNA, RNA, or cDNA, and may be delivered by a viral particle (e.g., lentiviral particle or adeno-associated viral particle). In some embodiments, the agent may modulate the interaction between GABARAP or a fragment thereof and any one of substrates described herein (e.g., increase or stabilize the interaction, or decrease or destabilize the interaction) (e.g., calreticulin). In addition, GABARAP is post-translationally modified (e.g., phosphorylated, etc.). Thus, an agent may increase the copy number, expression level, amount, and/or activity of GABARAP by modulating the post-translational modification of GABARAP. In some embodiments, the agent may decrease or reduce the turnover rate. In some embodiments, the agent may increase the stability of the mRNA and/or protein of GABARAP. In some embodiments, the agent comprises a small molecule compound, a peptide, a polypeptide, an aptamer, an antibody or antigen-binding fragment thereof, an intrabody or antigen-binding fragment thereof, and/or a nucleic acid. An antibody (including biparatopic or bispecific antibody) or antigen-binding fragment thereof may cluster GABARAP on cell surface and increase its activity. An antibody or intrabody (including biparatopic or bispecific) or antigen-binding fragment thereof may stabilize or increase the interaction between GABARAP and a substrate, thereby increasing its activity.

Purified GABARAP proteins are commercially available (Cat. #NM_007278 NM_007278 NM_007278 NM_007278 NM_007278 NM_007278) from Origene (Rockville, MD), Recombinant Human His6-GABARAP Protein, CF (UL-410) from R&D systems (Minneapolis, MN), and the like. Similarly, gene clones or ORF clones for human, mouse, and rat GABARAP are commercially available (cat #SC206295 MC200203 RN200743 SC115633 MG200511 MR200511 MR200511L1 MR200511L2 MR200511L3 MR200511L4 RC218961 RC218961L1 RC218961L2 RC218961L3 RC218961L4 RG218961 RR200743 RR200743L3 RR200743L4 MR200511L1V MR200511L2V MR200511L3V MR200511L4V RC218961L1V RC218961L2V RC218961L3V RC218961L4V RR200743L3V RR200743L4V) from Origene (Rockville, MD). In addition, gene clones or a fragment thereof in an expression vector or a viral vector (e.g., lentivirus, adenovirus, AAV (single-stranded AAV, self-complementary AAV), MMLV retrovirus, MSCV retrovirus, etc.) are commercially available from vendors such as VectorBuilder (Chicago, IL). Furthermore, anti-GABARAP antibodies for various methods described herein (e.g., treatment, diagnosis, and prognosis, etc.) are commercially available: Human GABARAP Antibody (MAB8574) from R&D systems (Minneapolis, MN), and anti-GABARAP antibodies (cat. #AP32182PU-N TA319834 TA332791 TA336614 TA336818 TA336870 TA339168 TA339169) from Origene (Rockville, MD).

The term "calreticulin," also known as Sicca Syndrome Antigen A, Endoplasmic Reticulum Resident Protein 60, Calregulin, CC1qR, CRP55, ERp60, HACBP, Grp60, CRT, CALR, SSA, RO, Epididymis Secretory Sperm Binding Protein Li 99n, Autoantigen Ro, HEL-S-99n, FLJ26680, or CRTC, refers to a highly conserved chaperone protein which resides primarily in the endoplasmic reticulum, and is involved in a variety of cellular processes, among them, cell adhesion. Additionally, it functions in protein folding quality control and calcium homeostasis. Calreticulin is also found in the nucleus, suggesting that it may have a role in transcription regulation. Calcium-binding chaperone that promotes folding, oligomeric assembly and quality control in the endoplasmic reticulum (ER) via the calreticulin/calnexin cycle. This lectin interacts transiently with almost all of the monoglucosylated glycoproteins that are synthesized in the ER. It interacts with the DNA-binding domain of NR3C1 and mediates its nuclear export. Involved in maternal gene expression regulation. May participate in oocyte maturation via the regulation of calcium homeostasis (By similarity). Systemic lupus erythematosus is associated with increased autoantibody titers against calreticulin. Recurrent mutations in calreticulin have been linked to various neoplasms, including the myeloproliferative type. Diseases associated with CALR include myelofibrosis, thrombocythemia 1, essential thrombocythemia, rubella, and congenital heat block. Among its related pathways are Neuroscience and Antigen processing-Cross presentation.

Calreticulin (CALR or CRT as used herein) is an endoplasmic reticulum (ER)-resident protein involved in a spectrum of cellular processes. In healthy cells, CRT operates as a chaperone and Ca2+ buffer to assist correct protein folding within the ER. Besides favoring the maintenance of cellular proteostasis, these cell-intrinsic CRT functions support Ca2+-dependent processes, such as adhesion and integrin signaling, and ensure normal antigen presentation on MHC Class I molecules. Moreover, cancer cells succumbing to immunogenic cell death (ICD) expose CRT on their surface, which promotes the uptake of cell corpses by professional phagocytes and ultimately supports the initiation of anticancer immunity. Thus, loss-of-function CRT mutations promote oncogenesis not only as they impair cellular homeostasis in healthy cells, but also as they compromise natural and therapy-driven immunosurveillance.

The term "calreticulin" is intended to include fragments, variants (e.g., allelic variants) and derivatives thereof. Calreticulin encompasses domains and motifs for its function, including ConA-like_dom_sf, Calret/calnex, Calret/calnex_CS, and calreticulin/calnexin P domain superfamily (Calreticulin/calnexin_P_dom_sf). CRT can be divided into a N-terminal globular domain, a proline-rich P-domain forming an elongated arm-like structure and a C-terminal acidic domain. The P-domain binds one molecule of calcium with high affinity, whereas the acidic C-domain binds multiple calcium ions with low affinity.

The nucleic acid and amino acid sequences of a representative human CRT is available to the public at the GenBank database (Gene ID 811) and is shown in Table 1 (e.g., GenBank database numbers NM_004343.4 and NP_004334.1). Nucleic acid and polypeptide sequences of CRT orthologs in organisms other than humans are well known and include, for example, Mouse (*Mus musculus*) CRT (NM_007591.3 and NP_031617.1), Chicken (*Gallus gallus*) CRT (XM_418262.4 and XP_418262.3), Lizard (*Anolis carolinensis*) CRT (Chromosome 2: 77,770,708-77,779,899), African clawed frog (*Xenopus laevis*) CRT (BC046699.1), Zebrafish (*Danio rerio*) CRT (NM_199713.1 and NP_956007.1), and rat CRT (NM_022399.2 and NP_071794.1).

The term "calreticulin activity" includes the ability of a CRT polypeptide (and its fragments, domains, and/or motifs thereof, discussed herein) to bind its substrate, and/or perform a chaperone activity. Since CRT operates as a Ca2+ buffer, and functions support Ca2+-dependent processes, CRT's Ca2+-binding activity is important for its function. As disclosed herein, the CRT activity also include facilitation of immunogenic cell death (ICD) and its activity that regulates immune response, e.g., maturation of a dendritic cell and/or increasing phagocytosis of cancer cells. CRT may be proteolytically modified, glycosylated, phosphorylated, ubiquitinylated, citrullinated, sumoylated, or otherwise disclosed herein, for it functions.

The term "calreticulin substrate(s)" includes binding partners of a calreticulin polypeptide (and its fragments, domains, and/or motifs thereof, discussed herein), e.g., the proteins including PDIA3/ERp57, SPACA9, TRIM21, NR3C1, PPIB, PDIA5, GABARAP, HLA-E-B2M, HLA-G-B2M, HLA-F, and CLCC1. CRT is also a component of an EIF2 complex at least composed of CELF1/CUGBP1, CALR, CALR3, EIF2S1, EIF2S2, HSP90B1 and HSPA5. Furthermore, CRT substrates may refer to downstream members in the pathways where CRT has a functional role.

The term "calreticulin-regulated pathway(s)" includes pathways in which calreticulin (and its fragments, domains, and/or motifs thereof, discussed herein) binds to at least one of its substrate, through which at least one cellular function and/or activity and/or cellular protein profiles is changed (e.g., immune response, immunogenic cell death). In some embodiments, CRT-regulated pathways include regulating immune response to cancer cells.

An agent that increases the copy number, expression level, amount, and/or activity of CRT includes any natural or non-natural agent prepared, synthesized, manufactured, and/or purified by human that is capable of increasing, improving, and/or enhancing the ability of a CRT polypeptide (and its fragments, domains, and/or motifs thereof, discussed herein). In some embodiments, the agent is a recombinant polypeptide. In some embodiments, the recombinant polypeptide is injected into a tumor mass, thereby inducing immune response of the intratumoral immune cells (e.g., dendritic cells, T cells). As demonstrated herein, exogenous incubation of recombinant CRT with cancer cells increases the immune response against the cancer cells. In some embodiments, the agent is a nucleic acid encoding CRT or a fragment thereof (e.g., a biologically active fragment thereof). Importantly, the nucleic acid or a fragment thereof may encode a wild-type protein, or may comprise one or more mutations that enhances its activity.

The mutation may be deletion, substation, addition, or other chemical modifications. Such mutation may lack a negative regulatory domain, or confer increased interaction with one of its substrates. The nucleic acid may be transiently expressed in the target cell (e.g., cancer cell), or it may be integrated into the target cell genome. Such nucleic acid may be DNA, RNA, or cDNA, and may be delivered by a viral particle (e.g., lentiviral particle or adeno-associated viral particle). In some embodiments, the agent may modulate the interaction between CRT or a fragment thereof and any one of substrates described herein (e.g., increase or stabilize the interaction, or decrease or destabilize the interaction) (e.g., GABARAP). In addition, CRT is post-translationally modified (e.g., glycosylated, ubiquitinylated, phosphorylated, etc.). Thus, an agent may increase the copy number, expression level, amount, and/or activity of CRT by modulating the post-translational modification of CRT. In some embodiments, the agent may decrease or reduce the turnover rate. In some embodiments, the agent may increase the stability of the mRNA and/or protein of CRT. In some embodiments, the agent comprises a small molecule compound, a peptide, a polypeptide, an aptamer, an antibody or antigen-binding fragment thereof, an intrabody or antigen-binding fragment thereof, and/or a nucleic acid. An antibody or intrabody (including biparatopic or bispecific) or antigen-binding fragment thereof may stabilize or increase the interaction between CRT and a substrate, thereby increasing its activity.

Purified CRT proteins are commercially available (Cat. #NM_004343 NM_004343 NM_004343 NM_004343 NM_004343 NM_004343 NM_007591) from Origene (Rockville, MD), Recombinant Human CRT Protein, cat. #NBP1-44499 from Novus Biologicals (Centennial, CO), and the like. Similarly, gene clones or ORF clones for human, mouse, and rat CRT are commercially available (cat #SC207887 MC208210 RN209415 SC320287 MG206584 MR206584 MR206584L3 MR206584L4 RC203222 RC203222L1 RC203222L2 RC203222L3 RC203222L4 RG203222 RR209415 RR209415L3 RR209415L4 MR206584L3V MR206584L4V RC203222L1V RC203222L2V RC203222L3V RC203222L4V RR209415L3V RR209415L4V) from Origene (Rockville, MD). In addition, gene clones or a fragment thereof in an expression vector or a viral vector (e.g., lentivirus, adenovirus, AAV (single-stranded AAV, self-complementary AAV), MMLV retrovirus, MSCV retrovirus, etc.) are commercially available from vendors such as VectorBuilder (Chicago, IL). Furthermore, anti-CRT antibodies for various methods described herein (e.g., treatment, diagnosis, and prognosis, etc.) are commercially available: Human/Mouse/Rat Calreticulin Antibody (MAB38981) from R&D systems (Minneapolis, MN), and anti-CRT antibody (cat. #AM00171PU-N AM06211SU-N AM31148PU-N AP00030PU-N AP05311PU-N AP17172PU-N AP33519PU-N CF813228 CF813229 CF813230 CF813231 SP1087P TA309300 TA312147 TA321646 TA321647 TA326909 TA327765 TA329122 TA329123 TA336667 TA336669 TA336776 TA344177 TA344447 TA344448 TA813228 TA813228S TA813229 TA813229S TA813230 TA813230S TA813231 TA813231S) from Origene (Rockville, MD).

Stimulator of interferon genes (STING) (also known as 173 (TMEM173) and MPYS/MITA/ERIS) is a transmembrane protein that in humans is encoded by the STING1 gene. In healthy cells, It is a facilitator of innate immune signaling that acts as a sensor of cytosolic DNA from bacteria and viruses and promotes the production of type I interferon (IFN-alpha and IFN-beta) Acts by binding cyclic dinucleotides: recognizes and binds cyclic di-GMP (c-di-GMP), a second messenger produced by bacteria, and cyclic GMP-AMP (cGAMP), a messenger produced by CGAS in response to DNA virus in the cytosol. Upon binding of c-di-GMP or cGAMP, STING1 oligomerizes, translocates from the endoplasmic reticulum and is phosphorylated by TBK1 on the pLxIS motif, leading to recruitment and subsequent activation of the transcription factor IRF3 to induce expression of type 1 interferon and exert a potent anti-viral state. The term "STING" is intended to include fragments, variants (e.g., allelic variants) and derivatives thereof.

The nucleic acid and amino acid sequences of a representative human STING is available to the public at the GenBank database (Gene ID 40061) and is shown in Table 1. Nucleic acid and polypeptide sequences of CRT orthologs in organisms other than humans are well known and include, for example, Mouse (Mus musculus) STING (AMD16372.1), Cow (Bos Taurus) STING (ANQ45218.1), Boar (Sus Scrofa) STING (ACJ70708.1), fly (Drosophila melanogaster) STING (AAD38655.1), Zebrafish (Danio rerio) STING (NP_001265766.1), and rat (Rattus norvegicus) STING(NP_001102592.1).

The term "STING activity" includes the ability of a STING polypeptide (and its fragments, domains, and/or motifs thereof, discussed herein) to bind its substrate, and/or perform a chaperone activity. As disclosed herein, the STING activity also include facilitation of immunogenic cell death (ICD) and its activity that regulates immune response, e.g., maturation of a dendritic cell and/or increasing phagocytosis of cancer cells. STING may be proteolytically modified, glycosylated, phosphorylated, ubiquitinylated, citrullinated, sumoylated, or otherwise disclosed herein, for it functions.

The term "STING-regulated pathway(s)" includes pathways in which STING (and its fragments, domains, and/or motifs thereof, discussed herein) binds to at least one of its substrate, through which at least one cellular function and/or activity and/or cellular protein profiles is changed (e.g., immune response, immunogenic cell death). In some embodiments, STING-regulated pathways include regulating immune response to cancer cells.

An agent that increases the copy number, expression level, amount, and/or activity of STING includes any natural or non-natural agent prepared, synthesized, manufactured, and/or purified by human that is capable of increasing, improving, and/or enhancing the ability of a STING polypeptide (and its fragments, domains, and/or motifs thereof, discussed herein). In some embodiments, the agent is a recombinant polypeptide. In some embodiments, the recombinant polypeptide is injected into a tumor mass, thereby inducing immune response of the intratumoral immune cells (e.g., dendritic cells, T cells). As demonstrated herein, exogenous incubation of recombinant STING with cancer cells increases the immune response against the cancer cells. In some embodiments, the agent is a nucleic acid encoding STING or a fragment thereof (e.g., a biologically active fragment thereof). Importantly, the nucleic acid or a fragment thereof may encode a wild-type protein, or may comprise one or more mutations that enhances its activity. The mutation may be deletion, substation, addition, or other chemical modifications. Such mutation may lack a negative regulatory domain, or confer increased interaction with one of its substrates. The nucleic acid may be transiently expressed in the target cell (e.g., cancer cell), or it may be integrated into the target cell genome. Such nucleic acid may be DNA, RNA, or cDNA, and may be delivered by a viral particle (e.g., lentiviral particle or adeno-associated viral particle). In some embodiments, the agent may modulate the interaction between STING or a fragment thereof and any one of it's substrates described herein. In some embodiments, the agent may decrease or reduce the turnover rate. In some embodiments, the agent may increase the stability of the mRNA and/or protein of STING. In some embodiments, the agent comprises a small molecule compound, a peptide, a polypeptide, an aptamer, an antibody or antigen-binding fragment thereof, an intrabody or antigen-binding fragment thereof, and/or a nucleic acid. In some embodiments, the agent is a STING agonist (e.g., ADUS-100, MK-1454, macrocycle-bridged STING agonist E7766, BMS-986301, GSK3745417, IMSA101, MK-2118, SB 11285, SNX281, TAK-676, or STING agonist-containing PTGFRN-expressing exosomes CDK002).

Purified STING proteins are commercially available (Cat. #TP308418) from Origene (Rockville, MD). Similarly, gene clones or ORF clones STING are commercially available (cat #RG237169, RC208418, RC208418L3V, MR227544, RG208418, MG227544, RC237169, and MR229327) from Origene (Rockville, MD). In addition, gene clones or a fragment thereof in an expression vector or a viral vector (e.g., lentivirus, adenovirus, AAV (single-stranded AAV, self-complementary AAV), MMLV retrovirus, MSCV retrovirus, etc.) are commercially available from vendors such as VectorBuilder (Chicago, IL). Furthermore, anti-STING antibodies for various methods described herein (e.g., treatment, diagnosis, and prognosis, etc.) are commercially available: Human/Mouse/Rat STING Antibody from R&D systems (Minneapolis, MN), and anti-STING antibody (cat. #CF50523, CF505024, TA505023AM, TA505023BM, CF505032, TA505024AM) from Origene (Rockville, MD).

The term "STC1," also known as Stanniocalcin 1, refers to a secreted, homodimeric glycoprotein. that is expressed in a wide variety of tissues and may have autocrine or paracrine functions. The gene contains a 5' UTR rich in CAG trinucleotide repeats. The encoded protein contains 11 conserved cysteine residues and is phosphorylated by protein kinase C exclusively on its serine residues. The protein may play a role in the regulation of renal and intestinal calcium and phosphate transport, cell metabolism, or cellular calcium/phosphate homeostasis. Overexpression of human stanniocalcin 1 in mice produces high serum phosphate levels, dwarfism, and increased metabolic rate. This gene has altered expression in hepatocellular, ovarian, and breast cancers, One molecular function of human Stanniocalcin-1 is a SUMO E3 ubiquitin ligase activity in the SUMOylation cycle. STC1 interacts with many proteins in the cytoplasm, mitochondria, endoplasmatic reticulum, and in dot-like fashion in the cell nucleus. The N-terminal region of STC1 is the function region which is responsible to establish the interaction with its partners, including SUMO1.

The term "STC1" is intended to include fragments, variants (e.g., allelic variants) and derivatives thereof. The nucleic acid and amino acid sequences of a representative human STC1 is available to the public at the GenBank database (Gene ID 6781) and is shown in Table 2. The nucleic acid encoding STC1 has been annotated in multiple NCBI Reference Sequences: NM_003155.3, NG_029711.1, KP455659.1, KP455658.1, KP455656.1, KP455655.1, AF242179.i, and BC029044.1.

Nucleic acid and polypeptide sequences of STC1 orthologs in organisms other than humans are well known and include, for example, chimpanzee STC1 (XM_528091.6), dog STC1 (XM_038435397.1 and XM_543238.7), rat STC1 (NM_031123.2 and NP_112385.1), mouse STC1 (NM_009285.3 and NP_033311.3), Cow (*Bos Taurus*) GABARAP (NM_001034048.1 and NP_001029220.1), Boar (*Sus Scrofa*) STC1 (NM_001103212.1 and NP_01096682.1), and zebrafish STC1 (NM_001045457.1 and NP_00038922.1).

The term "STC1 activity" includes the ability of a STC1 polypeptide (and its fragments, domains, and/or motifs thereof, discussed herein) to bind its substrate and/or function as a, for example, SUMO E3 ubiquitin ligase activity in the SUMOylation cycle. As discovered herein, the STC1 activity also includes inhibition of immunogenic cell death (ICD), binding to CALR and the activity to trap and/or increase levels of CALR in the mitochondria.

The term "STC1-regulated pathway(s)" includes pathways in which STC1 (and its fragments, domains, and/or motifs thereof, discussed herein) binds to at least one of its substrate, through which at least one cellular function and/or activity and/or cellular protein profiles is changed. In some embodiments, STC1-regulated pathways include regulating immune response to cancer cells.

An agent that decreases the copy number, expression level, amount, and/or activity of STC1 includes any natural or non-natural agent prepared, synthesized, manufactured, and/or purified by human that is capable of increasing, improving, and/or enhancing the ability of a STC1 polypeptide (and its fragments, domains, and/or motifs thereof, discussed herein). In some embodiments, the agent is a nucleic acid encoding STC1 or a fragment thereof (e.g., a biologically active fragment thereof). Importantly, the nucleic acid or a fragment thereof may encode a wild-type protein, or may comprise one or more mutations that enhances its activity. The mutation may be deletion, substation, addition, or other chemical modifications. Such mutation may lack a negative regulatory domain, or confer increased interaction with one of its substrates. The nucleic acid may be transiently expressed in the target cell (e.g., cancer cell), or it may be integrated into the target cell genome. Such nucleic acid may be DNA, RNA, or cDNA, and may be delivered by a viral particle (e.g., lentiviral particle or adeno-associated viral particle). In some embodiments, the agent may modulate the interaction between STC1 or a fragment thereof and any one of substrates described herein (e.g., increase or stabilize the interaction, or decrease or destabilize the interaction). An agent may decrease the copy number, expression level, amount, and/or activity of STC1 by modulating the post-translational modification of STC1. An agent may increase STC1's interaction with GABARAP and/or decrease STC1's interaction with CALR In some embodiments, the agent may increase the turnover rate. In some embodiments, the agent may decrease the stability of the mRNA and/or protein of STC1. In some embodiments, the agent comprises a small molecule compound, a peptide, a polypeptide, an aptamer, an antibody or antigen-binding fragment thereof, an intrabody or antigen-binding fragment thereof, and/or a nucleic acid. An antibody (including biparatopic or bispecific antibody) or antigen-binding fragment thereof may increase STC1's interaction with GABARAP and/or decrease STC1's interaction with CALR. An antibody or intrabody (including biparatopic or bispecific) or antigen-binding fragment thereof may stabilize or increase the interaction between STC1 and a substrate, thereby increasing its activity.

Purified STC1 proteins are commercially available (Cat. #NM_003155) from Origene (Rockville, MD), Recombinant Human Stanniocalcin 1/STC-1 Protein, CF, from R&D systems (Minneapolis, MN), and the like. Similarly, gene clones or ORF clones for human, mouse, and rat GABARAP are commercially available (cat #RC206573, RC206573L1V, RC206573L2V, RC206573L3V, RC206573L4V, MR203105, RG206573, MG203105, RR213324, MR203105L1, MR203105L3, RC20673L1, RC206573L4, RC206573L3, MR203105L1V, MR203105L2V, MR203105L3V, MR203105L4V, RR213324L3V, RR213324L4V, MR203105L2, MR203105L4, RC206573L2, RR213324L3, RR213324L4, MC206790 SC11027, SC324585, and RN2313324) from Origene (Rockville, MD). In addition, gene clones or a fragment thereof in an expression vector or a viral vector (e.g., lentivirus, adenovirus, AAV (single-stranded AAV, self-complementary AAV), MMLV retrovirus, MSCV retrovirus, etc.) are commercially available from vendors such as VectorBuilder (Chicago, IL). Furthermore, anti-STC1 antibodies for various methods described herein (e.g., treatment, diagnosis, and prognosis, etc.) are commercially available: Human STC1 Antibody (MAB2958) from R&D systems (Minneapolis, MN), and anti-STC1 antibodies (cat. #TA810025, TA311078, TA810025AM, and TA350454) from Origene (Rockville, MD).

"Aptamers" are oligonucleotide or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. The "Affimer protein", an evolution of peptide aptamers, is a small, highly stable protein engineered to display peptide loops which provides a high affinity binding surface for a specific target protein. It is a protein of low molecular weight, 12-14 kDa, derived from the cysteine protease inhibitor family of cystatins. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Additional exemplary immune responses include phagocytosis by macrophages and/or dendritic cells.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the reduce, decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

The term "inducer of immunogenic cell death (ICD)" or an "inducer of ICD" is art-recognized, and refers to an agent that induces ICD, a certain type of cell death that elicits immune response. ICD is characterized by the ability of dying cells to elicit robust adaptive immune responses against altered self-antigens/cancer-derived neo-epitopes, in the case of tumor cells, or against pathogen-derived antigens during the course of an infection. Besides antigenicity, another vital factor needed to unleash a genuine immune response is adjuvanticity, which is conferred by microorganism- and/or danger-associated molecular patterns (MAMPs and DAMPs, respectively). These are molecules that are exposed or released by dying cells and let the immune system know the existence of a menace to the organism. This "danger" state is sensed in the human body by pattern recognition receptors (PRRs) displayed by innate immune cells such as monocytes, macrophages and dendritic cells (DCs), hence promoting activation and maturation of these cells to engage the adaptive arm of the immune system. Despite some screening studies using large drug libraries having been performed, only a small group of candidates have emerged to be valid ICD inducers (Obeid et al., 2007; Martins et al., 2011; Menger et al., 2012; Sukkurwala et al., 2014). The chemical nature of these agents, is considerably diverse: oxazophorines like cyclophosphamide (Schiavoni et al., 2011); Pt-based compounds as oxaliplatin (Tesniere et al., 2009); anthracyclines (Minotti et al., 2004) such as idarubicin and doxorubicin; anthracenediones such as mitoxantrone and dipeptides such as bortezomib (Merin and Kelly, 2014). Similar to bortezomib, carfilzomib another proteasome inhibitor used in the treatment of MM, has also shown to expose CRT in different MM cell lines (Jarauta et al., 2016).

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM, IgG1, IgG2C, and the like) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy.

The "normal" level of expression of a biomarker is the level of expression of the biomarker in cells of a subject, e.g., a human patient, not afflicted with a cancer. An "overexpression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to an agent described herein in combination with an inducer of ICD, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to an agent described herein in combination with an inducer of ICD. Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular inhibitor/immunotherapy combination therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid.

Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to an agent" or "response to an inducer of ICD" (e.g., chemotherapeutic agents, radiation therapy, oxazophorines, platinum-based compounds, anthracyclines, anthracenediones, or proteasome inhibitors) relates to any response of the hyperproliferative disorder (e.g., cancer) to an agent or an inducer described herein, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a gene (e.g., negative regulator of GABARAP or CRT) by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a nucleic acid (e.g., encoding negative regulator of GABARAP or CRT) by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the nucleic acid (e.g., encoding negative regulator of GABARAP, CRT, STING, or STC1). In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of a nucleic acid expression" includes any decrease in expression or protein activity or level of the nucleic acid or protein encoded by the nucleic acid. The decrease may be of at least 30%, 40%, 50%, 60%, 70%, 80%, 90%, 95% or 99% or more as compared to the expression of a nucleic acid or the activity or level of the protein encoded by the nucleic acid which has not been targeted by an RNA interfering agent.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a nucleic acid (e.g., encoding negative regulator of GABARAP, CRT, STING, or STC1), e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "subject" refers to any healthy animal, mammal or human, or any animal, mammal or human afflicted with a cancer, e.g., brain, lung, ovarian, pancreatic, liver, breast, prostate, and/or colorectal cancers, melanoma, myeloma such as multiple myeloma, and the like.

The term "subject" is interchangeable with "patient." The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more anti-cancer agents (e.g., an agent described herein) can be greater than the sum of the separate effects of the anti-cancer agents/therapies alone.

The term "T cell" includes CD4$^+$ T cells and CD8$^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well-known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

TABLE 1

Gamma-Aminobutyric Acid Receptor-Associated Protein (GABARAP), such as from a mammal (e.g., a rodent, primate, or human)
Calreticulin, such as from a mammal (e.g., a rodent, primate, or human)

```
SEQ ID NO: 1 Human Gamma-Aminobutyric Acid Receptor-Associated Protein
(GABARAP) Amino Acid Sequence (NP_009209.1)
   1 mkfvykeehp fekrrsegek irkkypdrvp vivekapkar igdldkkkyl vpsdltvgqf
  61 yflirkrihl raedalfffv nnvipptsat mgqlyqehhe edfflyiays desvygl SEQ ID NO: 2 Human GABARAP cDNA sequence (NM_007278.2, CDS region from
position 120-473)
   1 gcaaattcgt ggatcgctcc gctgaatccg cccgcgcgtc gccgccgtcg tcgccgcccc
  61 ccgtcccggc cccctgggt tccctcagcc cagccctgtc cagcccggtt cccgggagga
 121 tgaagttcgt gtacaaagaa gagcatcgt tcgagaagcg ccgctctgag ggcgagaaga
 181 tccgaaagaa atacccggac cgggtgccgg tgatagtaga aaggctccc aaagctcgga
 241 taggagacct ggacaaaaag aaatacctgg tgccttctga tctcacagtt ggtcagttct
 301 acttcttgat ccggaagcga attcatctcc gagctgagga tgccttgttt ttctttgtca
 361 acaatgtcat tccacccacc agtgccacaa tgggtcagct gtaccaggaa caccatgaag
 421 aagacttctt tctctacatt gcctacagtg acgaaagtgt ctacggtctg tgaagctgct
 481 gccctgagc tggagggggg tctcattcta caaagagaga ggtggccccc ctttcttgac
 541 ctcctcctcc ttcaagctca aacaccacct cccttattca ggaccggcac ttcttaatgt
 601 ttgtggcttt ctctccagcc tctcttagga ggggtaatgg tggagttggc atcttgtaac
 661 tctccttttct cctttcttcc cctttctctg cccgcctttc ccatcctgct gtagacttct
 721 tgattgtcag tctgtgtcac atccagtgat tgttttggtt tctgttccct ttctgactgc
```

TABLE 1-continued

Gamma-Aminobutyric Acid Receptor-Associated Protein (GABARAP), such as from a
mammal (e.g., a rodent, primate, or human)
Calreticulin, such as from a mammal (e.g., a rodent, primate, or human)

```
 781 ccaaggggct cagaacccca gcaatccctt cctttcacta ccttcttttt tgggggtagt
 841 tggaagggac tgaaattgtg gggggaaggt aggaggcaca tcaataaaga ggaaaccacc
 901 aagctgaact gaattttgcc ttgtgttgct cccctcgtcc cgctgatttt aagtctttcc
 961 aaggtgtcag tgggttcag tggtggggaa agaagagtac tgggtacaag ctggagggat
1021 agaagtatat tttggtttat tctgttcatg tggggctttt ccctgtctgc aaaaagaggg
1081 tgcttttgtt gtgatggaat ggaatactga ggattatttc ttgaaacttt agttttataa
1141 cacgcatgtg aaactaaatg ttaaaaatgc tcatgtaaaa aaaaattttt ttttactgtg
1201 ggttcctgtg gagaaagttc cgaagtacct gctttaggtg aacatccaca tttgctagaa
1261 cattctaact aagatatttt catgtgtgca agctagtaaa acggctgttc tcagttgca
```

SEQ ID NO:3 Mouse GABARAP Amino Acid Sequence (NP_062723.1)
```
  1 mkfvykeehp fekrrsegek irkkypdrvp vivekapkar igdldkkkyl vpsdltvgqf
 61 yflirkrihl raedalfffv nnvipptsat mgqlyqehhe edfflyiays desvygl
```

SEQ ID NO: 4 Mouse GABARAP cDNA sequence (NM_019749.4, CDS region from
position 344-697)
```
   1 caactttgta ctgtgggaaa gggttttttca gttcactcga acaacagca accttatctg
  61 cgatgtcata tgtgtaaccc acaagttgat tccaaagcag ttacgctgaa ggcgtaagag
 121 gaccaggcta cgggttgcgc tagcaagctg agctagtggc gtatgttagc aggcggggcc
 181 ggtccgatgt tcggggcgg ggttgatgaa tagggaagtg gcgcaaattc gtggatcgct
 241 ccgccaagtc tgttcgtcga agccgcctcc gccgccgcc cctgtcccgg cccccccct
 301 gggttccctc agcccagctc ggtccagccc ggttctcggg agaatgaagt tcgtgtacaa
 361 agaggagcat ccgttcgaga agcgccgctc tgagggcgag aaaatccgaa agaaataccc
 421 agaccgggtc ccgtgatag tggaaaaagc ccccaaagct cggataggag acctggacaa
 481 aaagaaatac ctggtgcctt ctgatcttac agttggtcaa ttctacttct tgatccggaa
 541 gcgaattcat ctccgtgctg aagatgcctt gtttttcttt gtcaacaatg tcattccacc
 601 caccagtgcc acgatgggtc agctgtacca ggaacaccat gaagaagact tctttctata
 661 cattgcctac agtgatgaaa gcgtctatgg tctgtgaagc tgctgtacct gaggtggggg
 721 gttccattct acgaagagag gtggcgctcc ttccttgaca tccagttcct ccttcaggct
 781 caaacaccac ctcctttctt caggacctgc acttaatgtt tgaggctgtc tctccagtcc
 841 ctctcagcag gaggggtaat ggtagataca gcctccatac atctctttct ccccttgttt
 901 accctccatt cccactctga tttagacttc ttgattgtcg atctctgtca catccgatga
 961 ttgtttggt ttctattccc tttctaactg cccatcgggc tcagaacccc aataatccct
1021 tccttctcact atcttctttt tgggggtag gtggaaggga ttgacattgg atggggagg
1081 taggaggcac atcaataaaa aggaaaccac cgagctgaat tg
```

SEQ ID NO: 5 Rat GABARAP Amino Acid Sequence (NP_742033.1)
```
  1 mkfvykeehp fekrrsegek irkkypdrvp vivekapkar igdldkkkyl vpsdltvgqf
 61 yflirkrihl raedalfffv nnvipptsat mgqlyqehhe edfflyiays desvygl
```

SEQ ID NO: 6 Rat GABARAP cDNA sequence (NM_172036.3, CDS region from
position 50-403)
```
   1 cccctgggt tccctcagcc cagctcggtc cagcccggtt ctcggagaa tgaagttcgt
  61 gtacaaagag gagcatccgt tcgagaagcg ccgctctgag ggcgagaaaa tccgaaagaa
 121 atacccagac cgggtcccgg tgatagtgga aaaagctccc aaagctcgga taggggacct
 181 ggacaaaaag aaatacttgg tgccttctga tcttacaggt ggtcaattct acttcttgat
 241 ccggaagcga attcatctcc gtgctgaaga tgccttgttt ttctttgtca acaatgtcat
 301 tccaccacc agtgccacga tgggtcagct gtaccaggaa caccatgaag aagacttctt
 361 tctatacatt gcctacagtg atgaaagcgt ctacggtctg tgaagttgct gtcccggagg
 421 tggggttcc attctacaaa gagaggtggc gctccttcct tggcatccag ttcctccttc
 481 aggctcaaac accatctcct ttcttcagga cctgcactta atgtttgagg ctgtctctcc
 541 agtccctctg agcaggaggg gtaatggtag atgcagccgc tgtacatctc tcttcccct
 601 tgtttaccct ccattcccac tctgctttag acttctggat tgtcgatctc tgtcacatcg
 661 gatgattgtt ttggtttcta ttccctttct aactgcccac tgggctcaga ccccaataa
 721 accttcctt tcactacctt ctttttgggg ggtagatgga agggttgac attgggtggg
 781 ggaggtagga ggcacatcaa taaagaggaa accaccgagc tgaaataaaa aaaaaaaaa
 841 aaaaaaaaa aaa
```

SEQ ID NO: 7 Human Calreticulin Amino Acid Sequence (NP_004334.1)
```
  1 mllsvplllg llglavaepa vyfkeqfldg dgwtsrwies khksdfgkfv lssgkfygde
 61 ekdkglqtsq darfyalsas fepfsnkgqt lvvqftvkhe qnidcgggyv klfpnsldqt
121 dmhgdseyni mfgpdicpg tkkvhvifny kgnvlinkd irckddefth lytlivrpdn
181 tyevkidnsq vesgsleddw dflppkkikd pdaskpedwd erakiddptd skpedwdkpe
241 hipdpdakkp edwdeemdge weppviqnpe ykgewkprqi dnpdykgtwi hpeidnpeys
301 pdpsiyaydn fgvlgldlwq vksgtifdnf litndeayae efgnetwgvt kaaekqmkdk
361 qdeeqrlkee eedkkrkeee eaedkedded kdedeedeed keedeeedvp gqakdel
```

SEQ ID NO: 8 Human Calreticulin cDNA sequence (NM_004343.4, CDS region from
position 72-1325)
```
  1 gtccgtactg cagagccgct gccggagggt cgttttaaag ggcccgcgcg ttgccgcccc
 61 ctcggccgc catgctgcta tccgtgccgc tgctgctcgg cctcctggcc ctggccgtcg
121 ccgagcctgc cgtctacttc aaggagcagt ttctggacgg agacgggtgg acttccgct
181 ggatcgaatc caaacacaag tcagattttg gcaaattcgt tctcagtccc ggcaagttct
241 acggtgacga ggagaaagat aaaggttgc agacaagcca ggatgcacgc ttttatgctc
301 tgtcggccag tttcgagcct ttcagcaaca aaggccagac gctggtggtg cagttcacgg
361 tgaaacatga gcagaacatc gactgtgggg gcggctatgt gaagctgttt cctaatagtt
```

TABLE 1-continued

Gamma-Aminobutyric Acid Receptor-Associated Protein (GABARAP), such as from a mammal (e.g., a rodent, primate, or human)
Calreticulin, such as from a mammal (e.g., a rodent, primate, or human)

```
 421 tggaccagac agacatgcac ggagactcag aatacaacat catgtttggt cccgacatct
 481 gtggccctgg caccaagaag gttcatgtca tcttcaacta caagggcaag aacgtgctga
 541 tcaacaagga catccgttgc aaggatgatg agtttacaca cctgtacaca ctgattgtgc
 601 ggccagacaa cacctatgag gtgaagattg acaacagcca ggtggagtcc ggctccttgg
 661 aagacgattg ggacttcctg ccacccaaga agataaagga tcctgatgct tcaaaaccgg
 721 aagactggga tgagcgggcc aagatcgatg atcccacaga ctccaagcct gaggactggg
 781 acaagcccga gcatatccct gaccctgatg ctaagaagcc cgaggactgg gatgaagaga
 841 tggacggaga gtgggaaccc ccagtgattc agaaccctga gtacaagggt gagtggaagc
 901 cccggcagat cgacaaccca gattacaagg gcacttgcat ccacccagaa attgacaacc
 961 ccgagtattc tcccgatccc agtatctatg cctatgataa cttttggcgtg ctgggcctgg
1021 acctctggca ggtcaagtct ggcaccatct ttgacaactt cctcatcacc aacgatgagg
1081 catacgctga ggagtttggc aacgagacgt ggggcgtaac aaaggcagca gagaaacaaa
1141 tgaaggacaa acaggacgag gagcagaggc ttaaggagga ggaagaagac aagaaagca
1201 aagaggagga ggaggcagag gacaaggagg atgatgagga caaagatgag gatgaggagg
1261 atgaggagga caaggaggaa gatgaggagg aagatgtccc cggccaggcc aaggacgagc
1321 tgtagagagg cctgcctcca gggctggact gaggcctgag cgctcctgcc gcagagctgg
1381 ccgcgccaaa taatgtctct gtgagactcg agaactttca ttttttttcc ggctggttcg
1441 gatttggggt ggattttggt tttgttcccc tcctccactc tcccccaccc cctcccgcc
1501 cttttttttt tttttttta aactggtatt ttatctttga ttctccttca gccctcaccc
1561 ctggttctca tctttcttga tcaacatctt ttcttgcctc tgtcccttc tctcatctct
1621 tagctcccct caacctggg gggcagtggt gtggagaagc cacaggcctg agatttcatc
1681 tgctctcctt cctggagccc agaggagggc agcagaaggg ggtggtgtct ccaacccccc
1741 agcactgagg aagaacgggg ctcttctcat ttcaccccctc cctttctccc ctgcccccag
1801 gactgggcca cttctgggtg gggcagtggg tcccagattg gctcacactg agaatgtaag
1861 aactacaaac aaaatttcta ttaaattaaa ttttgtgtct c
```

SEQ ID NO: 9 Mouse Calreticulin Amino Acid Sequence (NP_031617.1)
```
  1 mllsvplllg llglaaadpa lyfkeqfldg dawtnrwves khksdfgkfv lssgkfygdl
 61 ekdkglqtsq darfyalsak fepfsnkgqt lvvqftvkhe qnidcgggyv klfpsgldqk
121 dmhgdseyni mfgpdicgpg tkkvhvifny kgknvlinkd irckddefth lytlivrpdn
181 tyevkidnsq vesgsleddw dflppkkikd pdaakpedwd erakiddptd skpedwdkpe
241 hipdpdakkp edwdeemdge weppviqnpe ykgewkprqi dnpdykgtwi hpeldnpeys
301 pdaniyayds favlgldlwq vksgtifdnf litndeayae efgnetwgvt kaaekqmkdk
361 qdeeqrlkee eedkkrkeee eaedkedddd rdededeede keedeeespg qakdel
```

SEQ ID NO: 10 Mouse Calreticulin cDNA sequence (NM_007591.3, CDS region from position 134-1384)
```
   1 ggctgtgtca ggttcgggtg agaggtaggt gaatataaat tgaagcggcg gtggccgcgt
  61 ccgtcaatac cgcagagccg ctgcctgaag atcgtcttaa aaggcctgtg tgccgccgcc
 121 ccctcggccc gccatgctcc tttcggtgcc gctcctgctt ggcctcctcg gcctggccgc
 181 cgcagaccct gccatctatt tcaaagagca gttcttggac ggagatgcct ggaccaaccg
 241 ctgggtcgaa tccaaacata gtccgatttt ggcaaattt gtcctcagtt ctggcaaatt
 301 ttacggggac ctggagaagg ataaagggct gcagacaagc caagatgccc gattttacgc
 361 actgtccgcc aaattcgaac ccttcagcaa taagggccag acactggtgg tacagttcac
 421 ggtgaagcat gagcagaata tcgactgtgg gggcggctac gtgaagctgt ttccgagtgg
 481 tttggaccag aaggacatgc atggagactc agaatataac atcatgtttg gtcctgacat
 541 ctgcggtcct ggcaccaaga aggttcatgt catctttaac tacaagggca agaatgtgct
 601 gatcaacaag gatatccggt gtaaggatga tgaattcaca cacctataca cactgattgt
 661 gcggccagac aacacctatg aggtgaaaat tgacaacagc caggtggagt caggctcctt
 721 ggaggatgat tgggactttc tgccacccaa gaagataaag gaccctgatg ctgccaagcc
 781 ggaagactgg gatgaacgag ccaagatcga tgacccccaca gattccaagc ctgaggactg
 841 ggacaagcca gagcacatcc ctgaccctga tgctaagaag cctgaggact gggatgaaga
 901 gatggatgga gagtgggaac caccagtgat tcaaaatcct gaatacaagg gcgagtggaa
 961 accacgtcaa attgacaacc cagattacaa gggtacctgg atacacccag aaattgacaa
1021 ccctgaatac tcccccgatg caaatatcta tgcctatgat agttttgctg tactgggcct
1081 agatctctgg caggtcaagt ccgggacaat ctttgacaat ttcctcatca ccaatgatga
1141 ggcctatgca gaggagtttg gcaatgagac gtgggggtgt taccaaggctg cagagaagca
1201 gatgaaggac aagcaggatg aggagcagag gcttaaggaa gaagaagagg acaagaagcg
1261 taaagaggaa gaaaggctg aggataaaga ggatgatgat gacagagatg aagatgggaa
1321 cgaagaagat gagaaggagg aagatgagga gaatcccct ggccaagcca aggatgagct
1381 gtagaggcca caccacctgc cttcagggct ggactgaggc ctgaacaccc tgccgcagag
1441 ctggctgctc ccaataatgt ctctatgaga ctcaagaact tttcatttt tccaggcagg
1501 ttcagatctg gggtagattc tgattttgtt ccctgcctc ccccattacc ccccccctt
1561 ttttttttta ctggtgttg tctttaattc tccttcagcc ctcatctggt ttctcatttt
1621 tgaatcaaca tcttttcctt ctgtcccctcc cttttctccat cttttggtca ctaccctcca
1681 actctaggaa caggggtgta gaggagaagc cctaggcttg agatttcatc tgctctcctt
1741 cctgcatctc agaggagggc aggagaaggg ggtgggtgtctt tcctcccccc cgcactgagg
1801 aagaatgggg ctcttctcat cccctttctc ccttgccccc aggactgggc cacttgtggg
1861 gcagccagtt ctagcacagc tcacactgag agtgtaagaa ctacaaacaa aatttctatt
1921 aaattaagtt ttgtgtcttc cot
```

SEQ ID NO: 11 Rat Calreticulin Amino Acid Sequence (NP_071794.1)
```
  1 mllsvplllg llglaaadpa lyfkeqfldg dawtnrwves khksdfgkfv lssgkfygdq
 61 ekdkglqtsq darfyalsar fepfsnkgqt lvvqftvkhe qnidcgggyv klfpggldqk
121 dmhgdseyni mfgpdicgpg tkkvhvifny kgknvlinkd irckddefth lytlivrpdn
181 tyevkidnsq vesgsleddw dflppkkikd pdaakpedwd erakiddptd skpedwdkpe
```

TABLE 1-continued

Gamma-Aminobutyric Acid Receptor-Associated Protein (GABARAP), such as from a mammal (e.g., a rodent, primate, or human)
Calreticulin, such as from a mammal (e.g., a rodent, primate, or human)

```
241 hipdpdakkp edwdeemdge weppviqnpe ykgewkprqi dnpdykgtwi hpeldnpeys
301 pdaniyayds favlgldlwq vksgtifdnf litndeayae efgnetwgvt kaaekqmkdk
361 qdeeqrlkee eedkkrkeee eaedkededd rdededeede keedeedatg qakdel
```

SEQ ID NO: 12 Rat Calreticulin cDNA sequence (NM_022399.2, CDS region from position 64-1314)
```
   1 cgcagagccg ctgcttgaag atcgttttaa agggccagtg tgccgccgcc ccctcggccc
  61 gccatgctcc tttcggtgcc gctcctgctt ggcctcctcg gcctggctgc cgcagaccct
 121 gccatctatt tcaaagagca gttcttggac ggagatgcct ggaccaaccg ctgggtcgaa
 181 tccaaacata agtctgattt tggcaaattc gtcctcagtt ctggcaaatt ctacggggac
 241 caggagaagg ataaagggtt gcagacaagc caagatgccc gattttacgc gctgtccgcc
 301 agattcgaac ccttcagcaa caagggccag acactggtgg tacagttcac cgtgaagcat
 361 gagcagaata tcgactgtgg gggcggctac gtgaagctgt ttccgggtgg cttggaccag
 421 aaggacatgc atgagactc agaatataac atcatgtttg tccggacat ctgcggtcct
 481 ggaccaaga aggttcatgt catctttaac tacaagggca agaacgtgct gatcaacaag
 541 gatatccggt gtaaggatga tgaattcaca catctataca cgctgattgt gcggccagac
 601 aacacctacg aggtgaaaat tgacaacagc caggtggagt cgggctcctt ggaggatgat
 661 tgggactttc tgccgcccaa gaagattaag gatcctgacg ctgccaagcc agaagactgg
 721 gatgaacgag ccaagattga tgccccaca gattccaagc tgaggactg gacaagcca
 781 gagcacatcc ctgaccctga tgctaagaag cctgaggact gggacgaaga gatggatgga
 841 gagtgggaac caccagtgat tcaaaatcct gaatacaagg gcgaatggaa gccacgtcaa
 901 attgacaacc cagattacaa gggtacctgg atacacccag agattgacaa tcctgaatac
 961 tcccccgatg cgaatatcta tgcctatgat agttttgctg tactgggctt agacctctgg
1021 caggtcaagt ctggcacaat tttgacaac ttcctcatca ccaatgatga ggcctatgca
1081 gaggagtttg gcaatgagac ctgggtgtc accaaggctg cagagaagca gatgaaggac
1141 aagcaggatg aggagcagag gcttaaggaa gaagaagcg acaagaagcg taaagaggaa
1201 gaggaggcca aggataaaga ggatgaggat gacagagatg aagatgaaga tgaagaggat
1261 gagaaggaag aagatgagga ggatgccact ggccaagcca aggatgagct gtagaggcca
1321 caccacctgc ctccagggct ggactgaggc ctgaacaccc cgccacagag ctggctgctc
1381 ccaataatgt ctctatgaga ctcaagaact tttcattttt cttccaggca ggttcaggtc
1441 tggggtggat tctgattttt gttccctgc ctccccatcc tccccacccc ccttttttt
1501 ttactggtgt ttgtctttaa ttcttcagcc ctcacctcct ggcctctcat ttttgaatca
1561 acattttttc tttctgtccc tttctccatc tcttggtcac tatcctccaa ctctaggaac
1621 aggtatggag gaaaagccct aggcttgaga tttcatctgc tctcctttct gaatcctcaga
1681 ggagggtagg agaaggggt ggtatcttcc ctccccccag cactgaggag gaatgggggct
1741 cttccccttt ctcccttgcc cccaggactg ggccatttgt ggggcagcca gttctagcac
1801 agctcacact gagagtgtaa gaactacaaa caaaatttct attaaattaa gttttgtgtc
1861 ttccc
```

SEQ ID NO: 19 Human STING Amino Acid Sequence (NP_938023.1)
```
   1 mphsslhpsi pcprghgaqk aalvllsacl vtlwglgepp ehtlrylvlh laslqlglll
  61 ngvcslaeel rhihsryrgs ywrtvraclg cplrrgalll lsiyfyyslp navgppftwm
 121 lallglsqal nillglkgla paeisavcek gnfnvahgla wsyylgylrl ilpelqarir
 181 tynqhynnll rgavsqrlyi llpldcgvpd nlsmadpnir fldklpqqtg dhagikdrvy
 241 snsiyellen gqragtcvle yatplqtlfa msqysqagfs redrleqakl fcrtledila
 301 dapesqnncr llayqepadd ssfslsqevl rhlrqeekee vtvgslktsa vpststmsqe
 361 pellisgmek plplrtdfs
```

SEQ ID NO: 20 Human Calreticulin cDNA sequence (MF622062.1)
```
   1 atgcccact ccagcctgca tcatccatc ccgtgtccca ggggtcacgg ggcccagaag
  61 gcagccttgg ttctgctgag tgcctgcctg gtgacccttt gggggctagg agagccacca
 121 gagcacactc tccggtacct ggtcctcac ctagcctccc tgcagctggg actgctgtta
 181 aacggggtct gcagctggc tgaggagctg cgccacatcc actccaggta ccggggcagc
 241 tactgcgagga ctgtgcgggc ctgcctgggc tgcccctcc gccgtggggc cctgttgctg
 301 ctgtccatct atttctacta ctcccctcca aatgcggtcg gccgcccctt cacttggatg
 361 cttgccctcc tggcctctc gcaggcactg aacatcctcc tgggcctcaa gggcctggcc
 421 ccagctgaga tctctgcagt gtgtgaaaaa ggaatttca acgtggccca tgggctggca
 481 tggtcatatt acatcggatct gcggctg atcctgccag agctccaggc ccggattcga
 541 acttacaatc agcattacaa caaccgcta cggggtgcag tgagccagcg gctgtatatt
 601 ctcctcccat tggactgtgg ggtgcctgat aacctgagta tggctgaccc caacattcgc
 661 ttcctggata aactgcccca gcagaccggt gaccgtgctg catcaagga tcgggtttac
 721 agcaacagca tctatgagct tctggagaac gggcagcggg cggccctg tgtcctggag
 781 tacgccaccc ccttgcagac tttgtttgcc atgtcacaat acagtcaagc tggctttagc
 841 cgggaggata ggcttgagca ggccaaactc ttctgccgga cacttgagga catcctggca
 901 gatgccctg agtctcagaa caactgccgc ctcattgcct accaggaacc tgcagatgac
 961 agcagcttct cgctgtccca ggaggttctc cggcacctgc ggcaggagga aaaggaagag
1021 gttactgtgg gcagcttgaa gacctcagcg gtgcccagta cctccacgat gtcccaagag
1081 cctgagctcc tcatcagtgg aatggaaag ccctcctc tccgcacgga tttctcttga
```

SEQ ID NO: 21 Mouse STING Amino Acid Sequence (AMD16372.1)
```
   1 mpysnlhpai prprghrsky valiflvasl milwvakdpp nhtlkyvglh lalhelglll
  61 knlcclaeel chvqsryqgs ywkavraclg cpihcmamil lsfyfyflqn tadmcllvls
 121 kslsmllglq sltpaevsav ceekklnvah glawsyyigy lrlilpglqa rirmfnqlhn
 181 nmlsgagsrr lyilfpldcg vpddlsvvdp nirfrdmlpq qnidragikn rvysnsvyei
```

TABLE 1-continued

Gamma-Aminobutyric Acid Receptor-Associated Protein (GABARAP), such as from a
mammal (e.g., a rodent, primate, or human)
Calreticulin, such as from a mammal (e.g., a rodent, primate, or human)

```
241 lengqpagvc ileyatplqt lfamsqdaka gfsredrleq aklfcrtlee iledvpesrn
301 ncrlivyqep tdgnsfslsq evlrhirqee keevtmnapm tsvapppsvl sqeprllisg
361 mdqplplrtd li SEQ ID NO: 22 Mouse STING cDNA sequence (KR-154221.1)
   1 atgccatact ccaacctgca tccagccatc ccacgccca gaggtcaccg ctccaaatat
  61 gtagccctca tctttctggt ggccagcctg atgatccttt gggtggcaaa ggatccacca
 121 aatcacactc tgaagtacgt aggacttcac ctagccttgc acgaacttgg actactgttg
 181 aaaaacctct gctgtctggc tgaagagctg tgccatgtcc agtccaggta ccagggaagc
 241 tactggaagg ctgtgcgcgc ctgcctggga tgccccatcc actgtatggc tatgattcta
 301 ctatcgtttt atttctattt cctccaaaac actgctgaca tgtgccttct ggtcctctct
 361 aagtccctaa gcatgctcct gggccttcag agcttgactc cagcggaagt ctctgcagtc
 421 tgtgaagaaa agaagttaaa tgttgcccac gggctggcct ggtcatacta cattggtac
 481 ttgcggttga tcttaccagg gctccaggcc cggatccgaa tgttcaatca gctacataac
 541 aacatgctca gtggtgcagg gagccgaaga ctgtacatcc tctttccatt ggactgtggg
 601 gtgcctgacg acctgagtgt ggttgacccc aacattcgat tccgagatat gctgccccag
 661 caaaacatcg accgtgctgg catcaagaat cgggtttatt ccaacagcgt ctacgagatt
 721 ctggagaacg gacagccagc aggcgtctgt atcctggagt acgccacccc cttgcagacc
 781 ctgtttgcca tgtcacagga tgccaaagct ggcttcagtc gggaggatcg gcttgagcag
 841 gctaaactct tctgccggac acttgaggaa atcctggaag atgtccccga gtctcgaaat
 901 aactgccgcc tcattgtcta ccaagaaccc acagatggaa acagtttctc actgtctcag
 961 gaggtgctcc ggcacattcg tcaggaagaa aaggaggagg ttaccatgaa tgcccccatg
1021 acctcagtgg cacctcctcc ctccgtactg tcccaagagc aagactcct catcagtggt
1081 atggatcagc ctctcccact ccgcactgac ctcatctga SEQ ID NO: 23 Rat STING Amino Acid Sequence (NP_001102592.1)
   1 mpysnlhpsi prprsyrfkl aafvllvgsl mslwmtgepp shtlhylalh vasqqqgqqq
  61 kklcclaeel chvqsryqgs ywkavracvg spicfmalil lsfyfycsle ntsdlrlawh
 121 lgilvlsksl smtldlqsla paevsavcee knfnvahgla wsyyigylkl ilpglqarir
 181 mfnqlhnnml sgagsrrlyi lfpldcgvpd dlsvadpnir frdmlpqqnt dragvknray
 241 snsvyellen gqpagacile yatplqtlfa msqdgkagfs redrleqakl fcrtleeila
 301 dvpesrnhcr livyqeseeg nsfslsqevl rhirqeekee vtmsgpptsv aprpsllsqe
 361 prllisgmeq plplrtdli SEQ ID NO: 24 Rat STING cDNA sequence (NM_001109122.1)
   1 ctctcctggg cttctactaa attcttagct tagagcccga gatttcagga agtagagtgt
  61 gctgtttacc ctctcaatct ctcctgtgca atcctccctc ctgatgtcct agggatagat
 121 agtggagggt ttgggggcat cttgaaatcc tgtgggggc cctgtcactt ggggtccttg
 181 tgtgagtcct gcctggtgtc tactgcagcg tgttgcatcc cacggacctt tagaggaatc
 241 cggagtgcgg ggctgtgact gctgtctgcc ctttgagagg ccacttgccg gtcgctacgg
 301 aagggttctt catagtctct ccagttccag gaacacttcg gtctaggaag cagaagatgc
 361 catactccaa cctgcatcca tccatcccac ggcccagaag ttaccgcttc aaactggcag
 421 ccttcgtctt gctggtgggc agcctgatga gcctttggat gacaggggaa ccaccaagtc
 481 acactctgca ttacctagca cttcacgtag cctcgcagca acttggatta ctgttgaaaa
 541 agctctgctg tctggctgaa gagttgtgcc atgtccagtc caggtaccag ggcagctact
 601 ggaaggctgt gcgcgcctgc gtggggagtc ccatctgctt tatggccctg atcctactgt
 661 catttattt ctactgctcc ctcgaaaata cttctgacct gcgccttgct ggcatcttg
 721 gcatcctggt cctttcaaag tccctaagca tgacctgga ccttcagagc ttggccccag
 781 cagaagtctc tgcggtctgt gaagaaaaga acttcaatgt gcccatggac tggcctggt
 841 cgtactacat tgggtacctg aagctgatct tgccaggact gcaggcccgg atccggatgt
 901 tcaatcagct acacaacaac atgctctcgg gtgcggggag ccggcggctg tatatcctct
 961 tcccattgga ctgtggggtg cctgatgatc tgagtgtggc tgaccccaat attcgattcc
1021 gagatatgct gccccagcaa aacacagacc gtgctggcgt caagaatcgg gcttattcca
1081 acagtgtcta tgaacttctg gagaatgggc agccggacgt gcctgtatcc ctggagtacg
1141 cccaccccctt gcagaccttg tttgccatgt cacaggatgg caaagctggc ttcagtcggg
1201 aggaccggct tgagcaggcc aaactcttct gtcggacact tgaggaaatt ctggctgatg
1261 tccctgagtc tcgaaaccac tgccgcctca ttgtctacca agaatccgaa gagggaaaca
1321 gtttctcgct gtctcaggag gtgctccggc acattcggca agaagaaaag gaggaagtta
1381 ccatgagtgg cccccccgacc tcagtggcac ctcgtccctc cctactgtcc caagagccga
1441 gacttctcat cagtggcatg gagcagcctc tccactccg cacggacctc atctgaggca
1501 tgagacagcc ttgcctgggt cccagtgacc cttcagcctc ttgactgggc tccccttta
1561 tggctggggg cctcatagag acttcacatc tccagatgag tcccacattc ccgggcaagc
1621 cacttcacct ctctgagcct cagcctgccc cactccaaag gccatcataa ggtattcct
1681 gcccactcag ggttttgtg aagacaatac atgtagaagt ttggtgtcaa tgcctggtaa
```

TABLE 1-continued

Gamma-Aminobutyric Acid Receptor-Associated Protein (GABARAP), such as from a
mammal (e.g., a rodent, primate, or human)
Calreticulin, such as from a mammal (e.g., a rodent, primate, or human)

```
1741 acttgagaga taggccaagt atttcccatg atgatcagca ttctccactc tctgttgact
1801 tgtgtgggtt gttccagcag acctctgacc cagcttctgg tcatgtgtgt tcaacgggag
1861 cctcagtaga tggagagagg gagaaggaac atgtgttctg taggcagtca cagtgggccg
1921 ccctgccagg ctgtcttctc agtaaacata tttattctca ggtttctaga atggtctctt
1981 ctccttgccc cagcactggt atttgtgtga cactggagta cttactgtct gtggtctctt
```

\* Included in Table 1 are RNA nucleic acid molecules (e.g., thymidines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

\* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

TABLE 2

SEQ ID NO: 13 Human Stanniocalcin 1 cDNA sequence (NM_003155.3 CDS region
from position 284 . . . 1027)

```
   1 agtttgcaaa agccagaggt gcaagaagca gcgactgcag cagcagcagc agcagcggcg
  61 gtggcagcag cagcagcagc ggcggcagca gcagcagcag cggaggcacc ggtggcagca
 121 gcagcatcac cagcaacaac aacaaaaaaa aatcctcatc aaatcctcac ctaagctttc
 181 agtgtatcca gatccacatc ttcactcaag ccaggagagg gaaagaggaa aggggggcag
 241 gaaaaaaaaa aaacccaaca acttagcgga aacttctcag agaatgctcc aaaactcagc
 301 agtgcttctg gtgctggtga tcagtgcttc tgcaacccat gaggcggagc agaatgactc
 361 tgtgagcccc aggaaatccc gagtggcggc tcaaaactca gctgaagtgg ttcgttgcct
 421 caacagtgct ctacaggtcg gctgcgggc ttttgcatgc ctggaaaact ccacctgtga
 481 cacagatggg atgtatgaca tctgtaaatc cttcttgtac agcgctgcta aatttgacac
 541 tcagggaaaa gcattcgtca aagagagctt aaaatgcatc gccaacgggg tcacctccaa
 601 ggtcttcctc gccattcgga ggtgctccac tttccaaagg atgattgctg aggtgcagga
 661 agagtgctac agcaagctga atgtgtgcag catcgccaag cggaaccctg aagccatcac
 721 tgaggtcgtc cagctgccca atcacttctc caacagatac tataacagac ttgtccgaag
 781 cctgctggaa tgtgatgaag acagtcag cacaatcaga gacagcctga tggagaaaat
 841 tgggcctaac atggccagct cttccacat cctgcagaca daccactgtg cccaaacaca
 901 cccacgagct gacttcaaca ggagacgcac caatgagccg cagaagctga aagtcctcct
 961 caggaacctc cgaggtgagg aggactctcc ctcccacatc aaacgcacat cccatgagag
1021 tgcataacca gggagaggtt attcacaacc tccaaaact agtatcattt taggggtgtt
1081 gacacaccag ttttgagtgt actgtgcctg gtttgatttt tttaaagtag ttcctatttt
1141 ctatccccct taaagaaaat tgcatgaaac taggcttctg taatcaatat ccaacattc
1201 tgcaatggca gcattcccac caacaaaatc catgtgacca ttctgcctct cctcaggaga
1261 aagtaccctc ttttaccaac ttcctctgcc atgttttcc cctgctcccc tgagaccacc
1321 cccaaacaca aaacattcat gtaactctcc agccattgta atttgaagat gtggatccct
1381 ttagaacggt tgccccagta gagttagctg ataaggaaac tttatttaaa tgcatgtctt
1441 aaatgctcat aaagatgtta aatgaattc gtgttatgaa tctgtgctgg ccatggacga
1501 atatgaatgt cacatttgaa ttcttgatct ctaatgagct agtgtccttat ggtcttgatc
1561 ctccaatgtc taattttctt tccgacacat ttaccaaatt gcttgagcct ggctgtccaa
1621 ccagactttg agcctgcatc ttcttgcatc taatgaaaaa caaaaagcta acatctttac
1681 gtactgtaac tgctcagagc tttaaaagta tctttaacaa ttgtcttaaa accagagaat
1741 cttaaggtct aactgtggaa tataaatagc tgaaaactaa tgtactgtac ataaattcca
1801 gaggactctg cttaaacaaa gcagtatata ataacttat tgcatataga tttagttttg
1861 taacttagct ttatttttct tttcctggga atggaataac tatctcactt ccagatatcc
1921 acataaatgc tccttgtggc cttttttata actaagggg tagaagtagt tttaattcaa
1981 catcaaaact taagatgggc ctgtatgaga caggaaaaac caacaggttt atctgaagga
2041 ccccaggtaa gatgttaatc tcccagccca cctcaaccca gaggctactc ttgacttaga
2101 cctatactga aagatctctg tcacatccaa ctggaaattc caggaaccaa aaagagcatc
2161 cctatgggct tggaccactt acagtgtgat aaggcctact atacattagt aaggtggcagt
2221 tctttactcg tcccctttca tcggtgcctg gtactctggc aaatgatgat ggggtgggca
2281 actttccatt aaatcaatca ggaatgagtc aatcagcctt taggtcttta gtccggggga
2341 cttggggctg agagagtata ataaccctg ggctgtccag ccttaataga cttctcttac
2401 attttcgtcc tgtagcacgc tgcctgccaa agtagtcctg gcagctggac catctctgta
2461 ggatcgtaaa aaaatagaaa aaaagaaaaa aaaaagaaag aaagagggaa aaagagctgg
2521 tggtttgatc atttctgcca tgatgtttac aagatggcga ccaccaaagt caaacgacta
2581 acctatctat gaacaacagt agtttctcag ggtcactgtc cttgaaccca acagtccctt
2641 atgagcgtca ctgcccacca aaggtcaatg tcaagagagg aagagaggga ggaggggtag
2701 gactgcaggg gccactccaa actcgcttag gtagaaacta ttggtgctca actctcacta
2761 ggctaaactc aagatttgac caaatcgagt gatagggatc ctggtgggag gagagagggc
2821 acatctccag aaaaatgaaa agcaatacaa ctttaccata aagcctttaa aaccagtaac
2881 gtgctgctca aggaccaaga gcaattgcag cagcccagc agcagcagca gcagcacaaa
2941 cattgctgcc tttgtcccca cacagcctct aagcgtgctg acatcagatt gttaagggca
3001 tttttatact cagaactgtc ccatcccag gtccccaaac ttatggacac tgccttagcc
3061 tcttggaaat caggtagacc atattctaag ttagactctt cccctccctc ccacacttcc
3121 cacccccagg caaggctgac ttctctgaat cagaaaagct attaaagttt gtgtgttgtg
3181 tccattttgc aaacccaact aagccaggac cccaatgcga caagtagttc atgagtattc
```

TABLE 2-continued

```
3241 ctagcaaatt tctctctttc ttcagttcag tagatttcct tttttcttt ctttttttt
3301 tttttttttt ttggctgtga cctcttcaaa ccgtggtacc cccccttttc tccccacgat
3361 gatatctata tatgtatcta caatacatat atctacacat acagaaagaa gcagttctca
3421 caatgttgct agttttttgc ttctctcttcc cccacccctac tccctccaat tccccccttaa
3481 acttccaaag cttcgtcttg tgtttgctgc agagtgattc gggggctgac ctagaccagt
3541 ttgcatgatt cttctccttgt gatttggttg cactttagac attttttgtgc cattatattt
3601 gcattatgta tttataattt aaatgatatt taggtttttg gctgagtact ggaataaaca
3661 gtgagcatat ctggtatatg tcattattta ttgttaaatt acatttttaa gctccatgtg
3721 catataaagg ttatgaaaca tatcatggta atgacagatg caagttattt tatttgctta
3781 ttttttataat taaagatgcc atagcataat atgaagcctt tggtgaattc cttctaagat
3841 aaaaataata ataaagtgtt acgtttta
```

SEQ ID NO: 14 Human Stanniocalcin 1 Amino Acid Sequence (AKK31754)
```
  1 mydicksfly saakfdtqgk afvkeslkci angvtskvfl airrcstfqr miaevqeecy
 61 sklnvcsiak rnpeaitevv qlpnhfsnry ynrlvrslle cdedtvstir dslmekigpn
121 maslfhilqt dhcaqthpra dfnrrrtnep qklkvllrnl rgeedspshi krtshesa
```

SEQ ID NO: 15 Rat Stanniocalcin 1 cDNA sequence (NM_031123.2, CDS region from position 258-1001)
```
    1 gaagcagcag cagcagcagc agcaacaaca acagcagcag tagcagcagc agcagcagca
   61 gcagcagcag cagcagcagc agcagccacc gccgccgctt gccagccagc cacacagcca
  121 cacaaaaatt cctcctcaaa tcctcaccta agctttcagt atatccagat ccacatcttc
  181 actcaagccg ggagagggaa agaggaaagg gggggaggaa aaaaaaagcc aacaacttag
  241 cggaaacttc tcagagaatg ctccaaaact cagcagtgat tctggcgctg gtcatcagtg
  301 ctgctgcagc tcacgaggcg gaacagaatg attctgtgag ccccagaaaa tcccggctgg
  361 cggctcaaaa ttcagctgaa gtggtccgct gcctcaacag tgccctacag gttggctgtg
  421 gggcttttgc atgcctggaa aactccacat gtgacacaga tgggatgtac gacatttgta
  481 aatccttctt gtacagtgct gctaaatttg acactcaggg aaaagcattt gtcaaagaga
  541 gcttaaagtg catcgccaat gggatcacct caaggtcttc cttgccatt cggaggtgtt
  601 ctactttcca gaggatgatc gccgaggtgc aggaggactg ctacagcaag ctcaatgttt
  661 gcagcattgc caagcgcaac ccggaagcca tcactgaagt catacagctc cccaatcact
  721 tctccaacag atactacaac agacttgtcc gaagccttct ggaatgtgat gaagatacgg
  781 tcagcacaat cagagacagc ctgatggaga gatcggccc aacatggcc agcctcttcc
  841 atatcctgca gacagaccac tgtgcccaga cacacccag agctgacttc aataggaggc
  901 gcacaaatga gccacagaag ctgaaagtcc tcctcaggaa cctccgaggt gaggggatt
  961 ctcccctcaca catcaaacgc acctcccaag agaatgcgta agcagggaga ggtattcaca
 1021 gcctcaccaa actaatagcg ttttagggt gtttacacac caactttgag tgtactgtgc
 1081 ctggtttgat ttttttttaa gtagtaccta tttctatcc cccttaaag aaaactgcat
 1141 gaaactaagc ttccatgatc aatatcccaa tattctgcaa tgacagcatt cttagcaata
 1201 gaatacatgt ggtcattctg cctcttctgg agagagaatg taccctcttc catccccct
 1261 ctctctcaat tcttttcaa gatccccatc tactctctgc aaacacaaaa cattcatgta
 1321 actgcccagt cattgtaatc tgaagatgta ggtcccttta gaatggtcac ccagtagagt
 1381 tagccaatac aaaaacaactt tatttaaatg catgtcttaa atgctcataa atatgttaaa
 1441 tggaattcgt gttatgaatc tgtgctggcc atggacgaat atgaatgtca tgtttgaatt
 1501 cttgatctct aatgagtctt atggtctcaa tcctccaatg tctaacttcc tttctgacat
 1561 atttaccaaa ttgctcaaac ctggttctcc aaccagattt tgagccagca tcttcttgca
 1621 tctaatgaaa aacaaaaagc taacatcttt atgtactgta actgctcaga gctttaaaag
 1681 tatctttaac aattgtctta aaaacagaga atcttaaggt ctaactgtgg aatataaata
 1741 gctgaaaact attgtactgt acataaaattc cagaggactc tgcttaacag agcagtctat
 1801 aataactttta tgcatatag atttagttttt gtaccttagc tttatttttcc tttcctggga
 1861 aatggaataa ctatctcact tccagatatc cgcgttcatg ctccttgtgg ccttttttat
 1921 aactaagggg gtagaagtag ttttaactca acatcagaac ttaagatggg cctatacttg
 1981 ataggaaaac ccaacaggtt atctgaagga ccccaggtga gatatcaatc tcccagccca
 2041 gctcaaccca gaggctacat ttgacttaga tgtatccgca aacagctctg tcacagccaa
 2101 ctgggaatta caggaatcaa agagatcatc cctctgggct ttgatcactt agtgtgacaa
 2161 ggcctactat ccccttggaa gtgcagttc ttggctcatt gccttccatc aatgcctggc
 2221 actctggtaa atgatggaat gggatattgt tccactaagc caatcaggaa tgagtcaatc
 2281 agcctttggg tctttagtcc tgggaacttg ggcttaaggg ggtataaaata accctgggct
 2341 gtccagcctt aatagactcc tcttacatct tttgtcctgt aacacgctgc ctgccaaagt
 2401 agtcctggca gctggaccat ctctgtagga tcttaaaaaa aaaaaaaaa aaaaaaaaaa
 2461 aaa
```

SEQ ID NO: 16 Rat Stanniocalcin 1 Amino Acid Sequence (EDM02180.1)
```
  1 mlqnsavila lvisaaaahe aeqndsvspr ksrvaaqnsa evvrclnsal qvgcgafacl
 61 enstcdtdgm ydicksflys aakfdtqgka fvkeslkcia ngitskvfla irrcstfqrm
121 iaevqedcys klnvcsiakr npeaiteviq lpnhfsnryy nrlvrsllec dedtvstird
181 slmekigpnm aslfhilqtd hcaqthprad fnrrrtnepq klkvllrnlr gegdspshik
241 rtsqena
```

SEQ ID NO: 17 Mouse Stanniocalcin 1 cDNA sequence (NM_009285.3, CDS region from position 102 to 845)
```
    1 agtatatcca gatccacatc ttcactcaag ccgggagagg gaaagaggaa aggggggag
   61 gaaaaaaaaa agccaacaac ttagcggaaa cttctcagag aatgctccaa aactcagcag
  121 tgattctggc gctggtcatc agtgcagctg cagcgcacga ggcggaacaa aatgattctg
  181 tgagccccag aaaatcccgg gtggcggctc aaaattcagc tgaagtggtt cgctgcctca
  241 acagtgccct gcaggttggc tgtggggctt ttgcatgcct ggaaaactcc acatgtgaca
  301 cagatgggat gtacgacatt tgtaaatcct tcttgtacag tgctgctaaa tttgacactc
  361 agggaaaagc atttgtcaaa gagagcttaa agtgcatcgc caatgggatc acctccaagg
  421 tattccttgc cattcggagg tgttcgactt tccagaggat gatcgccgag gtgcaggagg
  481 actgctacag caagcttaac gtttgcagca tcgccaagcg caacccggaa gccatcactg
```

TABLE 2-continued

```
 541 aagtcataca gctgcccaat cacttctcca acagatacta caacagactt gtccgaagcc
 601 ttctggaatg tgatgaagac acgtcagta caatcagaga cagcctgatg gagaagatcg
 661 ggcccaacat ggccagcctc ttccacatcc tgcagacaga ccactgtgcc cagacacacc
 721 ccagagctga cttcaatagg aggcgcacaa atgagccaca gaagctgaaa gtcctcctca
 781 ggaacctccg aggtgagggg gactctccct cacacatcaa acgcacctcc caagagagtg
 841 cgtaagcagg gagaggtatt cacagcctca ccaaactaat agcattttag gggtgttgac
 901 acaccaactt tgagtgtact gtgcctggtt tgattttttt taagtagtac ctattttcta
 961 tcccccgtt aaagaaaaat tgcatgaaac taggcttcca taatcaatat cccaacattc
1021 tgcaatgaca gcattcttac caacagaata catgtgtggt cattctgcct ctcctcaaga
1081 gagaatgtac cctcttccat cccccctctc tctgaattct tttcccagat ccctatctac
1141 tctccgcaaa cacaaaccat tcatgtaact acccagtcat tgtaatctga aaatgtagat
1201 ccctttagaa tggtcacctg gtagagttag ccaatacaaa acaactttat ttaaatgcat
1261 gtcttaaatg ctcataaata tgttaaatgg aattcgtgtt atgaatctgt gctggccatg
1321 gacgaatatg aatgtcatgt ttgaattctt gatctctaac gagtcttatg gtctctatcc
1381 tccaatgtct aatttccttt ctgacatatt taccaaattg ctcaaacctg gttctccaac
1441 cagactttga gctagcatct tcttgcatct aatgaaaaac aaaaagcta acatctttat
1501 gtactgtaac tgctcagagc tttaaaagta tcttaacaa ttgtcttaaa aaacggagaa
1561 tcttaaggtc taactgtgga atataaatag ctgaaaacta ttgtactgta cataaattcc
1621 agaggactct gcttaacaga gcagtctata ataacttat tgcatataga tttagttttg
1681 tacccttagct ttatttccct tttcctggga atggaataac tatctcactt ccagatatcc
1741 acattcatgc tccttgtggc ctttttata actaagggg tagaagtagt tttaactcaa
1801 catcagaact taagatgggc ctatacttga caggaaaacc caacaggtta tctgaaggac
1861 cccaggtaag acgttaatct cccagcccac ctcaaccgg aggctacgtt tgacttagat
1921 gtatcctgaa acagctctgt cacatccaac tgggaataac aagaatcaaa aagaccatcc
1981 ctttgggctt ggaccacttg gtgtgacaag gcctactatc cccttgaag tggcagttct
2041 tggctcatcg ccttccatca gtgcctggca ctctggtaaa tgatggagtg ggatattgtt
2101 ccactaagcc aatcaggaat gagtcaatca gcctttgggt ctttagtccg ggaaacttgg
2161 gcttaagggg gtatgaataa ccctgggctg tccagcctta atagactcct cttacatctt
2221 ttgtcctgta acatgctgcc tgccaaagta gtcctggcag ctggaccatc tctgtaggat
2281 cttaaaaaa aaagaaaaaa agaaaaaaaa aagaaaaaat atagagagaa tgaaggaggg
2341 cataagcgct ggtggtttga tcatttctgc tgtgatgttt acaggatggt agccaccaaa
2401 gccaaatgat taacctgtct acgaacaaca gtagttttctc agggtcattg tccttgaacc
2461 caacagcccc aattatgagt gtcactgctc accaaaggtc aatgctgaga gaggaagagg
2521 gaggggctgc tccaaactca tttgggtaga aactatcggt gcttgactct cactaggcta
2581 caccccagag ttgaccaaat tgagtgatag ggaccctggt gggaggaggg agggcacctc
2641 tccagggaaa tcaaaagcaa tacaacttta ccacaaagcc tttaaaacca gtaacatagt
2701 gctcaaggac caagatcaag cgtagcagct gcagctgcag cagcggcccc aaggctgcag
2761 cctctgtccc cacacagcct cgaagcgcgc tgacatcaga ttgttaaggg cattttcata
2821 cttagaactg tcccatcccc aggtcccaaa caaatggaca ctgccttagc ctcttggaaa
2881 tcaggtagca catattctaa gctagattca cccctctccc ccacccccaa cttcccaccc
2941 caggcaaggc tgacttcttt gaaccagaaa agctagtcaa gtgtgtgtgt gttgtgcatt
3001 gttgcaaacc cactaagcca gaagcccaaa gtggcaaata gcttatgaga attcctagta
3061 caattctctt aagttcagta aacttctttt ctctcttttc tcttttttt tatttttttt
3121 attttgctg tgaccttttc aatctgtgat atacectcct ttctccccac agtgacattg
3181 gtatatgtac caacaatgca catatctaca catatgaaaa gaagcagttc tcacaacgtt
3241 gctgggtttt tgtttttgttt tgttttttgg tttttgtttt ttgttttttg cttcttttt
3301 ccccctcccc ctgcccctct ccacctcctt cttgaacttc caaagctttg tctcgtgttt
3361 gctgcagagc gattcgggga ctgacctaga cctgtttgca tgatctcctc tcttgtgatt
3421 tggttgcact ttagaacatt tttgtgccgt attatttgca ttatgtattt ataatttaaa
3481 tgatatttag gtttttggct gagtactgga ataaacagtg agcatatctg gtatatgtca
3541 ttatttattg ttaaattaca tttttaagct ccatgtgcat ataaaagtta tgaaacatat
3601 catggtaatg acagatgcaa gttatttat ttgcttattt ttataattaa agatgccata
3661 gcataatttg aagcctttgg tgaattcctt ctacgataat aataataata ataaagtgtt
3721 aacgttttat ttgttccccc tcc
```

SEQ ID NO: 18 Mouse Stanniocalcin 1 Amino Acid Sequence (EDL35955.1)

```
   1 mlqnsavila lvisaaaahe aeqndsyspr ksrvaaqnsa evvrclnsal qvgcgafacl
  61 enstcdtdgm ydicksflys aakfdtqgka fvkeslkcia ngitskvfla irrcstfqrm
 121 laevqedcys klnvcsiakr npeaiteviq lpnhfsnryy nrlvrsllec dedtvstird
 181 slmekigpnm aslfhilqtd hcaqthprad fnrrrtnepq klkvllrnlr gegdspshik
 241 rtsqesa
```

* Included in Table 2 are RNA nucleic acid molecules (e.g., thymidines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 2, or a portion thereof. Such nucleic acid molecules can have a function of the full-length nucleic acid as described further herein.
* Included in Table 2 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 2, or a portion thereof. Such polypeptides can have a function of the full-length polypeptide as described further herein.

II. Vaccine

The present invention provides a vaccine useful for promoting ICD, such as a cancer vaccine, comprising cells, such as cancer cells, wherein the cells are modified to comprise an increased copy number, expression level, and/or activity of one or more biomarkers listed in Table 1 or a fragment thereof. The exemplary description provided below is directed to cancer cells as exemplary, but may be adapted by the ordinarily skilled artisan to many other cell types useful for promoting ICD. In some embodiments, cells are cancer cells and may be derived from a solid or hematological cancer (e.g., MM). In some embodiments, the cancer cells are derived from a subject. For example, the cancer cells may be derived from a myeloma, such as a multiple myeloma. In another embodiment, the cancer cells are derived from a cancer cell line. The cancer cells may be from any cancer cell line or primary cancer cells. For example, the cancer cells may be derived from a cell line selected from the group consisting of AMO1, H929, 5TGM1, and KMS11 cells. The cancer cells may have different kinds of additional genetic mutations. The cancer cells may be derived from the subject who is treated with the cancer vaccine. The cancer cells may also be derived from a different subject who is not treated with the cancer vaccine. The cancer cells may be derived from a cancer that is the same type as the cancer treated with the cancer vaccine. The cancer cells may also be derived from a cancer that is a different type from the cancer treated with the cancer vaccine. The cancer cells may be derived from a cancer that has the same genetic mutations as the cancer treated with the cancer vaccine. The cancer cells may also be derived from a cancer that has different genetic mutations from the cancer treated with the cancer vaccine.

a. Cancer Cell Isolation and Purification

In some embodiments, the cancer cells are derived from a subject. Isolation and purification of tumor cell from various tumor tissues such as surgical tumor tissues, ascites or carcinous hydrothorax is a common process to obtain the purified tumor cells. Cancer cells may be purified from fresh biopsy samples from cancer patients or animal tumor models. The biopsy samples often contain a heterogeneous population of cells that include normal tissue, blood, and cancer cells. Preferably, a purified cancer cell composition can have greater than 10%, 20% 30%, 40%, 50%, 60%, 70%, 75%, 80%, 85%, 90%, 95%, 99%, or more, or any range in between or any value in between, total viable cancer cells. To purify cancer cells from the heterogeneous population, a number of methods can be used.

In one embodiment, laser microdissection is used to isolate cancer cells. Cancer cells of interest can be carefully dissected from thin tissue slices prepared for microscopy. In this method, the tissue section is coated with a thin plastic film and an area containing the selected cells is irradiated with a focused infrared laser beam pulse. This melts a small circle in the plastic film, causing cell binding underneath. Those captured cells are removed for additional analysis. This technique is good for separating and analyzing cells from different parts of a tumor, which allows for a comparison of their similar and distinct properties. It was used recently to analyze pituitary cells from dissociated tissues and from cultured populations of heterogeneous pituitary, thyroid, and carcinoid tumor cells, as well as analyzing single cells found in various sarcomas.

In another embodiment, fluorescence activated cell sorting (FACS), also referred to as flow cytometry, is used to sort and analyze the different cell populations. Cells having a cellular marker or other specific marker of interest are tagged with an antibody, or typically a mixture of antibodies, that bind the cellular markers. Each antibody directed to a different marker is conjugated to a detectable molecule, particularly a fluorescent dye that may be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and related lineage cells is well-known in the art and described in, for example, U.S. Pat. Nos. 5,137,809; 5,750,397; 5,840,580; 6,465,249; Manz et al. (202) Proc. Natl. Acad. Sci. U.S.A. 99:11872-11877; and Akashi et al. (200) Nature 404:193-197. General guidance on fluorescence activated cell sorting is described in, for example, Shapiro (2003) Practical Flow Cytometry, 4th Ed., Wiley-Liss (2003) and Ormerod (2000) Flow Cytometry: A Practical Approach, 3rd Ed., Oxford University Press.

Another method of isolating useful cell populations involves a solid or insoluble substrate to which is bound antibodies or ligands that interact with specific cell surface markers. In immunoadsorption techniques, cells are contacted with the substrate (e.g., column of beads, flasks, magnetic particles, etc.) containing the antibodies and any unbound cells removed. Immunoadsorption techniques may be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads may be readily isolated by a magnetic separator (see, e.g., Kato and Radbruch (1993) Cytometry 14:384-92). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations. One of the most common uses of this technology is for isolating circulating tumor cells (CTCs) from the blood of breast, NSC lung cancer, prostate and colon cancer patients using an antibody against EpCAM, a cell surface glycoprotein that has been found to be highly expressed in epithelial cancers.

FACS and most batch wise immunoadsorption techniques may be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that may be employed is use of antibody/complement treatment or immunotoxins to remove unwanted cells.

In still another embodiment, microfluidics, one of the newest technologies, is used to isolate cancer cells. This method used a microfluidic chip with a spiral channel that can isolate circulating tumor cells (CTCs) from blood based upon their size. A sample of blood is pumped into the device and as cells flow through the channel at high speeds, the inertial and centrifugal forces cause smaller cells to flow along the outer wall while larger cells, including CTCs, flow along the inner wall. Researchers have used this chip technology to isolate CTCs from the blood of patients with metastatic lung or breast cancer.

Fluorescent nanodiamonds (FNDs), according to a recently published article (Lin et al. Small (2015) 11:4394-4402), can be used to label and isolate slow-proliferating/ quiescent cancer stem cells, which, according to study authors, have been difficult to isolate and track over extended time periods using traditional fluorescent markers. It was concluded that nanoparticles do not cause DNA damage or impair cell growth, and that they outperformed EdU and CFSE fluorescent labels in terms of long-term tracking capability.

It is to be understood that the purification or isolation of cells also includes combinations of the methods described above. A typical combination may comprise an initial procedure that is effective in removing the bulk of unwanted cells and cellular material. A second step may include isolation of cells expressing a marker common to one or more of the progenitor cell populations by immunoadsorption on antibodies bound to a substrate. An additional step providing higher resolution of different cell types, such as FACS sorting with antibodies to a set of specific cellular markers, may be used to obtain substantially pure populations of the desired cells.

b. Cancer Cell Modification and Gene Delivery

The cancer cells is modified to comprise an increased copy number, expression level, and/or activity of one or more biomarkers listed in Table 1 or a fragment thereof. An exemplary way to increase the copy number, expression level, and/or activity of a gene (e.g., GABARAP and/or CRT or fragments thereof) is to use gene delivery methods to introduce nucleic acid into cells (e.g., an exogenous nucleic acid molecule encoding a biomarker). Any means for the introduction of a polynucleotide into mammals, human or non-human, or cells thereof may be adapted to the practice of this invention for the delivery of the various constructs of the present invention into the intended recipient. In some embodiments of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al. Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), lentivirus, and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In certain embodiments of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In other embodiments, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147 154, 1992. Other vehicles which can optionally be used include DNA-ligand (Wu et al., J. Biol. Chem. 264:16985 16987, 1989), lipid-DNA combinations (Felgner et al., Proc. Natl. Acad. Sci. USA 84:7413 7417, 1989), liposomes (Wang et al., Proc. Natl. Acad. Sci. 84:7851 7855, 1987) and microprojectiles (Williams et al., Proc. Natl. Acad. Sci. 88:2726 2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In preferred embodiments, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In still other embodiments, the introduced nucleic acid may be present inside the target cancer cell transiently (thereby providing transient increase in expression of a biomarker). Alternatively, the nucleic acid may integrate randomly or at a specific locus (the integration can be engineered, e.g., by flanking the nucleic acid with the target genomic sequence to induce homologous recombination), thereby providing a longer-term increase in expression of a biomarker.

III. Subjects

In one embodiment, the subject for whom predicted likelihood of efficacy of an agent described herein, is a mammal (e.g., mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or immunotherapies. In still another embodiment, the subject has undergone treatment, such as chemotherapy, radiation therapy, targeted therapy, and/or immunotherapies.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to an agent described herein, and immunotherapy combination treatment of many different cancers in subjects such as those described herein.

IV. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. In some embodiments, the control sample comprises two wild-type copies of GABARAP. In some embodiments, the control sample comprises two wild-type copies of CRT. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins), evaluate a response to an agent described herein and an inducer of ICD, and/or evaluate a response to agent described herein and an inducer of ICD combination treatment with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more agents that alter the copy number, expression level, and/or activity of one or more biomarkers listed in Table 1 and an inducer of ICD, alone or in combination with other anti-cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

V. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N Y, 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. U.S.A.* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. U.S.A.* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553-6556; Lemaitre et al., 1987, *Proc. Natl. Acad. Sci. U.S.A.* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. U.S.A.* 87:2264-2268, modified as in Karlin and Altschul (1993) *Proc. Natl. Acad. Sci. U.S.A.* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the following address on the World Wide Web:.ncbi.nlm.nih.gov. Another preferred, non-limiting example of a mathematical algorithm utilized for the comparison of sequences is the algorithm of Myers and Miller, (1988) *ComputAppl Biosci*, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. U.S.A.* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. U.S.A.* 89:7811-7815; Delgrave et al., 1993, *Protein Engineering* 6(3):327-331). An isolated polypeptide or a fragment thereof (or a nucleic acid encoding such a polypeptide) corresponding to one or more biomarkers encompassed by the present disclosure, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein). While there are commercially available antibodies against GABA-RAP or CRT, generation of an antibody as described herein may provide additional detection tools for the diagnostic and prognostic methods described herein. Furthermore, generation of an antibody or bispecific antibody/intrabody (e.g., those stabilizing the interaction between the biomarker and its substrate to increase the activity of the biomarker) may be useful for the methods described herein.

In some embodiments, the immunotherapy utilizes an inhibitor of at least one immune checkpoint, such as an antibody binds substantially specifically to an immune checkpoint, such as PD-1, and inhibits or blocks its immunoinhibitory function, such as by interrupting its interaction with a binding partner of the immune checkpoint, such as PD-L1 and/or PD-L2 binding partners of PD-1. In some embodiments, an antibody or an intrabody (e.g., bispecific), binds substantially specifically to one or more biomarkers listed in Table 1 and one or more of its substrate(s), such that the antibody or intrabody stabilizes and increases the interaction between the biomarker and the substrate, thereby increasing the biological activity of the one or more biomarkers listed in Table 1.

For example, a polypeptide immunogen typically is used to prepare antibodies by immunizing a suitable subject (e.g., rabbit, goat, mouse or other mammal) with the immunogen. A preferred animal is a mouse deficient in the desired target antigen. For example, a PD-1 knockout mouse if the desired antibody is an anti-PD-1 antibody, may be used. This results in a wider spectrum of antibody recognition possibilities as antibodies reactive to common mouse and human epitopes are not removed by tolerance mechanisms. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in *Monoclonal Antibodies: A New Dimension In Biological Analyses*, Plenum Publishing Corp., New York, New York (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically. In some embodiments, the immunization is performed in a cell or animal host that has a knockout of a target antigen of interest (e.g., does not produce the antigen prior to immunization).

Any of the many well-known protocols used for fusing lymphocytes and immortalized cell lines can be applied for the purpose of generating a monoclonal antibody against one or more biomarkers encompassed by the present disclosure, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, MD. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody encompassed by the present disclosure are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. U.S.A.* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. U.S.A.* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well-known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention described herein. However, the ordinarily skilled artisan will appreciate that some deviation from the exact CDR sequences may be possible while still retaining the ability of the antibody, especially an introbody, to bind a desired target, such as one or more biomarkers listed in Table 1, and/or a binding partner thereof, either alone or in combination with an immunotherapy, such as the one or more biomarkers, the binding partners/substrates of such biomarkers, or an immunotherapy effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

For example, the structural features of non-human or human antibodies (e.g., a rat anti-mouse/anti-human antibody) can be used to create structurally related human antibodies, especially introbodies, that retain at least one functional property of the antibodies of the present invention, such as binding to one or more biomarkers listed in Table 1, the binding partners/substrates of such one or more biomarkers, and/or an immune checkpoint. Another functional property includes inhibiting binding of the original known, non-human or human antibodies in a competition ELISA assay.

Antibodies, immunoglobulins, and polypeptides encompassed by the present disclosure can be used in an isolated (e.g., purified) form or contained in a vector, such as a membrane or lipid vesicle (e.g. a liposome). Moreover, amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Similarly, modifications and changes may be made in the structure of the antibodies described herein, and in the DNA sequences encoding them, and still obtain a functional molecule that encodes an antibody and polypeptide with desirable characteristics. For example, antibody glycosylation patterns can be modulated to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, 0-galactosidase, or acetylcholinesterase; examples of suitable prosthetic group complexes include a flag tag, a myc tag, an hemagglutinin (HA) tag, streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}I$, $^{131}I$, $^{35}S$, or $^3H$. As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. U.S.A.*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers encompassed by the present disclosure, including one or more biomarkers listed in Table 1, or a fragment thereof. In one embodiment, the bispecific antibody could specifically bind to both a polypeptide or a fragment thereof and its natural binding partner(s) or a fragment(s) thereof.

Techniques for modulating antibodies, such as humanization, conjugation, recombinant techniques, and the like are well-known in the art.

In another aspect of this invention, peptides or peptide mimetics can be used to antagonize the activity of one or more biomarkers encompassed by the present disclosure, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. U.S.A.* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers encompassed by the present disclosure, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences described herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187;

Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments encompassed by the present disclosure. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides described herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci*. pp. 463-468 (general review); Hudson, D. et al. (1979) *Int. J. Pept. Prot. Res*. 14:177-185 (—CH2NH—, CH2CH2-); Spatola, A. F. et al. (1986) *Life Sci*. 38:1243-1249 (—CH2-S); Hann, M. M. (1982) *J. Chem. Soc. Perkin Trans. L* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett*. 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett*. (1983) 24:4401-4404 (—C(OH)CH2-); and Hruby, V. J. (1982) *Life Sci*. (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present disclosure are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anti-cancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. U.S.A.* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. U.S.A.* 89:1865-1869) or on phage (Scott and Smith (1990) *Science* 249:386-390); (Devlin (1990) *Science* 249:404-406); (Cwirla et al. (1990) *Proc. Natl. Acad. Sci. U.S.A.* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

Chimeric or fusion proteins can be prepared for one or more biomarkers listed in Table 1, and/or agents for the immunotherapies described herein. As used herein, a "chimeric protein" or "fusion protein" comprises one or more biomarkers encompassed by the present disclosure, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers encompassed by the present disclosure, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ 4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein encompassed by the present disclosure is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

The fusion proteins encompassed by the present disclosure can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers encompassed by the present disclosure, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences encompassed by the present disclosure may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol.* 20:446-448; Brummelkamp et al. (2002) *Science* 296:550-553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. U.S.A. 84:648-652; PCT Publication No. WO88/09810) or the blood-brain barrier (see, e.g., PCT Publication No. WO89/10134), hybridization-triggered cleavage agents. (See, e.g., Krol et al. (1988) BioTech. 6:958-976) or intercalating agents. (See, e.g., Zon (1988) Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215:327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells, or piwiRNAs. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nat. Biotechnol. 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug et al. (1984) Science 224:574-578; Zaug et al. (1986) Science 231:470-475; Zaug et al. (1986) Nature 324:429-433; WO 88/04300; and Been et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein.

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion E. coli expression vectors include pTrc (Amann et al., 1988, *Gene* 69:301-315) and pET 11d (Studier et al., p. 60-89, In Gene *Expression Technology: Methods in Enzymology* vol. 185, Academic Press, San Diego, C A, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in E. coli is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, C A, 1990. Another strategy is to alter the nucleic acid sequence of the nucleic acid to be inserted into an expression vector so that the individual codons for each amino acid are those preferentially utilized in E. coli (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast S. cerevisiae include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. U.S.A.* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

VI. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 2, 3, 4, 5, 6, 7, 8, 9, or 10 is predictive of better outcome of a treatment with an inducer of ICD.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. U.S.A.* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci U.S.A.* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. U.S.A.* 86: 1173), self-sustained sequence replication (Guatelli, et al. (1990) *Proc. Nat. Acad. Sci. U.S.A.* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) Proc. Natl. Acad. Sci. U.S.A. 86: 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS U.S.A. 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. U.S.A., 87, 1874 (1990)); and transcription amplification (see, e.g., Kwoh et al., Proc. Natl. Acad. Sci. U.S.A. 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos: 6,618,6796; 6,379,897; 6,664,377; 6,451,536; 548,257; U.S. 20030157485 and Schena et al. (1995) Science 20, 467-470; Gerhold et al. (1999) Trends In Biochem. Sci. 24, 168-173; and Lennon et al. (2000) Drug Discovery Today 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an agent described herein in combination with an inducer of ICD. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I) carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule for the treatment, diagnostic, and prognostic methods described herein.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. U.S.A. 87:1874-1878), transcriptional amplification system (Kwoh, D. Y. et al. (1989) Proc. Natl. Acad. Sci. U.S.A. 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. U.S.A.* 74:560 or Sanger (1977) *Proc. Natl. Acad Sci. U.S.A.*

74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. U.S.A.* 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci U.S.A.* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. U.S.A.* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a new restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci U.S.A.* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The agent described herein may be used in combination with one or more additional anti-cancer therapies, such as another immune checkpoint inhibitor. In some embodiments, an agent described herein can be administered to a subject indicated as being a likely responder. In other embodiments, administration of an agent described herein can be avoided once a subject is indicated as not being a likely responder and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy. In addition, any representative embodiment of an agent to modulate a particular target can be adapted to any other target described herein by the ordinarily skilled artisan (e.g., monospecific antibodies, bispecific antibodies, non-activating forms, small molecules, peptides, interfering nucleic acids, and the like).

The term "targeted therapy" refers to administration of agents that selectively interact with a chosen biomolecule to thereby treat cancer. One example includes immunotherapies such as immune checkpoint inhibitors, which are well-known in the art. For example, anti-PD-1 pathway agents, such as therapeutic monoclonal blocking antibodies, which are well-known in the art and described above, can be used to target tumor microenvironments and cells expressing unwanted components of the PD-1 pathway, such as PD-1, PD-L1, and/or PD-L2.

For example, the term "PD-1 pathway" refers to the PD-1 receptor and its ligands, PD-L1 and PD-L2. "PD-1 pathway inhibitors" block or otherwise reduce the interaction between PD-1 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, PD-1 inhibitors can block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2, such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect anti-immune checkpoint inhibitors block or otherwise reduce the immunoinhibitory signaling generated by the interaction between the immune checkpoint and at least one of its ligands. For example, an inhibitor can block the interaction between PD-1 and one or both of its ligands without necessarily directly blocking the interaction between PD-1 and one or both of its ligands. For example, indirect inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

Similarly, agents may inhibit a negative regulator of GABARAP, CRT and/or STING and may alter the interaction of the negative regulator with its substrate. Agents may potentiate a negative regulator of STC1 or may alter the interaction of the negative regulator with its substrate. Exemplary agents include monospecific or bispecific blocking antibodies, especially intrabodies, against the one or more negative regulators and/or their substrate(s) that block the interaction between the one or more biomarkers and their substrate(s); a non-active form of such one or more biomarkers and/or their substrate(s) (e.g., a dominant negative polypeptide), small molecules or peptides that block the interaction between such one or more biomarkers and their substrate(s) or the activity of such one or more biomarkers; and a non-activating form of a natural biomarker and/or its substrate(s).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well-known adoptive cell-based immunotherapeutic modalities, including, without limitation, Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa-super repressor overexpression, NFKB decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

Nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used with in combination with an agent described herein in combination with an inducer of ICD to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well-known in the art.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci U.S.A. 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. U.S.A. 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. U.S.A. 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02, 806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as agents described herein that increases the copy number, expression level, and/or activity of GABARAP and/or CRT, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection.

Response may be recorded in a quantitative fashion like percentage change in tumor volume or cellularity or using a semi-quantitative scoring system such as residual cancer burden (Symmans et al., J. Clin. Oncol. (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to immunotherapies, such as anti-immune checkpoint therapies, are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any immunotherapy, such as anti-immune checkpoint therapy. The outcome measurement may be pathologic response to therapy given in the neoadjuvant setting. Alternatively, outcome measures, such as overall survival and disease-free survival can be monitored over a period of time for subjects following immunotherapies for whom biomarker measurement values are known. In certain embodiments, the same doses of immunotherapy agents, if any, are administered to each subject. In related embodiments, the doses administered are standard doses known in the art for those agents used in immunotherapies. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an immunotherapy can be determined using methods such as those described in the Examples section.

5. Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays and xenograft animal model assays. In one embodiment, the assays provide a method for identifying whether a cancer is likely to respond to an agent described herein in combination with an inducer of ICD, such as in a human by using a xenograft animal model assay, and/or whether an agent can inhibit the growth of or kill a cancer cell that is unlikely to respond to an inducer of ICD.

In one embodiment, the present invention relates to assays for screening test agents which bind to, or modulate the biological activity of, at least one biomarker described herein (e.g., in the tables, figures, examples, or otherwise in the specification). In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C, or $^{3}$H, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to new agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker described herein in the context of a biological sample (e.g., blood, serum, cells, or tissue) to thereby determine whether an individual afflicted with a cancer is likely to respond to an agent described herein in combination with an inducer of ICD, such as in a cancer. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect of the present invention pertains to monitoring the influence of agents (e.g., drugs, compounds, and small nucleic acid-based molecules) on the expression or activity of a biomarker described herein. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to an agent described herein in combination with an inducer of an ICD. In some embodiments, the present invention is useful for classifying a sample (e.g., from a subject) as associated with or at risk for responding to or not responding to an inducer of ICD using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to an agent described herein in combination with an inducer of an ICD (e.g., chemotherapeutic agents, radiation therapy, oxazophorines, platinum-based compounds, anthracyclines, anthracenediones, or proteasome inhibitors) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immunotherapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to an inducer of ICD), a biological sample from the subject during remission, or a biological sample from the subject during treatment for developing a cancer progressing despite being treated chemotherapy and/or radiation therapy.

d. Prognostic Assays

The diagnostic methods described herein can furthermore be utilized to identify subjects having or at risk of developing a cancer that is likely or unlikely to be responsive to an inducer of ICD. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The therapeutic compositions described herein, such as the combination of an agent described herein and an inducer of ICD, can be used in a variety of in vitro and in vivo therapeutic applications using the formulations and/or combinations described herein. In some embodiments, the therapeutic agents can be used to treat cancers determined to be responsive thereto. In some embodiments, single or multiple agents may be used to treat cancers in subjects identified as likely responders thereto.

Modulatory methods of the present invention involve contacting a cell, such as an immune cell with an agent that inhibits or blocks the expression and/or activity of such one or more biomarkers and an immunotherapy, such as an immune checkpoint inhibitor (e.g., PD-1). Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a condition that would benefit from an increased immune response, such as an infection or a cancer like colorectal cancer.

Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), a parasitic infection, and an immunosuppressive disease.

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents. In one preferred embodiment, agents that upregulate the immune response described herein are useful for modulating the arginase/iNOS balance during *Trypanosoma cruzi* infection in order to facilitate a protective immune response against the parasite.

Immune responses can also be enhanced in an infected patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that pre-existing tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

6. Administration of Agents

The agent(s) of the present disclosure are administered to subjects in a biologically compatible form suitable for pharmaceutical administration in vivo, to enhance immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agent(s) described herein may be administered to the subject in combination with another cancer therapy (e.g., in a combination dosage form or by simultaneous administration of single agents), according to a schedule that results in effective amounts of each modulatory agent present in the patient at the same time.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9)

oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present disclosure. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. U.S.A. 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment, an agent encompassed by the present disclosure is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

7. Kits

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXAMPLES

Example 1: Materials and Methods for Examples 2-3 a. Cell Culture

Multiple myeloma cell line human H929, murine JAWSII, and 293T were purchased from the American Type Culture Collection (ATCC); AMO1 was purchased from DSMZ; KMS11 were obtained by Japanese Collection of Research Bioresources (National Institute of Health Sciences; Japan); and murine 5TGM1 cells were kindly provided by Dr. Irene Ghobrial (Dana-Farber Cancer Institute, Boston). Cell lines were tested to rule out *Mycoplasma* contamination using the MycoAlert™ *Mycoplasma* Detection Kit (Lonza) and authenticated by Short Tandem Repeats DNA typing. Human MM cell lines were cultured in RPMI/1640 media containing 10% fetal bovine serum (FBS) (GIBCO; ThermoFisher Scientific), 2 µmol/L glutamine, 100 U/mL penicillin, and 100 µg/mL streptomycin (GIBCO; ThermoFisher Scientific). 293T cells were maintained in DMEM culture media with 10% FBS and 1% penicillin-streptomycin. Murine JAWSII cells were cultured in Alpha minimum essential medium with ribonucleosides, deoxyribonucleosides, 4 mM L-glutamine, 1 mM sodium pyruvate, 20% FBS, 1% penicillin-streptomycin, and 5 ng/ml murine GM-CSF(PeproTech). Murine 5TGM1 cells were maintained in Iscove's Modified Dulbecco's Media (IMDM) media (ThermoFisher Scientific) supplemented with 10% FBS and 1% penicillin-streptomycin.

b. Drugs

Bortezomib was purchased from Selleckchem (S1013) and resuspended in DMSO for in vitro and in vivo studies. Recombinant calreticulin was purchased from Sigma (SRP8001) and used at a concentration of 3 ug/$10^6$ cells following the manufacturer's instructions.

c. Apoptosis Assay

Apoptosis was evaluated by Annexin-V/7-Aminoactinomycin D (7-AAD) staining and flow cytometric analysis using the PE Annexin V Apoptosis Detection Kit I (BD Biosciences), following the manufacturer's instructions.

d. Cell Surface Exposure of CRT

Multiple myeloma (MM) cells were seeded in 12-well plates ($2 \times 10^5$ per well), treated with BTZ for 16 h at indicated concentrations, and then stained with Alexa Fluor647® anti-calreticulin antibody (ab196159, Abcam) and 7-AAD. Analysis of fluorescence intensity on 7-AAD negative cells was assessed using BD LRSFortessa™ X-20 flow cytometer.

e. Generation of Monocyte-Derived DCs (Mo-DCs) and Phagocytosis Assay

Mo-DCs were generated from CD14+ peripheral blood monocytes were positively selected using magnetic beads (Miltenyi Biotec) and cultured for 6 days in mo-DC differentiation medium containing GM-CSF and IL-4 (130-094-812; Miltenyi Biotec) to generate Mo-DCs. AMO1, KMS11 and H929 cells lines, as well as patient MM cells, were stained with CellTrace™ Far Red (ThermoFisher Scientific), cultured with or without BTZ (for 16 h), and then incubated in 48-well plates for 4 h at 1:1 ratio with CellTrace™ CFSE stained Mo-DCs. Cells were then collected, and phagocytosis analysis was performed by flow cytometry and confocal microscopy. Analagous phagocytosis experiments was performed using 5TGM1 murine MM and immature murine DC line JAWSII.

f. Flow Cytometry-Based Assay

Collected cells were analyzed using the BD LRS-Fortessa™ X-20 flow cytometer. Mo-DCs that engulfed MM cells were CFSE and FAR-RED double positive. Fold increase in percentage of double positive DCs after co-culture with BTZ treated vs untreated MM cells was compared.

g. Generation of CRISPR KO MM Cells

Single guide RNA (sgRNA) targeting murine calr and human and murine GAPARAP were used to generate 5TGM1 calr$^{KO}$, AMO1 GABAPAR$^{KO}$, H929 GABARAP$^{KO}$, and 5TGM1 GABARAP$^{KO}$ cells. Cell lines were transfected via electroporation (Neon™ Transfection System; ThermoFisher Scientific) using All-in-one vectors (pCLIP-ALL-hCMV-ZsGreen) containing a sgRNA and a Cas9 (Transomic Technologies). 48 hours (48 h) after electroporation, cells were ZsGreen-sorted and plated as monoclones in 96-well plates. After expansion, monoclones were screened for either CRT or GABARAP expression by western blot analysis. Sequences of sgRNAs are as follows:

```
Calr Mus Musculus:
sgRNA#1: TATGTTTGGATTCGACCCAG sgRNA#2: ATAGATGGCAGGGTCTGCGG sgRNA#3: CGTAAAATTTGCCAGAACTG Non targeting control: GGAGCGCACCATCTTCTTCA GABARAP Homo Sapiens:
sgRNA#1: GGATCTTCTCGCCCTCAGAG sgRNA#2: GCGAATTCATCTCCGAGCTG sgRNA#3: GTTCGAGAAGCGCCGCTCTG Non targeting control: GGAGCGCACCATCTTCTTCA GABARAP Mus Musculus:
sgRNA#1: AAAGCCCCCAAAGCTCGGAT sgRNA#2: GTTCGAGAAGCGCCGCTCTG sgRNA#3: CCGAAAGAAATACCCAGACC Non targeting control: GGAGCGCACCATCTTCTTCA
``` h. Stable Overexpression of GABARAP

Human cDNA open reading frame (ORF) of GABARAP gene cloned into a lentiviral expression vector was purchased from Dharmacon (Clone Id: PLOHS_ccsb-BEn_02679; Cat. #: OHS5898-224626368). Virus was generated by transfecting HEK293T cells with 4 μg of DNA and packaging vectors (4 μg of psPAX2 and 2 μg of pMD2.G) using Lipofectamine™ 2000 (ThermoFisher Scientific). Supernatant containing viral particles was harvested after 48 h and sterile filtered with 0.45 μm filters. KMS11 or AMO1 GABARAP$^{KO}$ clones were spinoculated for 1 h with media containing lentiviral particles at a multiplicity of infection (MOI) of 2 in the presence of 8 μg/ml polybrene. Media was then changed, and cells were selected with blasticidin (Sigma-Aldrich) at a concentration of 10 μg/ml. After selection, efficient overexpression was evaluated by Western blot analysis.

i. Immunoblotting

Cell lysis was performed in RIPA buffer (Boston Bio Products) supplemented with Halt™ protease and phosphatase inhibitor cocktail (Thermo Fisher Scientific). Immunoblot analysis was performed to evaluate expression levels of total protein and phospho-specific isoforms. SDS-PAGE was performed on NuPage™ Bis-Tris gels (ThermoFisher Scientific) using MOPS or MES running buffer. Gels were dry transferred onto 0.45 μm nitrocellulose membranes using the iBlot® Dry Blotting System (ThermoFisher Scientific). The following antibodies (Abs) were used and purchased from Cell Signaling Technology: CRT (Cat. #12238) and GABARAP (Cat. #13733). GAPDH (Cat. #2118) was used as loading controls.

j. Analysis of T Cell Priming

DCs were generated from freshly isolated PBMCs as previously described. T cells were negatively selected from CD14− PBMCs using the Pan T cell Isolation Kit (Miltenyi Biotec) and frozen until immature DCs were generated. Either untreated or BTZ-treated MM cells were co-cultured with DCs and T cells for 5 days. T cells and DCs were also cultured in the absence of MM cells and in the presence of BTZ to assess the direct effects of drug on T cells and DCs. After 5 day co-culture, cells were treated with Dynabeads™ Human T-Activator CD3/CD28 (Cat. #11131D, ThermoFisher Scientific) 5 h before analysis, and with GolgiStop™ and GolgiPlug™ (Cat. #554724 and Cat. #555029, BD Biosciences) 3 h before analysis, following the manufacturer's instructions. Cells were then collected and T cell populations were analyzed by CyTOF analysis.

k. In Vivo Studies 6-week old female immunodeficient NOD.CB17-Prkdcscid/NCrCrl (NOD/SCID) mice (Charles River) and immunocompetent C57BL/KaLwRijHsd (Envigo) mice were housed in an animal facility at the Dana-Farber Cancer Institute (DFCI). All experiments were performed after approval by the Animal Ethics Committee of the DFCI and performed using institutional guidelines.

l. In Vivo Studies for Tumor Growth Analysis after BTZ Treatment

To assess the effect of BTZ in the absence of an immune system, NOD/SCID mice were subcutaneously injected with $1\times10^6$ 5TGM1 WT cells in a 1:1 ratio with Matrigel® (Corning); to assess BTZ in an immunocompetent host, C57BL/KaLwRijHsd mice were injected with $1\times10^6$ 5TGM1 either WT or calrKO in the same ratio with Matrigel®. When tumor became measurable, mice (5/group) were randomized to receive either PBS or BTZ administered intra peritoneally (i.p.) 0.5 mg/kg twice/week for 2 weeks. Tumor sizes were measured and mice were sacrificed when tumors reached 2 cm in diameter or ulceration or major compromise in quality of life. A parallel experiment was performed to allow for tumor harvesting after two injections i.p. of BTZ for RNA-seq analysis, as detailed below.

m. Vaccination Studies $5\times10^5$ 5TGM1 WT or calrKO were treated with BTZ (7.5 nM) in vitro for 16 h. C57BL/KaLwRijHsd mice (n=8 per group) were then either vaccinated in the left flank with dying 5TGM1 WT, 5TGM1calrKO, 5TGM1 gabarapKO or not vaccinated. After 1 week, $1\times10^6$ WT 5TGM1 cells were injected in the contralateral flank and tumor growth was monitored over time. In a parallel experiment under the same conditions, spleens from mice were harvested 10 days after rechallenge and ELISPOT assay was performed to assess T cell specific reactivity against MM cells (Translational Immunogenomics Laboratory, DFCI).

n. RNA-Seq Analysis from Mouse Tumors

Tumors growing from both 5TGM1 WT or calrKO cells in C57BL/KaLwRijHsd mice treated with either PBS or BTZ (3/group) were harvested and used to extract RNA using the RNeasy® kit (Qiagen). After passing quality control, RNAseq was performed using Illumina NextSeq 500 Single-End 75 bp (SE75) and analyzed following the VIPER NGS analysis pipeline (Cornwell et al. (2018) *BMC Bioinform.* 19:135) comparing BTZ-treated mice vs PBS in each experimental setting. Listing of differentially expressed genes (DEGs) were applied to gene set enrichment analysis (GSEA) and Cytoscape (Bindea et al. (2009) *Bioinform.* 25:1091-1093; Bindea et al. (2013) *Bioinform.* 29:661-663) software to reveal biological pathways modulated by BTZ.

o. Analysis of RNAseq data of MM Patients

RNAseq from CD138+MM cells from 327 newly-diagnosed clinically annotated MM patients from IFM/DFCI 20019 clinical trial (NCT01191060) was used. After QC controls, all RNAseq data were quantified with Salmon. Raw counts and TPM values were summed to gene leves using tximport, and DESeq2 was used for all differential gene expression analysis. Centered and scaled data was used for clustering with ward. D2 algorithm. All figures were created with pheatmap or ggplot2. Survival analysis was performed using survival package in R, and log rank test was used to compare groups. As a validation dataset, gene expression data of 152 MM patients performed with microarray platform was downloaded from GEO (GSE9782) and pre-processed and normalized with affy and limma packages in R.

p. Statistical Analysis

All in vitro experiments were repeated at least 3 times and performed in triplicate. Statistical significance of differences was determined using Student t test or using ANOVA pairwise for multiple comparison where specified. Statistical significance of the in vivo growth inhibition was determined using Student t test. All statistical analyses and graphs were performed using GraphPad software.

Example 2: Loss-of-Function of GABARAP Impairs Bortezomib-Induced Anti-Tumor Immunity in Multiple Myeloma Immune escape underlies progression of disease and resistance to therapy in multiple myeloma (MM). Conversely, restoration of anti-tumor immunity primed by immunogenic cancer cells and intratumoral dendritic cells (DCs) may be exploited to convert the immunologically "cold" MM into a "hot" MM; and may lead to long-term clinical benefit, even in patient subgroups with high-risk (HR) cytogenetics and poor survival. It is investigated herein the mechanisms, biologic sequelae, and clinical benefits of bortezomib (BTZ)-induced immunogenic cell death (ICD), the immunogenic consequence of apoptosis resulting in specific anti-MM immunity via T-cell priming by DCs.

It is demonstrated herein that BTZ can induce hallmarks of ICD in human and murine MM cell lines (n=5), including exposure of endoplasmic reticulum protein calreticulin (CRT) that functions as an "eat me signal". Specifically, the data presented herein show that co-culture with BTZ-treated MM cells can induce phenotypic and functional changes in immature DCs including higher expression of CD86/CD83 on cell surface and enhanced uptake of BTZ-treated MM cells, as assessed by flow cytometry- and confocal-based phagocytosis assay, respectively. Notably, it is demonstrated herein that CRT has a key role in BTZ-induced immunogenicity, since these functional sequelae were abrogated in vitro when DCs were co-cultured with $CRT^{KO}$MM cells. These findings are validated in 2 different in vivo syngeneic models. First, the anti-MM activity of BTZ resulted in more potent 5TGM1 tumor cell shrinkage in immunocompetent hosts; and that this effect was directly linked to ICD induction, since it was abrogated in mice bearing $CRT^{KO}$ tumors. Second, the in vitro BTZ-treated 5TGM1 cells were used as a vaccine to enhance an anti-MM immune response: injection of live tumor cells resulted in palpable tumors in non-vaccinated mice by 1 week; conversely, injection of live tumor cells in vaccinated mice did not result in detectable tumor after 30 days. In contrast, in mice similarly vaccinated with BTZ-treated $CRT^{KO}$ 5TGM1 cells and challenged with injection of live WT cells, only 50% of vaccinated mice were tumor-free at day 30.

Next, RNAseq analysis was performed using BTZ-treated vs untreated tumors from both immunodeficient or immunocompetent mice; and also carried out an integrative analysis of RNAseq data from newly diagnosed and clinically annotated MM patients (n=360) uniformly treated with BTZ-based regimes (IFM/DFCI 2009; see Attal et al. (2017) *New Engl. J. Med.* 376:1311-1320 for details). Importantly, increased expression of the human orthologs of the immune genes induced in mice by BTZ was strongly and positively correlated with clinical outcome (OS p value=0.00089). The predictive value of this signature was confirmed in an independent dataset (GSE9782) (OS p value=0.024). Moreover, by interrogating the IFM/DFCI patient dataset, it is identified herein the gamma-aminobutyric acid receptor-associated protein (GABARAP) as a top differentially expressed gene among patients with longer survival rate (>5 years) as compared to those with poor survival (<1.5 years) after BTZ-based treatment. It is discovered herein that low level of GABARAP, located on chr17p13.1, is associated with poor clinical outcome in MM patients (EFS, p=0.0032); and that its prognostic value is still maintained even excluding HR patients with 17p deletion (EFS, p=0.018). Surprisingly, KMS11 cells that carry monoallelic deletion of GABARAP were resistant to induction of ICD by BTZ; and stable overexpression of the gene in these cells restored the functional sequelae of ICD induction upon drug exposure. In some embodiments, GABARAP expression useful according to the present disclosure is the level that is more than a control, such as the baseline expression in a cell and/or subject (e.g., one or more additional copy numbers compared to a baseline, such as a diploid, triploid, etc. copy number as compared to a monoallelic baseline). Moreover, GABARAP$^{KO}$ in 2 ICD-sensitive cell lines abrogated the induction of ICD by BTZ; add-back experiments by pre-treatment with recombinant CALR (rCRT) or stable overexpression of GABARAP in KO clones confirmed the on-target effect GABARAP$^{KO}$. Finally, mass cytometry (CyTOF) after T cell co-culture with mature DCs primed by both WT and GABARAP$^{KO}$ AMO1 clones showed that treatment of MM cells with BTZ switched CD4+ T cells towards an effector memory function; in contrast to treatment of GABARAP$^{KO}$ clones with BTZ, which led to T cell exhaustion.

In conclusion, the studies presented herein demonstrate the clinical benefits of BTZ-induced ICD in MM; and that loss-of-function of GABARAP, particularly in HR patients with 17p deletion, abrogates induction of antitumor immunity after drug exposure. These studies provide the framework for novel combination treatments to trigger anti-MM immunity and improve patient outcome in MM.

Example 3: Identification of Specific Genetic Alterations That May Impair Induction of ICD by BTZ Recent evidence suggests that the clinical success of anti-cancer treatment is not solely related to tumor cytotoxicity, but also results from immunogenic effects of tumor cell death. The induction of immunogenic cell death (ICD) is believed to be critical for better outcome of patients. However, the role of ICD in myelomas like MM has not been defined yet. Example 1 of the present disclosure demonstrates that the induction of ICD by BTZ (bortezomib) in MM is associated with better and more prolonged anti-tumor response; identified an IFNs-I ICD-related signature that predicts clinical outcome in MM patients; and found a specific loss-of-function associated with del(17p) that impairs immunogenicity of cell death after BTZ treatment.

Figure 13A:
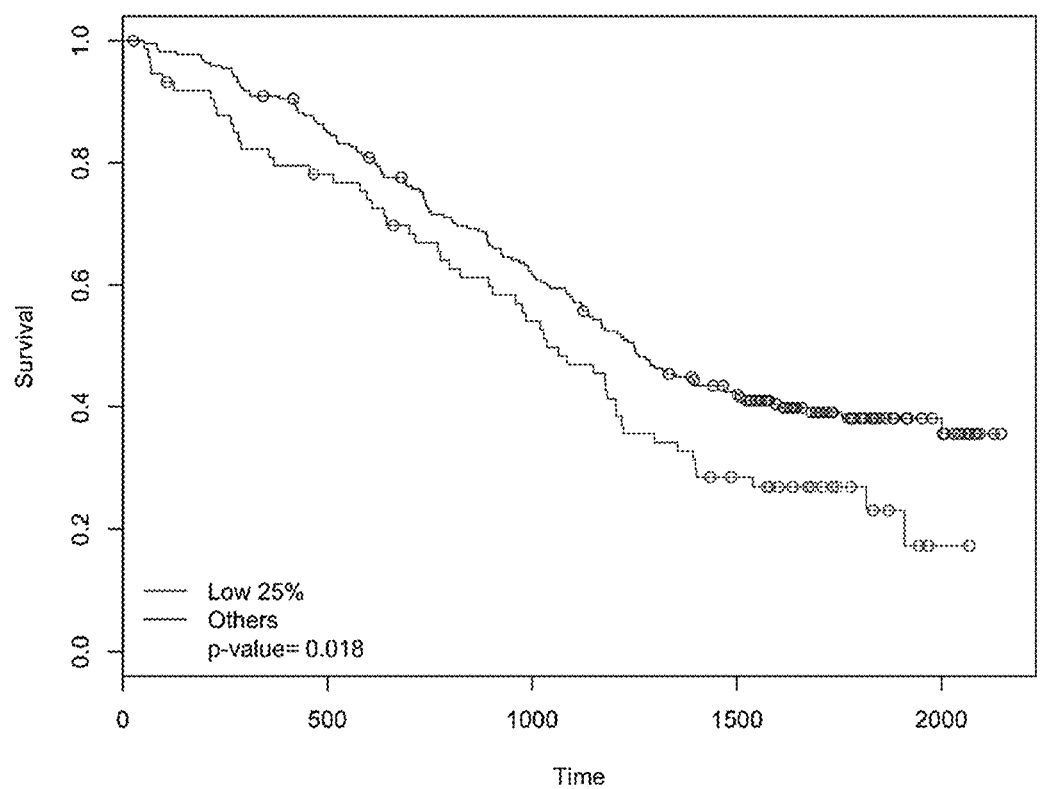
Figure 13B:
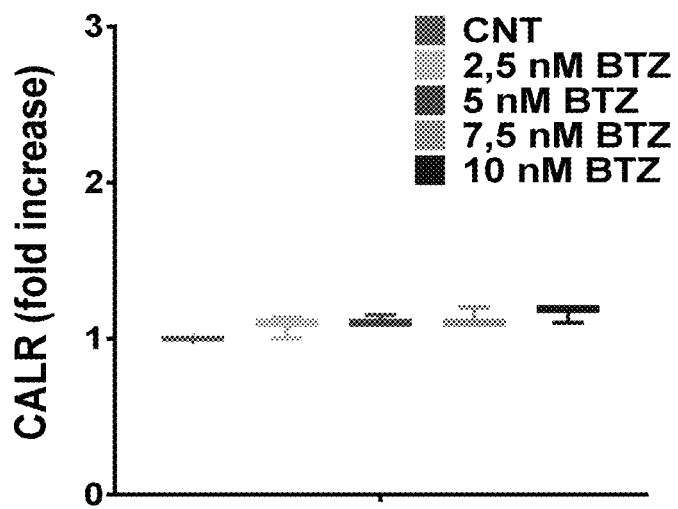
Figure 13C:
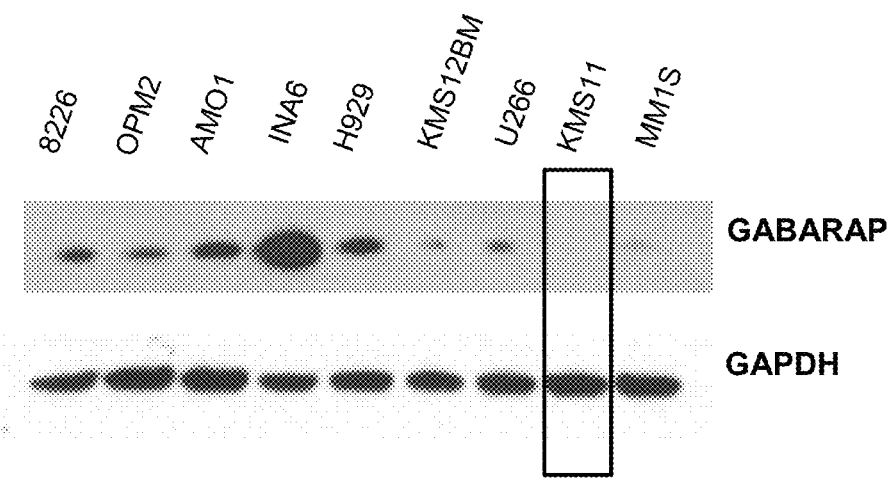
Figure 13D:
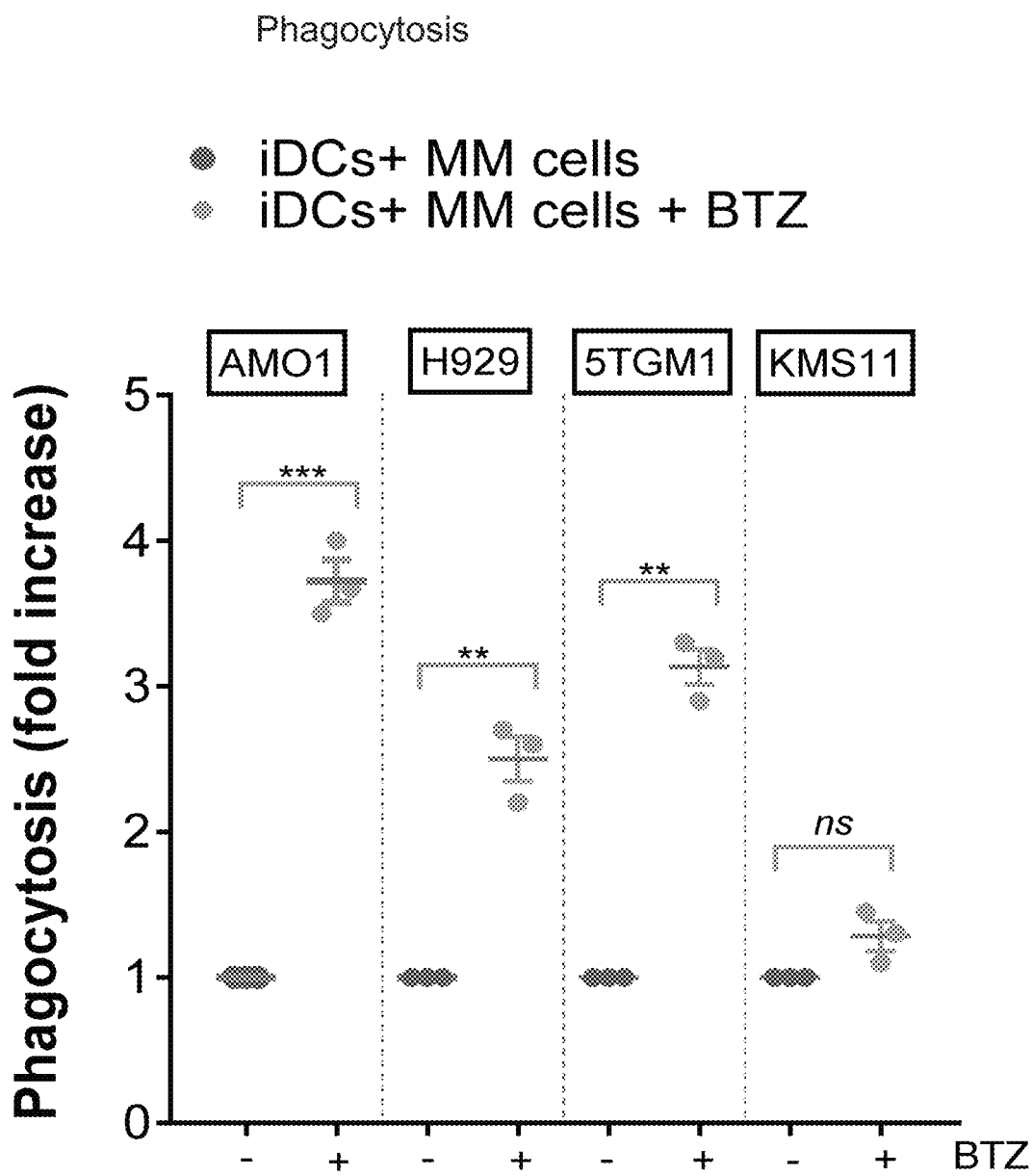

As demonstrated herein, CRT exposure is necessary for ICD induction by BTZ in MM; however, the exact mechanisms of CRT translocation from endoplasmic reticulum to cell surface (exposure of CRT) are still unclear. CRT is a high affinity ligand of gamma-aminobutyric acid receptor-associated protein (GABARAP), that belongs to the LC3/GABARAP family proteins, the major players in the autophagy process which in turn regulates intracellular vesicular transport. This gene is located on chromosome 17p13.1, and as demonstrated herein, its deletion confers poor prognosis in MM patients. Analysis of GABARAP expression in MM patients enrolled in the IFM/DFCI 2009 clinical study confirmed that lower GABARAP expression was associated with poor clinical outcome (EFS, p=0.0032). In a similar analysis excluding patients with 17p deletion, it is confirmed herein its prognostic role to identify high-risk disease independent of deletion of 17p itself (EFS, p=0.018) (FIG. 13A). Surprisingly, BTZ treatment in KMS11 cells, which carry monoallelic deletion of GABARAP gene, did not lead to an increase of CRT exposure or functional maturation of co-cultured DCs, as shown by phagocytosis assays (FIG. 13D); and stable overexpression of GABARAP in KMS11 cells restored the functional sequelae of ICD induction after BTZ (FIG. 13E).

Figure 14A:
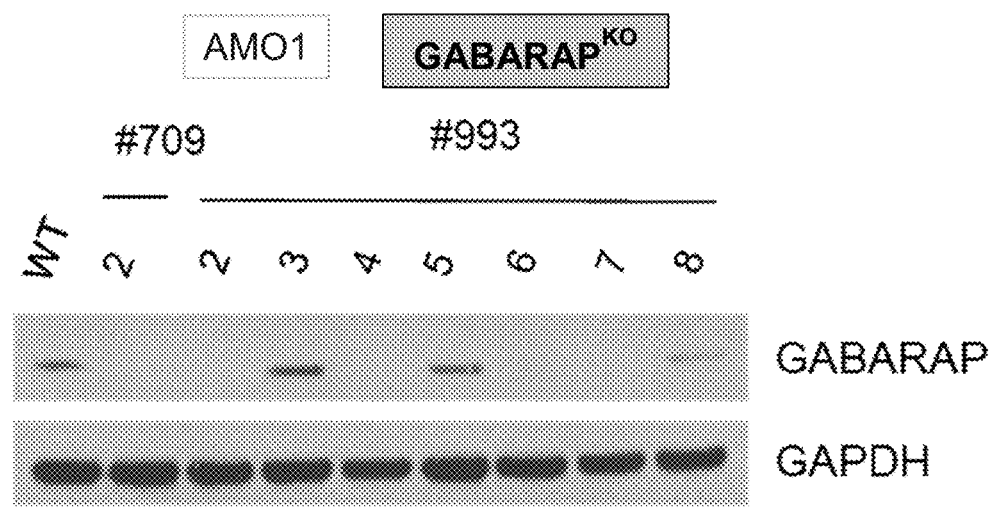
FIG. 14A-FIG. 14E show that GABARAP knock out impairs induction of ICD by BTZ. GABARAP$^{KO}$ blocks CALR exposure upon BTZ in AMO1 and H929 cell lines.
Figure 14A:
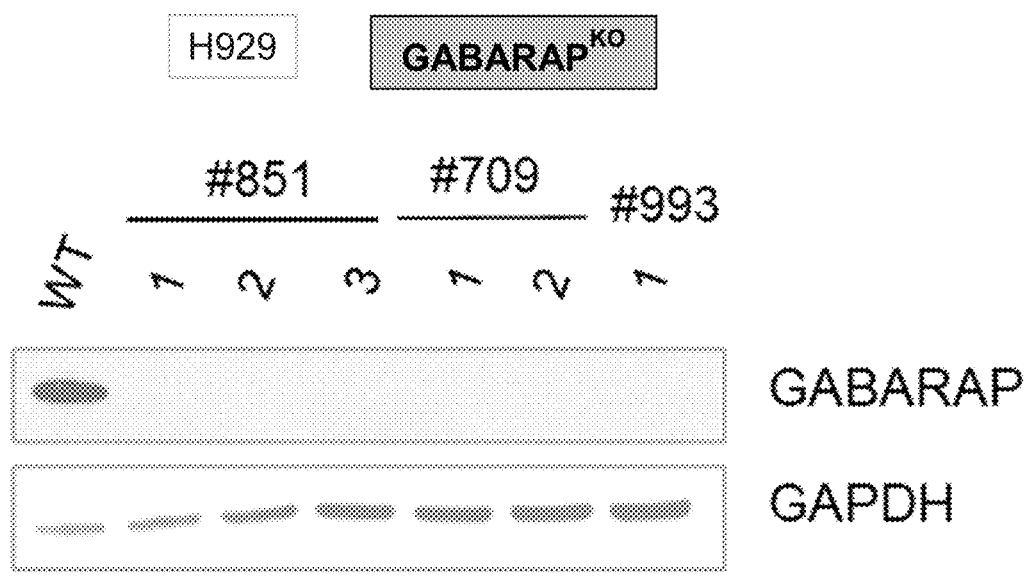
Figure 14B:
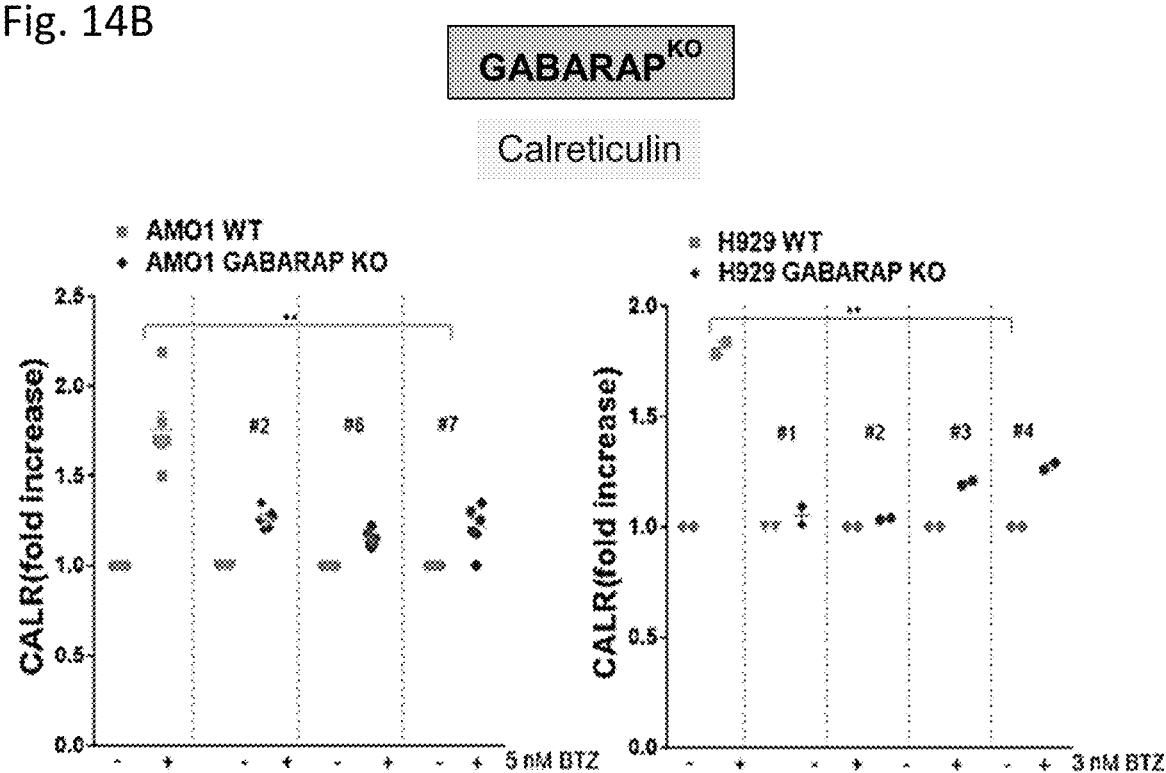
Figure 14C:
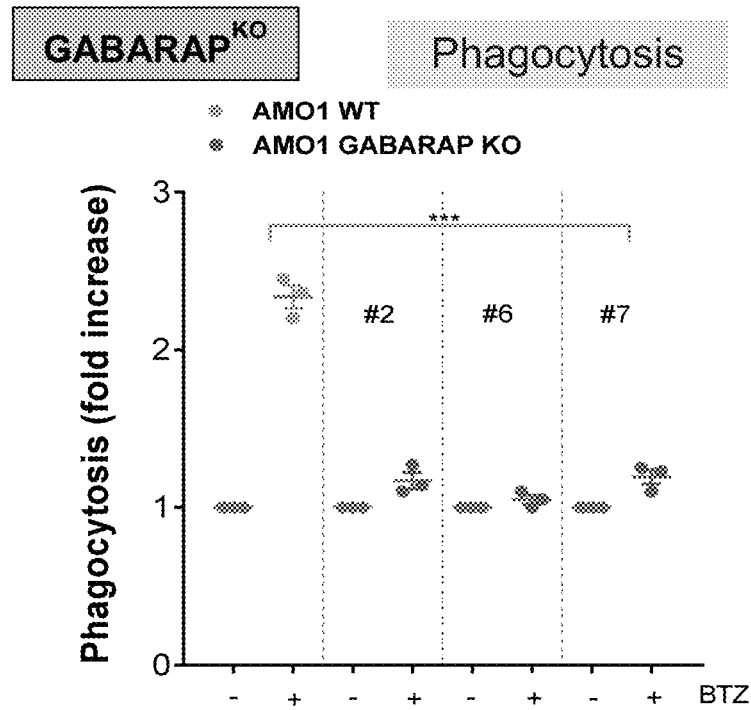
Figure 14D:
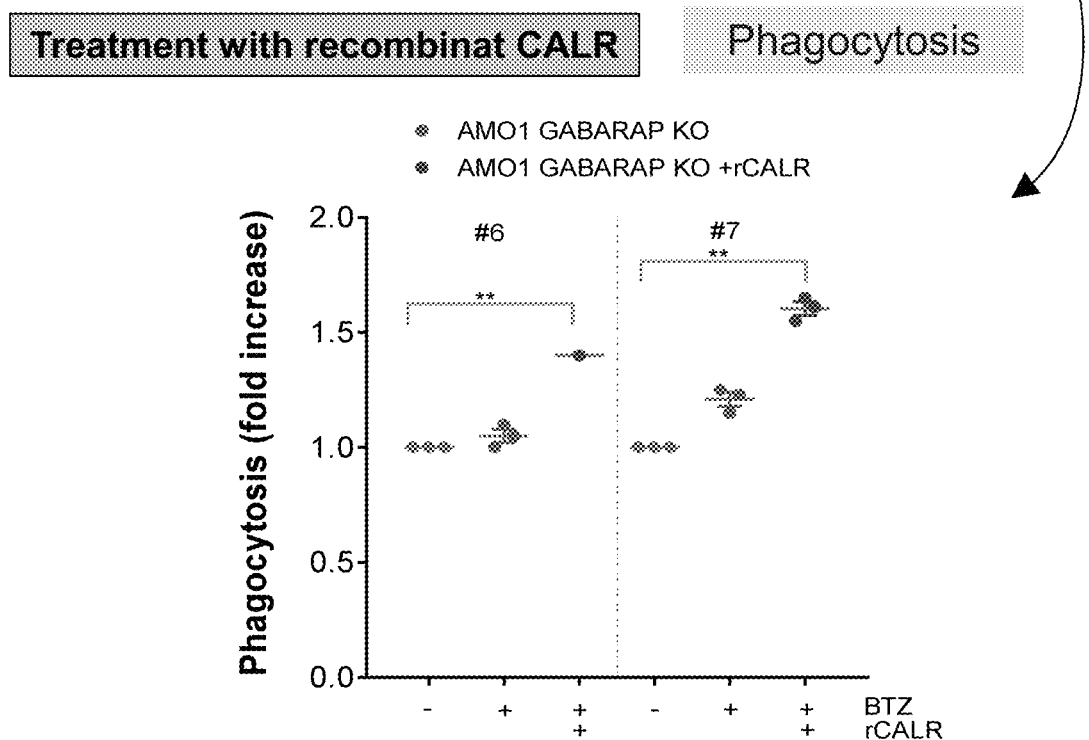
Figure 14E:
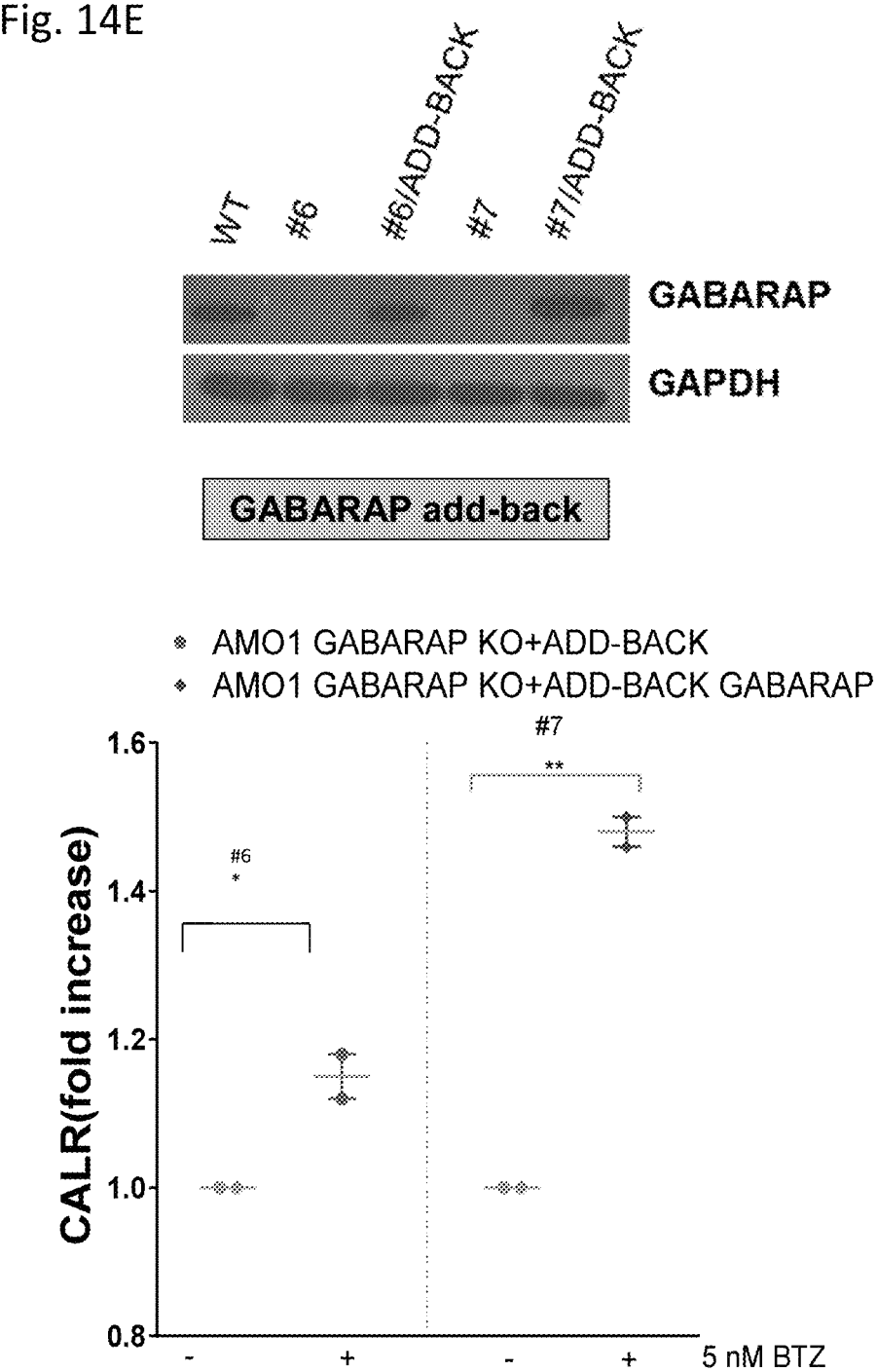
Figure 15A:
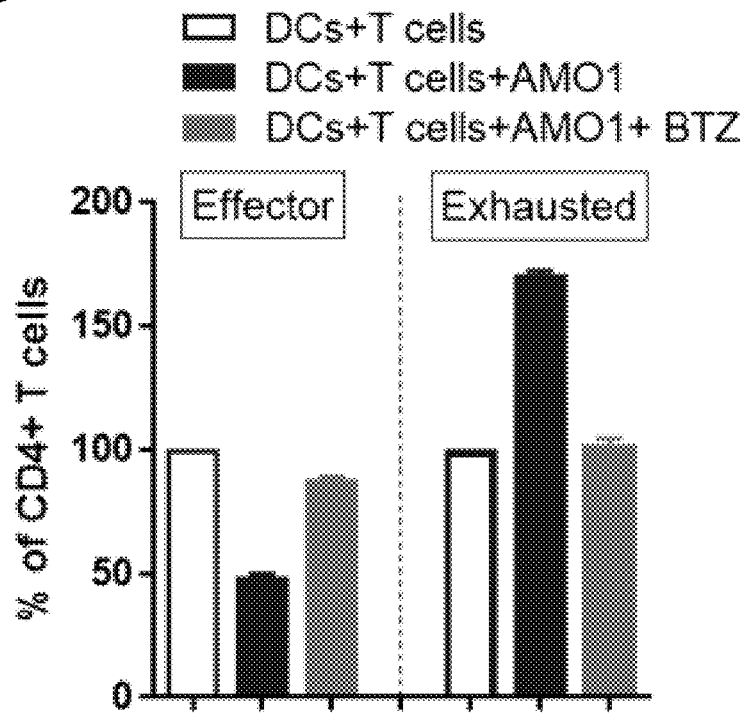
FIG. 15A-FIG. 15C show that GABARAP$^{KO}$ blocks T cell priming by DCs after BTZ treatment in MM. AMO1 WT or GABARAP$^{KO}$ were treated with BTZ and then co-cultured with DCs. After 24 h, the negative fraction of PBMCs used for DCs generation was added to the co-culture for 48 h. At the time of collection, CyTOF was performed. Histograms show percentage of CD4+ T cells induced by AMO1 WT (FIG. 15A) or GABARAP$^{KO}$ (FIG. 15B) alone or pre-treated with BTZ.
Figure 15B:
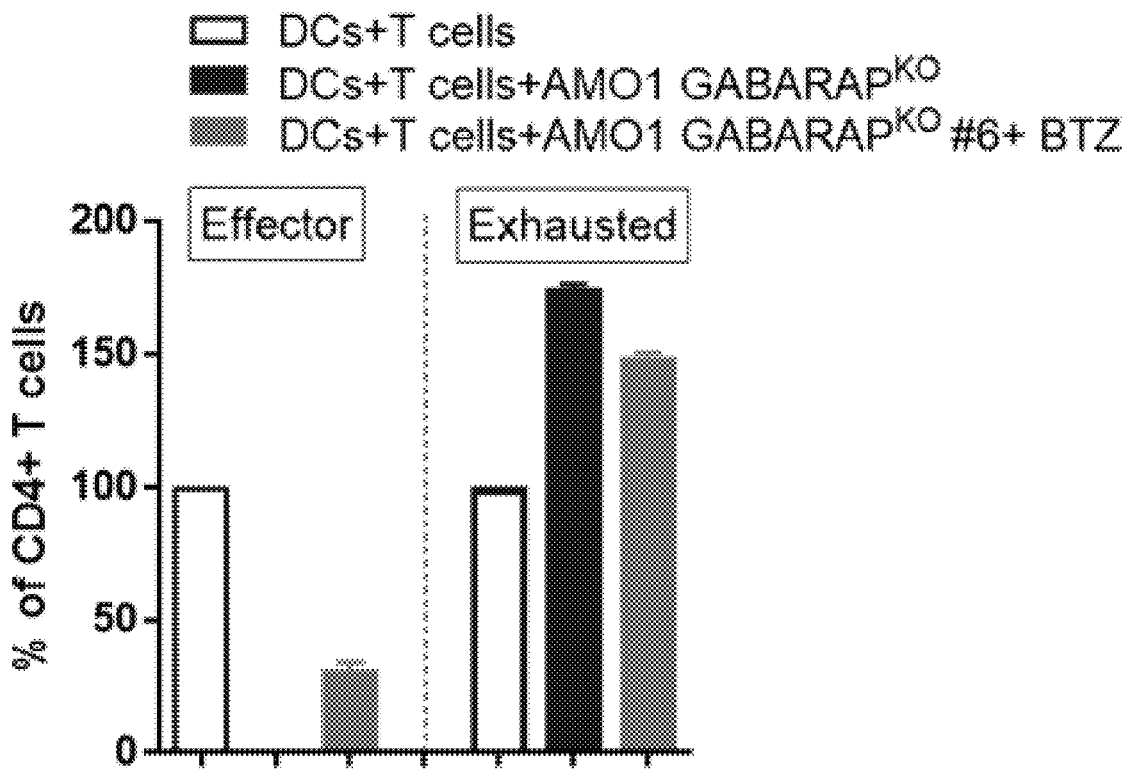
Figure 15C:
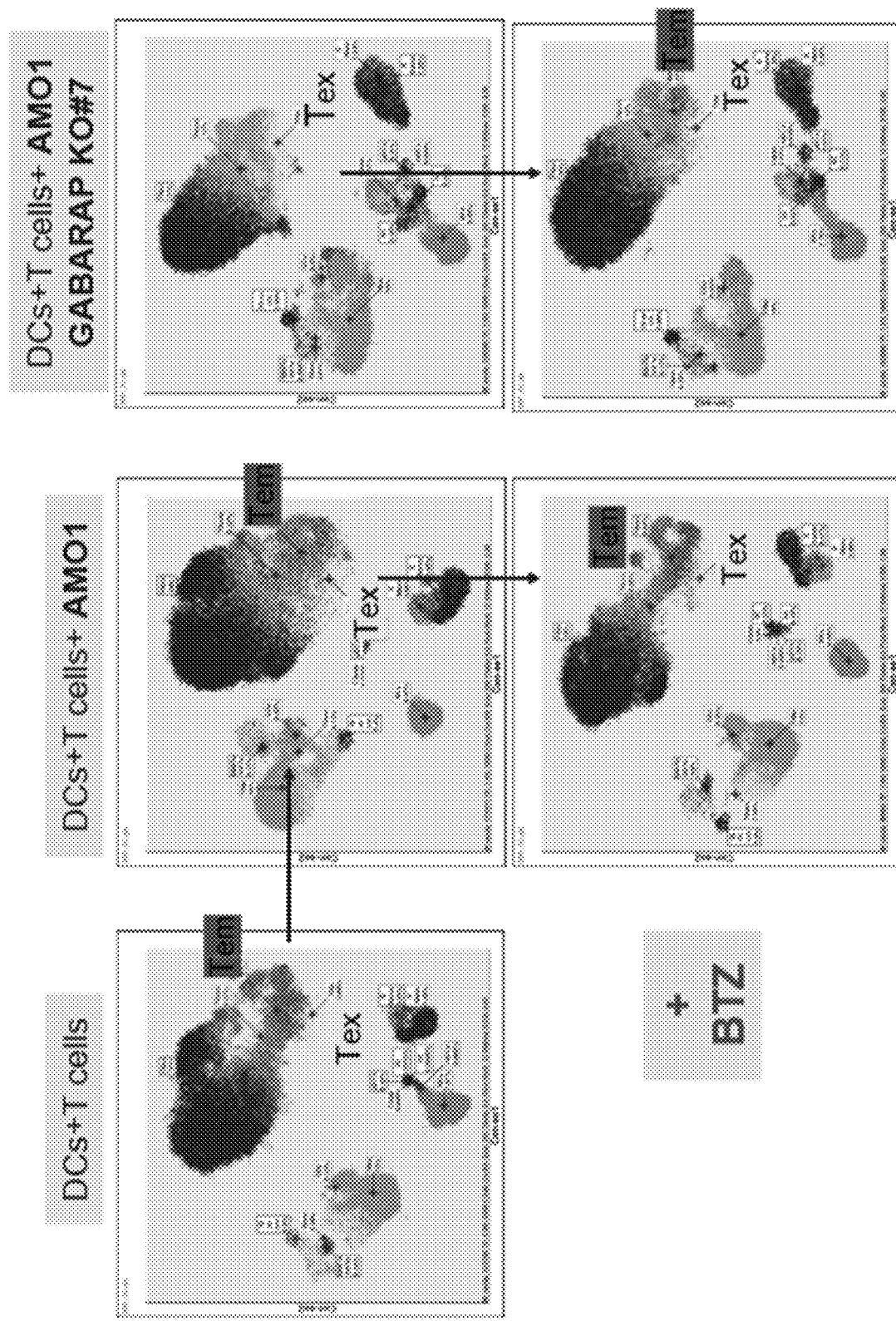

To test the specific role of loss-of-function of GABARAP in ICD induction, the AMO1 and H929 cell lines GABARAP$^{KO}$ cells (FIG. 14A) were generated. BTZ did not increase CRT exposure in AMO1 and H929 KO clones (FIG. 14B) and did not stimulate phagocytosis by DCs (FIG. 14C). Add-back experiments by treatment with recombinant CRT (rCRT) or GABARAP overexpression in KO cells restored phagocytosis of MM cells after BTZ (FIGS. 14D-14E). Next, mass cytometry (CyTOF) was performed for functional and phenotypic analysis of T cells after coculture with DCs primed by both WT and GABARAP KO AMO1. Importantly, treatment of MM cells with BTZ switched CD4+ T cells towards an effector memory function (FIG. 15A); in contrast, BTZ treatment of GABARAPKO clones with BTZ led to T cell exhaustion (FIG. 15B).

Figure 16A:
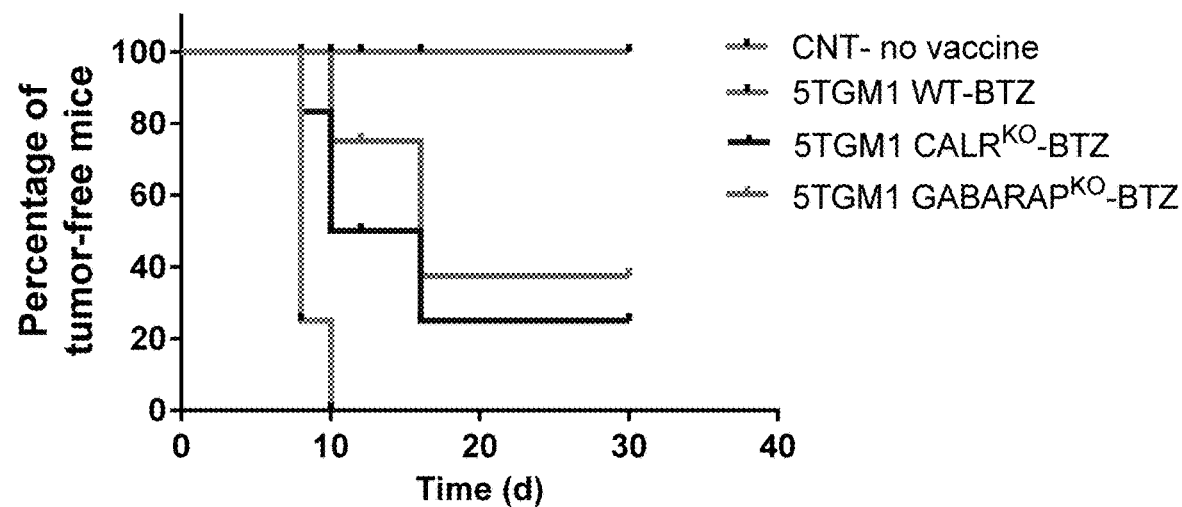
FIG. 16A and FIG. 16B show that GABARAP$^{KO}$ cells treated with BTZ fail to protect against tumor re-challenge in vivo.
Figure 16B:
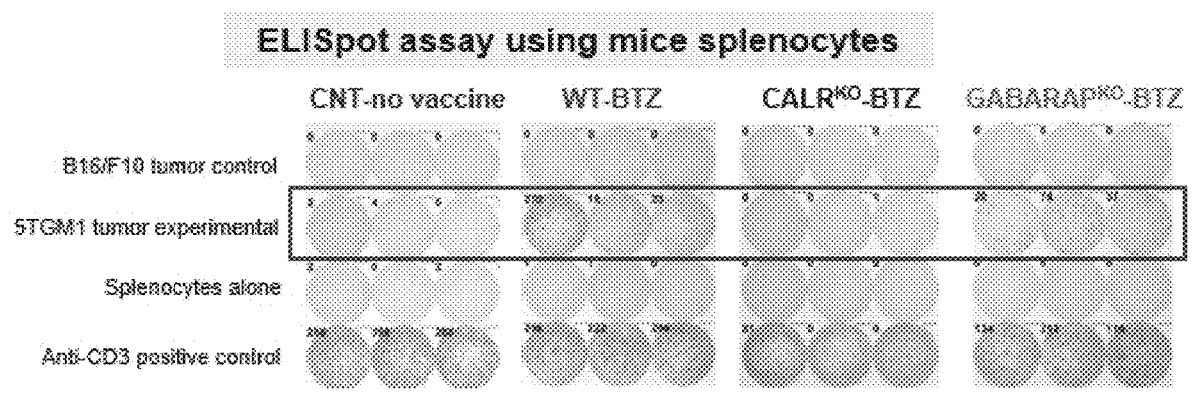

To confirm the role of GABARAP in ICD induction by BTZ in vivo, a vaccination study was performed. In vitro BTZ-treated 5TGM1 cells were used as a vaccine to enhance an anti-MM immune response in vivo: injection of live tumor cells resulted in palpable tumors in non-vaccinated mice by 1 week; conversely, similar injection in vaccinated mice did not result in detectable tumor after 30 days. Mice were similarly vaccinated with BTZ-treated crt KO and gabarap KO 5TGM1 and challenged with injection of live WT cells: only 40% of vaccinated mice were tumor-free at day 30 in gabarap KO group (FIG. 16A).

Various combination of BTZ with other drugs may restore the induction of ICD in GABARAP deleted patients, such as those high-risk patients carrying del(17p). In some embodiments, such subjects carrying del(17p) and/or cell thereof are treated/contacted with an agent described herein.

The following Examples further support and confirm the results described above.

Example 4: Bortezomib Induces Anti-Multiple Myeloma Immune Response Mediated by cGAS/STING Pathway Activation Multiple myeloma (MM) is a malignancy of plasma cells in the bone marrow (BM)(Gulla and Anderson (2020) *Haematologica* doi 10.3324/haematol.2020.247015; Kumar et al. (2017) *Nat Rev Dis Primers;* 3:17046). Despite remarkable improvement in patient survival due to the development of proteasome inhibitors (PIs) and immunomodulatory drugs (IMiDs), the clinical management of MM patients remains challenging. Constitutive and ongoing genetic complexity of MM cells, coupled with the tumor promoting, immunosuppressive BM microenvironment, underlie relapse of disease and remain an obstacle to cure (Nakamura et al. (2020) *Blood*; doi 10.1182/blood.2020006540). More recently, integration of monoclonal antibodies into the treatment of both newly-diagnosed and relapsed/refractory MM has further improved patient outcome (See Guilla A. et al. (2017) cited above; Wudhikarn et al. (2020) *Best Pract Res Clin Haematol;* 33(1):101143). However, dysfunction of innate and adaptive immunity, specifically involving the T cell compartment, highlights the need for novel approaches to enhance anti-MM immunity and achieve more durable responses.

Specific anti-tumor immunity can be triggered by therapeutic agents via "immunogenic cell death" (ICD) (Galluzzi et al. (2015) *Cancer Cell;* 28(6):690-714; Kroemer et al. (2013) *Annu Rev Immunol;* 31:51-72; Casares et al. (2005)

*J Exp Med;* 202(12):1691-701). During treatment-related induction of ICD, endogenous tumor cell proteins are recognized as damage-associated molecular patterns (DAMPs) and activate cancer-specific immune responses (Galluzzi et al. (2020) *J Immunother Cancer;* 8(1); Bloy et al. (2017) *Immunol Rev;* 280(1):165-74). Among several DAMPs, endoplasmic reticulum (ER) protein calreticulin (CALR) exposure on the tumor cell surface is triggered by activation of the unfolded protein response (UPR) and represents a potent "eat me signal", allowing for efficient phagocytosis of dying cancer cells by dendritic cells (DCs) and induction of a specific anti-tumor immune response (Obeid et al. (2007) *Nat Med;* 13(1):54-61). The clinical efficacy of ICD inducers is therefore due to their ability to redirect the patient's immune system against their own tumor (Bloy et al. (2017) *Immunol Rev;* 280(1):165-74; Zitvogel L et al. (2008) *J Clin Invest;* 118(6):1991-2001). To date, identification of immunogenic properties of conventional therapeutics, such as anthracyclines and oxaliplatin, has informed their clinical application in combination with immune therapies to enhance responses in immunologically "cold" solid tumors (Galluzzi L et al. (2020) *Nat Rev Clin Oncol;* Kepp et al. (2019). Oncoimmunology; 8(10):e1637188).

The PI bortezomib (BTZ) is an effective anti-MM agents (Richardson et al. (2007) *Blood;* 110(10):3557-60; Richardson et al. (2005) *N Engl J Med;* 352(24):2487-98). Excessive protein overload in MM cells renders them dependent on proteasome activity; conversely, PIs induce accumulation of misfolded proteins, endoplasmic reticulum (ER) stress, and MM cell death (Bianchi et al. (2009) *Blood;* 113(13): 3040-9). Indeed, proteasome inhibition impacts the quality control of proteins critical for MM survival (Gandolfi et al. (2017) *Cancer Metastasis* Rev; 36(4):561-84), including those involved in DNA repair (Neri et al (2011) Blood; 118(24):6368-79). Extensive preclinical studies have defined the mechanisms of action of BTZ on tumor cells and accessory cells, i.e. osteoclasts, in the BM milieu (Gandolfi et al (2017) *Cancer Metastasis Rev;* 36(4):561-84; Accardi et al. (2015) FBiomed Res Int; 2015:172458). However, the mechanism whereby BTZ triggers ICD, as well as its biological and clinical significance, are not fully characterized (Spisek et al. (2007) Blood; 109(11):4839-45; Serrano-Del Valle et al. (2019) Front Cell Dev Biol; 7:50; Jarauta et al. (2016) Cancer Lett; 382(1):1-10; De Beck, et al. (2018) Oncoimmunology; 7(10):e1484981). The mechanistic details regarding the immunotherapeutic role of BTZ in multiple myeloma are provided herein. Also provided herein are validation of STING signaling mediating BTZ-induced anti-tumor immunity, providing the preclinical rationale for clinical trials evaluating BTZ-STING agonist combination therapy to improve patient outcome in multiple myeloma.

BTZ Induces ICD and Stimulates Anti-Cancer Immunity In Vitro.

Figure 17A:
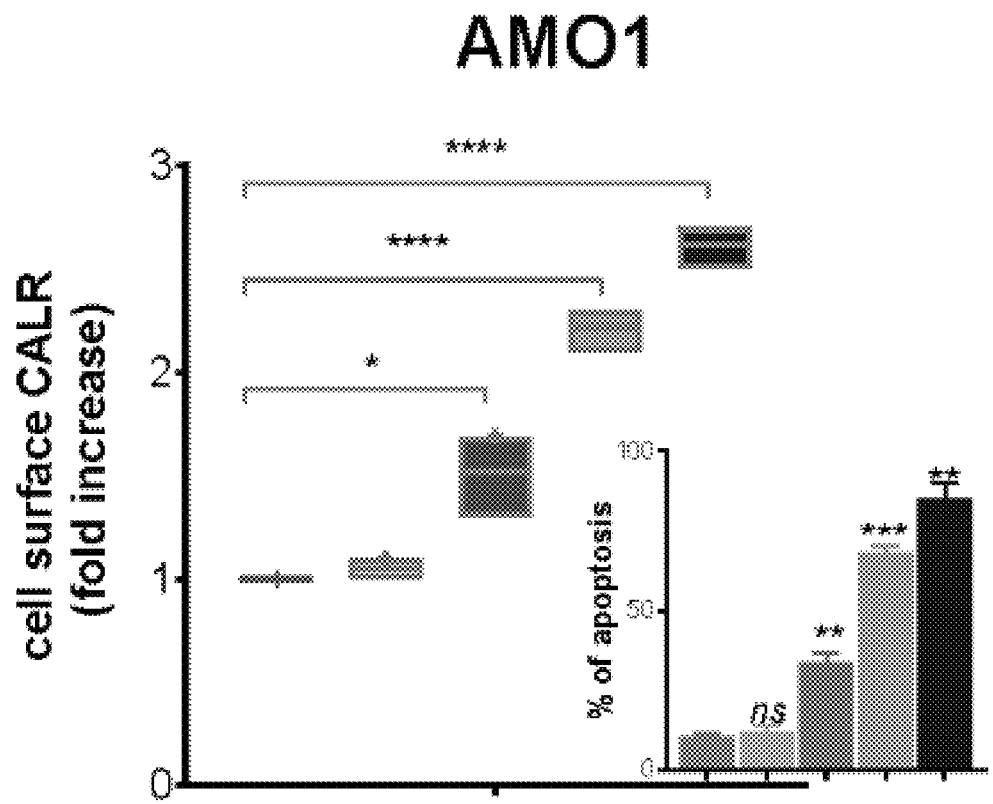
FIG. 17A to FIG. 17G Bortezomib (BTZ) induces immunogenic cell death (ICD) in MM cells in vitro.
Figure 17A:
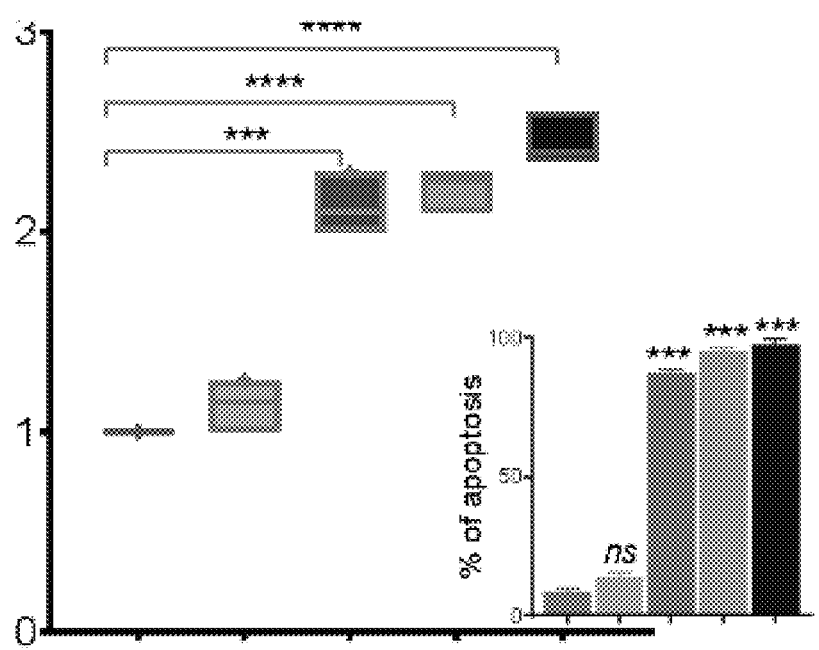
Figure 17A:
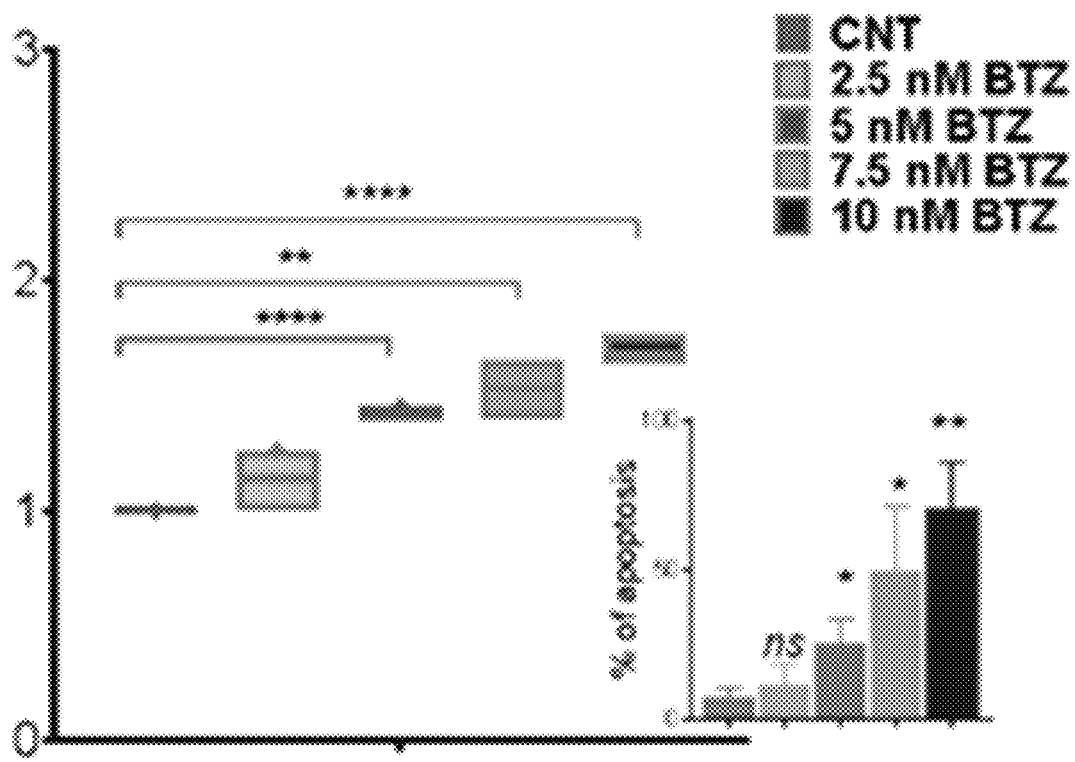
Figure 17B:
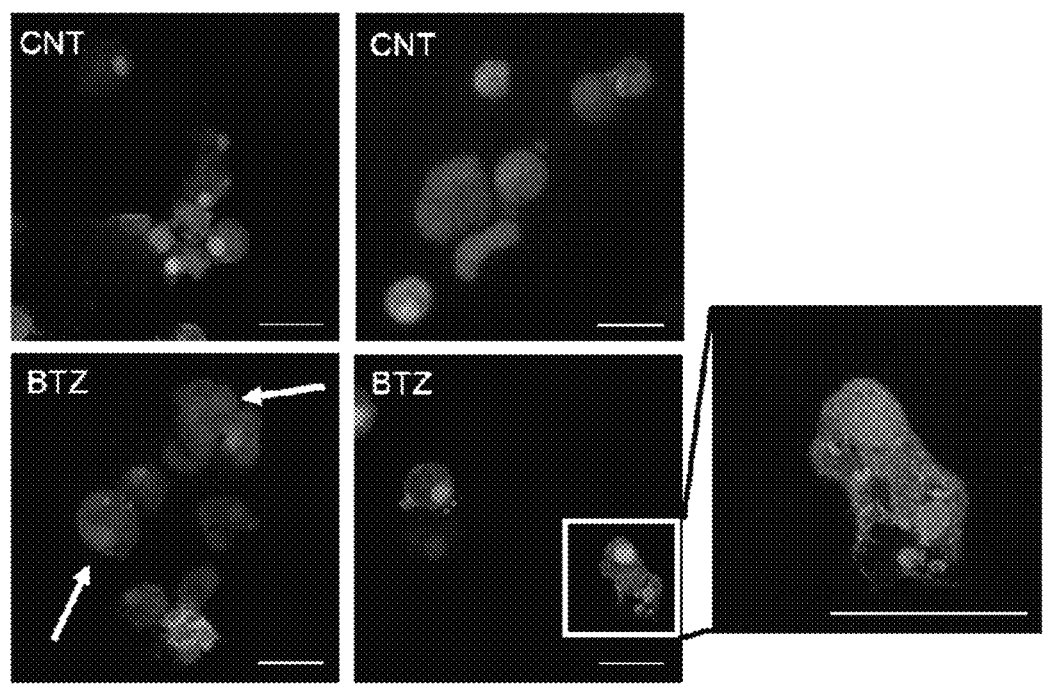
Figure 17C:
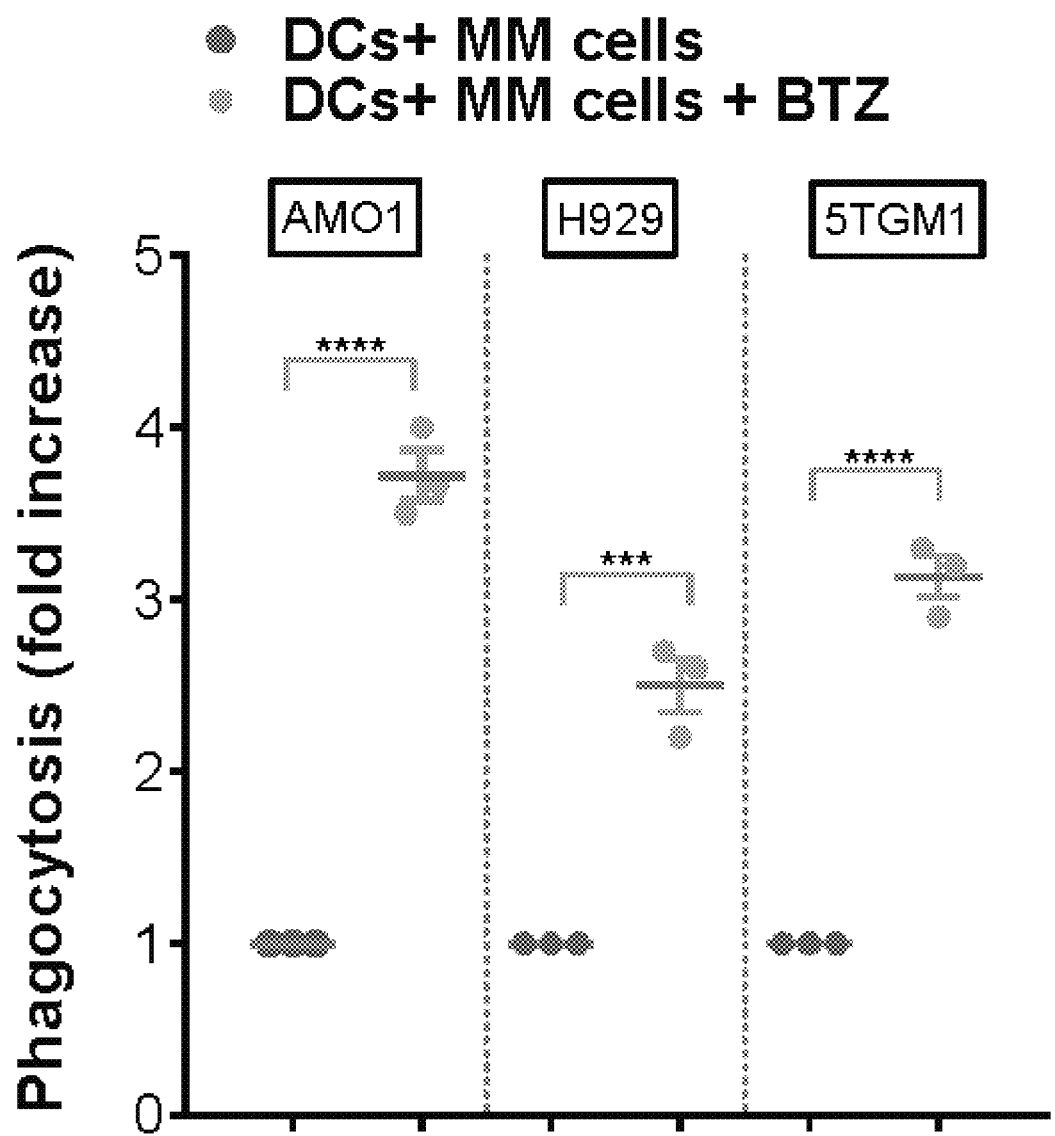
Figure 17D:
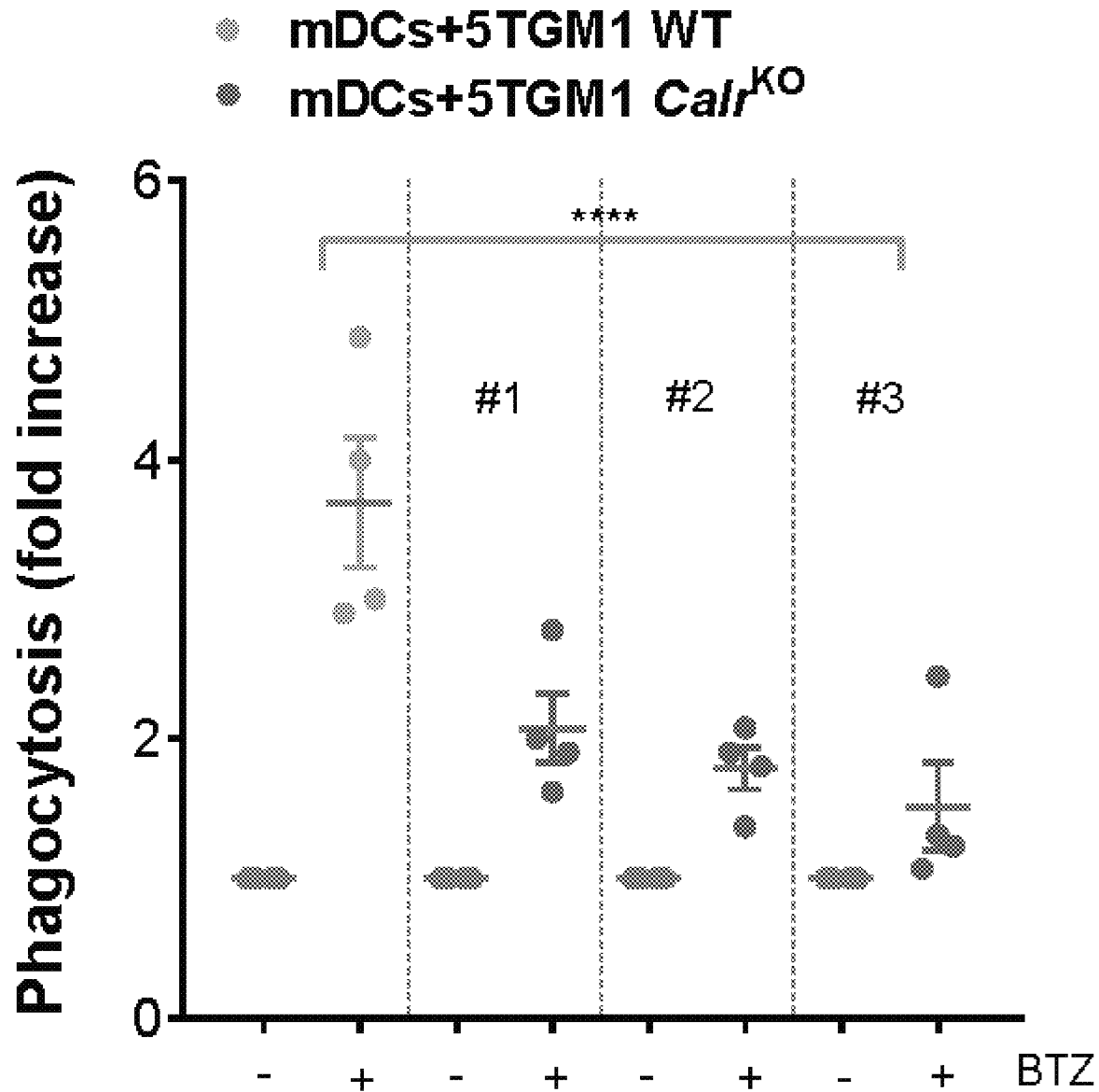
Figure 17E:
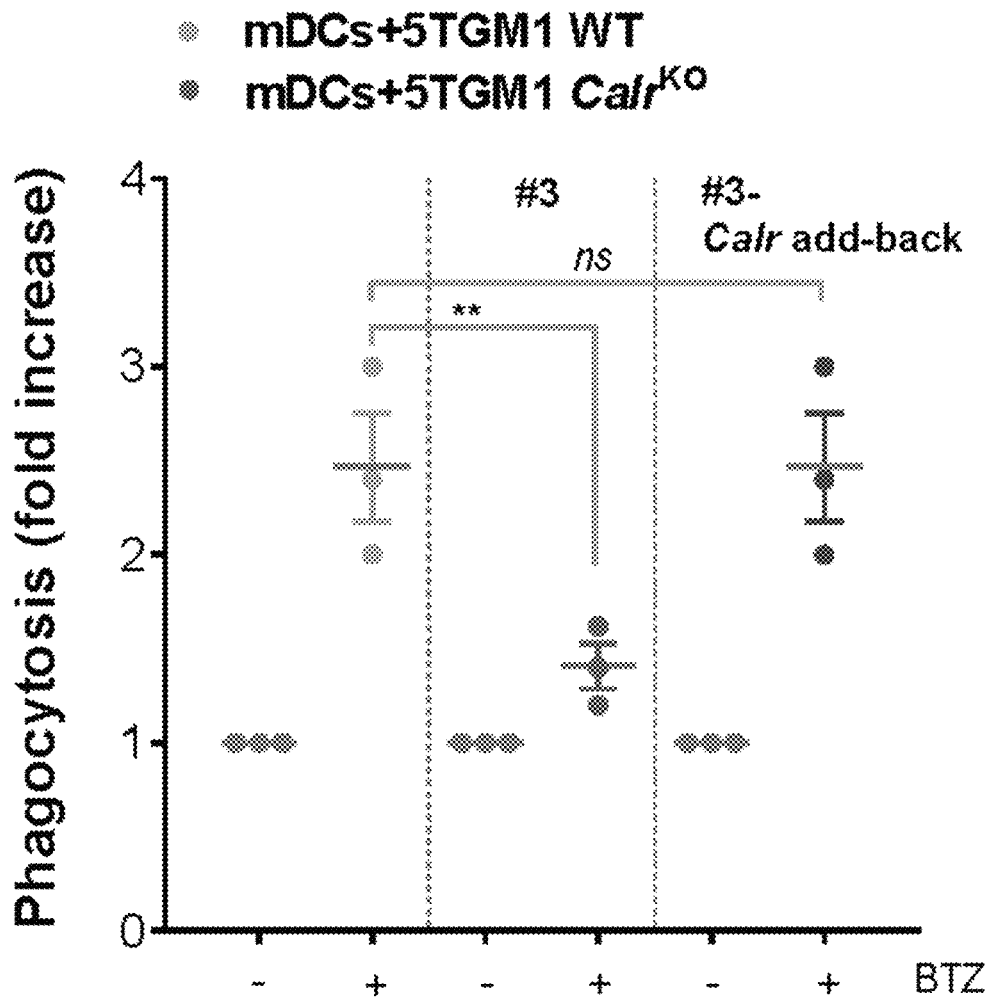
Figure 17E:
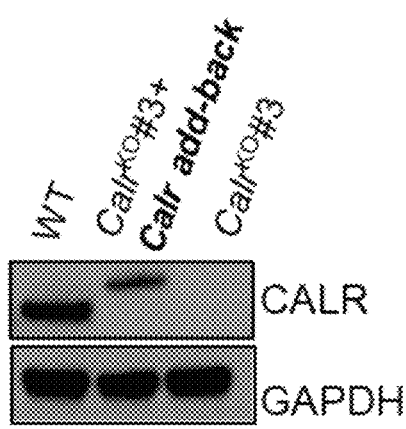
Figure 23A:
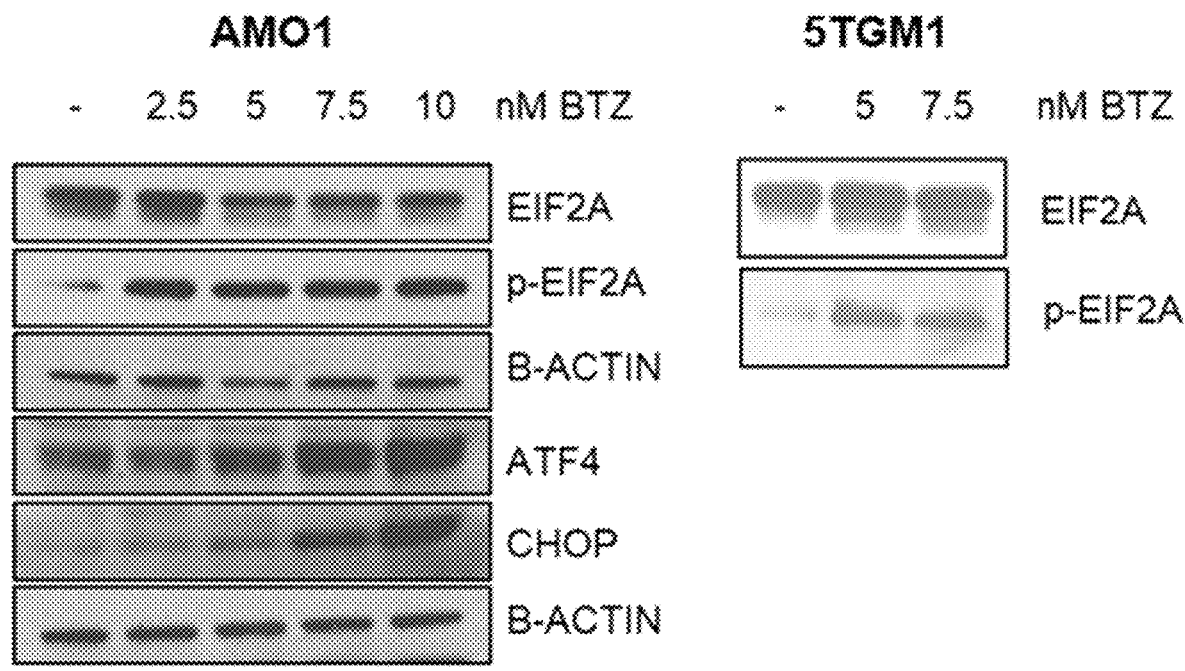
FIG. 23A to FIG. 23F shows bortezomib (BTZ) induces immunogenic cell death (ICD) in vitro.
Figure 23B:
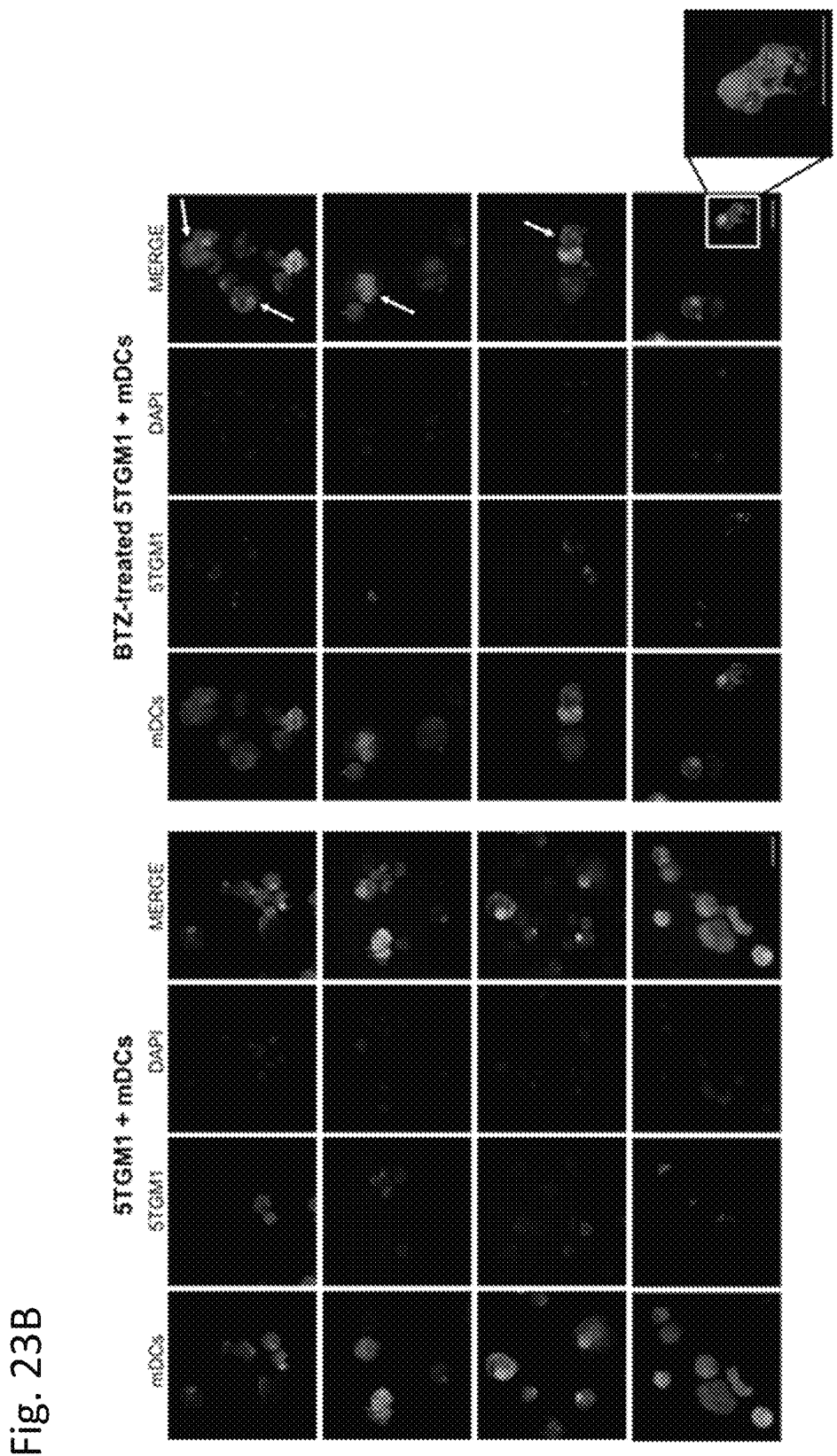
Figure 23C:
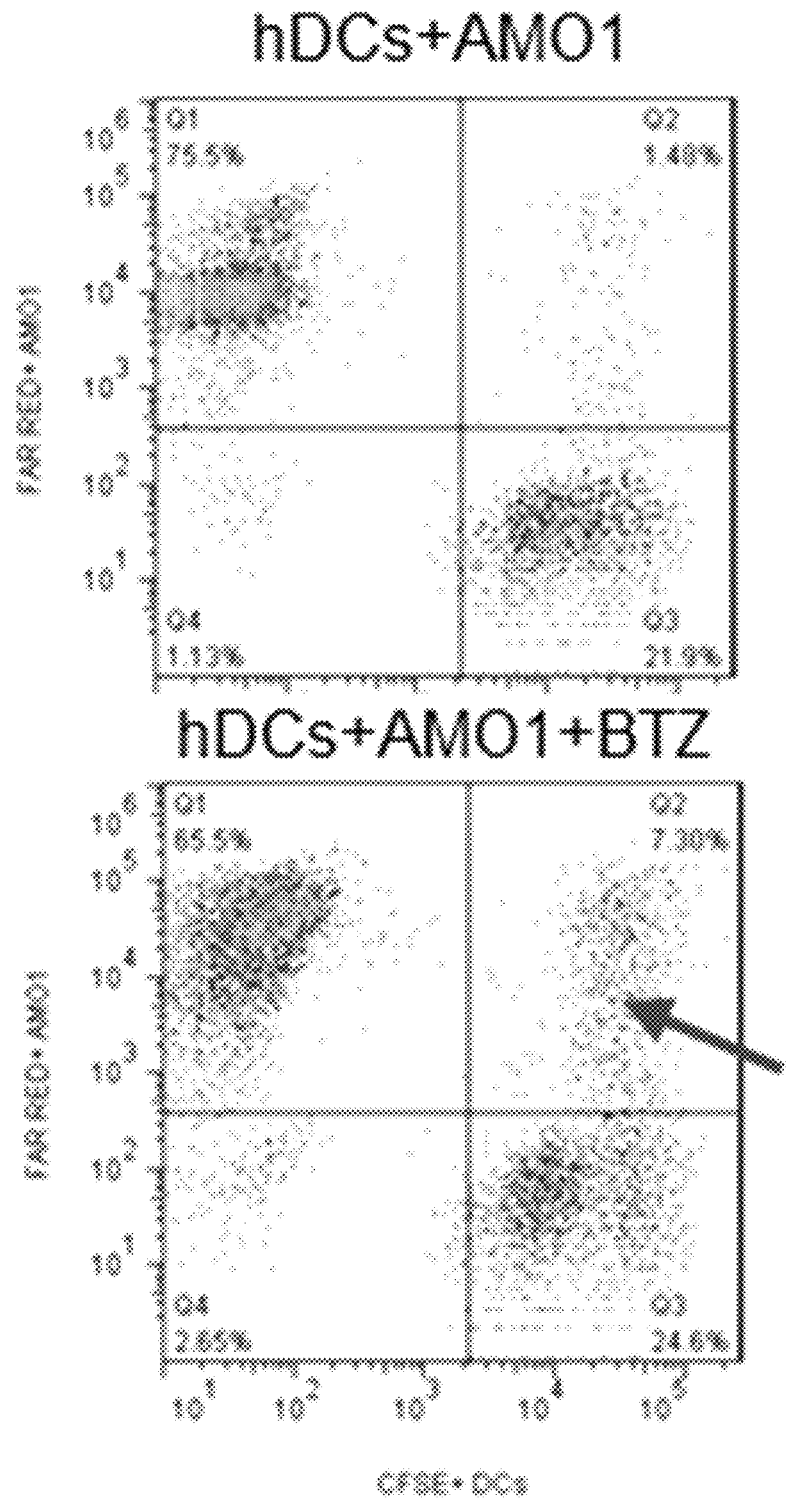
Figure 23D:
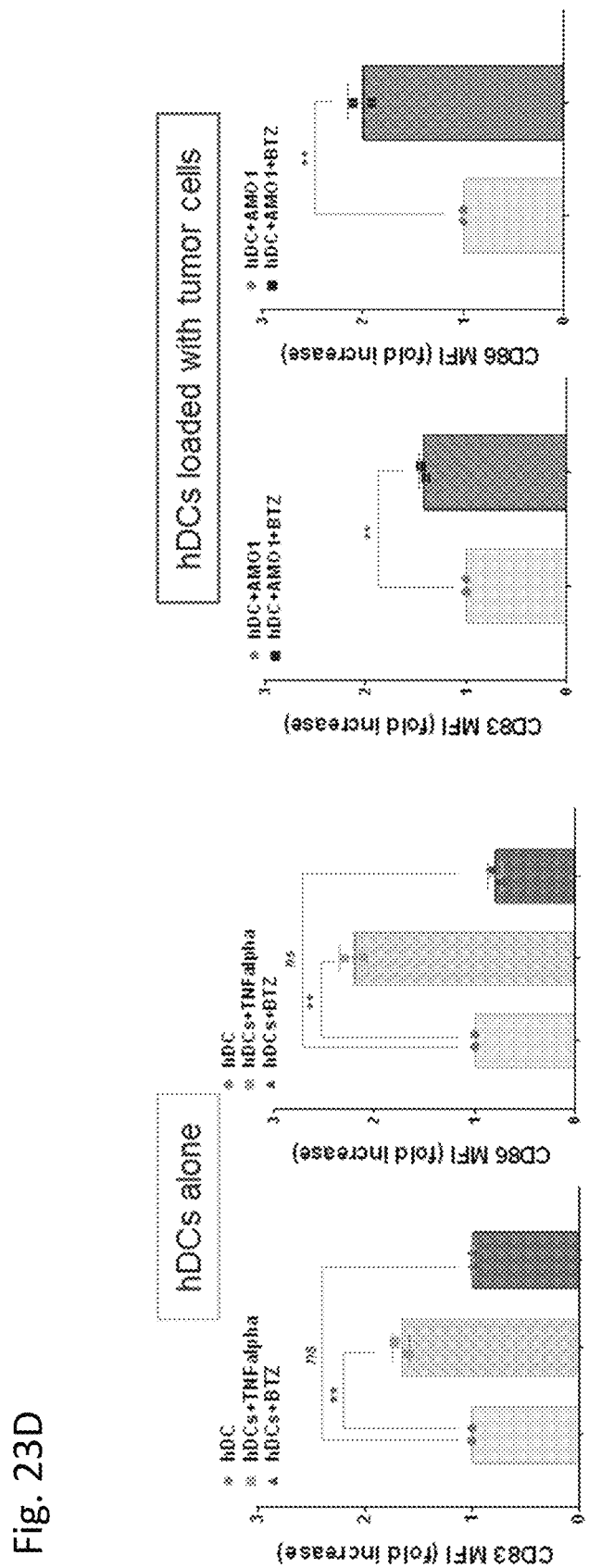
Figure 23E:
Figure 23F:
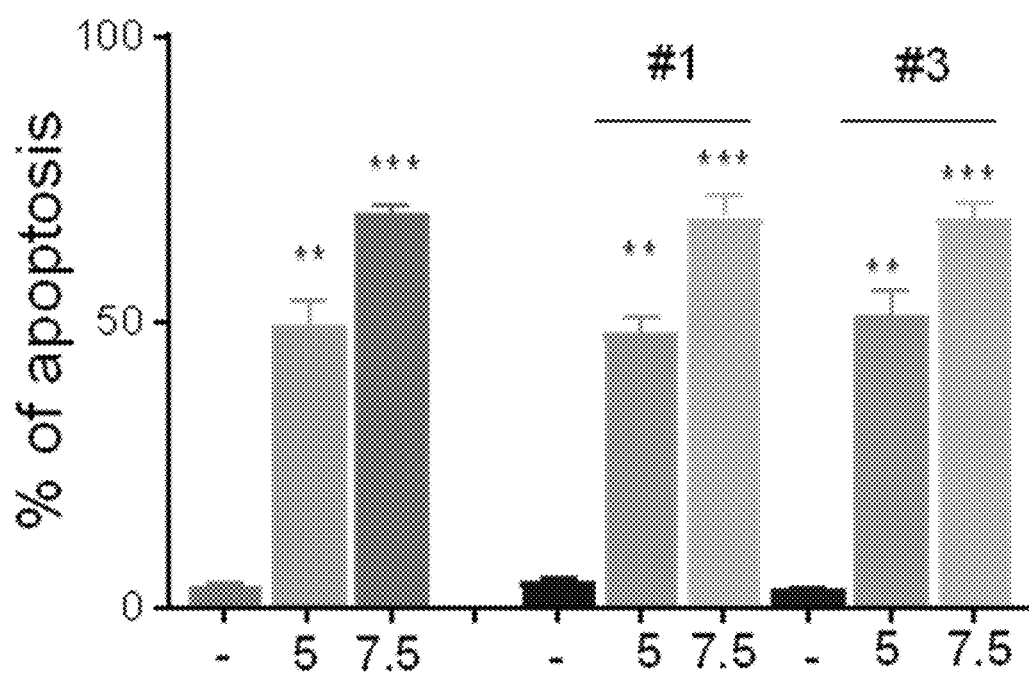

The effect of BTZ treatment on human AMO1 and NCI-H929 was assessed, as well as murine 5TGM1, multiple myeloma cell lines. BTZ induced multiple myeloma cell death in a dose-dependent manner, as measured by phosphatidylserine exposure (FIG. 17A, internal panel). As seen in FIG. 17A, BTZ also triggered a dose-dependent increase of CTLR exposure on the outer leaflet of multiple myeloma cell plasma membranes; and consistently activated the UPR transducer PERK pathway, evidenced by increased phosphorylation of the translation initiation factor eIF2-α (p-eIF2-α) and increased levels of CHOP and ATF4 proteins (FIG. 23A). Confocal analysis showed that BTZ-treated multiple myeloma cells, but not untreated cells, were engulfed by monocyte-derived DCs after 4 h of co-culture (FIG. 17B and FIG. 23B); and flow cytometry-based phagocytosis assay confirmed this effect in both human (AMO1 and NCI-H929) and murine 5TGM1 multiple myeloma cells (FIG. 17C and FIG. 23C). Phagocytosis of BTZ-treated AMO1 cells stimulated maturation of DCs, as shown by increased expression of CD83 and CD86 maturation markers, which was not triggered by either untreated multiple myeloma cells or BTZ alone (FIG. 23D). To confirm the essential role of CALR on phagocytosis by DCs, murine 5TGM1 Calr knock-out (Calr$^{KO}$) cells were generated (FIG. 17E). Although BTZ triggered apoptosis in both 5TGM1 WT cells and the Calr$^{KO}$ clones at the same extent (FIG. 17F), phagocytosis of BTZ-treated Calr$^{KO}$ multiple myeloma cells by DCs was inhibited (FIG. 17D). To confirm the specific on-target role of Calr loss in mediating suppression of phagocytosis, Calr in knock-out cells was re-expressed, which efficiently restored multiple myeloma cell phagocytosis by DCs (FIG. 17E) and confirmed the obligate role of CALR exposure in this process.

Figure 17F:
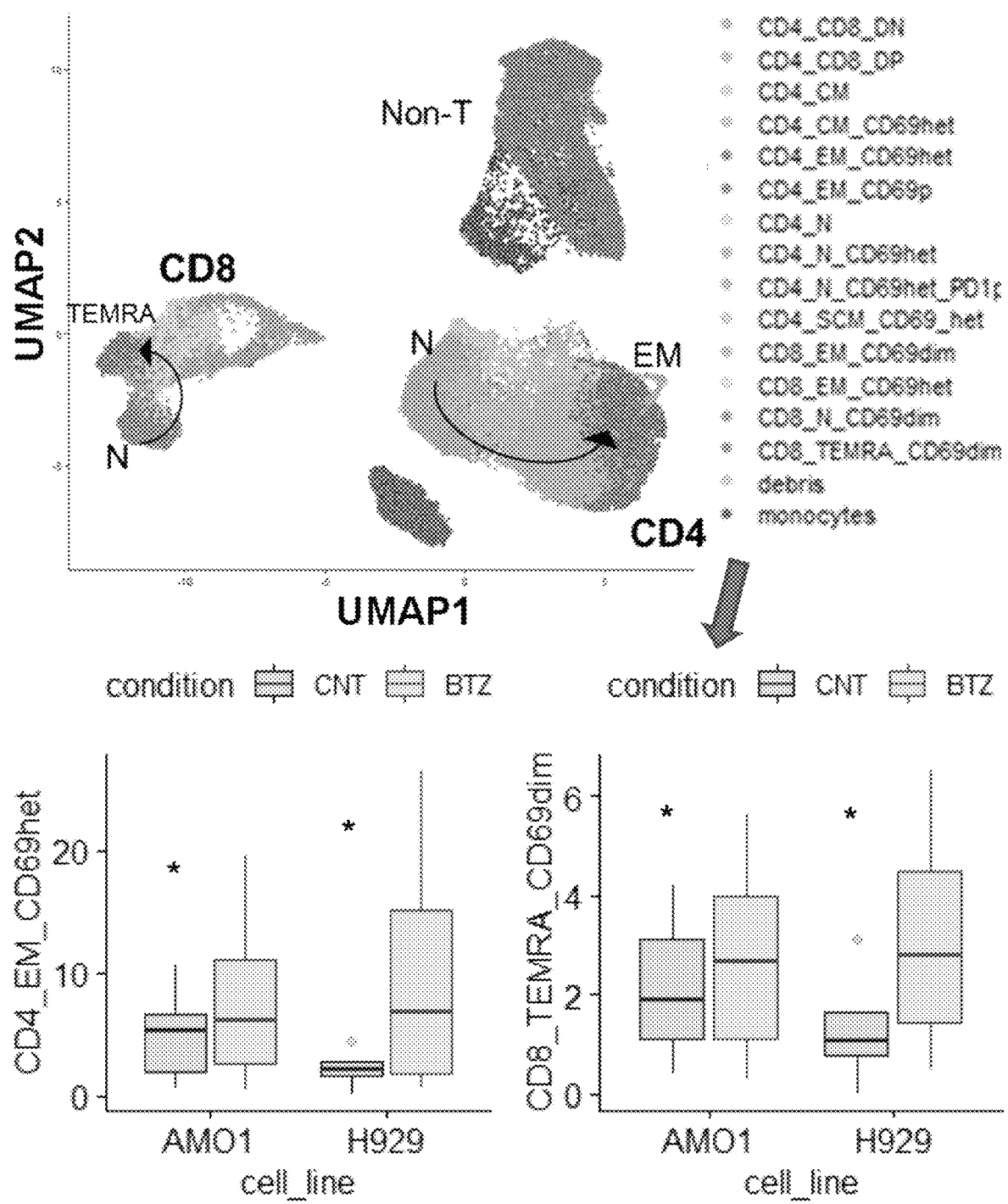
Figure 17G:
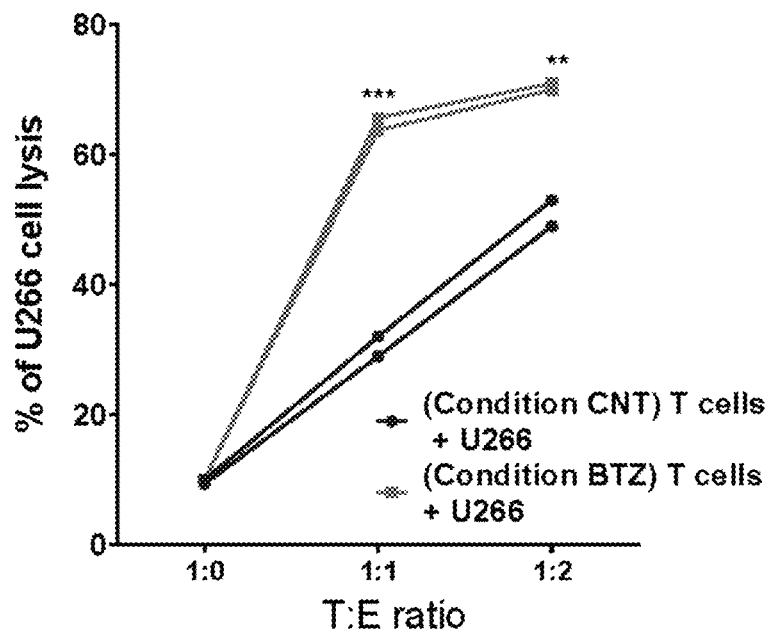
Figure 17G:
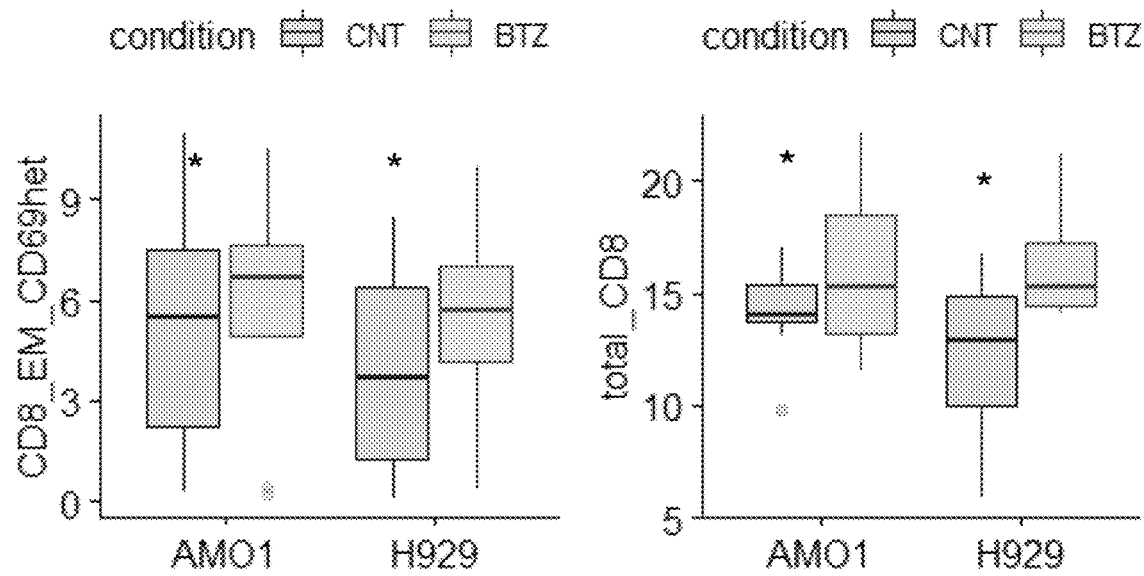
Figure 18A:
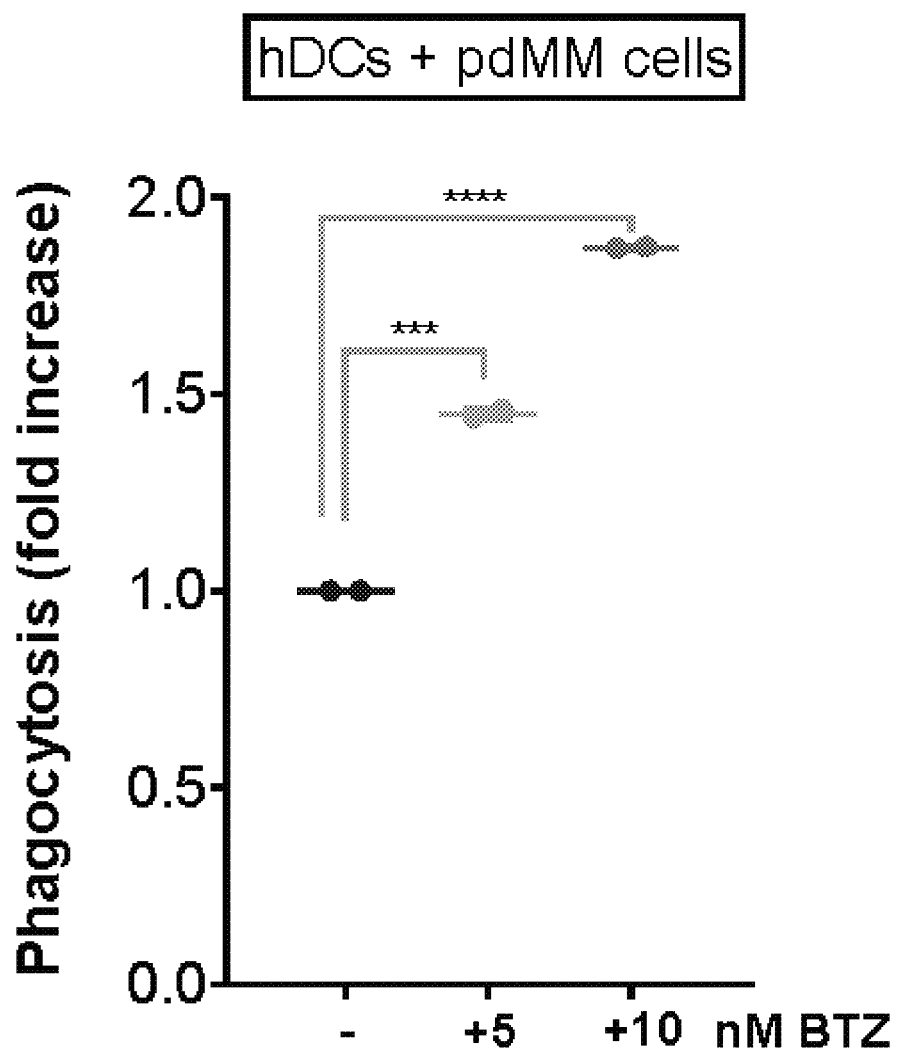
FIG. 18A to FIG. 18B shows BTZ-mediated induction of immune response in patient-derived MM cells in vitro.
Figure 18B:
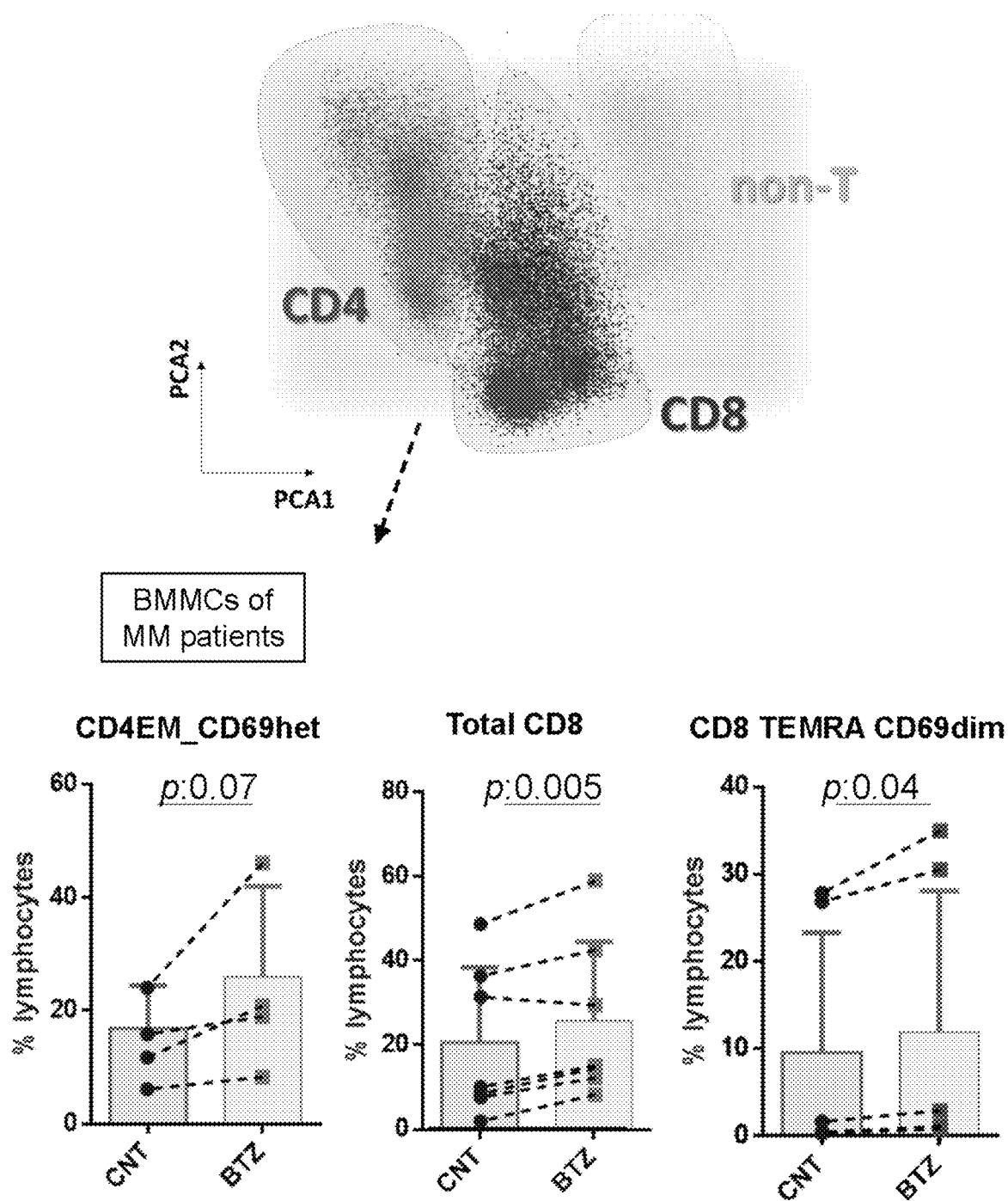
Figure 19A:
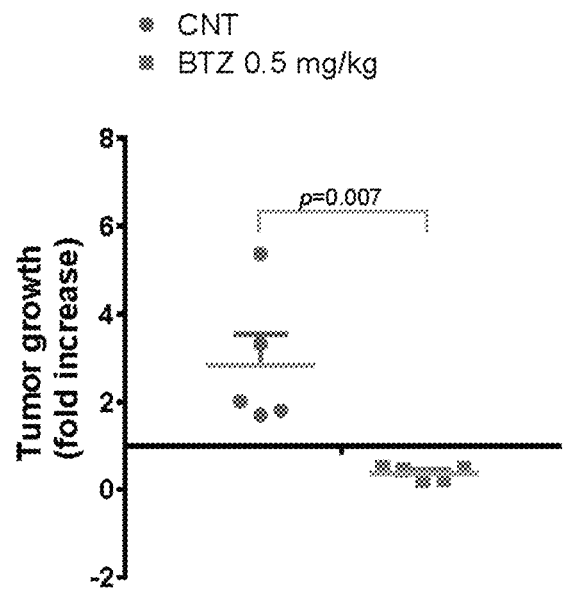
FIG. 19A to FIG. 19G shows BTZ induces ICD in a syngeneic murine model of MM.
Figure 19B:
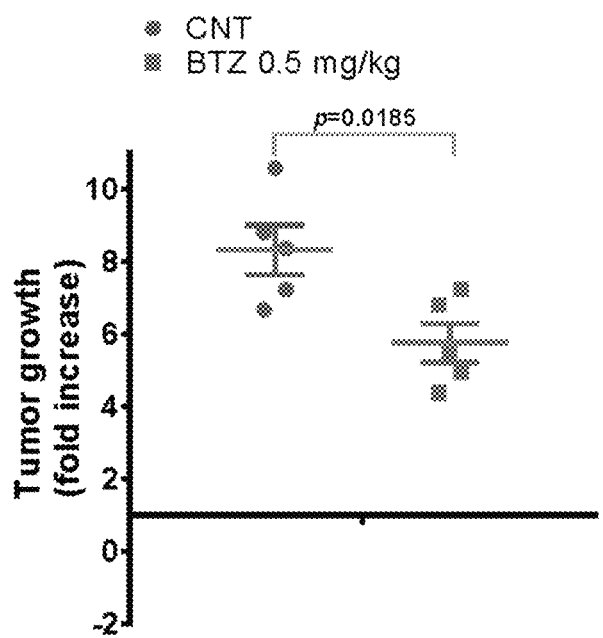
Figure 24A:
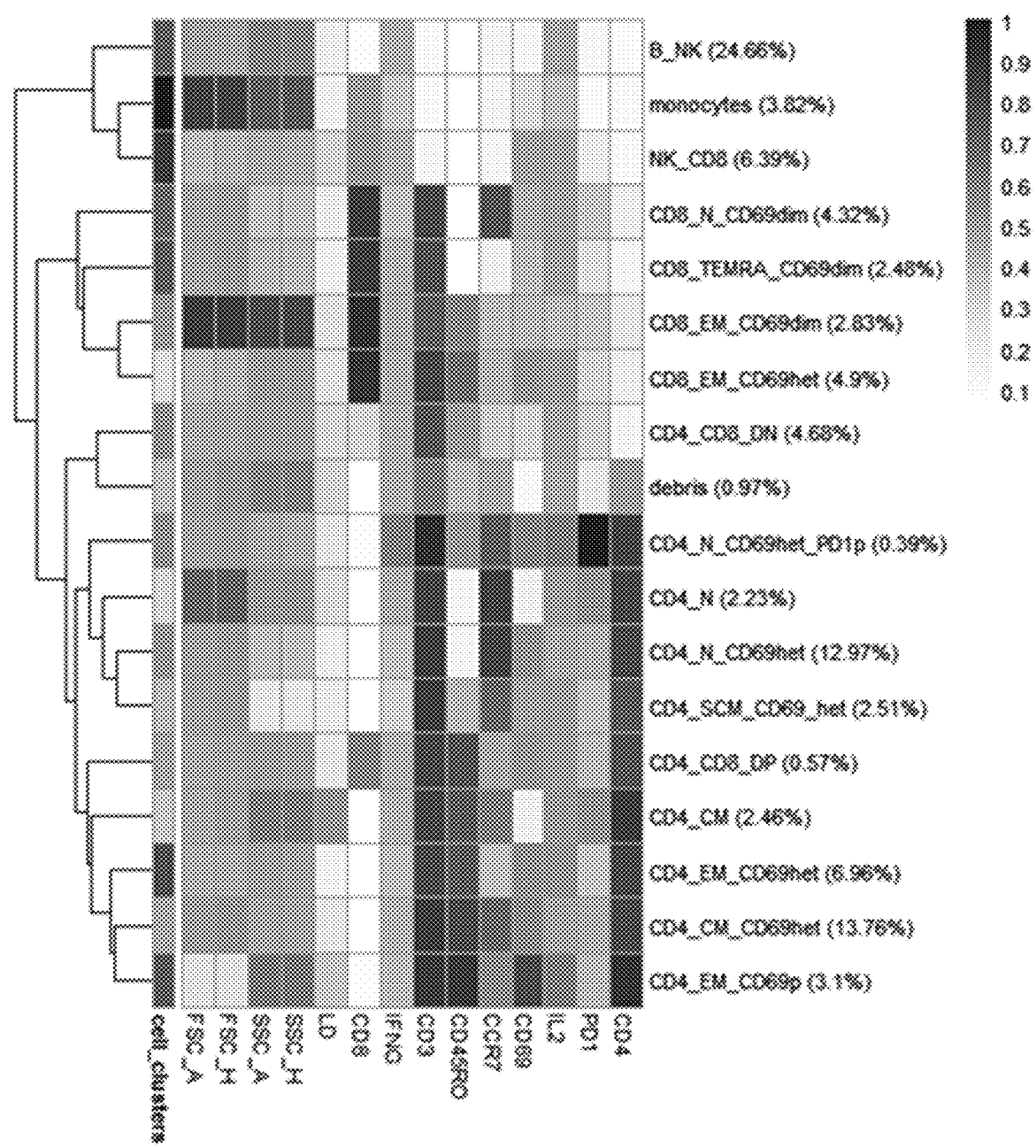
FIG. 24A to FIG. 24C shows BTZ treatment of co-culture of DCs and T cells does not induce T cell maturation.
Figure 24B:
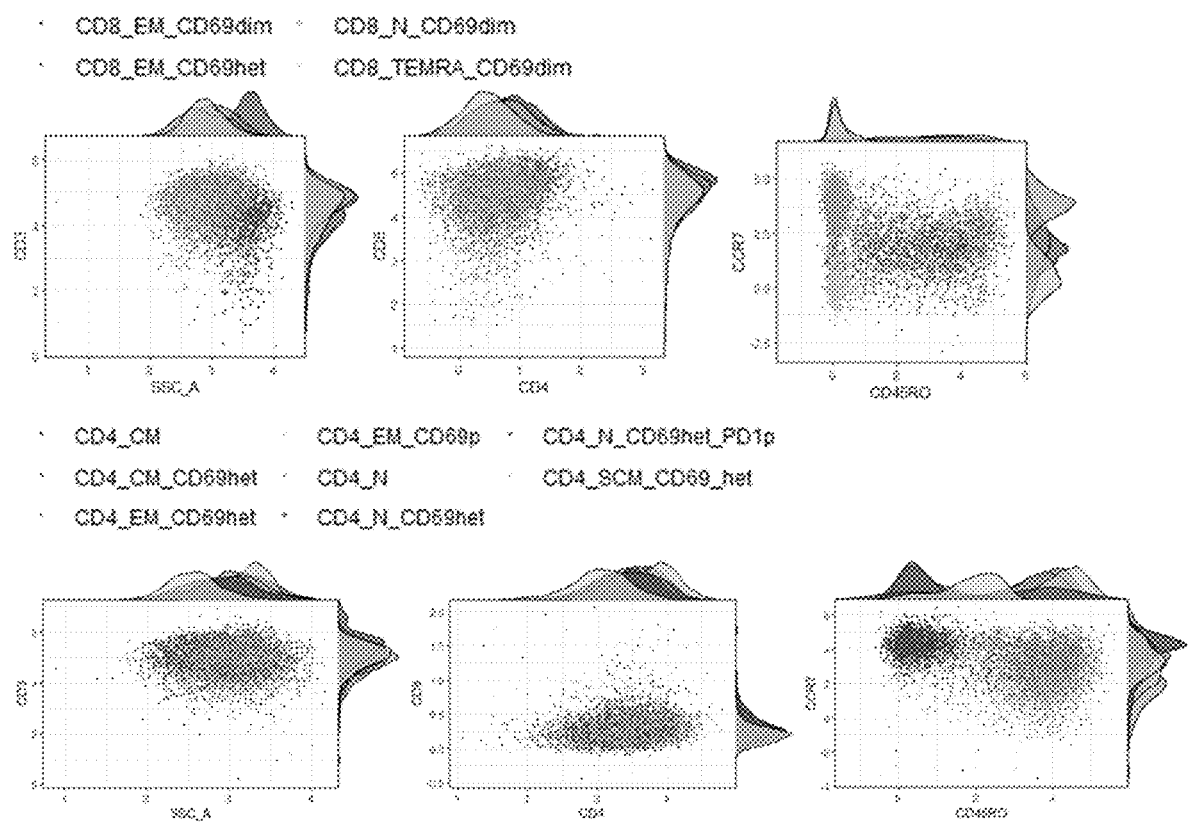
Figure 24C:
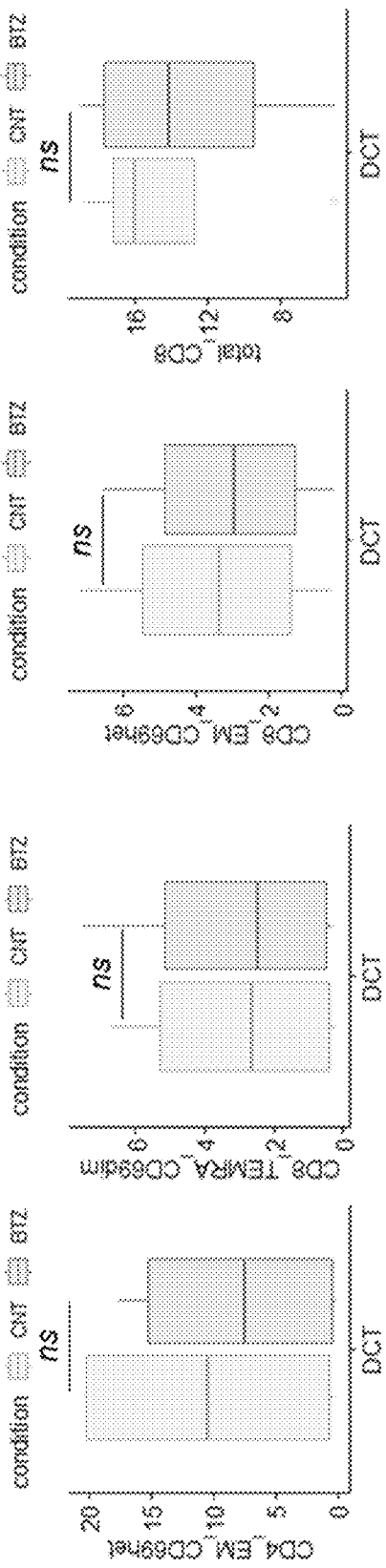
Figure 25A:
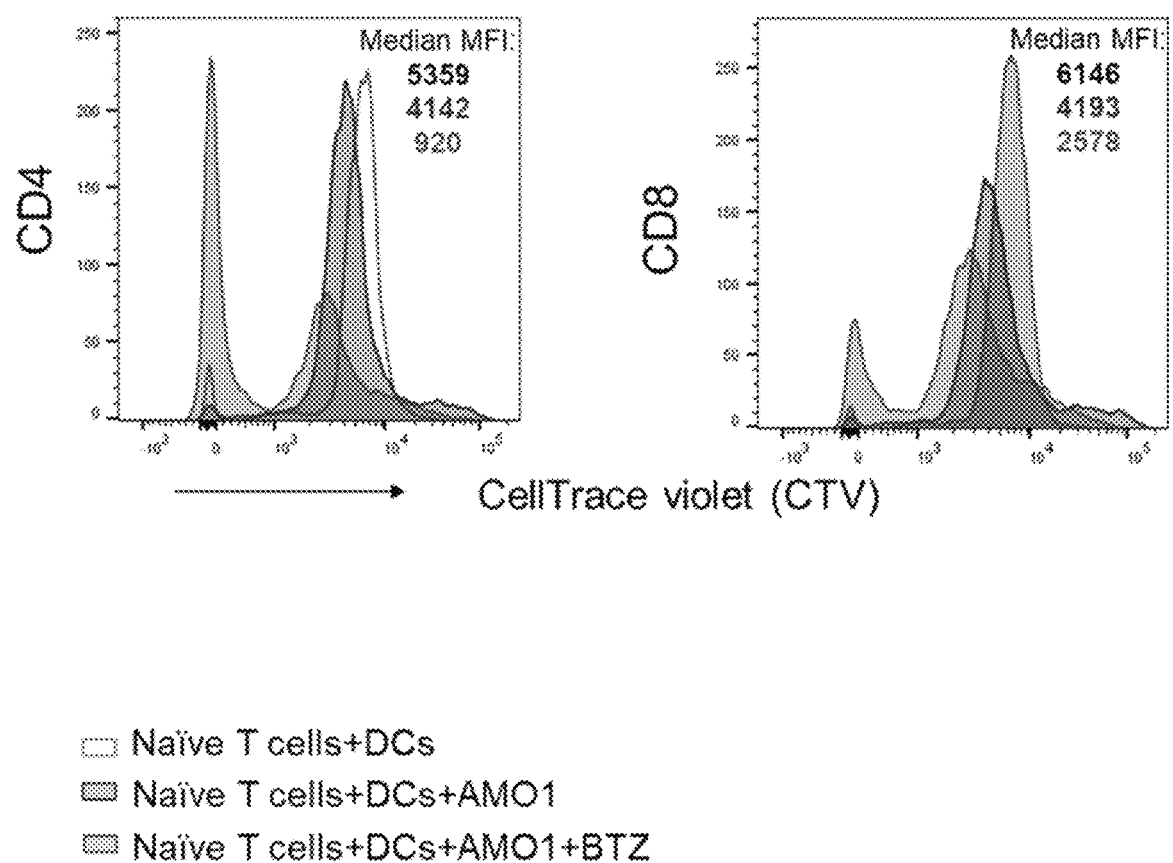
FIG. 25A and FIG. 25B shows BTZ-induced MM cell death promotes proliferation of CD4+ and CD8+ naïve T cells.
Figure 25B:
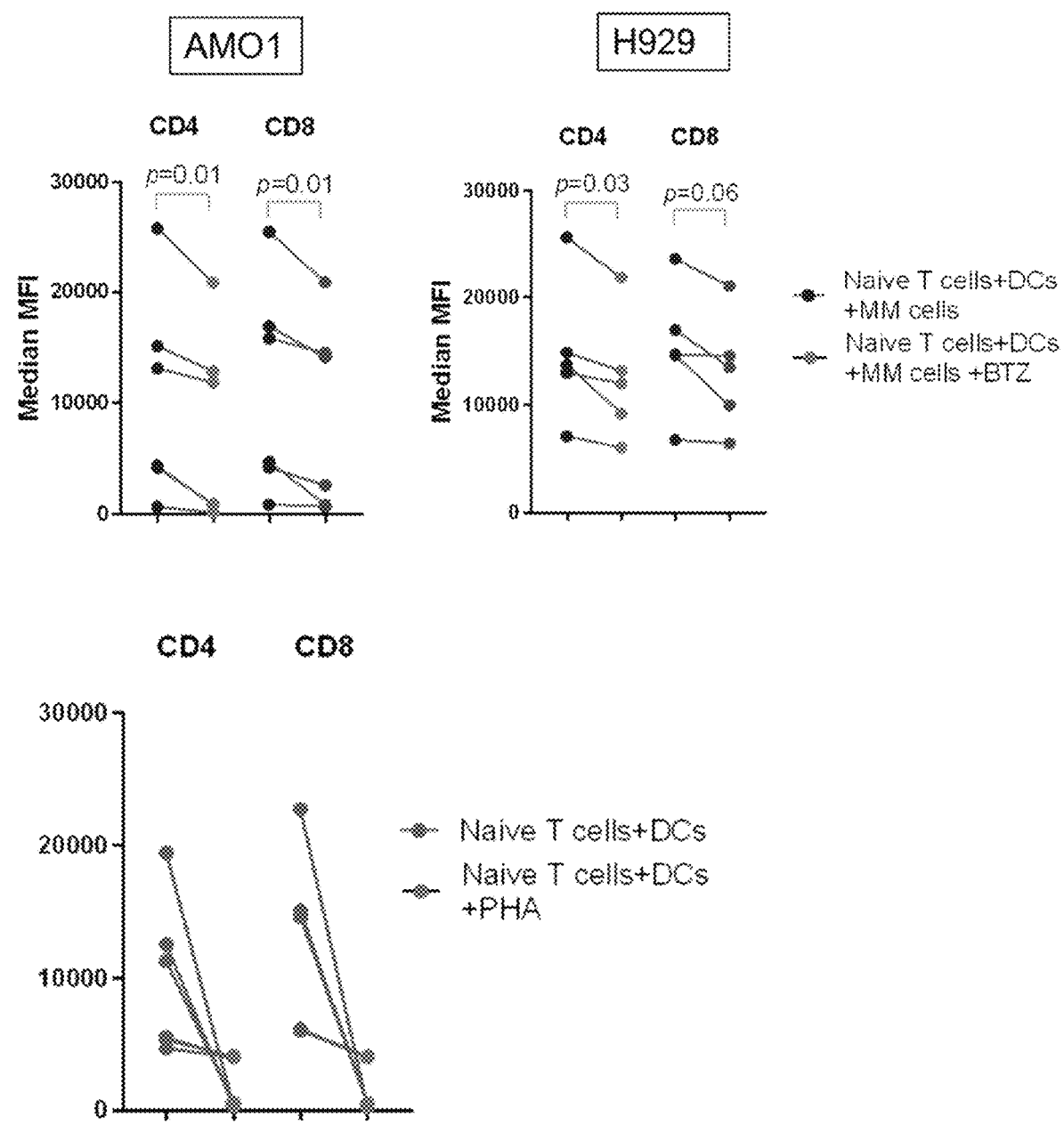

Next, the stimulation of T cells by DCs loaded with BTZ-treated multiple myeloma cells was assessed. In vitro culture of BTZ-treated multiple myeloma cells, DCs, and T cells increased maturation and activation of both CD4+ and CD8+ T cell populations (FIG. 17F and FIG. 24A-B). Specifically, induction of ICD by BTZ resulted in a significant increase of CD4+ effector memory (EM); total CD8+; CD8+EM and CD8+ terminally differentiated EM (TEMRA) cells, which was not observed by treating DCs and T cells with BTZ in the absence of multiple myeloma cells (FIG. 24C). Similarly, isolated T cells after co-cultures showed the presence of multiple myeloma specific cytotoxic T-lymphocytes (CTLs) that were able to efficiently induce lysis of multiple myeloma cells (FIG. 17G). To characterize specificity of the T cell response, a parallel experiment analyzed the effects of BTZ-induced cell death specifically on the naïve T cell population. An increased proliferation of both CD4+ and CD8+ naïve T cells was observed after coculture with BTZ-treated AMO1 or NCI-H929 cells and DCs (FIG. 19A-B). Similar results were obtained using primary cells derived from multiple myeloma patients (pdMM). A dose-dependent increase in phagocytosis of BTZ-treated pdMM cells by DCs was observed (FIG. 18A). Consistently, treatment of BMMCs from MM patients with BTZ confirmed the phenotypic changes in both CD4+ and CD8+ T cell populations (FIG. 19B). Together these data show that BTZ increases the immunogenicity of MM cells, thereby stimulating an anti-MM immune response in vitro. Bortezomib Stimulates Anti-MM Immunity In Vivo Via Induction of ICD.

Figure 19C:
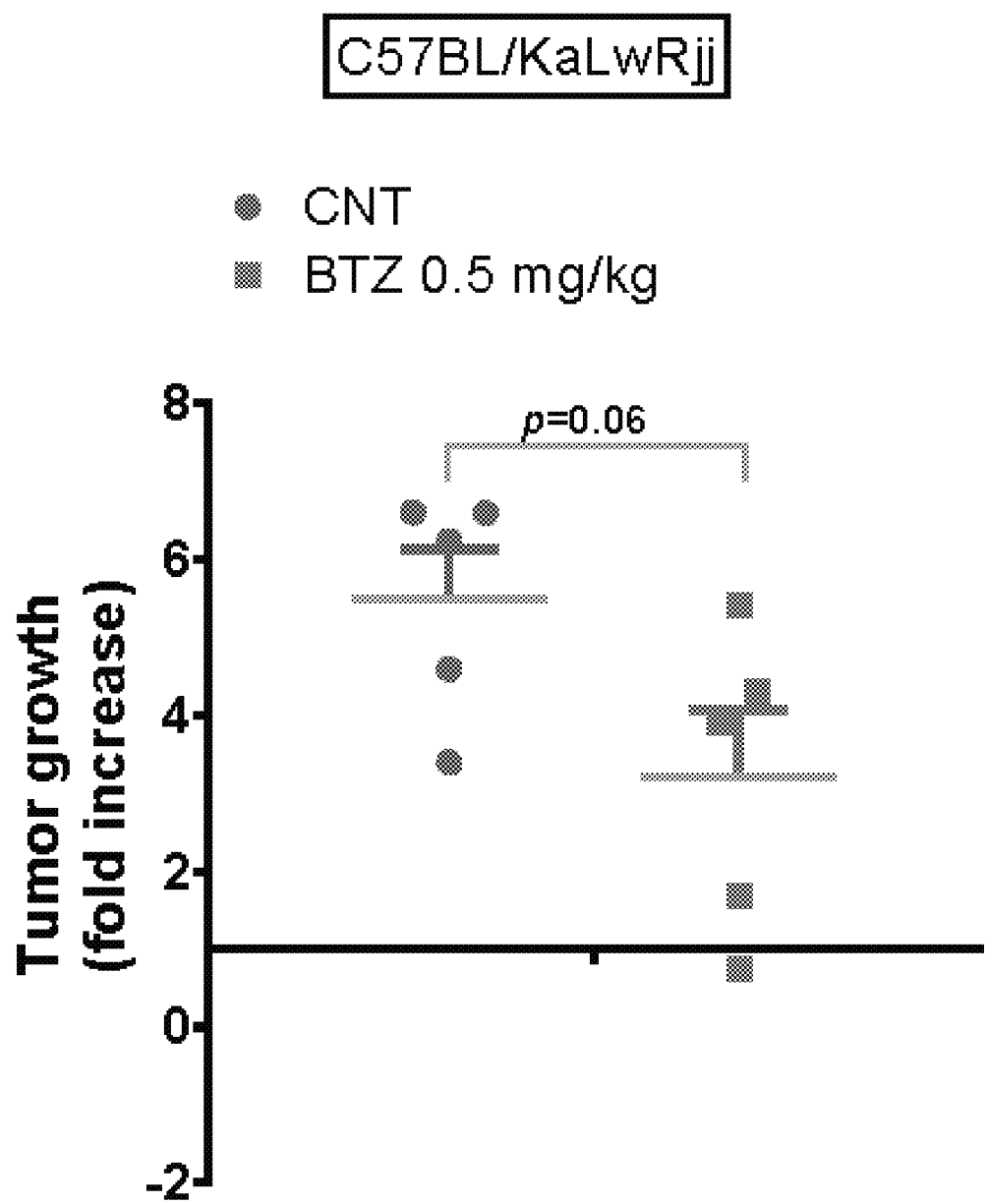
Figure 19D:
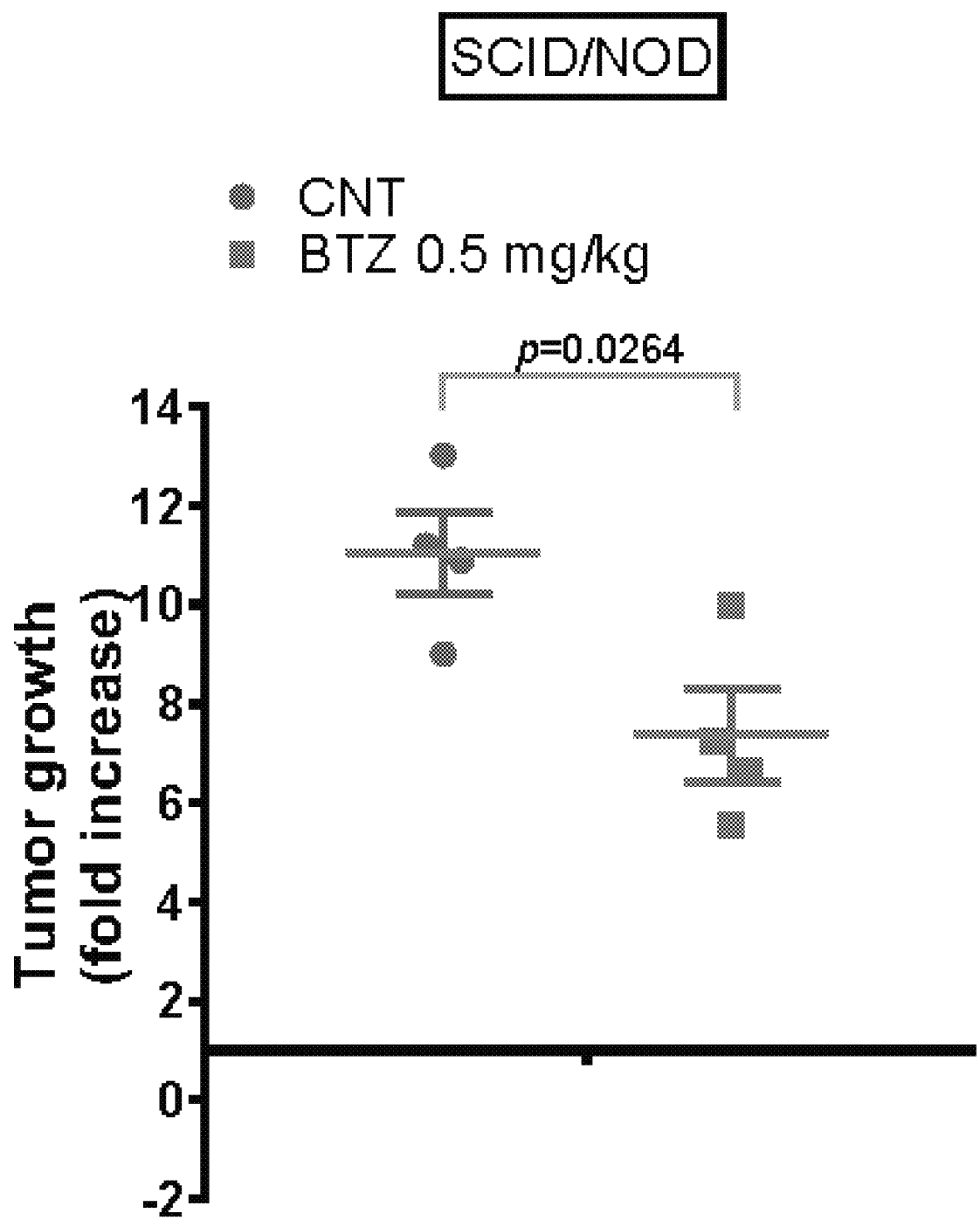

To test the relevance of ICD in BTZ-induced anti-multiple myeloma activity in vivo, the syngeneic immunocompetent 5T murine model of multiple myeloma was used. It was found that low doses of BTZ (0.5 mg/kg twice/week for 2 weeks) inhibited growth of 5TGM1 WT cells engrafted in immunocompetent (C57BL/KaLwRij) mice (FIG. 19A) to a greater extent than when these cells were engrafted in immunodeficient hosts (SCID/NOD) (FIG. 19B). Importantly, this effect was directly linked to ICD induction, since it was abrogated in immunocompetent mice bearing 5TGM1 Calr$^{KO}$ tumors (FIG. 19C), in which the delay of tumor growth was similar to that observed in the immunodeficient hosts (FIG. 19D). Taken together, these results suggest that the effects of BTZ are mediated, at least in part, by the immune system.

Figure 19E:
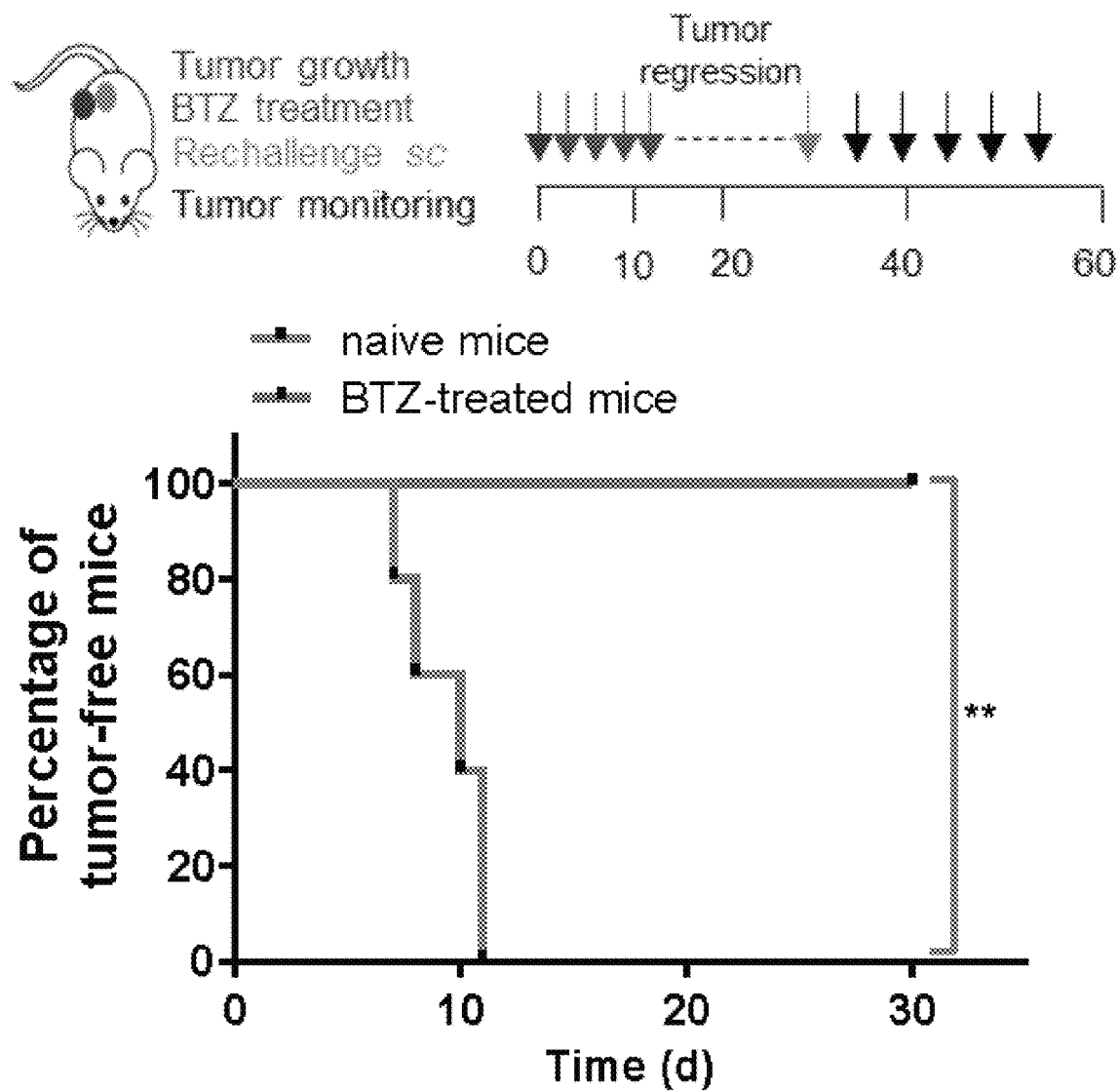
Figure 19F:
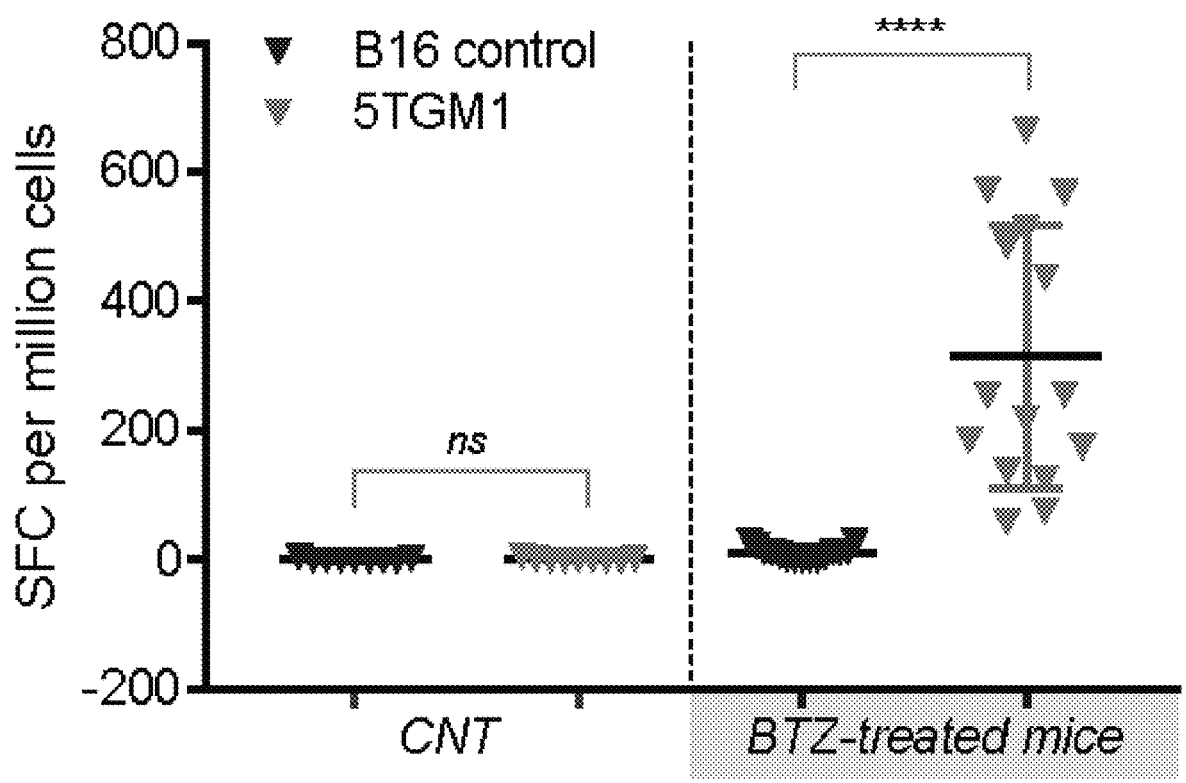
Figure 19G:
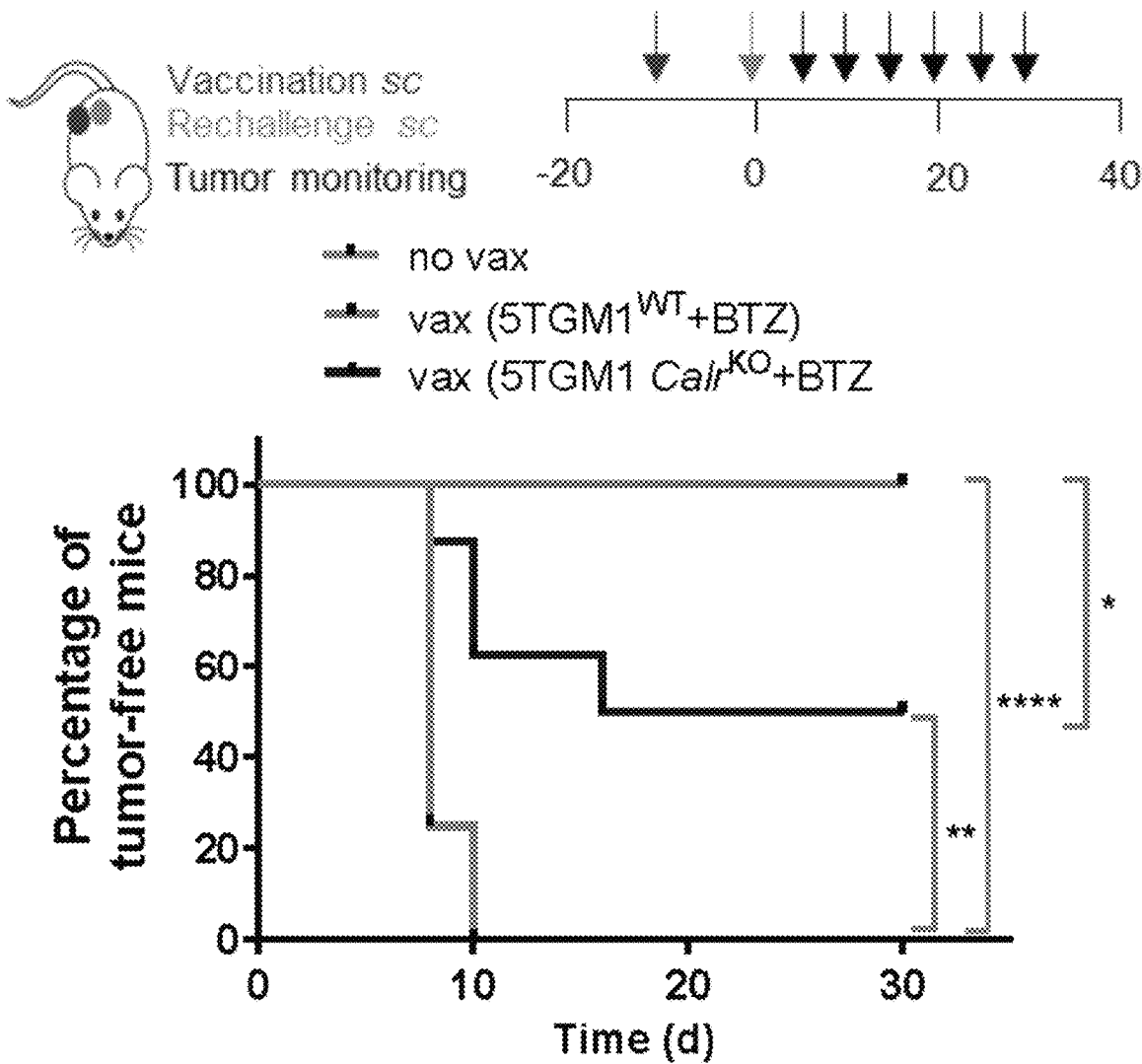
Figure 26:
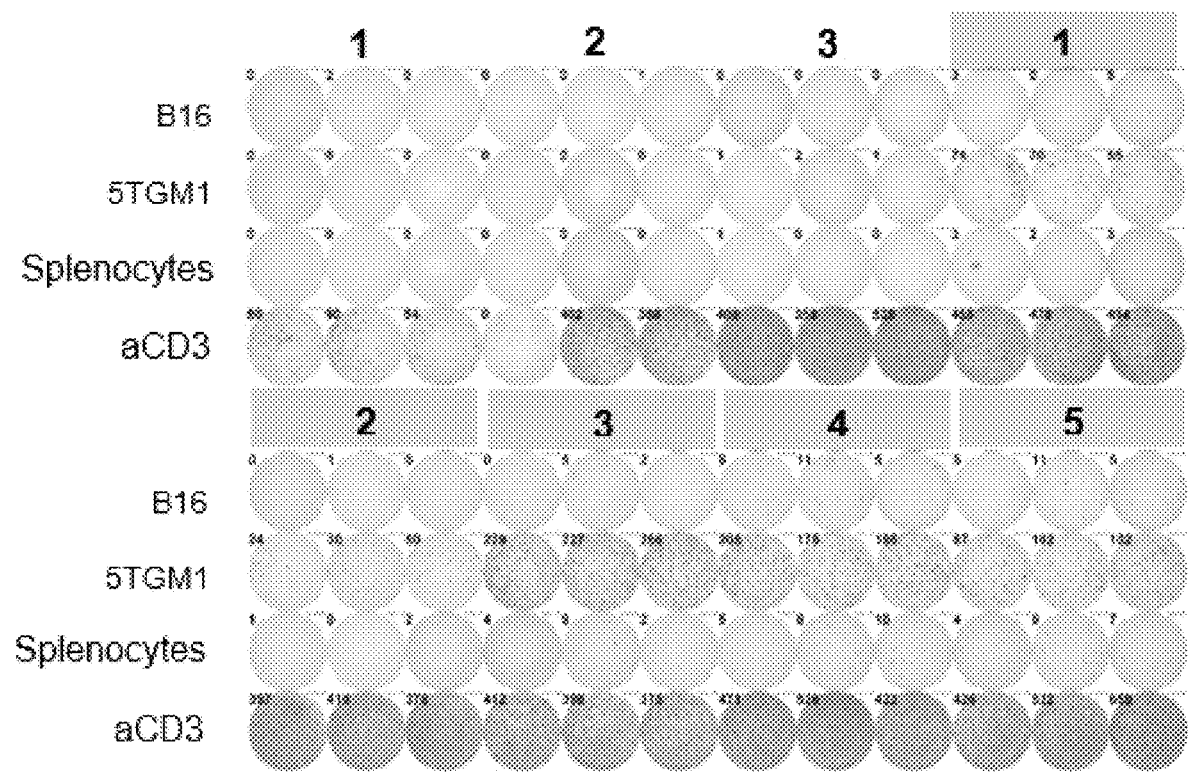
FIG. 26 shows BTZ treatment generates a robust immune response against MM cells. Ex vivo IFNγ ELISPOT of splenocytes harvested from naïve immunocompetent C57BL/KaLwRjj mice bearing 5TGM1 tumors (n=3) and BTZ-treated mice that were rechallenged with viable 5TGM1 cells after tumor regression and didn't develop tumors (n=5, highlighted in red). Splenocytes were stimulated with B16 cell line as negative control, with 5TGM1 or with anti-CD3 as positive control. ELISPOT experiments were performed in triplicate wells per sample. Statistical analysis of Spot forming colonies among the two groups is shown in FIG. 19F.

It was next tested whether, after the regression of tumor growth, the mice were further protected against a tumor rechallange. Injection of live 5TGM1 WT two weeks after BTZ-induced tumor regression did not result in tumor development, and 100% of mice were alive at the end of observation (day 30 after rechallange) (FIG. 19E). Ex vivo enzyme-linked immunospot (ELISPOT), using splenocytes harvested from mice treated under the same conditions, confirmed the generation of a robust immune response against multiple myeloma cells that could protect against rechallenge (FIG. 19F and FIG. 26A). In a similar attempt to prove the induction of immunological memory after BTZ-induced cell death, it was also assessed whether vaccination of C57BL/KaLwRij mice with in vitro BTZ-treated 5TGM1 cells could protect mice against challenge with viable 5TGM1 cells. Non vaccinated mice developed palpable tumors 1 week after 5TGM1 injection, whereas no tumor developed in vaccinated mice even after 30 days (FIG. 19G). Mice were next similarly vaccinated with BTZ-treated 5TGM1 Calr$^{KO}$ cells and challenged one week later with injection of live WT 5TGM1 cells: only 50% of vaccinated mice were tumor-free at day 30 (FIG. 19G). Altogether, these data indicate that induction of ICD by BTZ induces a protective anti-tumor response in vivo.

An ICD-Related Signature Predicts Clinical Outcome in Multiple Myeloma Patients after Bortezomib Treatment.

Figure 20A:
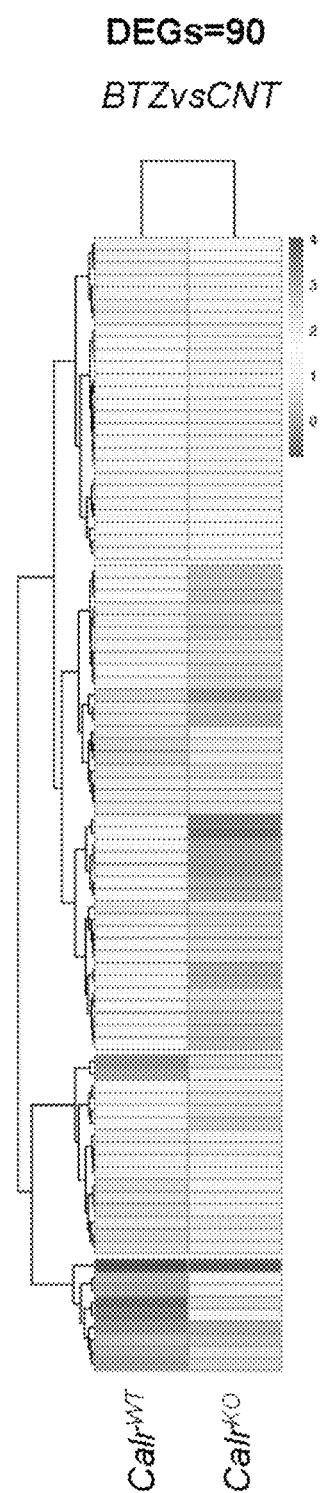
FIG. 20A to FIG. 20E shows an ICD-related signature predicts clinical outcome in MM patients after BTZ treatment.
Figure 20B:
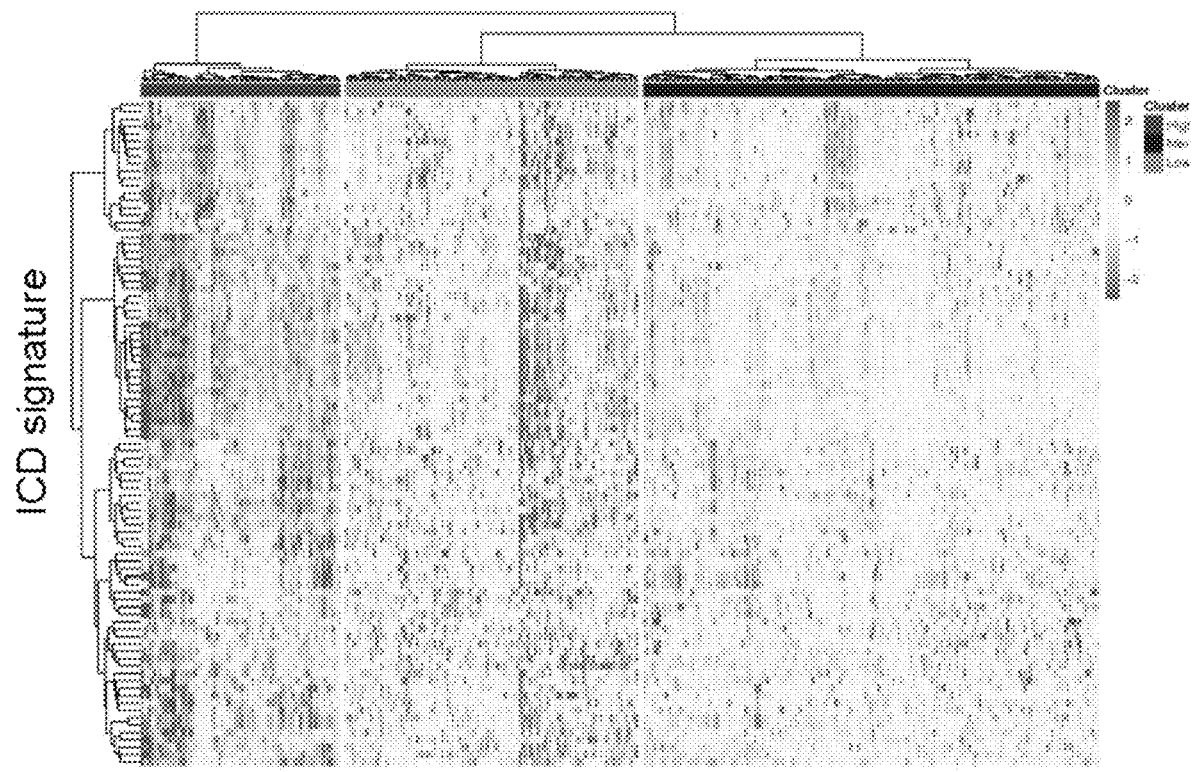
Figure 20C:
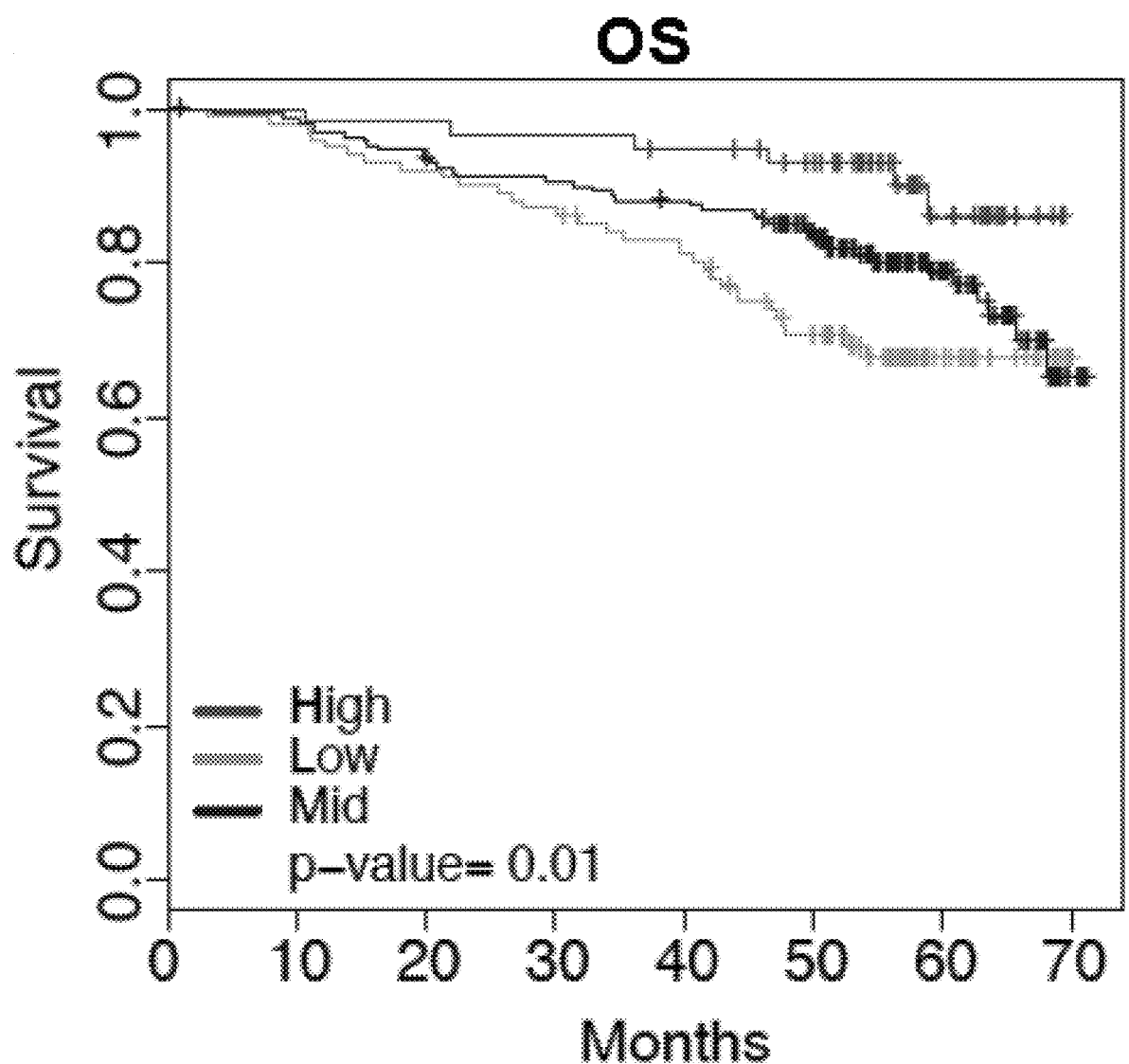
Figure 20D:
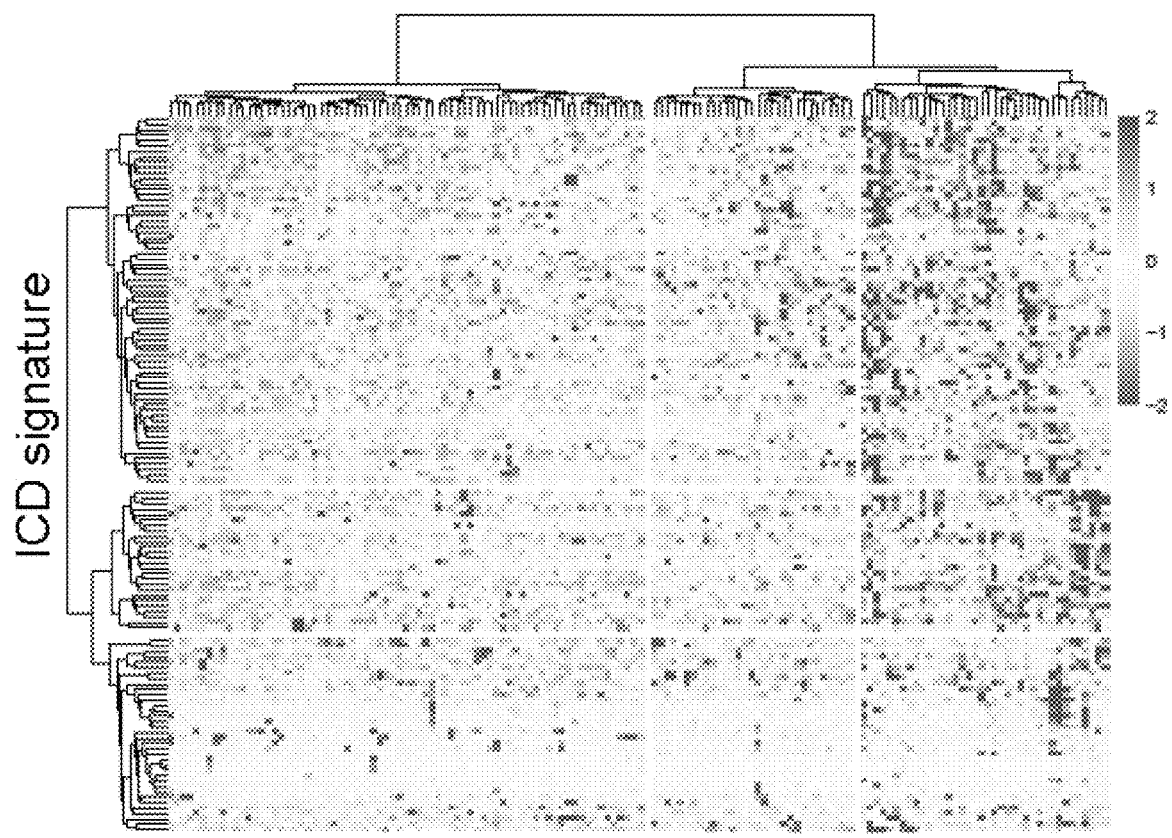
Figure 20E:
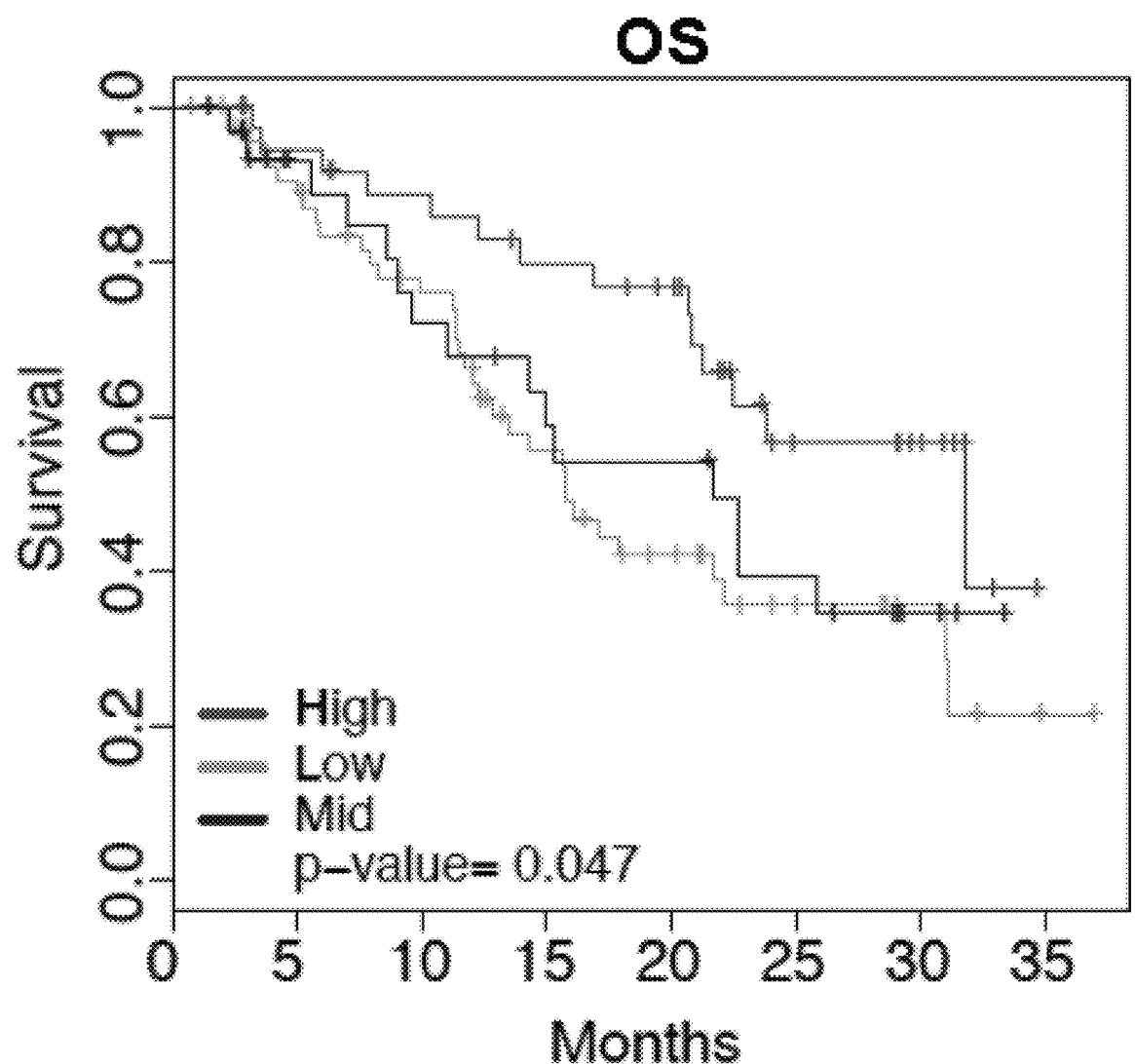
Figure 27:
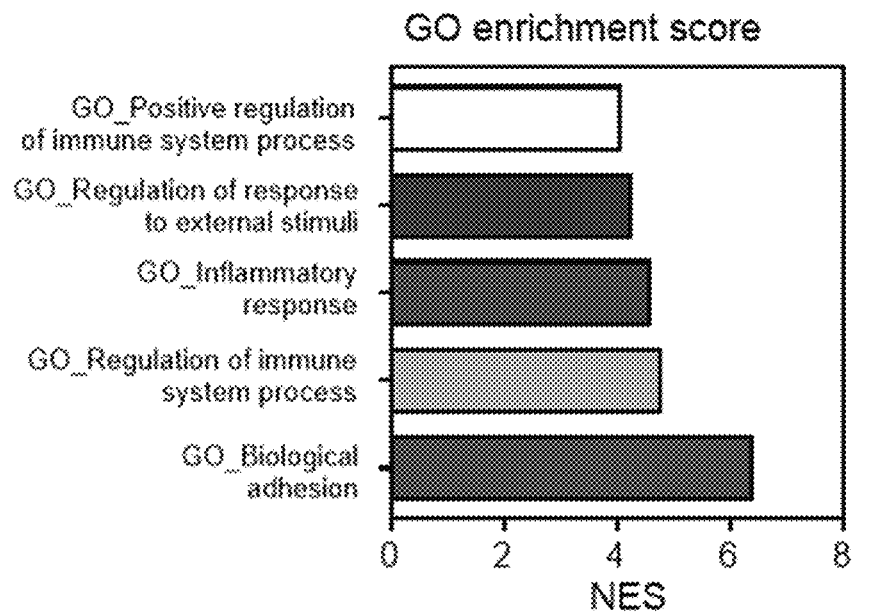
FIG. 27 shows enrichment analysis of top pathways upregulated by BTZ in vivo. GSEA Gene Ontology (GO) analysis of pathways significantly upregulated in 5TGM1 Calr$^{WT}$ (left) and Calr$^{KO}$ (right) tumors collected after BTZ treatment (0.5 mg/kg twice/week, i.p.). For all pathways shown, FRD<25%.
Figure 27:
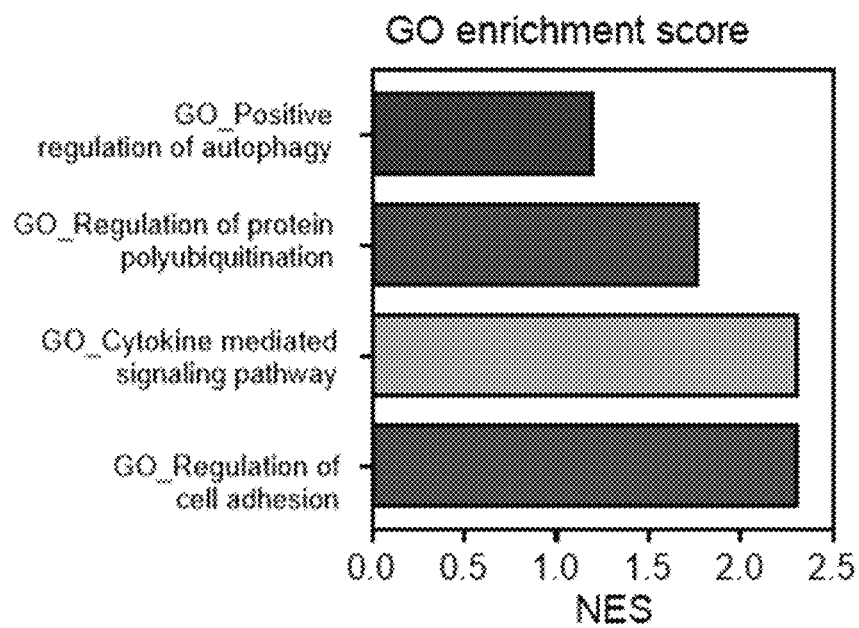
Figure 28:
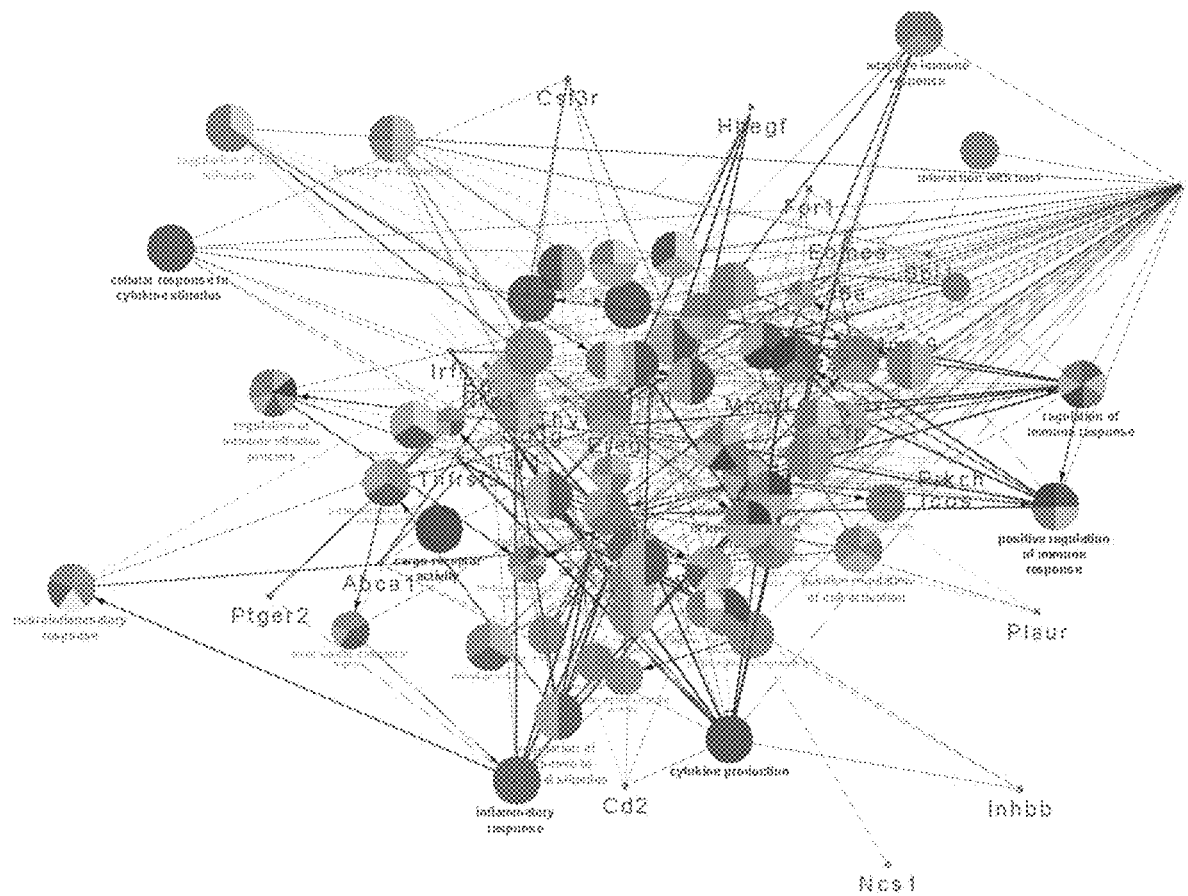
FIG. 28 shows GO analysis of ICD signature genes. The cytoscape ClueGO plugin was used to identify enriched GO biological processes amongst the 90 ICD gene list. Each node represents an enriched gene set, which were then grouped based on similarity of their associated genes. ClueGo parameters were set as indicated: Go Term Fusion selected; only display pathways with p values<0.01; and kappa score of 0.42. Enrichment results were mapped as a network of gene sets (nodes); and edges reflect the relationships between the nodes, according to the similarity of the included genes. Node size is proportional to the node significance. The CluePEDIA plugin was also used to visualize the relationship of each gene included in the ICD-signature with the nodes. Highlighted on the right are 57 interferon stimulated genes (ISGs), which are similarly represented in pathways involved in the inflammatory response.

To confirm the biological sequalae of ICD induction by BTZ in tumors in vivo, a RNA-seq analysis of 5TGM1 WT and 5TGM1 Calr$^{KO}$ tumors grown in C57BL/KaLwRij immunocompetent mice was performed. The transcriptional changes induced by BTZ in 5TGM1 WT tumors were consistent with activation of an immune response (i.e. Inflammatory response, Regulation of immune system process); whereas loss of Calr in 5TGM1 tumors decreased this effect, and revealed instead an enrichment in signaling related to direct BTZ cytotoxicity (i.e. Regulation of protein polyubiquitination, Positive regulation of autophagy) (FIG. 27A). Focused analysis of the most upregulated genes after BTZ treatment in mice bearing 5GTM1 WT tumors identified a set of 90 immune-related genes composing an ICD-signature, which was not similarly modulated in 5GTM1 Calr$^{KO}$ tumors (FIG. 20A and Table 3 below). It was found that high expression of the human orthologs of the murine ICD gene signature was strongly positively correlated with clinical outcome of MM patients uniformly treated with BTZ-based regimens in the IFM/DFCI clinical study (IFM/DFCI 2009) (Attal et al. (2017) N Engl J Med; 376(14): 1311-20) (OS p value=0.01) (FIGS. 20B and 20C). The predictive value of the identified ICD signature was also confirmed in an independent dataset (GSE9782) (Mulligan et al. (2007) Blood; 109(8):3177-88) (OS p value=0.047), in which patients received only BTZ as frontline therapy (FIG. 20D-E). To gain further insight into the biological significance of the genes included in the ICD signature, gene ontology (GO) analysis showing enrichment was performed in the following pathways: inflammatory response, regulation of immune effector process, cellular response to cytokine stimulus, cell adhesion, cargo activity receptor, cytokine production, and positive regulation of immune response. Interestingly, 57 of 90 genes were identified as interferon stimulated genes (ISGs) using the "Interferome" database (Rusinova (2013) Nucleic Acids Res 41) (FIG. 28A). These data suggest that induction of ICD by BTZ treatment contributes to a clinical benefit in MM patients; and that an inflammatory response involving ISGs may be an important mediator of this outcome.

TABLE 3

Immune genes regulated after treatment with BTZ in vivo. List of 90 immune-related genes differentially expressed in 5TGM1$^{WT}$ and Calr$^{KO}$ tumors

| Gene list | Gene ID | Description |
| --- | --- | --- |
| TNFRSF9 | ENSG00000049249.8 | TNF Receptor Superfamily Member 9 |
| TNFRSF1B | ENSG00000028137.16 | TNF Receptor Superfamily Member IB |
| DHRS3 | ENSG00000162496.8 | Dehydrogenase/Reductase 3 |
| FGR | ENSG00000000938.12 | FGR Proto-Oncogene, Src Family Tyrosine Kinase |
| PTAFR | ENSG00000169403.11 | Platelet Activating Factor Receptor |
| CSF3R | ENSG00000119535.17 | Colony Stimulating Factor 3 Receptor |
| CSF1 | ENSG00000184371.13 | Colony Stimulating Factor 1 |
| CD2 | ENSG00000116824.4 | CD2 |
| SHE | ENSG00000169291.9 | Src Homology 2 Domain Containing E |
| SYT11 | ENSG00000132718.8 | Synaptotagmin 11 |
| CD247 | ENSG00000198821.10 | CD247 |
| SELP | ENSG00000174175.16 | Selectin P |
| SELL | ENSG00000188404.8 | Selectin L |
| IL10 | ENSG00000136634.5 | Interleukin 10 |
| NLRP3 | ENSG00000162711.16 | NLR Family Pyrin Domain Containing 3 |
| CD8A | ENSG00000153563.15 | CD8A |
| ZAP70 | ENSG00000115085.13 | Zeta Chain Of T Cell Receptor Associated Protein Kinase 70 |
| IL1R1 | ENSG00000115594.11 | Interleukin 1 Receptor Type 1 |
| MARCO | ENSG00000019169.10 | Macrophage Receptor With Collagenous Structure |
| INHBB | ENSG00000163083.5 | Inhibin Subunit Beta B |
| ICOS | ENSG00000163600.12 | Inducible T Cell Costimulator |
| EOMES | ENSG00000163508.12 | Eomesodermin |
| CCRL2 | ENSG00000121797.9 | C-C Motif Chemokine Receptor Like 2 |
| STAB1 | ENSG00000010327.10 | Stabilin 1 |
| PROK2 | ENSG00000163421.8 | Prokineticin 2 |
| EREG | ENSG00000124882.3 | Epiregulin |
| CXCL9 | ENSG00000138755.5 | C-X-C Motif Chemokine Ligand 9 |
| SPP1 | ENSG00000118785.13 | Secreted Phosphoprotein 1 |
| TLR2 | ENSG00000137462.6 | Toll Like Receptor 2 |
| IL7R | ENSG00000168685.14 | Interleukin 7 Receptor |
| OSMR | ENSG00000145623.12 | Oncostatin M Receptor |
| FYB | ENSG00000082074.15 | FYN Binding Protein 1 |
| HBEGF | ENSG00000113070.7 | Heparin Binding EGF Like Growth Factor |
| LCP2 | ENSG00000043462.11 | Lymphocyte Cytosolic Protein 2 |

TABLE 3-continued

Immune genes regulated after treatment with BTZ in vivo. List of 90 immune-related genes differentially expressed in 5TGM1$^{WT}$ and Calr$^{KO}$ tumors

| Gene list | Gene ID | Description |
|---|---|---|
| RNF144B | ENSG00000137393.9 | Ring Finger Protein 144B |
| TNFRSF21 | ENSG00000146072.6 | TNF Receptor Superfamily Member 21 |
| INHBA | ENSG00000122641.9 | Inhibin Subunit Beta A |
| EGFR | ENSG00000146648.15 | Epidermal Growth Factor Receptor |
| FGL2 | ENSG00000127951.5 | Fibrinogen Like 2 |
| SERPINE1 | ENSG00000106366.8 | Serpin Family E Member 1 |
| CLEC5A | ENSG00000258227.6 | C-Type Lectin Domain Containing 5A |
| SLC7A2 | ENSG00000003989.16 | Solute Carrier Family 7 Member 2 |
| GCNT1 | ENSG00000187210.12 | Glucosaminyl (N-Acetyl) Transferase 1 |
| ABCA1 | ENSG00000165029.15 | ATP Binding Cassette Subfamily A Member 1 |
| NCS1 | ENSG00000107130.9 | NCS1 |
| IL2RA | ENSG00000134460.15 | Interleukin 2 Receptor Subunit Alpha |
| NRP1 | ENSG00000099250.17 | Neuropilin 1 |
| PRF1 | ENSG00000180644.6 | Perforin 1 |
| IFIT2 | ENSG00000119922.8 | Interferon Induced Protein With Tetratricopeptide Repeats 2 |
| IFITM3 | ENSG00000142089.15 | Interferon Induced Transmembrane Protein 3 |
| SPI1 | ENSG00000066336.11 | Hematopoietic Transcription Factor PU. 1 |
| SERPING1 | ENSG00000149131.15 | Serpin Family G Member 1 |
| IL18BP | ENSG00000137496.17 | Interleukin 18 Binding Protein |
| P2RY2 | ENSG00000175591.11 | Purinergic Receptor P2Y2 |
| CD3E | ENSG00000198851.9 | CD3E |
| CD3G | ENSG00000160654.9 | CD3G |
| THY1 | ENSG00000154096.13 | Thy-1 Cell Surface Antigen |
| CD4 | ENSG00000010610.9 | CD4 |
| C3AR1 | ENSG00000171860.4 | Complement C3a Receptor 1 |
| OLR1 | ENSG00000173391.8 | Oxidized Low Density Lipoprotein Receptor 1 |
| IFNG | ENSG00000111537.4 | Interferon Gamma |
| CMKLR1 | ENSG00000174600.13 | Chemerin Chemokine-Like Receptor 1 |
| MMP14 | ENSG00000157227.12 | Matrix Metallopeptidase 14 |
| GZMB | ENSG00000100453.12 | Granzyme B |
| PTGER2 | ENSG00000125384.6 | Prostaglandin E Receptor 2 |
| PRKCH | ENSG00000027075.13 | Protein Kinase C Eta |
| HIF1A | ENSG00000100644.16 | Hypoxia Inducible Factor 1 Subunit Alpha |
| GPR65 | ENSG00000140030.5 | G Protein-Coupled Receptor 65 |
| MEFV | ENSG00000103313.11 | MEFV Innate Immunity Regulator, Pyrin |
| IRF8 | ENSG00000140968.10 | Interferon Regulatory Factor 8 |
| SCARF1 | ENSG00000074660.15 | Scavenger Receptor Class F Member 1 |
| PIK3R5 | ENSG00000141506.13 | Phosphoinositide 3-kinase regulatory subunit 5 |
| CCL2 | ENSG00000108691.9 | C-C Motif Chemokine Ligand 2 |
| ITGB3 | ENSG00000259207.7 | Integrin Subunit Beta 3 |
| IFI30 | ENSG00000216490.3 | lysosomal thiol reductase |
| SCN1B | ENSG00000105711.10 | Sodium Voltage-Gated Channel Beta Subunit 1 |
| AXL | ENSG00000167601.11 | AXL Receptor Tyrosine Kinase |
| PLAUR | ENSG00000011422.11 | Plasminogen Activator, Urokinase Receptor |
| PTGIR | ENSG00000160013.8 | Prostaglandin I2 Receptor |
| C5AR1 | ENSG00000197405.7 | Complement C5a Receptor 1 |
| FPR1 | ENSG00000171051.8 | Formyl Peptide Receptor 1 |
| CST7 | ENSG00000077984.5 | Cystatin F |
| SAMHD1 | ENSG00000101347.8 | SAM And HD Domain Containing Deoxynucleoside Triphosphate Triphosphohydrolase 1 |
| TGM2 | ENSG00000198959.11 | Transglutaminase 2 |
| MMP9 | ENSG00000100985.7 | Matrix Metallopeptidase 9 |
| ITGB2 | ENSG00000160255.16 | Integrin Subunit Beta 2 |
| COL6A1 | ENSG00000142156.14 | Collagen Type VI Alpha 1 Chain |
| OSM | ENSG00000099985.3 | Oncostatin M |
| IL2RB | ENSG00000100385.13 | Interleukin 2 Receptor Subunit Beta |
| CFP | ENSG00000126759.12 | Complement Factor Properdin |

BTZ Activates a "Viral Mimicry" State in Multiple Myeloma Cells, which is Required for its Activity In Vivo.

Figure 29A:
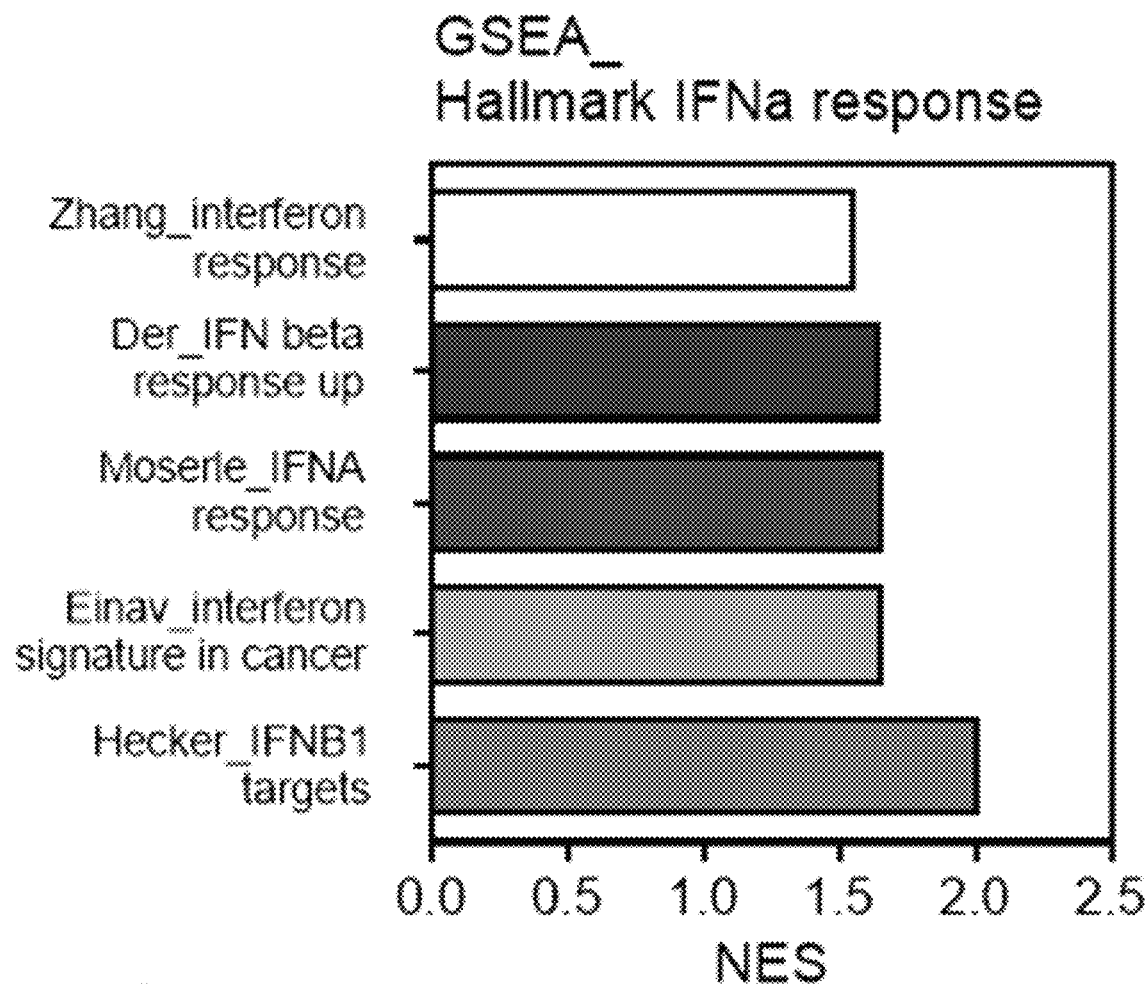
FIG. 29A to FIG. 29E shows MM cells engage in a type I IFN response after treatment with BTZ.
Figure 29B:
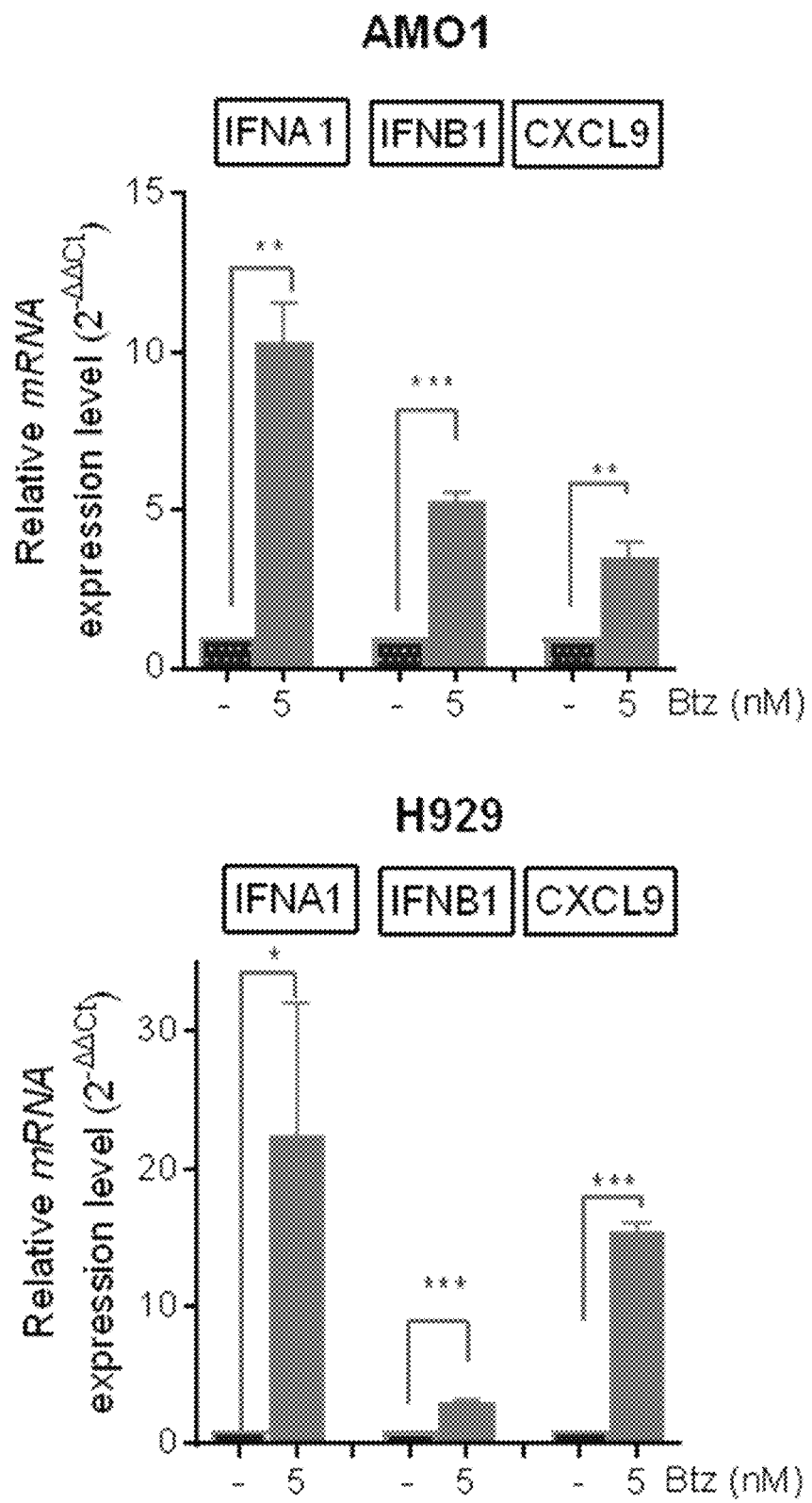
Figure 29C:
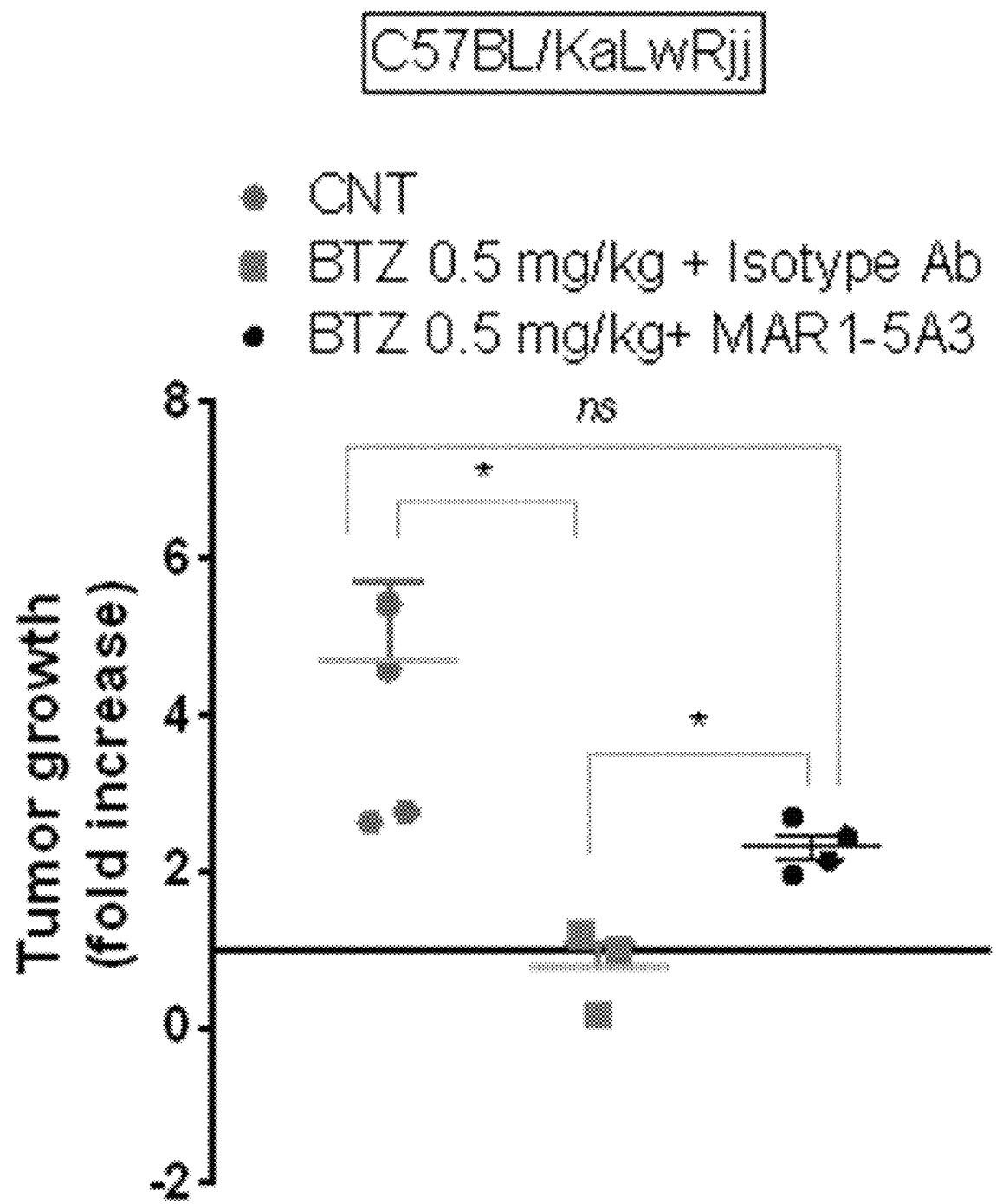
Figure 29D:
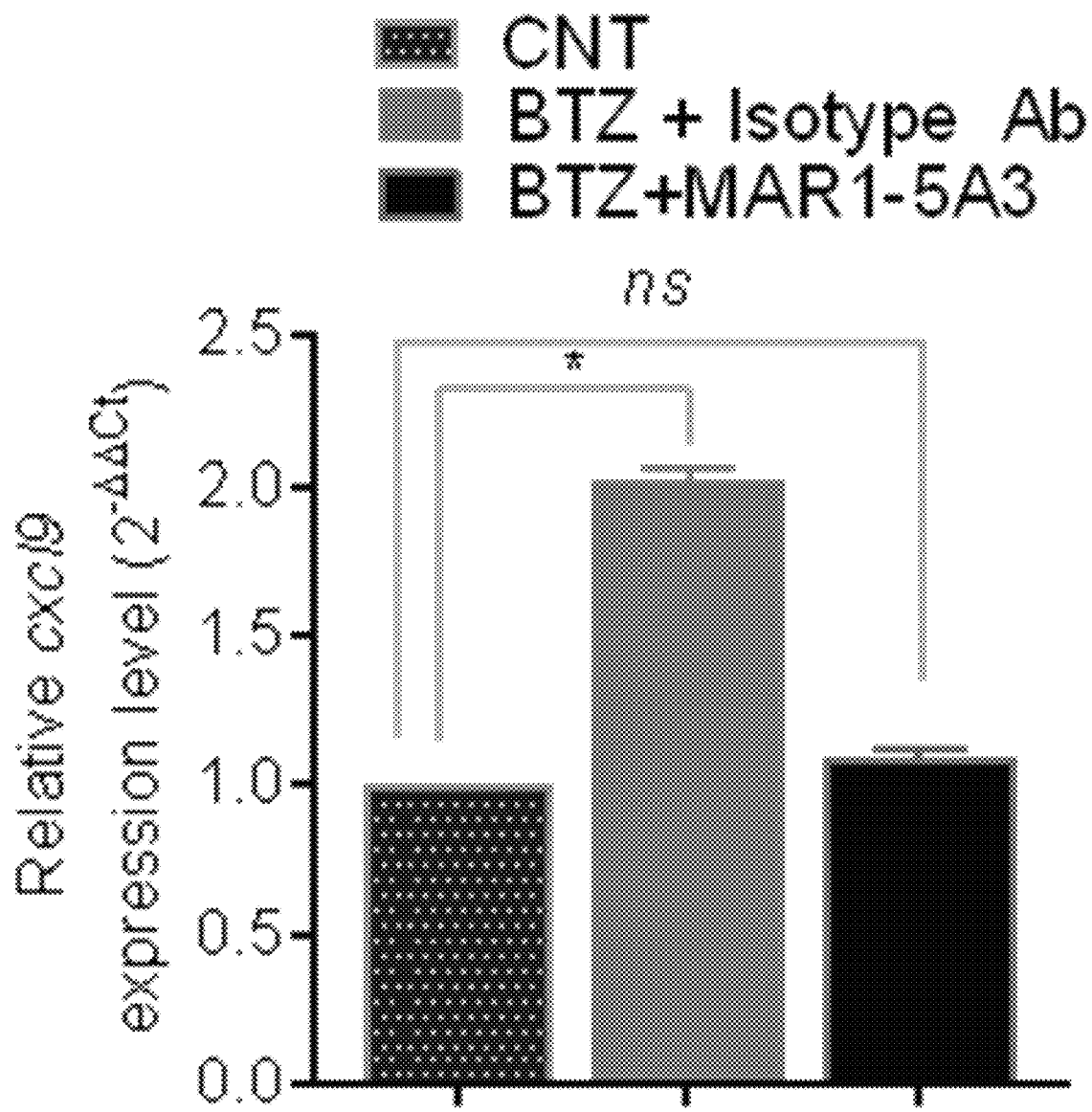
Figure 29E:
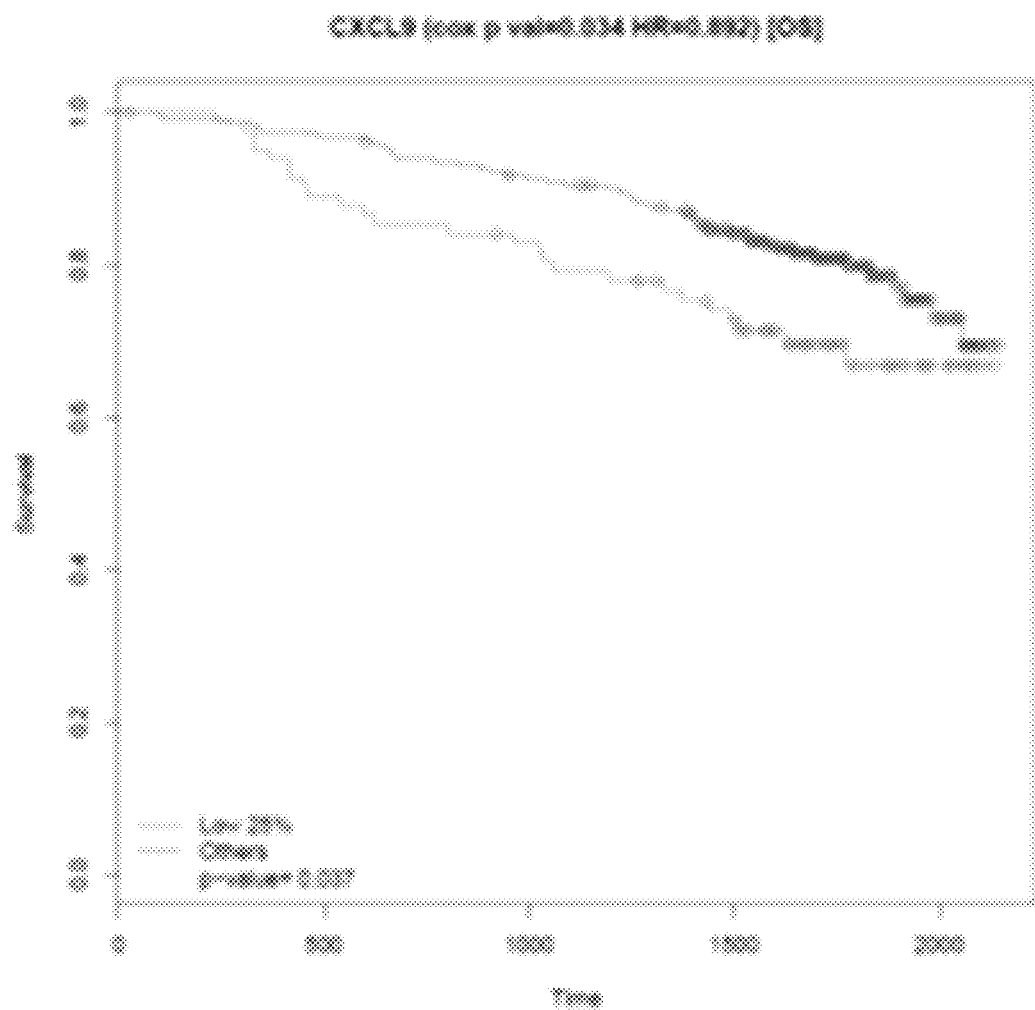

Transcriptional activation of ISGs by inducers of ICD is consistent with a "viral mimicry" state (Vacchelli et al. (2015) *Oncoimmunology;* 4(8):e988042 doi 10.4161/2162402X.2014.988042; Sistigu et al. (2014) *Nat Med* 2014; 20(11):1301-9). Specifically, type I interferon (IFN) response and inflammatory chemokines (such as CXCL9) create an inflammatory microenvironment and are required for optimal therapeutic efficacy of agents inducing ICD (Zitvogel et al. (2015) *Nat Rev Immunol;* 15(7):405-14 doi 10.1038/nri3845). Next, induction of a type-I IFN response was examined by treating AMO1 and NCI-H929 MM cells with BTZ in vitro. RNA-seq analysis of AMO1 cells treated with BTZ confirmed positive enrichment of gene sets included in the type-I IFN response hallmark signature (FIG. 29A); which was also validated by qRT-PCR showing increased IFNA1, IFNB1 and CXCL9 transcripts in AMO1 and NCI-H929 MM cells after BTZ treatment (FIG. 29B). The contribution of this type I IFNs response to the anti-MM activity of BTZ in vivo was then assessed. Neutralization of type-I IFN signaling in both multiple myeloma and host cells, using type-I IFNs receptor 1 (IFNAR1)-specific MAR1-5A3 monoclonal antibody (moAb), significantly decreased the efficacy of BTZ against 5TGM1 tumors, as compared to isotype control moAb (FIG. 29C). Quantitative RT-PCR analysis on harvested tumors confirmed that MAR1-5A3 moAb blocked Cxcl9 transcript accumulation in tumors from BTZ-treated mice (FIG. 29D). In a parallel analysis of multiple myeloma patients uniformly treated with BTZ containing regimens (IFM/DFCI 2009), it was found that low expression of CXCL9 transcript in CD138+ MM cells independently correlates with poor clinical outcome (OS p value=0.037) (FIG. 29E). These studies indicate that BTZ induces a "viral mimicry state" in multiple myeloma cells, and that this type-I IFN response is required for optimal in vivo response.

BTZ Induces Type-I IFN Signaling Via Activation of the cGAS/STING Pathway.

Figure 21A:
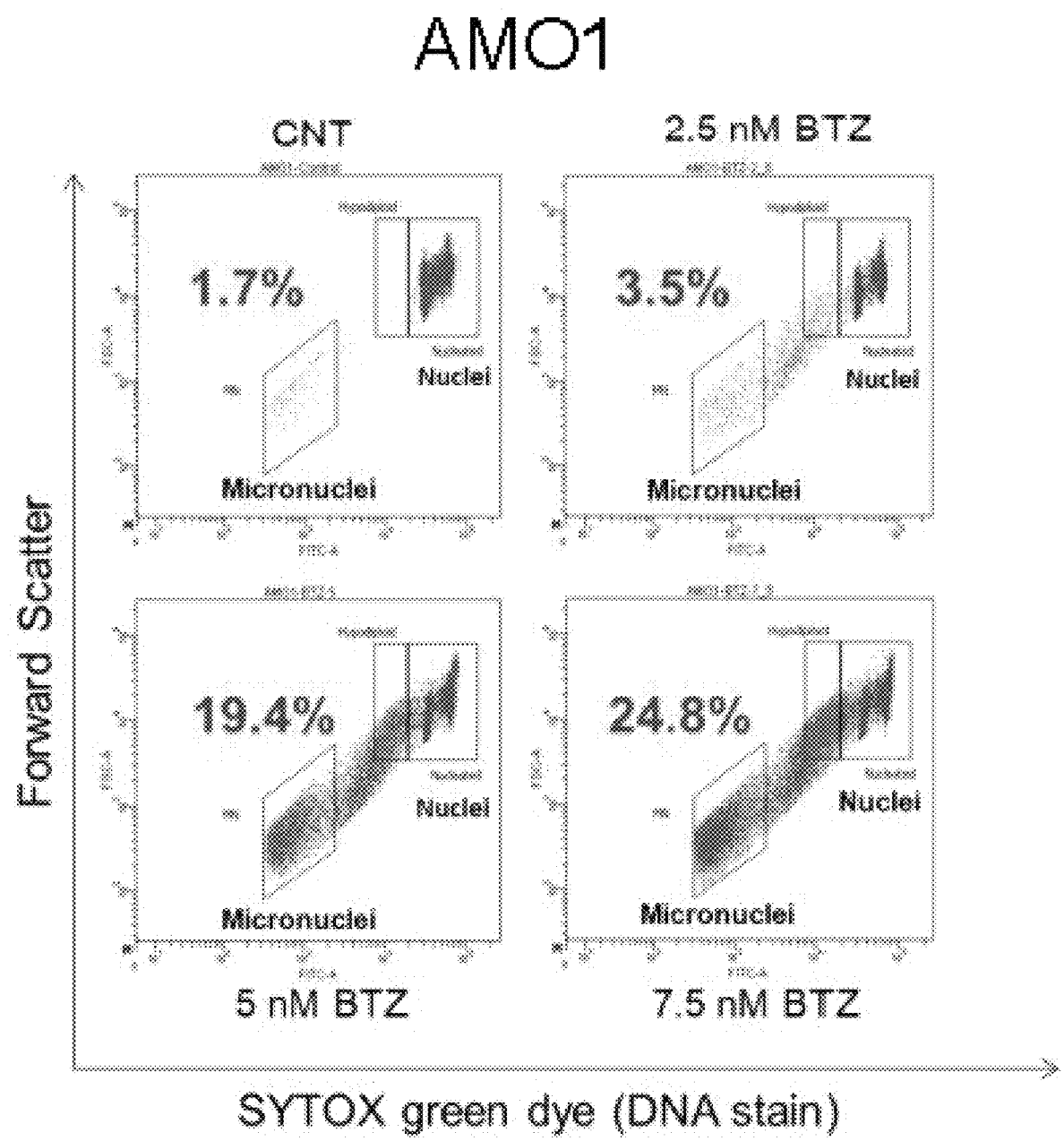
FIG. 21A to FIG. 21G shows BTZ induces IFN-I signaling and promotes T cell activation via cGAS/STING pathway.
Figure 21B:
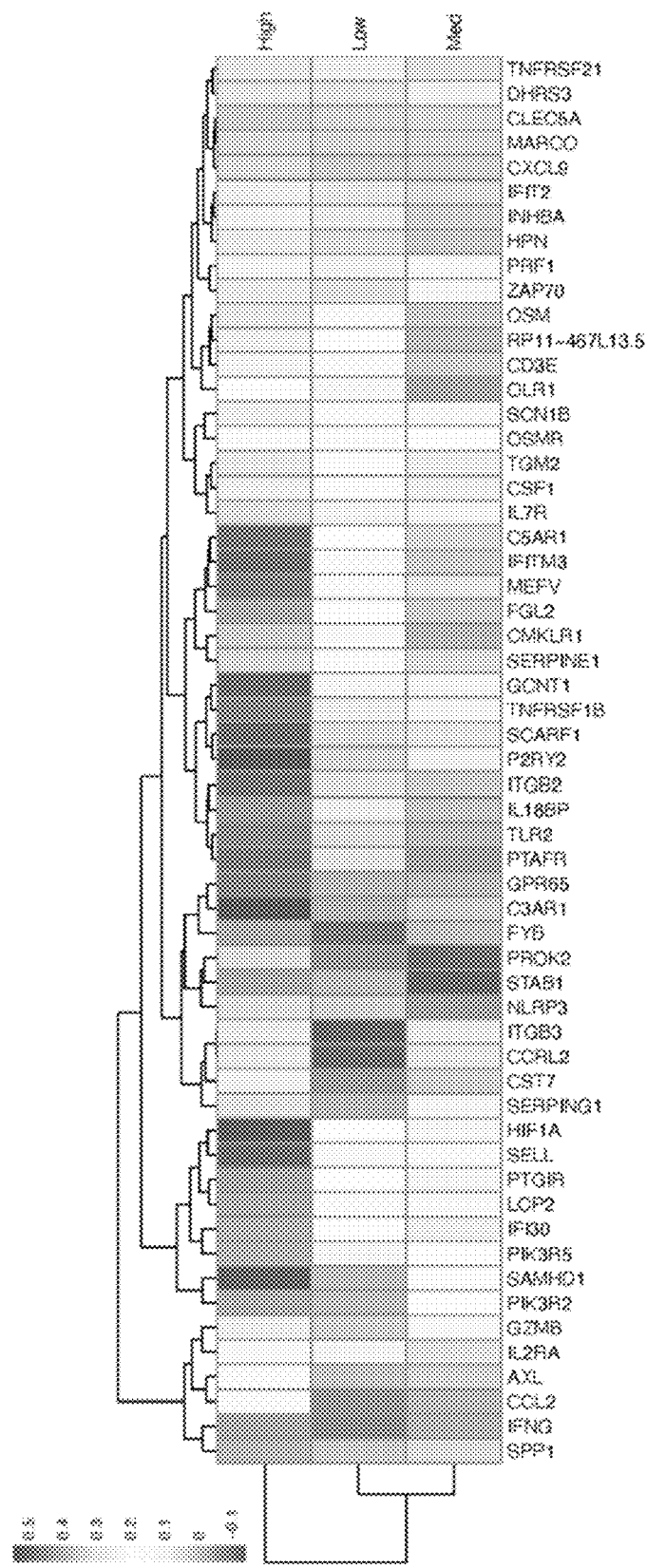
Figure 21C:
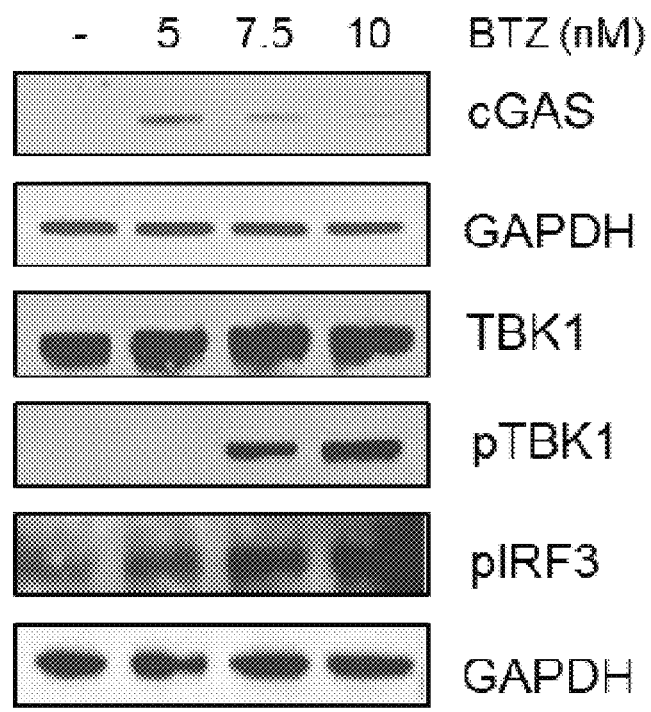
Figure 21D:
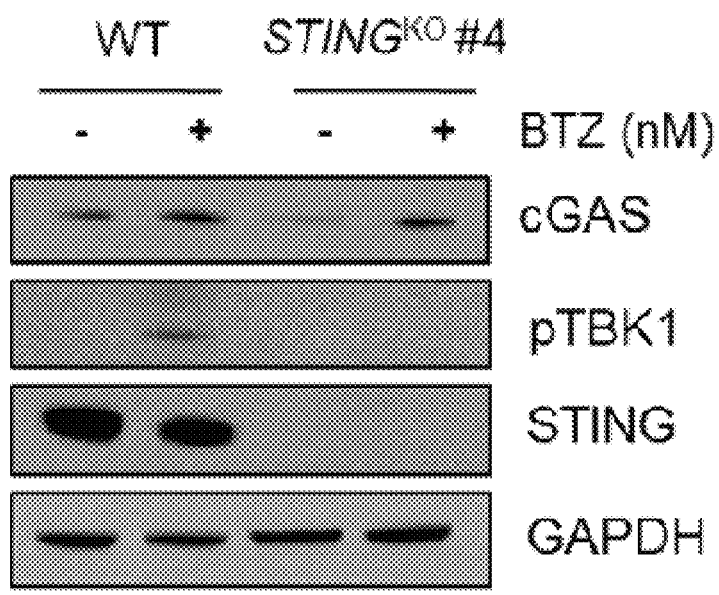
Figure 21E:
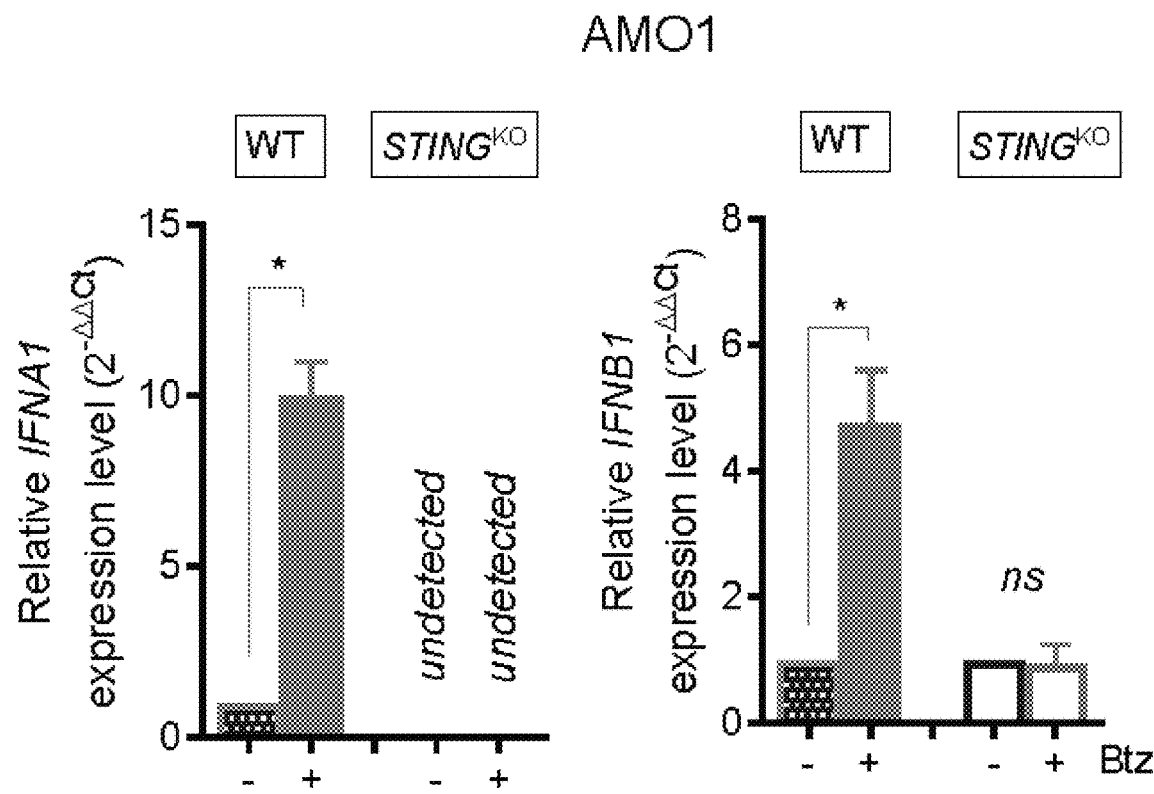
Figure 21F:
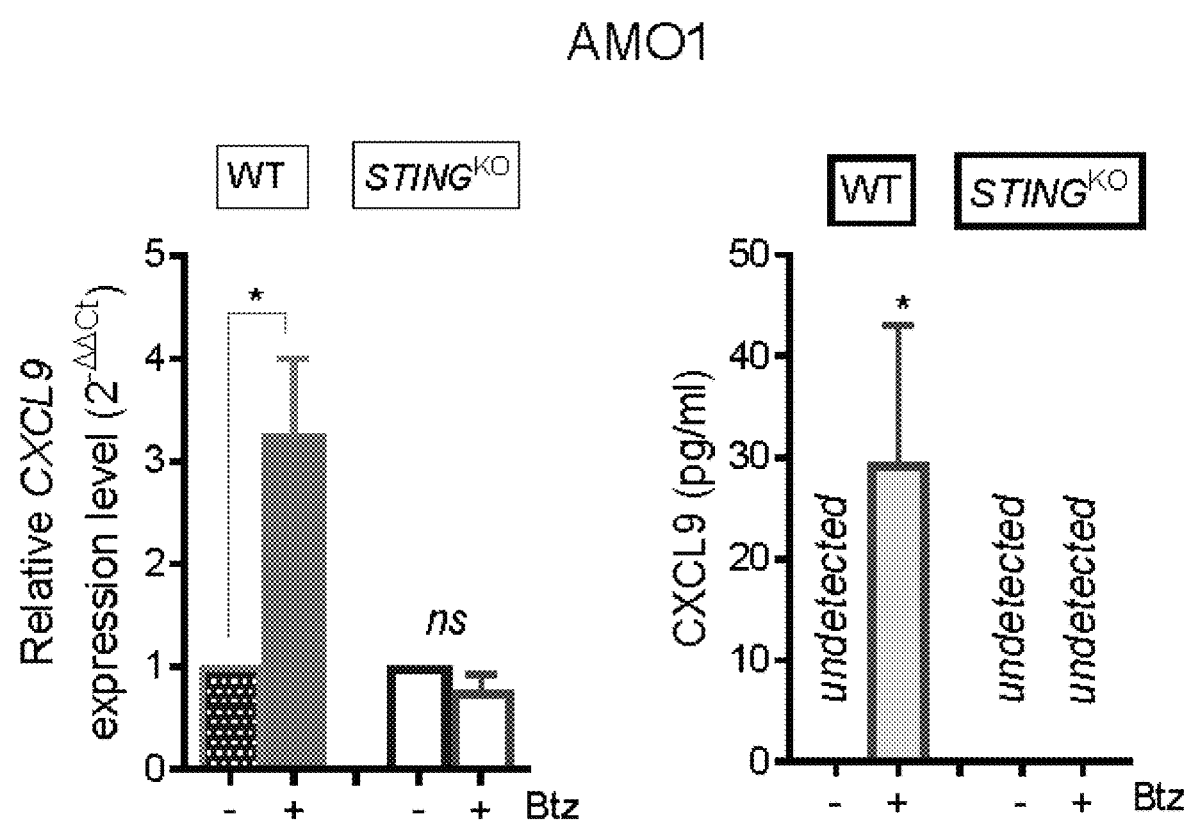
Figure 21G:
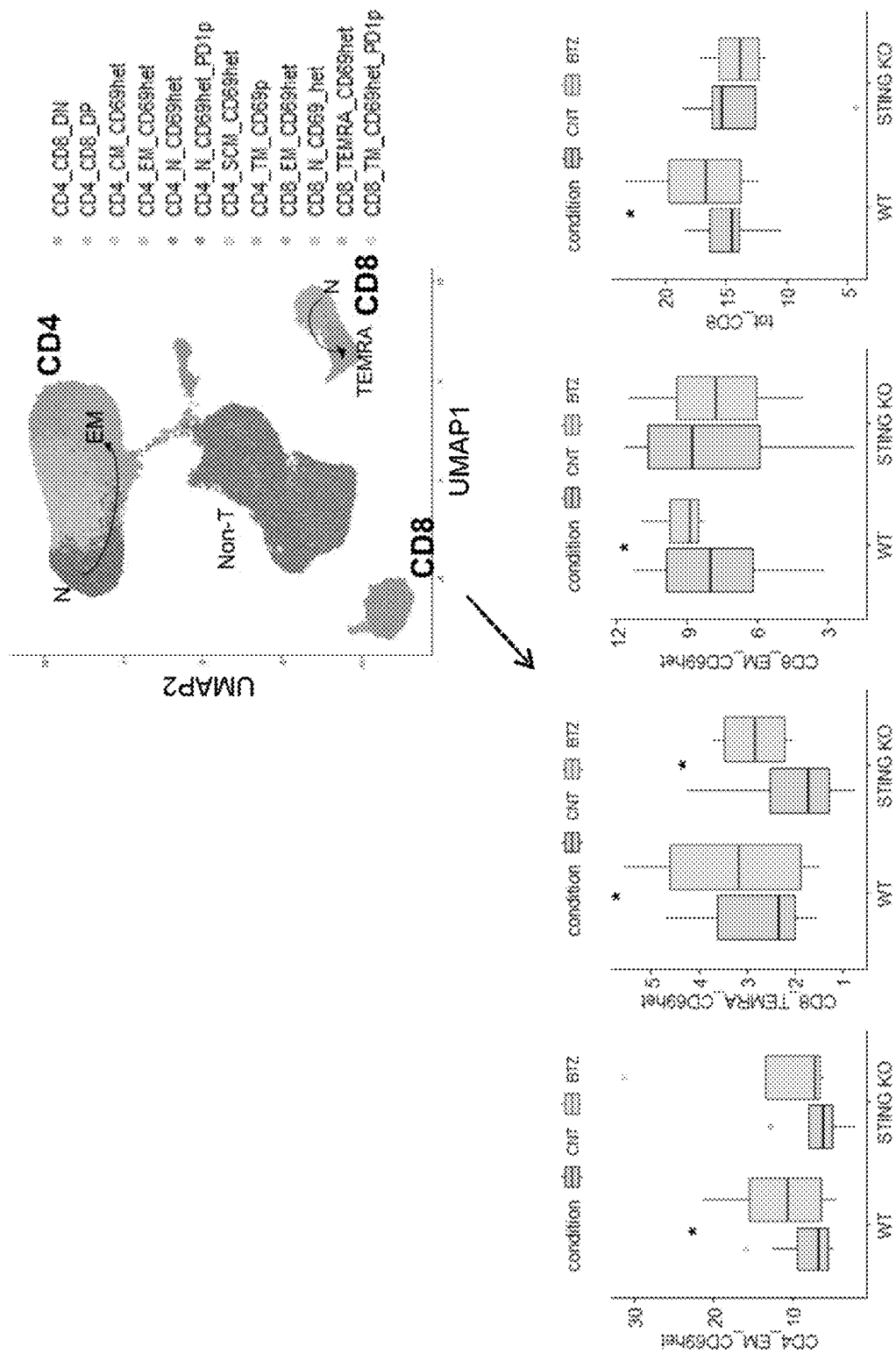
Figure 30A:
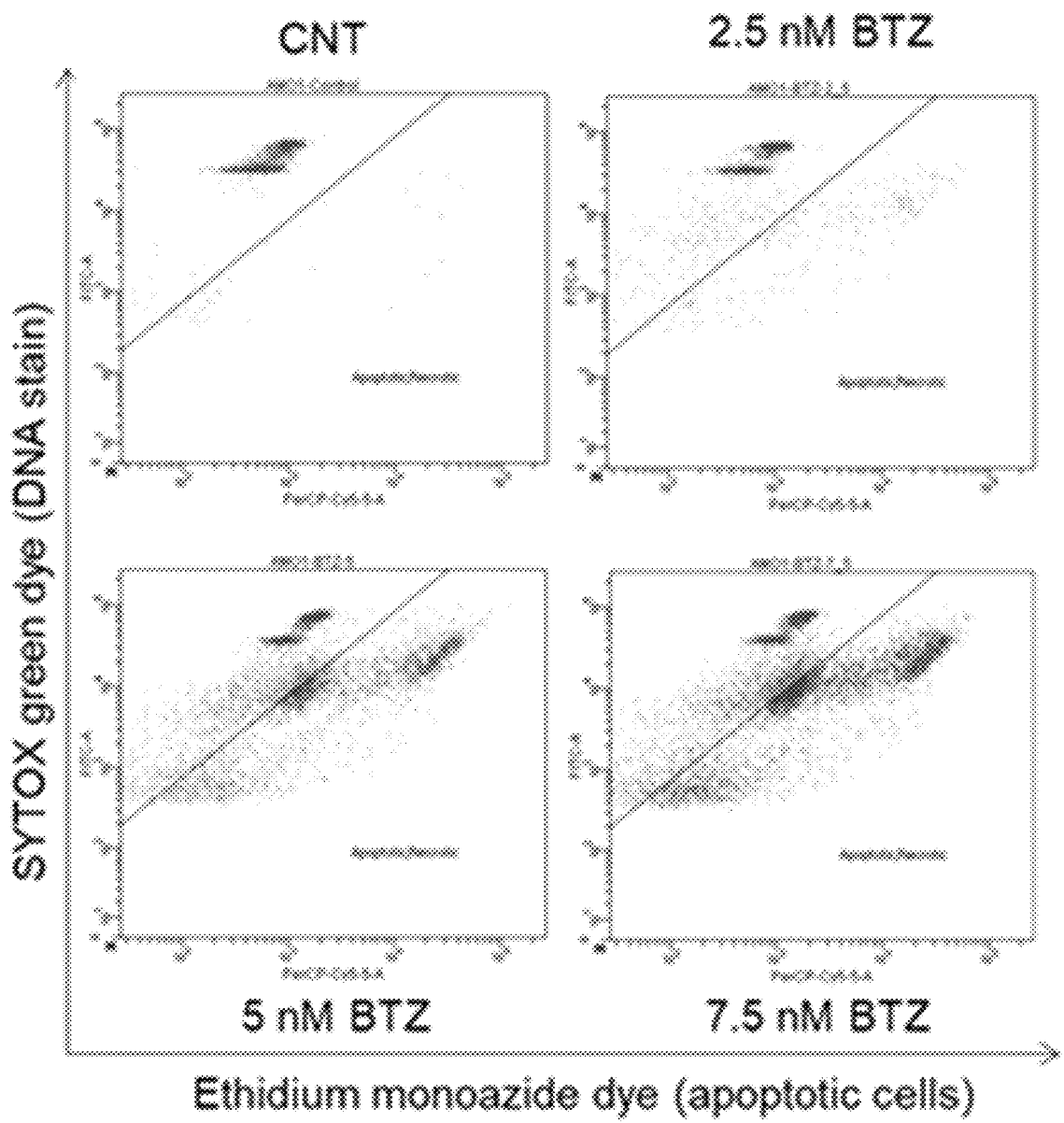
FIG. 30A to FIG. 30H show Type I IFN response after BTZ in MM is STING dependent.
Figure 30A:
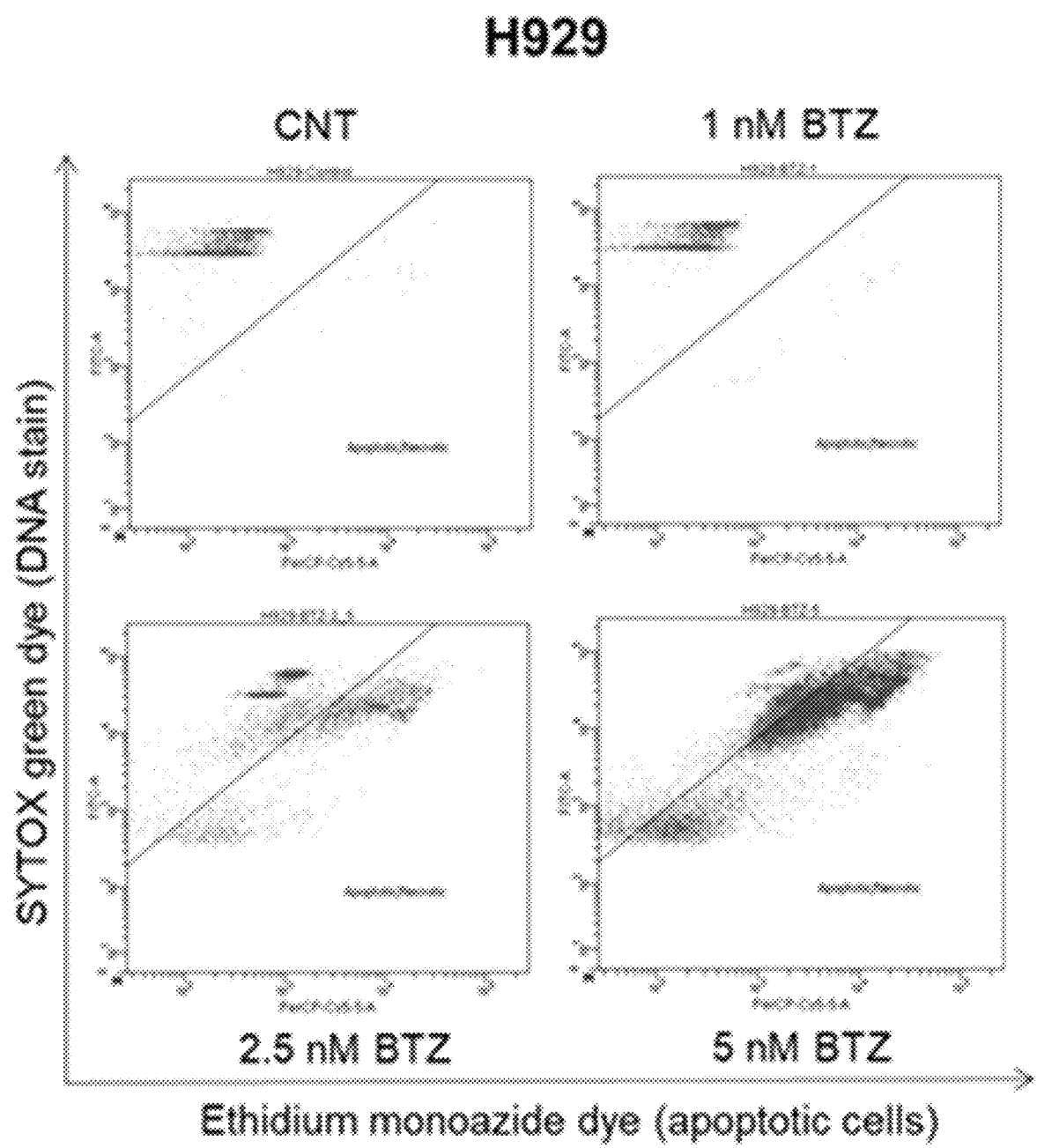
Figure 30B:
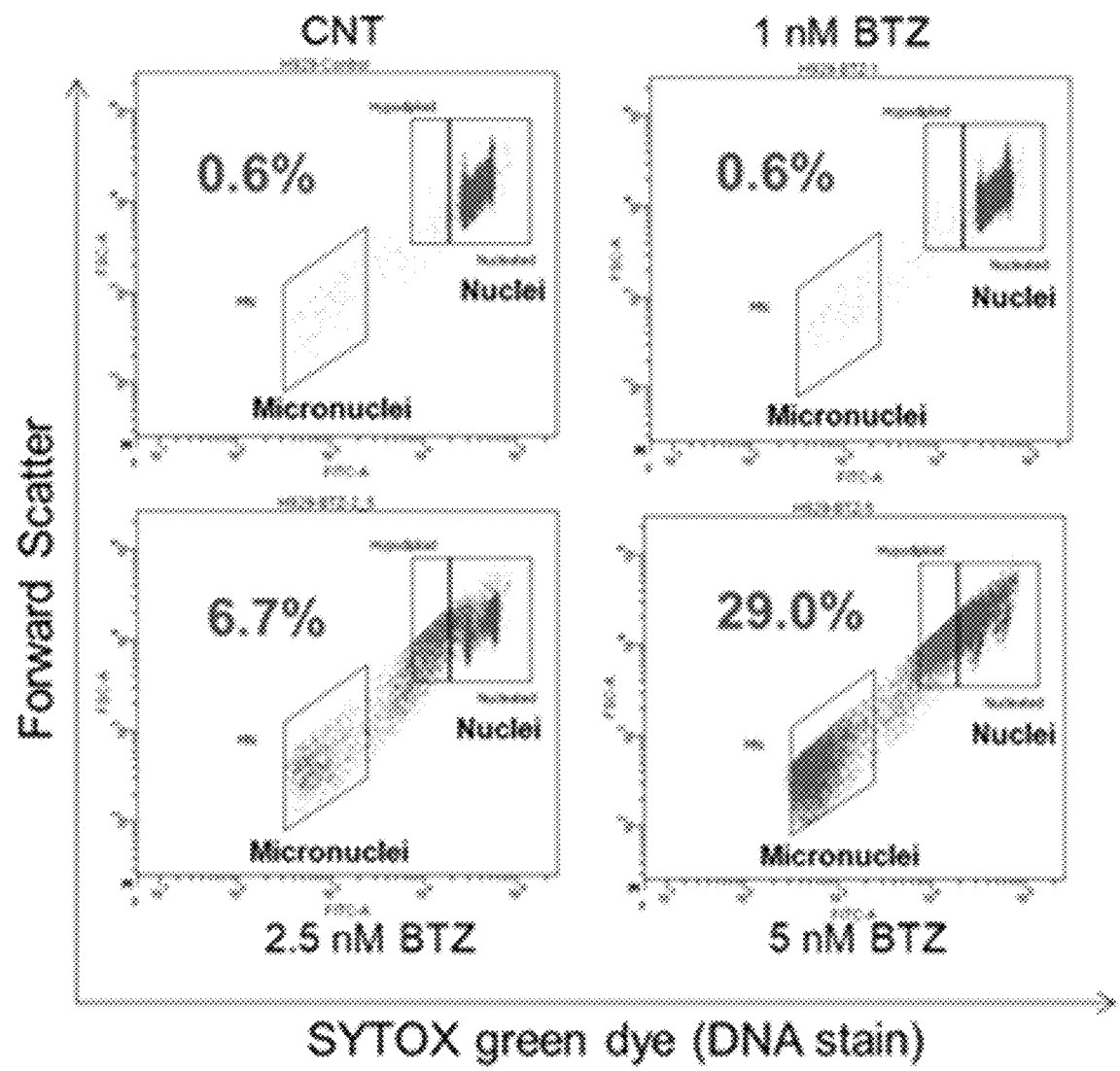
Figure 30C:
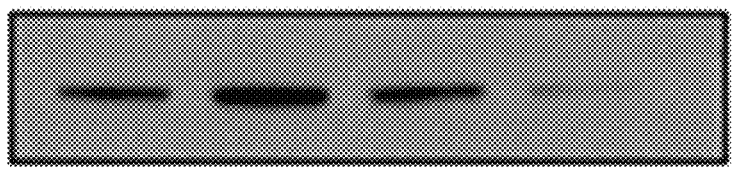
Figure 30C:
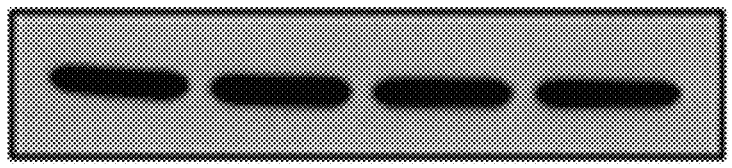
Figure 30C:
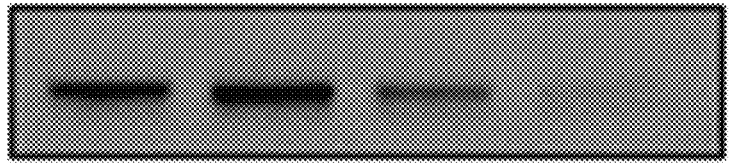
Figure 30C:
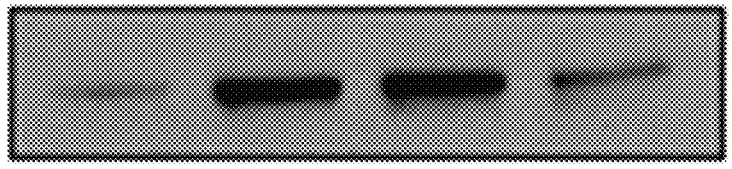
Figure 30C:
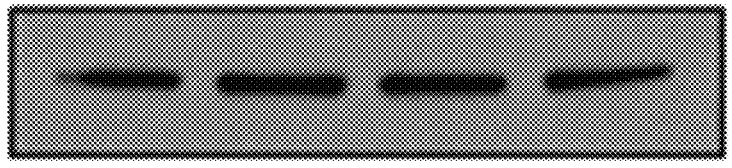
Figure 30D:
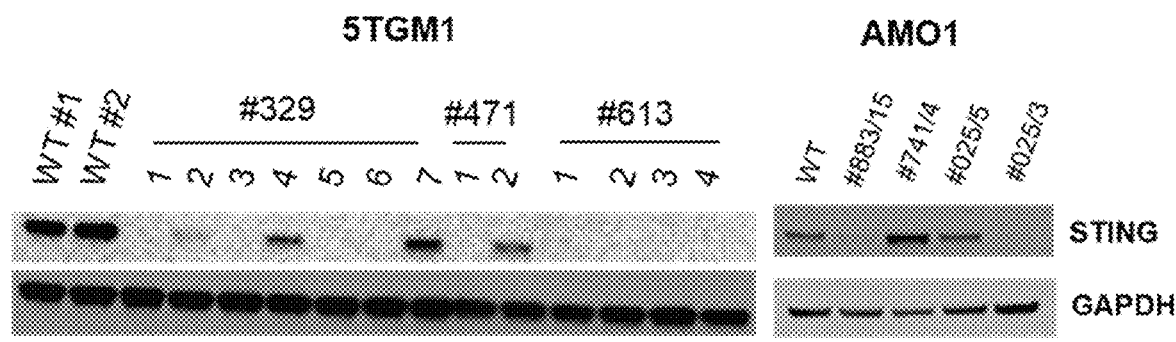
Figure 30E:
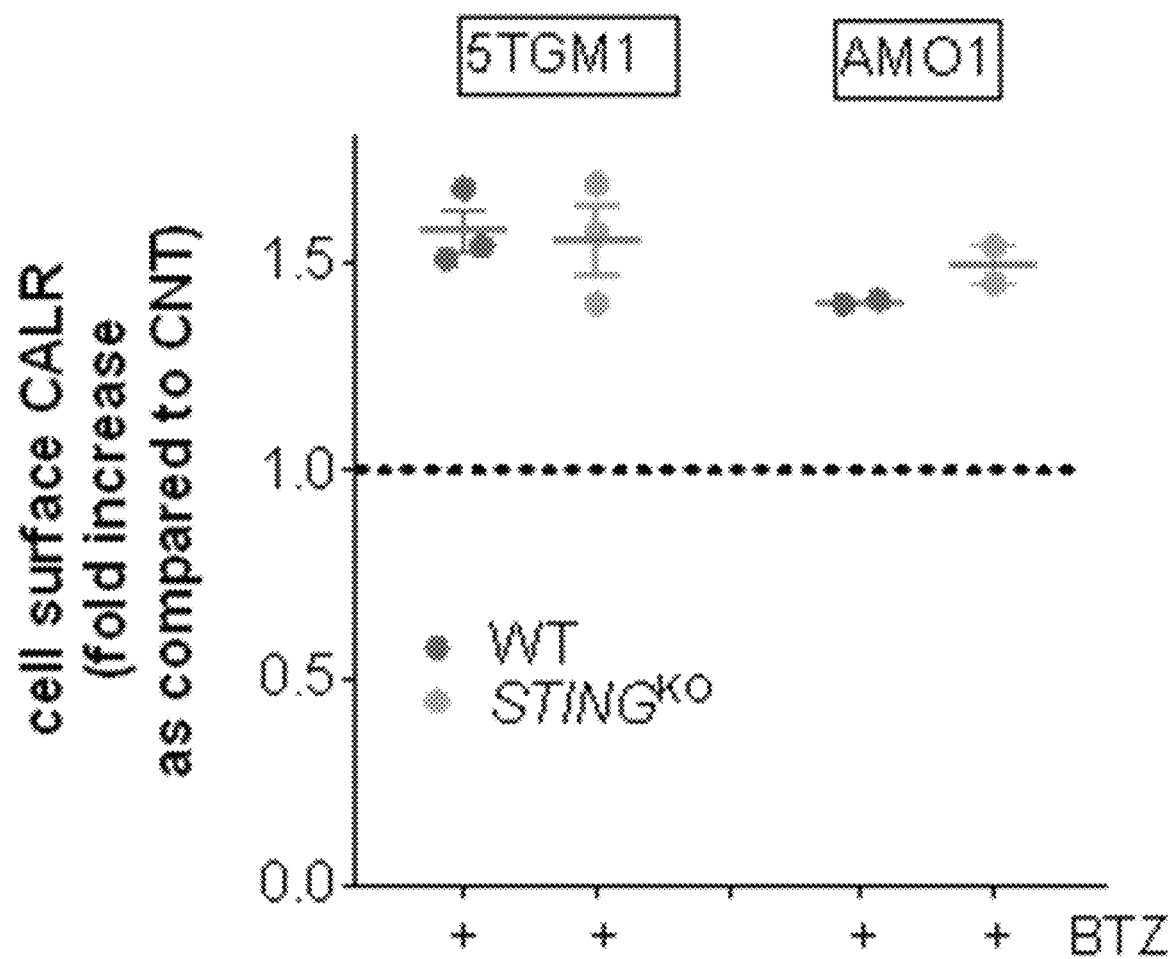
Figure 30F:
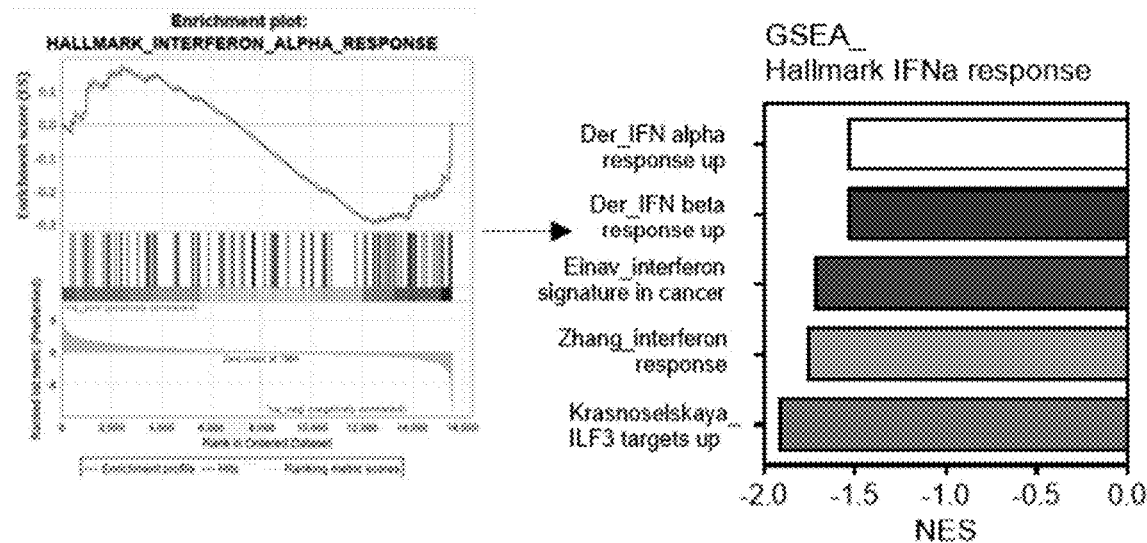
Figure 30G:
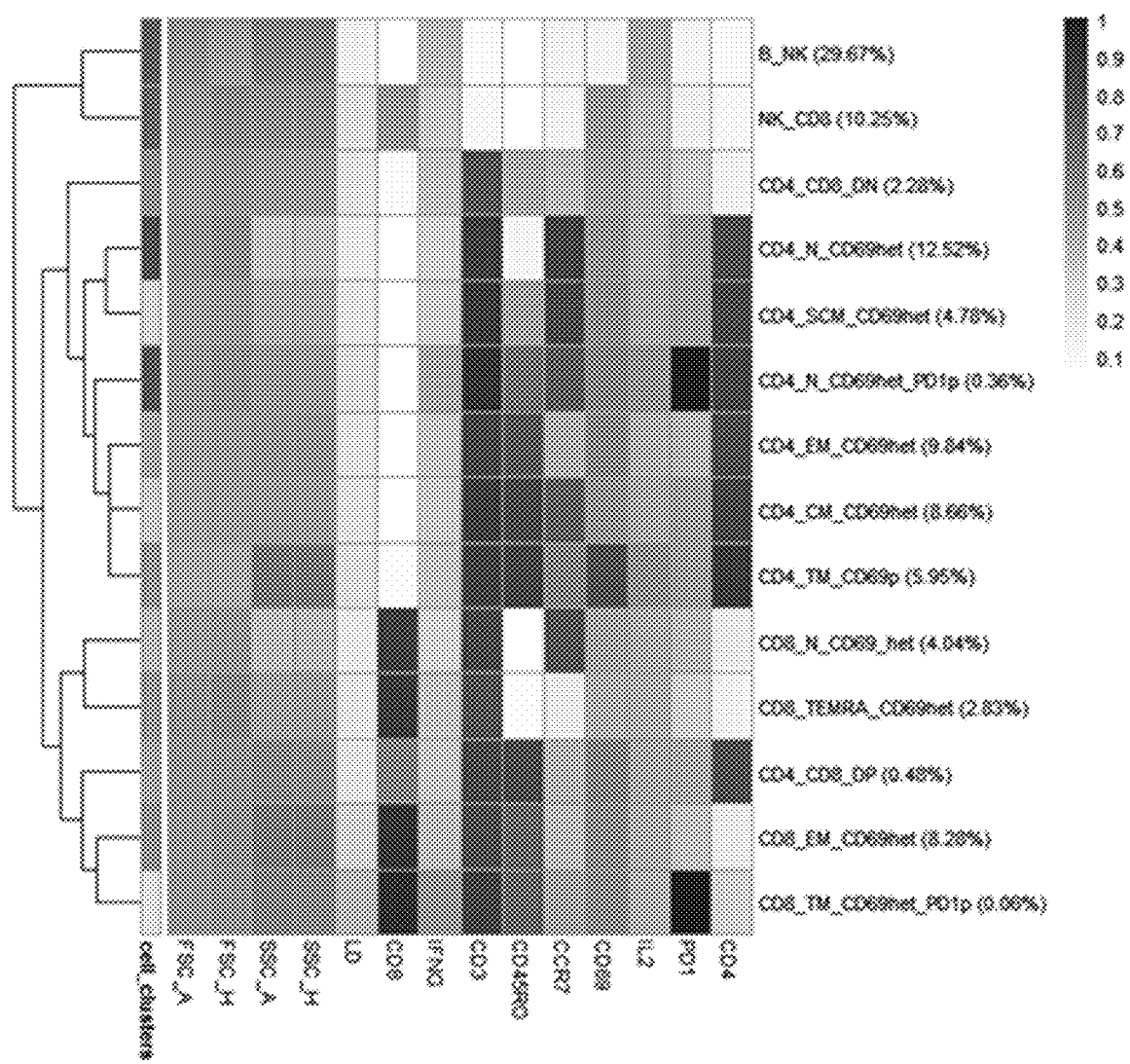
Figure 30H:
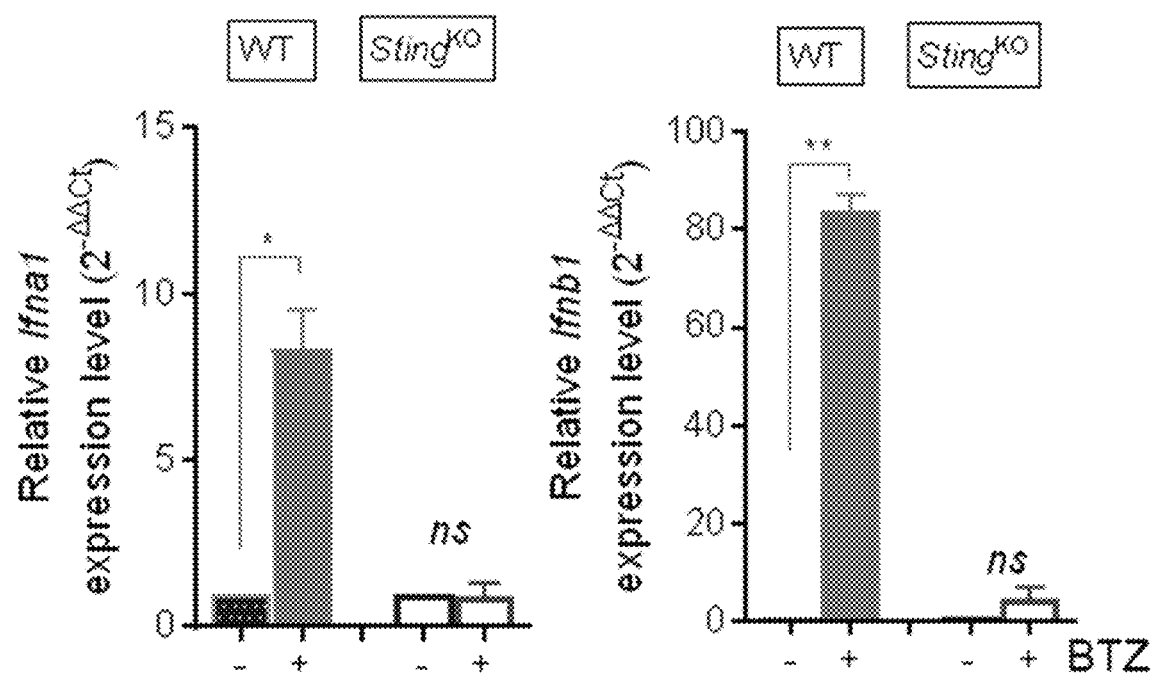

BTZ induces genomic instability and inhibits DNA repair in MM cells (Neri et al. (2011) Blood; 118(24):6368-79). Recent studies show that damaged DNA can be detected outside the nucleus and induce an immune stimulatory response, mimicking a viral attack and activating a type-I IFN response (Zhang C Z, Spektor A, Cornils H, Francis J M, Jackson E K, Liu S, et al. Chromothripsis from DNA damage in micronuclei. Nature 2015; 522(7555):179-84; Mackenzie K J, Carroll P, Martin C A, Murina O, Fluteau A, Simpson D J, et al. cGAS surveillance of micronuclei links genome instability to innate immunity. Nature 2017; 548 (7668):461-5). BTZ induced a dose-dependent increase of DNA content in the cytoplasm of AMO1 and NCI-H929 MM cells, detected in the form of micronuclei by flow cytometry (FIGS. 21A and 30A-B). Previous studies demonstrated that cGAS can directly sense micronuclei formation and link genomic instability to innate immunity by directly activating the STING/TMEM173 pathway (Mackenzie et al. (2017) Nature; 548(7668):461-5; Motwani et al. (2017) Immunity; 47(4):616-7 doi 10.1016/j.immuni.2017.09.020; Reislander et al. (2020) Mol Cell. Importantly, it was found that expression of the ISGs included in the ICD-signature was positively correlated with STING expression in the cluster of patients with high levels of ICD signature genes (FIG. 21B). Moreover, it also found that BTZ treatment of both AMO1 and NCI-H929 multiple myeloma cells induces accumulation of the cytosolic DNA sensor cGAS, which activates the adaptor molecule STING and in turn leads to phosphorylation by TBK1 kinase of IRF3, a well-known transcription factor of type I IFN genes (Hopfner et al. (2020) Nat Rev Mol Cell Biol; doi 10.1038/s41580-020-0244-x). (FIG. 21C and FIG. 30C). It was therefore hypothesized that BTZ may induce type-I IFNs signaling via activation of the cGAS/STING pathway. To test this possibility, human AMO1 STING$^{KO}$ and murine 5TGM1 Sting$^{KO}$ multiple myeloma cell lines were generated (FIG. 30D); and confirmed that KO of STING did not alter CALR exposure process after treatment with BTZ in both edited cell lines (FIG. 30E). Although BTZ treatment significantly accumulated cGAS, knockout of STING blocked activation of downstream signaling including p-TBK1 in AMO1 cells (FIG. 21D). The impairment of STING pathway activation was consistent with abrogation of a type I IFN response after BTZ treatment, and RNA-seq analysis showed that BTZ treatment in AMO1 multiple myeloma cells lacking STING did not activate transcription of genes in the IFNs response or increase the levels of IFNA1 and IFNB1 transcripts, as detected by qRT-PCR (FIG. 21E and FIG. 30F). Likewise, abrogation of IFN response after BTZ treatment was also confirmed in 5TGM1 Sting$^{KO}$ cells (FIG. 30G). Moreover, neither CXCL9 transcript or its secreted form were detected after treatment of AMO1 STING$^{KO}$ clones with BTZ (FIG. 21E-21F). This block of type-I IFNs response in myeloma cells resulted in impaired T cell response: no significant increase of CD4+EM; total CD8+; and CD8+EM cells were noted after co-culture of DCs with BTZ-treated AMO1 STING$^{KO}$ cells, as compared to BTZ-treated AMO1 WT clones (FIGS. 21G and 30H). These findings indicate that type-I IFN response in multiple myeloma cells triggered by BTZ is mediated by the cGAS/STING pathway and enhances anti-multiple myleoma T cell responses.

STING Agonists Potentiate BTZ-Induced Anti-Tumor Immunity.

Figure 22A:
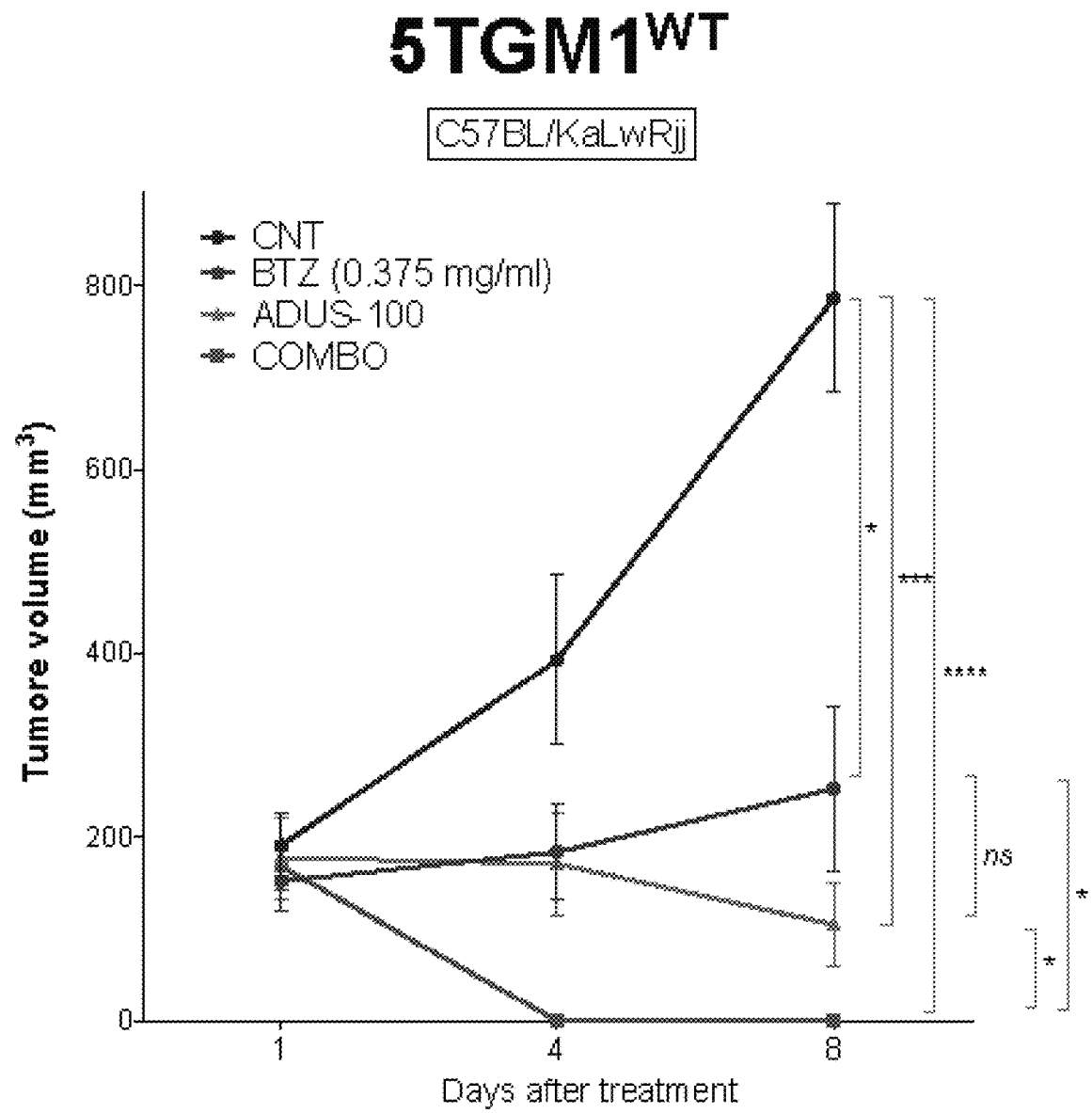
FIG. 22A to FIG. 22E shows STING agonists potentiate BTZ-induced anti-tumor immunity.
Figure 22B:
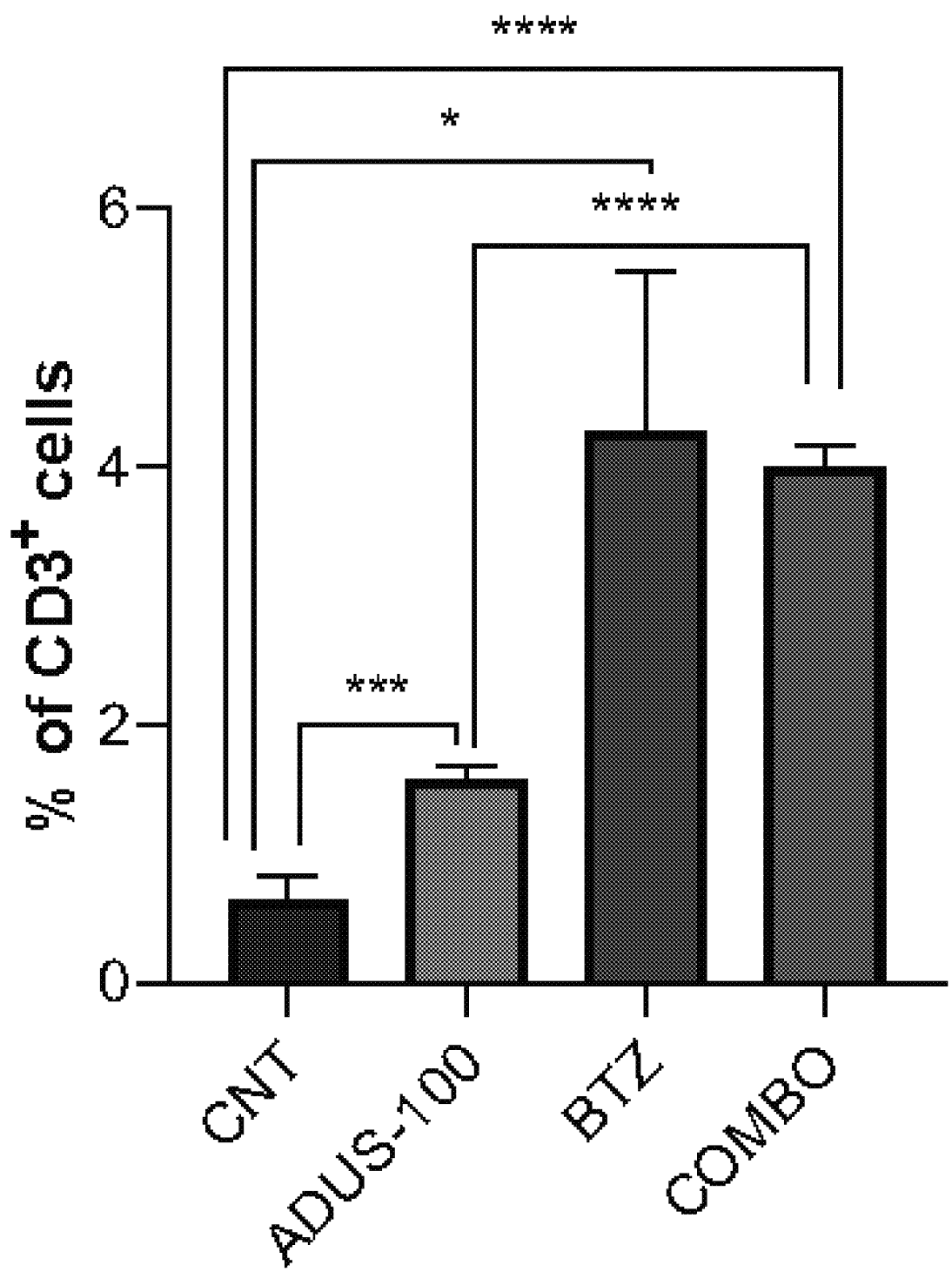
Figure 22B:
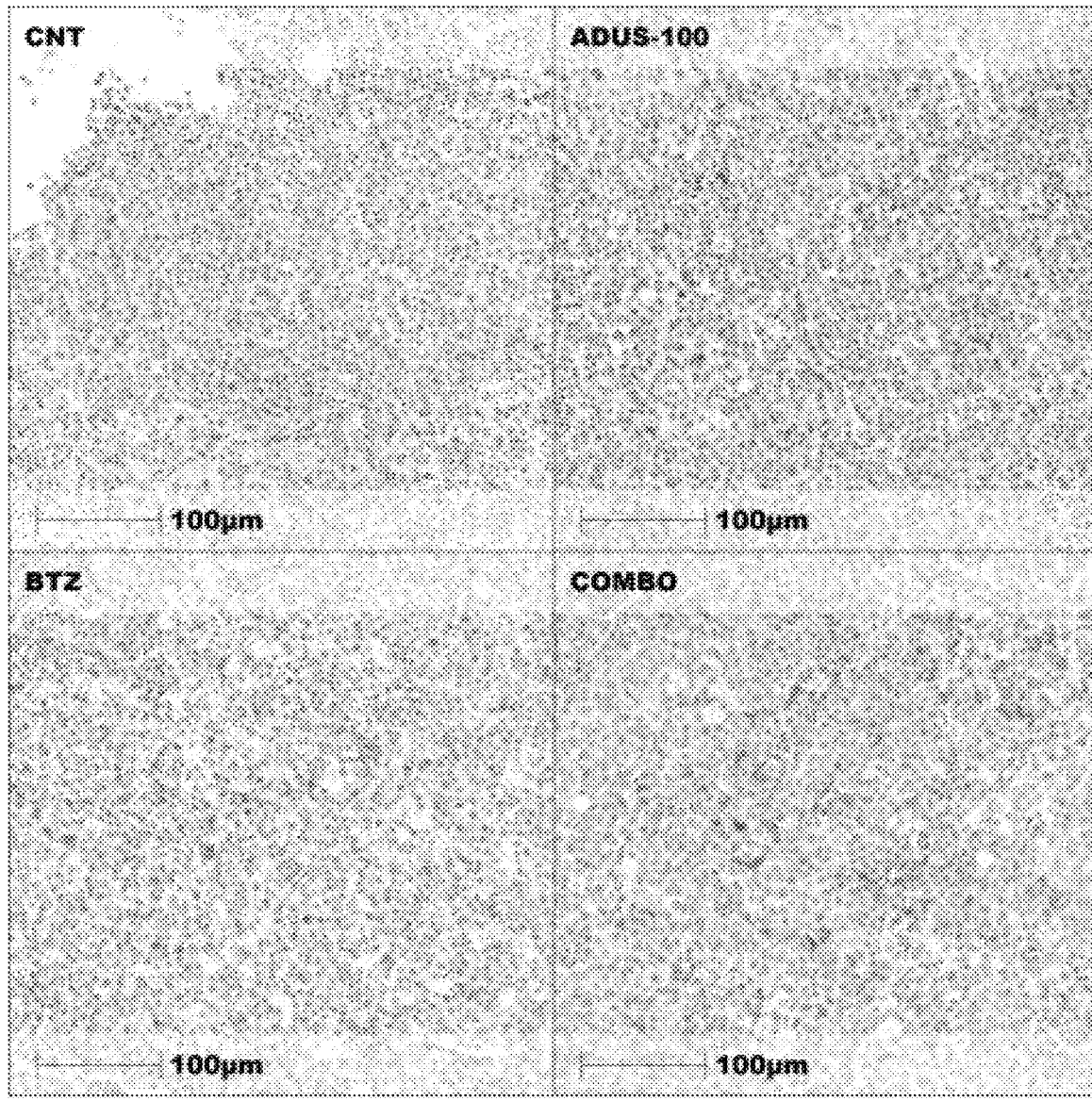
Figure 22C:
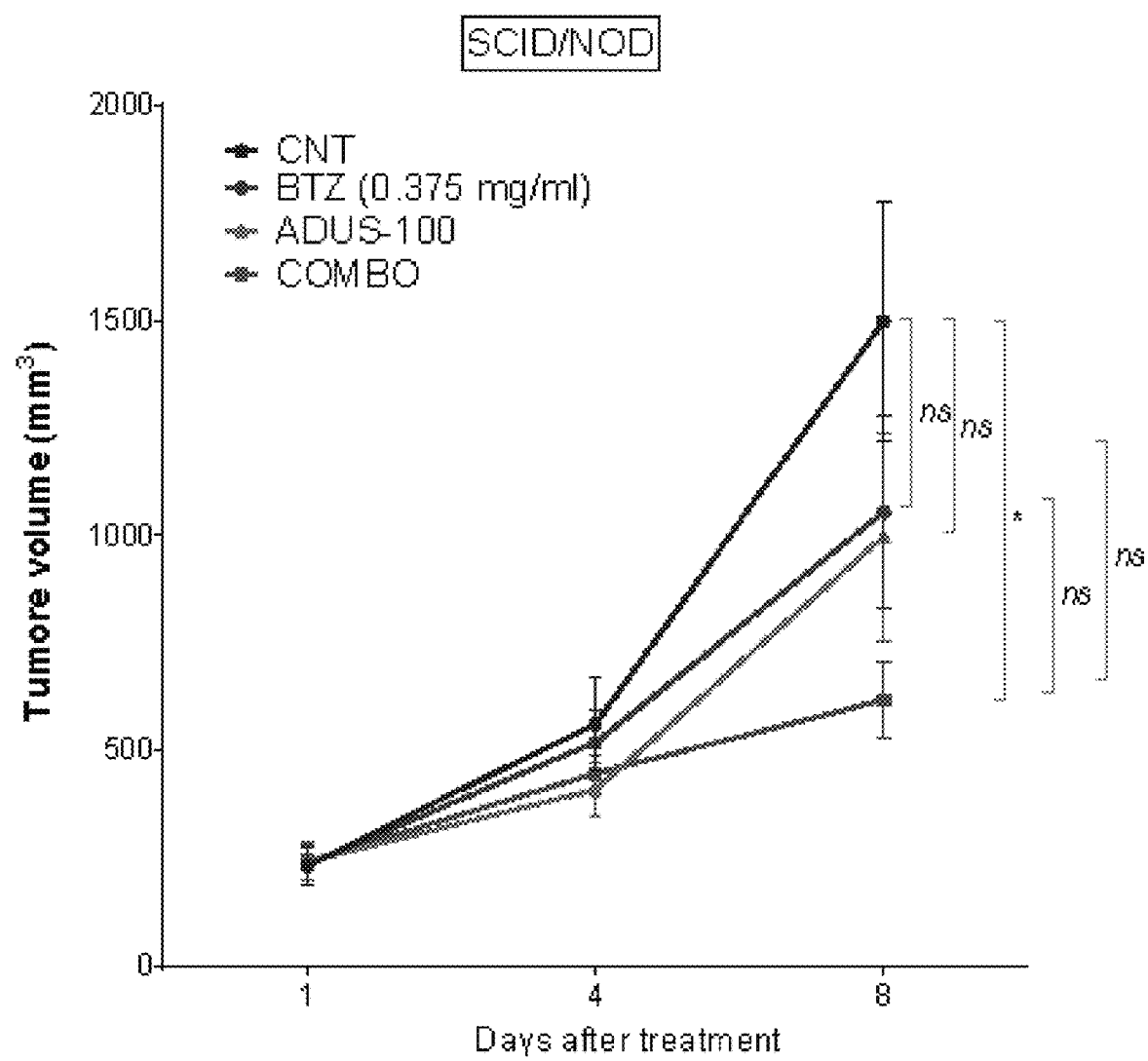
Figure 22D:
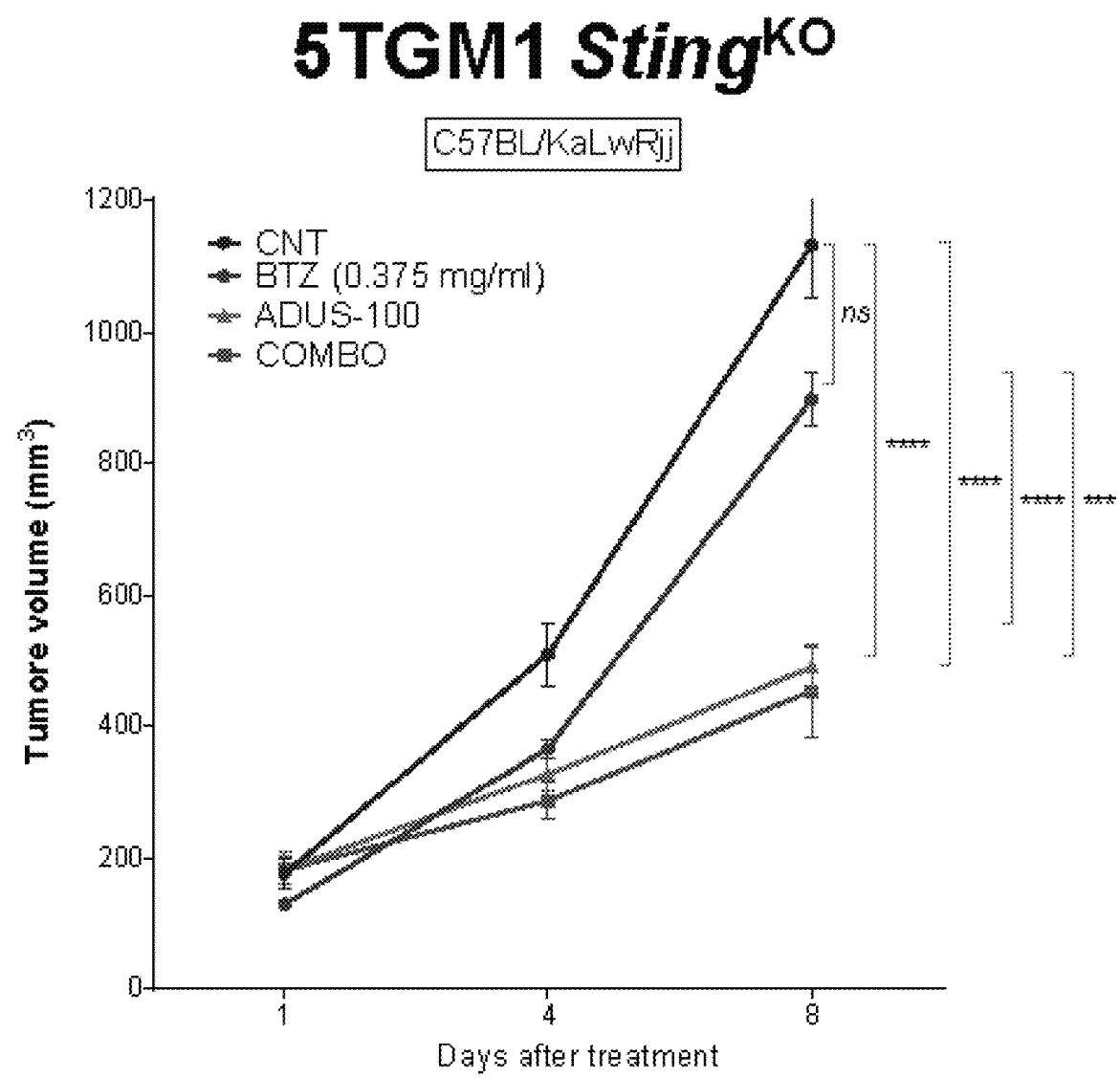
Figure 22E:
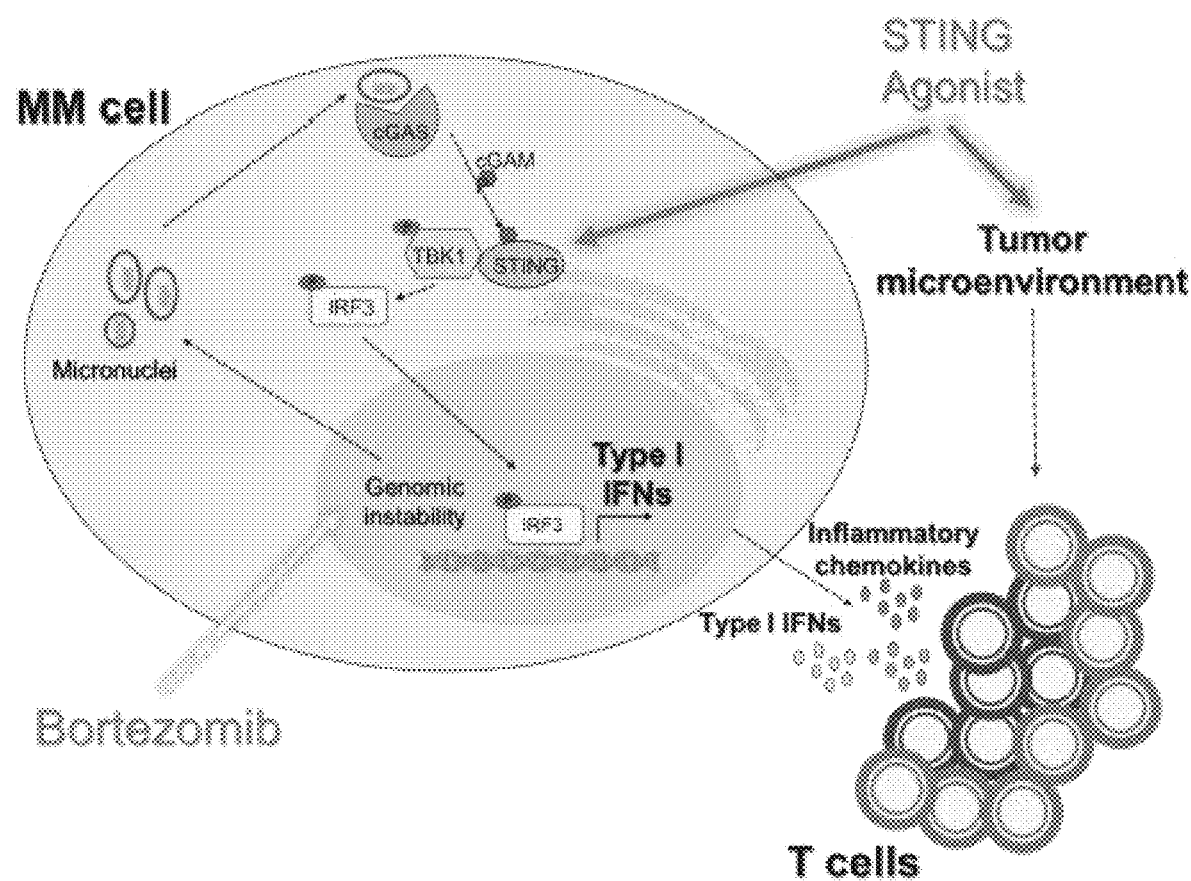
Figure 31A:
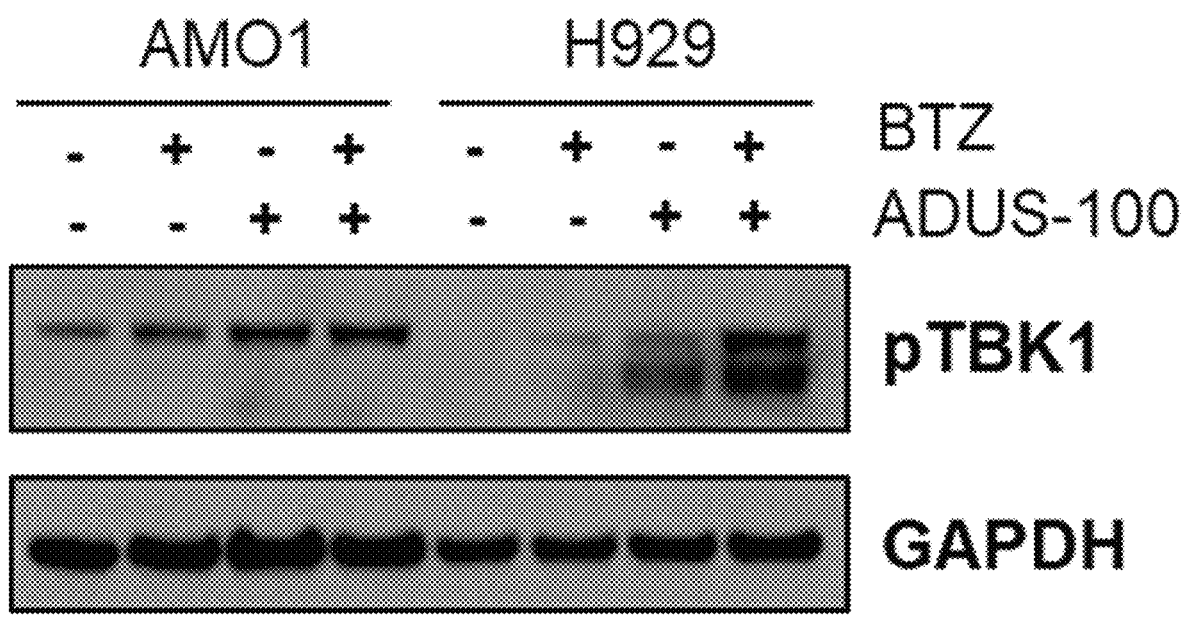
FIG. 31A to FIG. 31C shows STING agonists potentiate BTZ-induced anti-tumor immunity.
Figure 31B:
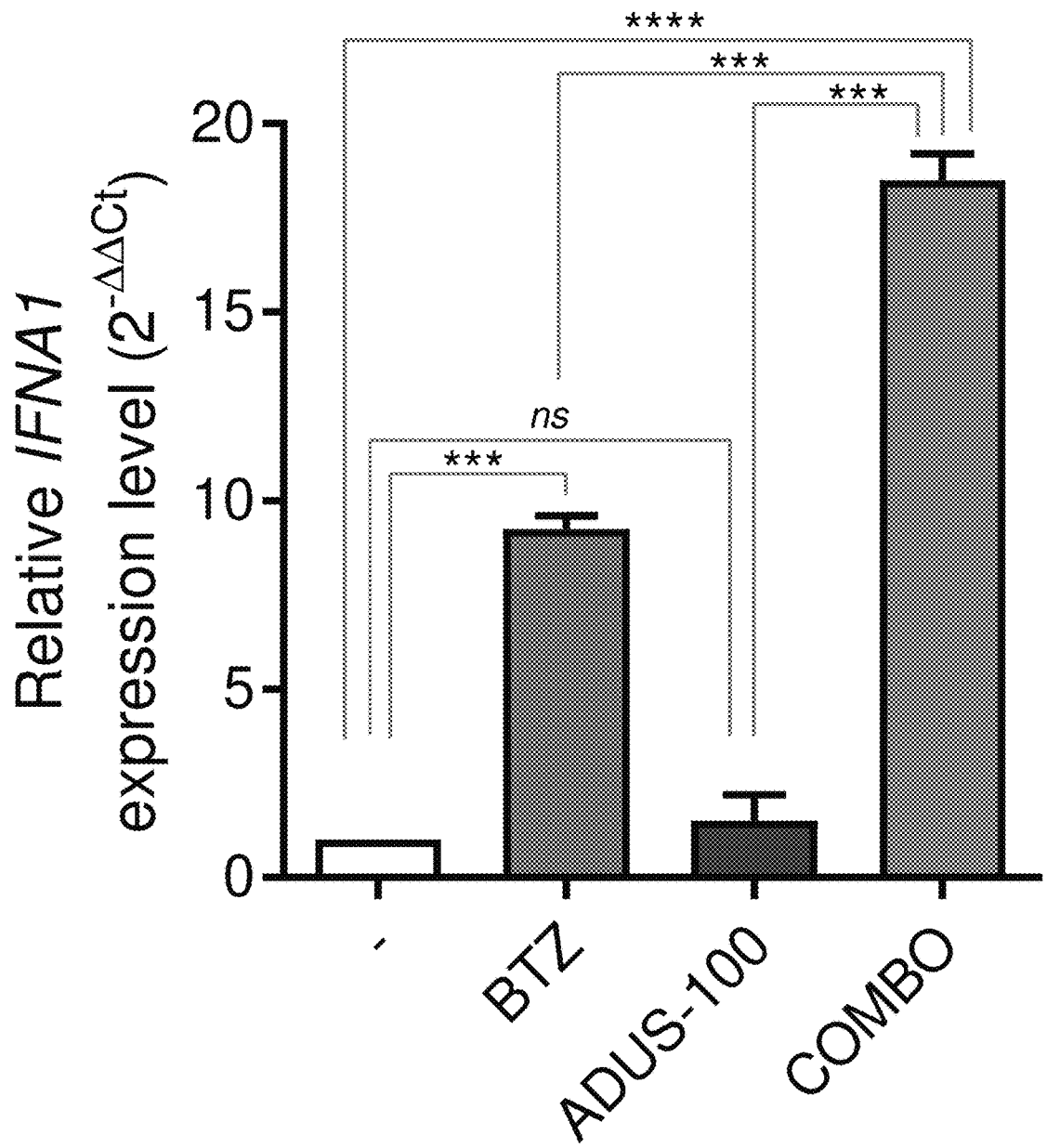
Figure 31B:
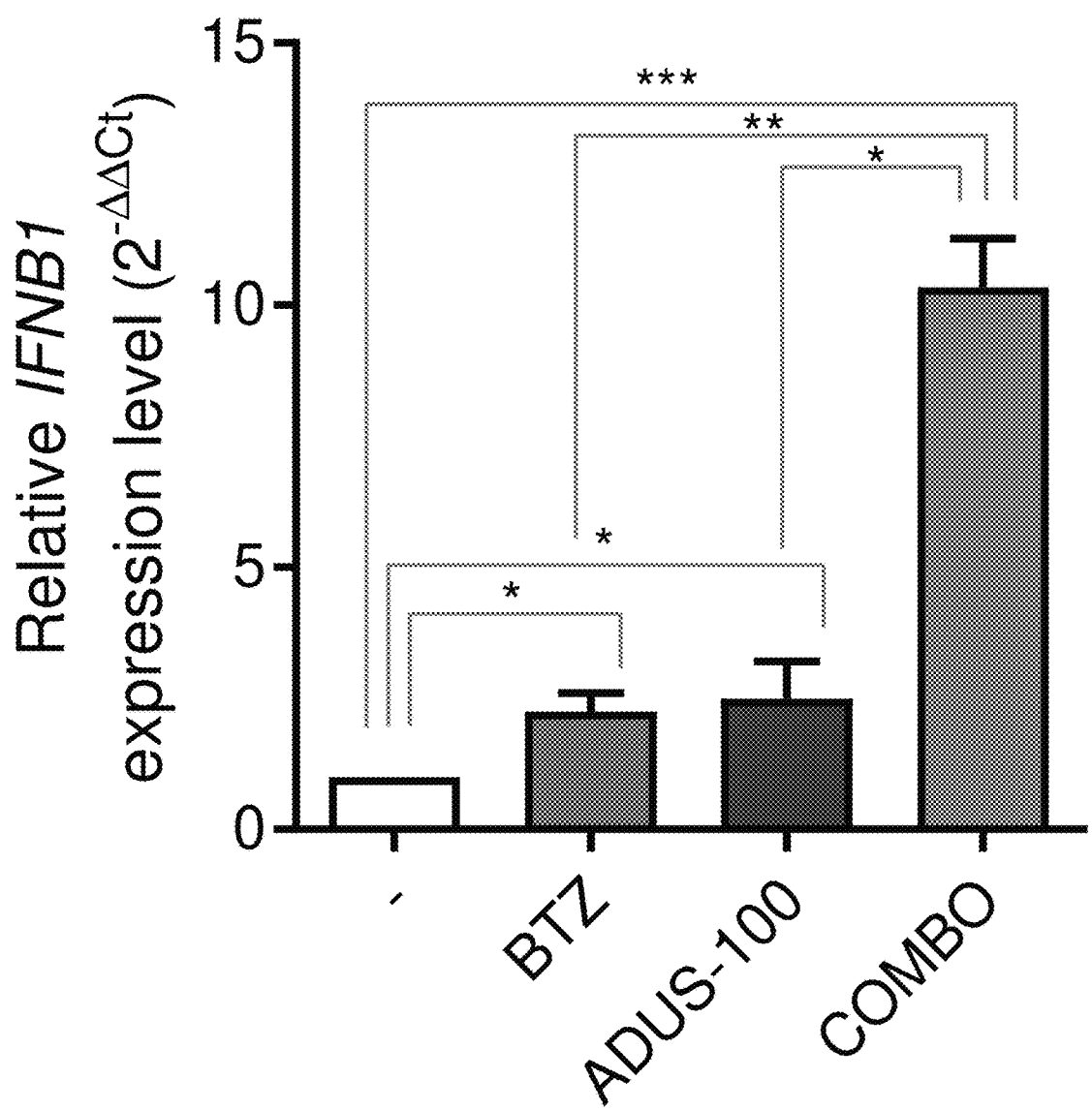
Figure 31C:
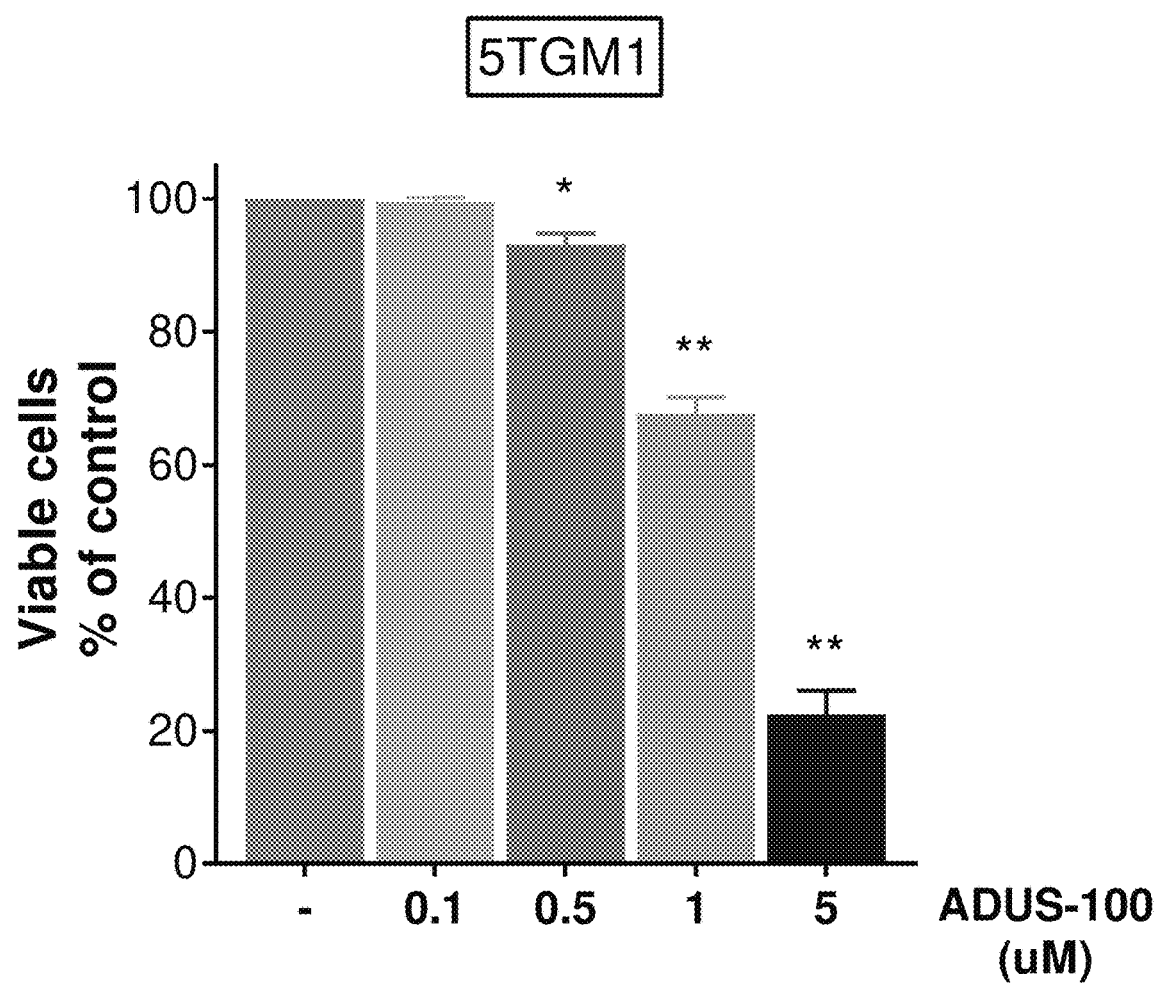

Pharmacological activation of the STING pathway represents a promising strategy to overcome immunosuppression in the tumor microenvironment (Flood et al. (2019) Immunol Rev; 290(1):24-38; Corrales et al. (2016) J Clin Invest; 126(7):2404-1; Sivick et al. (2019) Cell Rep; 29(3): 785-9 doi 10.1016/j.celrep.2019.09.089). It was found that the synthetic cyclic dinucleotide STING agonist ADU-S100 (Sivick et al. (2019) Cell Rep; 29(3):785-9; Corrales et al. (2015) Cell Rep; 11(7):1018-30) can significantly increase the activation of the STING signaling after BTZ treatment in vitro, as evidenced by higher levels of phosphorylated TBK1 kinase (FIG. 31A) and increased transcription of IFNA1 and IFNB1 (FIG. 31B). Thus, it was tested whether combining BTZ and ADU-S100 could increase the tumor T cell infiltration and enhance the anti-tumor activity in vivo. C57BL/KaLwRij immunocompetent mice bearing 5TGM1 tumors were randomized to receive 1) BTZ alone (0.375 mg/kg twice/week for 2 weeks), 2) peri-tumoral administration of ADU-S100 (100 ug on day 1 and 2) 3) both drugs or 4) PBS as control. Mice treated with the combination showed the most significant reduction of tumor growth, with a complete regression of the tumors (COMBO vs BTZ p=0.029; COMBO vs ADU-S100 p=0.05) (FIG. 22A). IHC analysis of tumors retrieved after one administration of the drugs showed that treatment with either BTZ or ADS-100 alone or in combination increased CD3+ T cell infiltration within tumors (FIG. 22B). Murine 5TGM1 cells are sensitive to a direct killing by ADU-S100 treatment in vitro (FIG. 31C). Thus, an identical in vivo study in immunodeficient NOD/SCID mice was done to examine whether ADU-S100 antagonizes multiple myeloma growth in vivo via an immunomodulatory activity or via a direct cytotoxicity. As shown in FIG. 22C, the absence of the immune system abrogated the anti-tumor effects of both BTZ and ADU-S100 (100 ug on day 1 and 2), indicating that the observed tumor regression in the presence of the immune system was primarily due to an anti-tumor immune response. To further confirm the role of the intrinsic stimulation of intratumoral STING in mediating the immune activation, the effect of BTZ-STING agonist combination in immunocompetent mice bearing Sting$^{KO}$ tumors was also tested. Anti-tumor activity of BTZ was significantly abrogated against tumors lacking Sting (FIG. 22D); whereas ADU-S100 still retained a partial anti-multiple myeloma activity most likely due to stimulation of STING pathway in the immune microenvironment cells (Corrales et al. (2016) J Clin Invest; 126(7):2404-11; Sivick et al. (2019) Cell Rep; 29(3):785-9). Taken together, these results indicate a central role of STING in mediating the anti-multiple myeloma immune response induced by BTZ; and show that STING agonist augments this effect by further promoting an immunogenic microenvironment (FIG. 22E).

DISCUSSION

Immune dysfunction poses a challenge to effective anti-multiple myeloma therapy and complete elimination of minimal residual disease (Nakamura et al. (2020) *Blood*; doi 10.1182/blood.2020006540). Although the mechanisms of action of anti-multiple myeloma agents have been characterized, their in vivo effects on the dynamic interplay between tumor cells and immune system are yet to be defined (Nakamura K et al. (2020) Blood; doi 10.1182/blood.2020006540); and may inform optimal combination treatment approaches in patients. In this context, the extraordinary clinical benefits of BTZ treatment have to date been attributed to the exquisite intrinsic dependency of multiple myeloma cells on proteasome activity (Gandolfi et al. (2017) *Cancer Metastasis Rev;* 36(4):561-84). Here, this notion was challenged by characterizing BTZ as an immunotherapeutic agent, and delineating novel mechanisms whereby BTZ triggers a specific anti-multiple myeloma immune response. The first major conclusion of this study is that BTZ efficacy is due to the activation of the immune system: while the drug can efficiently delay tumor growth in immunodeficient mice, it requires a competent immune system to induce tumor regression. To explain this effect, a tumor-intrinsic mechanism of immune activation, specifically the induction of ICD, was examined. Although early in vitro studies have suggested an immunogenic role of BTZ (Spisek R, et al. (2007) Blood; 109(11):4839-45), its biologic, functional, and clinical significance is not fully characterized (De Beck et al. (2018) Oncoimmunology; 7(10):e1484981). In these studies, BTZ treatment led to the exposure of the "eat-me" molecule CALR on the cell surface of both human and murine multiple myeloma cell lines, and the obligate role of this DAMP as a major pro-phagocytic checkpoint in multiple myeloma both in vitro and in vivo was confined. Analysis of transcriptomic changes in murine multiple myeloma cells after BTZ treatment identified an ICD-signature. Most importantly, clinical significance was confirmed, since the analogous ICD signature was positively correlated with improved outcome of multiple myeloma patients treated with BTZ in two independent datasets. Multiple clinical trials have shown that treatment with BTZ is effective in reducing tumor burden in multiple myeloma patients, including multiple myeloma with high-risk cytogenetics such as t(4;14) (Avet-Loiseau et al. (2010). *J Clin Oncol;* 28(30):4630-4). Based on these data, and without being bound to any particular theory, it is speculated that clinical responses to BTZ may be mediated via the induction of an efficient anti-myeloma immune response. Further characterization of the genes included in the BTZ-induced ICD signature identified a multiple myeloma cell-autonomous type-I IFN response. This finding is consistent with a previous report showing that activation of a "viral mimicry" state in multiple myeloma cells increases the anti-multiple myeloma immune response to therapy in the murine Vk*MYC model of multiple myeloma (Chesi et al. (2016) *Nat Med;* 22(12):1411-20). Moreover, IFN-alpha has in the past been used, either alone or in combination, to treat patients with multiple myeloma; although it demonstrated efficacy, its clinical utility was limited by toxicity (Zhang et al. (2017) *Exp Hematol Oncol;* 6:20).

The second major conclusion of this study is that BTZ stimulates the immunogenicity of multiple myeloma cells by activating the cGAS/STING innate immune response signaling pathway (Mackenzie et al. (2017) *Nature;* 548(7668): 461-5; Hopfner et al. (2020) Nat Rev Mol Cell Biol; doi 10.1038/s41580-020-0244-x). The release of cytosolic DNA after BTZ-induced multiple myeloma cell death is a trigger for the STING pathway; and an increased genomic instability, due to inhibition of the DNA repair machinery, is also recognized as a downstream effect of proteasome inhibition (Neri et al. (2011) Blood; 118(24):6368-79). Here, it is shown that the expression of STING positively correlates with the expression of ICD-related ISGs in multiple myeloma patients, implicating this pathway in BTZ-induced IFN response. Loss of IFN response has been described as an additional mechanism of tumor immune escape (Zaretsky et al. (2016) N Engl J Med; 375(9):819-29); and it was found that multiple myeloma patients with low STING/ISGs expression do not efficiently respond to ICD induction after BTZ treatment. Indeed, immune response after BTZ treatment was significantly reduced in vivo against multiple myeloma tumors lacking Sting. Importantly, activation of the STING pathway is an emerging immunotherapeutic approach, and Phase I and II clinical trials of several STING agonists are currently ongoing in solid tumors or lymphoma, alone or in combination with immunotherapies (NCT04144140, NCT03937141, NCT02675439, NCT03172936, NCT03010176). The prior use of IFN stimulation in anti-MM therapy, coupled with the current data, suggested that STING agonists may also represent a promising therapeutic strategy in multiple myeloma; and that their combined use with BTZ may increase their immunogenic effect, especially in patients with low basal level of STING expression. Indeed, it was shown that combination of BTZ with the STING agonist ADU-S100 significantly enhanced the immunogenic effect of BTZ in vivo. These studies both validate STING as a therapeutic target, and provide the framework for clinical trials evaluating BTZ and STING agonist combination therapy in multiple myeloma.

Methods for Example 4

Cell Culture

Multiple myeloma cell lines U266, NCI-H929, murine JAWSII and 293T were purchased from the American Type Culture Collection (ATCC); AMO1 was purchased from DSMZ; and murine 5TGM1 cells were kindly provided by Dr. Irene Ghobrial (DFCI, Boston). Cell lines were tested to rule out *Mycoplasma* contamination using the MycoAlert *Mycoplasma* Detection Kit (Lonza) and authenticated by Short Tandem Repeats DNA typing. Human multiple myeloma cell lines were cultured in RPMI/1640 media containing 10% fetal bovine serum (FBS) (GIBCO; ThermoFisher Scientific), 2 µmol/L glutamine, 100 U/mL penicillin, and 100 µg/mL streptomycin (GIBCO; ThermoFisher Scientific). 293T cells were maintained in DMEM culture media with 10% FBS and 1% penicillin-streptomycin. Murine JAWSII cells were cultured in Alpha minimum essential medium with ribonucleosides, deoxyribonucleosides, 4 mM L-glutamine, 1 mM sodium pyruvate, 20% FBS, 1% penicillin-streptomycin, and 5 ng/ml murine GM-CSF(PeproTech). Murine 5TGM1 cells were maintained in Iscove's Modified Dulbecco's Media (IMDM) media (ThermoFisher Scientific) supplemented with 10% FBS and 1% penicillin-streptomycin.

Patient Multiple Myeloma Cells and Normal Donor Samples.

Multiple myeloma patients BM aspirates and normal donor peripheral blood mononuclear cells (PBMCs) were obtained after written informed consent, in accordance with the declaration of Helsinki and under the approval by the Institutional Review Board of the Dana-Farber Cancer Institute. BMMCs and PBMCs were separated by Ficoll-Paque PLUS (GE Healthcare). Multiple myeloma cells from BMMCs were enriched by CD138-positive selection using magnetic microbeads (Miltenyi Biotec).

Drugs and Reagents

Bortezomib was purchased from Selleckchem (S1013) and resuspended in DMSO. Anti-mouse IFNAR1 (Clone: MAR1-5A3) (#BE0241) MoAb and mouse IgG1 Isotype CNT MoAb were purchased from BioXCell and resuspended in InVivoPure Diluition Buffer following manufacturer's instructions. ADU-S100 (#CT-ADUS100) was purchased from ChemieTek.

Proliferation Assay

Cell viability was evaluated by Cell Counting Kit-8 (CCK-8) assay (Dojindo Molecular Technologies).

Apoptosis Assay

Apoptosis was evaluated by Annexin-V/7-Aminoactinomycin D (7-AAD) staining and flow cytometric analysis using the PE Annexin V Apoptosis Detection Kit I (BD Biosciences).

Cell Surface Exposure of CALR

MM cells were seeded in 12-well plates ($2\times10^5$ per well), treated with BTZ for 16 h at indicated concentrations, and then stained with Alexa Fluor647® anti-calreticulin antibody (ab196159, Abcam) and 7-AAD. Analysis of fluorescence intensity on 7-AAD negative cells using BD LRSFortessa X-20 flow cytometer.

Generation of Monocyte-Derived DCs (Mo-DCs) and Phagocytosis Assay.

Mo-DCs were generated from CD14+ peripheral blood monocytes from healthy donors, positively selected using magnetic beads (Miltenyi Biotec), cultured for 6 days in mo-DC differentiation medium containing GM-CSF and IL-4 (130-094-812; Miltenyi Biotec). AMO1 and NCI-H929 cells lines, as well as patient MM cells, were stained with CellTrace™ Far Red (ThermoFisher Scientific), cultured with or without BTZ for 16 h, and then incubated in 48-well plates for 4 h at 1:1 ratio with CellTrace™ CFSE stained Mo-DCs. Cells were then collected, and phagocytosis analysis was performed by flow cytometry and confocal microscopy. Analagous phagocytosis experiments were performed using 5TGM1 murine multiple myeloma and JAWSII cell line that was used as source of immature murine DCs.

Flow cytometry-based assay: Collected cells were analyzed using the BD LRSFortessa X-20 flow cytometer. Mo-DCs that engulfed MM cells were CFSE and FAR-RED double positive. Fold increase in percentage of double positive DCs after co-culture with BTZ treated vs untreated MM cells was compared.

Confocal microscopy-based assay: 5TGM1 cells (15000) were cytospun for 7 min at 300 rpm, fixed in 4% paraformaldehyde for 20 min at RT, and washed three times with 1% FBS in PBS. After washes, nuclear content was stained with Fluoro-gel II mounting medium with DAPI (ThermoFisher Scientific). Slides were examined using Yokogawa Spinning Disk Confocal/TIRF System, and analyzed with ImageJ software.

DCs Maturation Assay

Immature DCs were generated as described above ("Generation of Mo-DCs" section). DCs were cultured alone or with untreated or BTZ pretreated-AMO1 (5 nM) for 24 h. DCs alone were cultured i) without maturation stimuli; ii) with 50 ng/ml of TNFalpha (Millipore Sigma); or iii) with 5 nM of BTZ. After 24 h, cells were harvested and analyzed by flow cytometry using the following Abs: anti-CD83-APC (#551073), CD86-FITC (#555657) and 7-AAD from BD Biosciences and CD11c-BV650 (#563404, Biolegend). Dead cells were excluded by 7-AAD positivity, and CD83 and CD86 expression was evaluated on CD11c+ cells.

Generation of CRISPR KO MM Cells

Single guide RNA (sgRNA) targeting murine Calr, murine Sting/Tmem173 and human STING/TMEM173 were used to generate 5TGM1 Calr$^{KO}$, 5TGM1 Sting$^{KO}$ and AMO1 STING$^{KO}$ cells. Both cell lines were transfected via electroporation (Neon™ Transfection System; ThermoFisher Scientific) using All-in-one vectors (pCLIP-ALL-hCMV-ZsGreen) containing a sgRNA and a Cas9 (Transomic technologies). 48 h after electroporation, cells were ZsGreen-sorted and plated as monoclones in 96-well plates. After expansion, monoclones were screened for either CALR or STING expression by WB. SgRNA sequences:

```
Calr Mus Musculus:
sgRNA#1: TATGTTTGGATTCGACCCAG sgRNA#2: ATAGATGGCAGGGTCTGCGG sgRNA#3: CGTAAAATTTGCCAGAACTG Non targeting control: GGAGCGCACCATCTTCTTCA Sting/Tmem173 Mus Musculus:
sgRNA#1: TATCTCGGAATCGAATGTTG sgRNA#2: GAAGGCCAAACATCCAACTG sgRNA#3: CTACATAACAACATGCTCAG STING/TMEM173 Homo Sapiens:
sgRNA#1: ACAGCAGCAACAGGGCCCCA sgRNA#2: ATAGATGGACAGCAGCAACA sgRNA#3: GCAGCAACAGGGCCCCACGG
```

Stable Overexpression of Calreticulin in 5TGM1 Calr$^{KO}$ Clones

The pRetroX-CRT-GPI-IRES-DsRed plasmid containing full-length murine calreticulin cDNA was kindly provided by Chen X(Chen X, Fosco D, Kline D E, Kline J. Calreticulin promotes immunity and type I interferon-dependent survival in mice with acute myeloid leukemia. Oncoimmunology 2017; 6(4):e1278332). Virus was generated by transfecting HEK293T cells with 4 ug of DNA and packaging vectors (4 ug of psPAX2 and 2 ug of pMD2.G) using lipofectamine 2000 (ThermoFisher Scientific). Supernatant containing viral particles was harvested after 48 h and sterile 0.45 μm filtered. 5TGM1 Calr$^{KO}$ clones were spinoculated for 1 h with media containing lentiviral particles at a multiplicity of infection (MOI) of 2 in the presence of 8 μg/ml polybrene. Media was then changed, and cells were DsRed-sorted using M Aria II SORP UV (BD Biosciences). After sorting, efficient overexpression was evaluated by WB.

Immunoblotting

Cell lysis was performed in RIPA buffer (Boston Bio Products) supplemented with Halt protease and phosphatase inhibitor cocktail (ThermoFisher Scientific). SDS-PAGE was performed on NuPage Bis-Tris gels (ThermoFisher Scientific) using MOPS or MES running buffer. Gels were dry transferred onto 0.45 μm nitrocellulose membranes using the iBlot® Dry Blotting System (ThermoFisher Scientific). The following Abs were purchased from Cell Signaling Technology: EIF2A (#5324), p-EIF2A (#3398), ATF4 (#11815), CHOP (2895), CALR (#12238), cGAS (#15102), TBK1 (#3504), pTBK1 (#5483), pIRF3 (#29047), STING (#13647). GAPDH (#2118) and B-ACTIN (#4970) were used as loading controls.

Reverse Transcription and Quantitative Real-Time PCR

Total RNA from multiple myeloma cells was prepared with TRIzol™ (ThermoFisher Scientific) and RNA Clean and Concentrator™-5 kit (Zymo Research) following the product instructions. RNA integrity and quantity was assessed by NanoDrop Spectrophotometer (ThermoFisher Scientific). For analysis of mRNA expression, oligo-dT-primed cDNA was obtained using the High Capacity cDNA Reverse Transcription Kit (ThermoFisher Scientific), and used as template to quantify: human and murine IFNA1 (Hs03044218_g1, Mm03030145_gH), human and murine IFNB1 (Hs01077958_s1, Mm00439552_s1), human and murine CXCL9 (Hs00171065_m1, Mm00434946_m1), and human and murine GAPDH (Hs02786624_g1, Mm99999915_g1). Analysis was determined by RT-PCR using TaqMan®Fast Universal PCR Master Mix on a 7500 Fast Real-Time PCR System (ThermoFisher Scientific). Comparative RT-PCR was performed in triplicate. Relative expression was calculated using the comparative cross threshold (Ct) method.

Analysis of T Cell Priming

DCs were generated from healthy donors PBMCs as described above ("Generation of Mo-DCs" section). T cells were negatively selected from CD14-PBMCs from the same donors using the Pan T cell Isolation Kit (Miltenyi Biotec) and frozen until immature DCs were generated. Either untreated or BTZ-treated multiple myeloma cells were co-cultured with DCs and T cells for 5 days. T cells and DCs were similarly cultured in the absence of multiple myeloma cells and in the presence of BTZ. Before analysis, cells were treated with Dynabeads™ Human T-Activator CD3/CD28 (#11131D, ThermoFisher Scientific), and with GolgiStop™ and GolgiPlug™ (#554724 and #555029, BD Biosciences). T cell populations were analyzed using 10 color flow-cytometry with the following Abs: CD3-BV605 (#317322), CD8-FITC (#344704), CD4-PerCP/Cyanine5.5 (#317428), CD45RO-APC (#304210), CCR7-PE (#353204), CD69-PE/Cyanine7 (#310912), and IL-2-BV785 (#500348), IFNγ-BV421 (#502532) (BioLegend); and PD1-Super Bright 702 (#67-998-582). LIVE/DEAD™ Fixable Aqua dead Cell Stain(#L34966) (ThermoFisher Scientific) was also added to discriminate dead cells. Intracellular staining for IL-2 and IFNγ was performed using the Fixation/Permeabilization Solution Kit (BD Biosciences).

When T cell experiments were performed using patient multiple myeloma cells, the entire population of autologous BMMCs was cultured in presence and absence of BTZ and analyzed after 5 days. Data from experiments performed using multiple myeloma cell lines were analyzed with a bioinformatic semiautomated pipeline (Perez et al. (2020) Blood; 136(2):199-209). Briefly, flow cytometry files were entered in a custom R script which includes different bioinformatic algorithms and has been designed to reduce the impact of technical and instrumental differences, minimize the variability of manual analysis, and reveal full cellular diversity based on automatic semi-supervised clustering. Data from primary MM patients were manually analyzed by using Infinicyt 2.0 (Cytognos, Salamanca, Spain).

Analysis of Naïve T Cell Proliferation

DCs were generated from healthy donors PBMCs as described above ("Generation of Mo-DCs" section). Naïve T cells were negatively selected from CD14-PBMCs from the same donors using the Naive Pan T Cell Isolation Kit (Miltenyi Biotec) and frozen. When DCs were generated, either untreated or BTZ-treated multiple myeloma cells were co-cultured with DCs and naïve T cells labeled with Cell-Trace™ Violet Cell Proliferation Kit (ThermoFisher Scientific) for 5 days. Naïve T cells were also cultured in the absence of multiple myeloma cells and in the presence of phytohemagglutinin (PHA) (20 ug/ml) as positive control. Before analysis, cells were stained with: CD8-FITC (#344704), CD4-PerCP/Cyanine5.5 (#317428) (BioLegend); and LIVE/DEAD™ Fixable Aqua dead Cell Stain (#L34966) (ThermoFisher Scientific). Proliferating CD4 and CD8 T cell subsets were then analyzed using the FlowJo software (Becton, Dickinson & Company).

Cytotoxicity Assay

After coculture of HLA-matched DCs and T cells from healthy donors with either untreated or BTZ-treated U266 cells for 5 days, T cells were negatively selected using the Pan T cell Isolation Kit (Miltenyi Biotec) and plated in round bottom 96-well plates with naïve U266 cells pre-stained with CFSE dye (ThermoFisher Scientific) at different target:effector (T:E) ratios for 24 h in the presence of IL-2 (#130-097-74, Miltenyi Biotec). Then cells were 7AAD-stained, and detection of viable CFSE-gated cells was performed using BD LRSFortessa X-20 cytometer.

Micronuclei Assay

Cells were analyzed for micronuclei formation using a flow cytometry-based Micronucleus Assay (MicroFlow kit), according to manufacturer's protocol. Briefly, nonviable cells were removed by Ficoll gradient centrifugation. Viable cells were then stained with photoactivated Nucleic Acid Dye A (ethidium monoazide) that crosses the compromised outer membrane of apoptotic and necrotic cells and stains them red. Cells were then washed twice and lysed with a detergent containing buffer to break open cytoplasmic membranes and release nuclei and micronuclei. Nucleic Acid Dye B (SYTOX green) is then added to label DNA from both nuclei and micronuclei. Flow cytometry analysis was used to distinguish DNA from dead (dual stained with Dye A and B) and live (single stained with Dye B) cells. After removing dead cells from analysis, micronuclei were quantified and plotted as a percent of 2N nuclei based on Dye B (SYTOX green) staining intensity, and exhibit 1/100th to 1/10th the fluorescent intensity of 2N nuclei.

ELISA

AMO1$^{WT}$ and STING$^{KO}$ cells were either untreated or treated with BTZ for 24 h. Supernatant was collected, and secretion of CXCL9 chemokines was analyzed by MIG (CXCL9) Human Instant ELISA™ Kit (#BMS285INST, ThermoFisher Scientific).

In Vivo Studies 6-week old female immunodeficient NOD.CB17-Prkdcscid/NCrCrl (NOD/SCID) (Charles River) and immunocompetent C57BL/KaLwRijHsd (Envigo) mice were housed in the animal facility at DFCI. All experiments were performed after approval by the Animal Ethics Committee of the DFCI and performed using institutional guidelines.

In Vivo Studies for Tumor Growth Analysis

NOD/SCID and C57BL/KaLwRijHsd mice were subcutaneously (sc) injected with 1×10$^6$ 5TGM1 either WT or Calr$^{KO}$ cells in PBS. When tumor became measurable, mice were randomized to receive either PBS or BTZ administered intra peritoneally (i.p.) 0.5 mg/kg twice/week for 2 weeks. Tumor sizes were measured as previously described (46), and mice were sacrificed when tumors reached 2 cm in diameter or ulceration or major compromise in quality of life. A parallel experiment was performed to allow for tumor harvesting after two injections ip of BTZ for RNA-seq analysis, as detailed below. For BTZ and STING agonist combination studies, C57BL/KaLwRijHsd (n=5/group) and SCID/NOD (n=6/group) mice bearing 5TGM1 WT and C57BL/KaLwRijHsd mice (n=5/group) bearing 5TGM1

Sting$^{KO}$ tumors were randomized to receive: PBS, BTZ (0.375 mg/kg twice a week for 2 weeks, i.p.), ADU-S100 (100 µg) administered in the peritumoral area (day 1 and 2), or a combination. Tumor sizes were measured as described above. A parallel experiment in C57BL/KaLwRijHsd mice was performed to allow for tumor harvesting after one administration of either BTZ or ADU-S100. Tumors were fixed in 10% formalin for 24 h, and then maintained in 70% ethanol prior to paraffin embedding and processing for IHC to detect CD3 (#nb600 Ab, Novus Bio).

In Vivo Rechallenge of Viable 5TGM1 Cells in BTZ-Treated Mice

C57BL/KaLwRijHsd mice bearing 5TGM1 WT tumors were treated with BTZ as above. 2 weeks after observation of tumor regression, treated (n=5) as well as naïve mice (n=5), were rechallenged with viable 1×10$^6$ 5TGM1 WT cells, and tumor growth was monitored over time. In a parallel experiment, spleens were harvested 2 weeks after tumor rechallenge from both groups to test T cell specific reactivity against multiple myeloma cell by ELISPOT assay (Translational Immunogenomics Laboratory, DFCI).

Vaccination Studies

5×10$^5$ 5TGM1 WT or Calr$^{KO}$ cells were treated with BTZ (7.5 nM) in vitro for 16 h. C57BL/KaLwRijHsd mice (n=8/group) were then either vaccinated sc with dying 5TGM1 WT or 5TGM1Calr$^{KO}$ cells or not vaccinated. After 1 week, viable 1×10$^6$ WT 5TGM1 cells were injected sc, and tumor growth was monitored over time.

RNA-Seq Analysis from Mouse Tumors

Tumors growing from both 5TGM1 WT or Calr$^{KO}$ cells in C57BL/KaLwRijHsd mice treated with either PBS or BTZ (3/group) were harvested and used to extract RNA using the RNeasy kit (Qiagen). After passing quality control, RNAseq was performed using Illumina NextSeq 500 Single-End 75 bp (SE75) and analyzed following the VIPER NGS analysis pipeline (Cornwell et al. (2018) *BMC Bioinformatics;* 19(1): 135), comparing BTZ-treated mice vs PBS in each experimental setting. Lists of DEGs were applied to gene set enrichment analysis (GSEA) and Cytoscape (Bindea et al. (2009) Bioinformatics; 25(8):1091-3, Bindea et al. (2013). Bioinformatics; 29(5):661-3) software to reveal biological pathways modulated by BTZ. Focused analysis were conducted on the list of differentially expressed genes included in the genesets of the Hallmarks collection of the Molecular Signature Database (MSigDB) conveying immune processes and enriched in 5TGM1 WT tumors after treatment with BTZ. Analysis of expression of human orthologs of these 90 genes in MM patients and correlation with patient clinical outcome was then analyzed as detailed below. RNAseq data have been submitted to Gene Expression Omnibus (accession number: GSE171837).

RNA-Seq Analysis of AMO1 MM Cells after Treatment with BTZ

AMO1 WT and STING$^{KO}$ were cultured for 16 h in the presence of absence of BTZ (5 nM). RNA was extracted as previously described and submitted to NovaSeq RNAseq analysis followed by VIPER NGS Analysis pipeline (Cornwell et al. (2018) *BMC Bioinformatics;* 19(1):135). Lists of DEGs were applied to the GSEA software. RNAseq data have been submitted to Gene Expression Omnibus (accession number: GSE171837).

Analysis of RNAseq Data of MM Patients

RNAseq from CD138+ multiple myeloma cells from a previously published dataset of 327 newly-diagnosed clinically annotated multiple myeloma patients from IFM/DFCI 2009 clinical trial (NCT01191060) was used (Samur et al. (2018) *Leukemia;* 32(12):2626-35). After QC controls, all RNAseq data were quantified with Salmon. Raw counts and TPM values were summed to gene leves using tximport, and DESeq2 was used for all differential gene expression analysis. Centered and scaled data was used for clysering with ward. D2 algorithm. All figures were created with pheatmap or ggplot2. Survival analysis was performed using survival package in R, and log rank test was used to compare groups. As validation dataset, gene expression data of 152 multiple myeloma patients performed with microarray platform was downloaded from GEO (GSE9782)(26) and pre-processed and normalized with affy and limma packages in R.

Statistical Analysis

All in vitro experiments were repeated at least 3 times and performed in triplicate. Statistical significance of differences was determined using Student t test (unless otherwise specified). All statistical analyses and graphs were performed using GraphPad software.

Example 5: Identification of Novel Therapeutic Target for Cancer

Applicant has shown that the proteasome inhibitor bortezomib (BTZ) is an immunogenic cell death (ICD) inducer in myeloma (Gulla A et al. (2021) *Blood Cancer Discov.* September; 2(5):468-483. doi: 10.1158/2643-3230.bcd-21-0047. Epub 2021 Apr. 23. PMID: 34568832; PMCID: PMC8462183); and Applicant used this drug as a tool to investigate mechanisms underlying ICD resistance. This analysis led to the identification of GABARAP as a novel modulator of ICD; and it was found that Bortezomib did not induce CALR exposure in MM cells due to GABARAP deletion. Interestingly, deletion of GABARAP occurs in all patients with deletion of chromosome 17p, which confers poor prognosis and defines high-risk (HR) MM patients. Based on these data, it was hypothesized that impaired anti-tumor immunity may underlie poor clinical outcome in HR patients, specifically those with del(17p) and low GABARAP. Importantly, the definition of the molecular mechanisms underlying CALR loss in this subgroup of patients may identify novel therapeutic target to restore ICD and improve patient outcome.

Figure 32A:
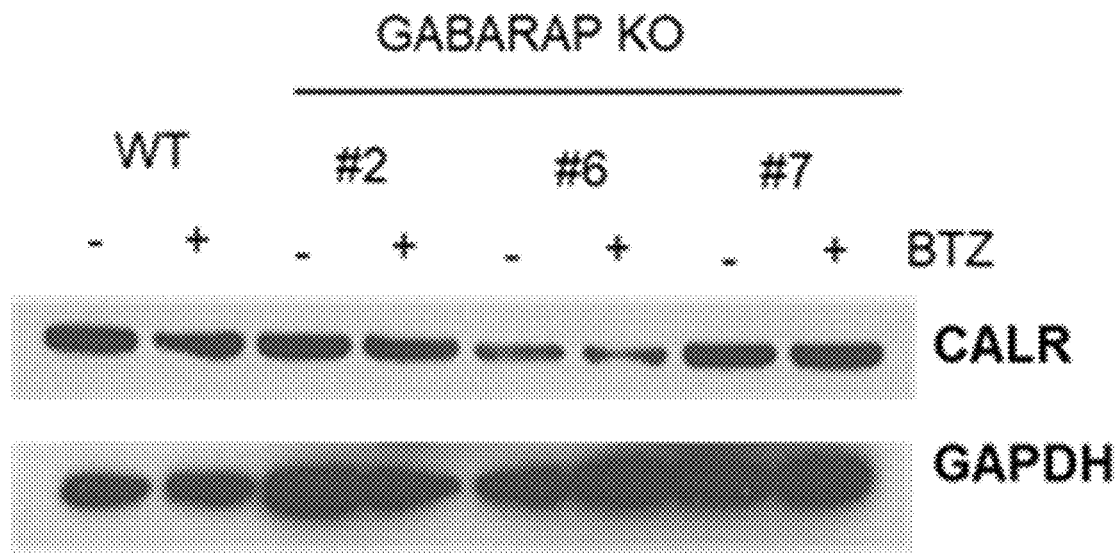
FIG. 32A and FIG. 32B show that CALR localizes to the mitochondria after treatment with BTZ in GABARAP KO cells.
Figure 32B:
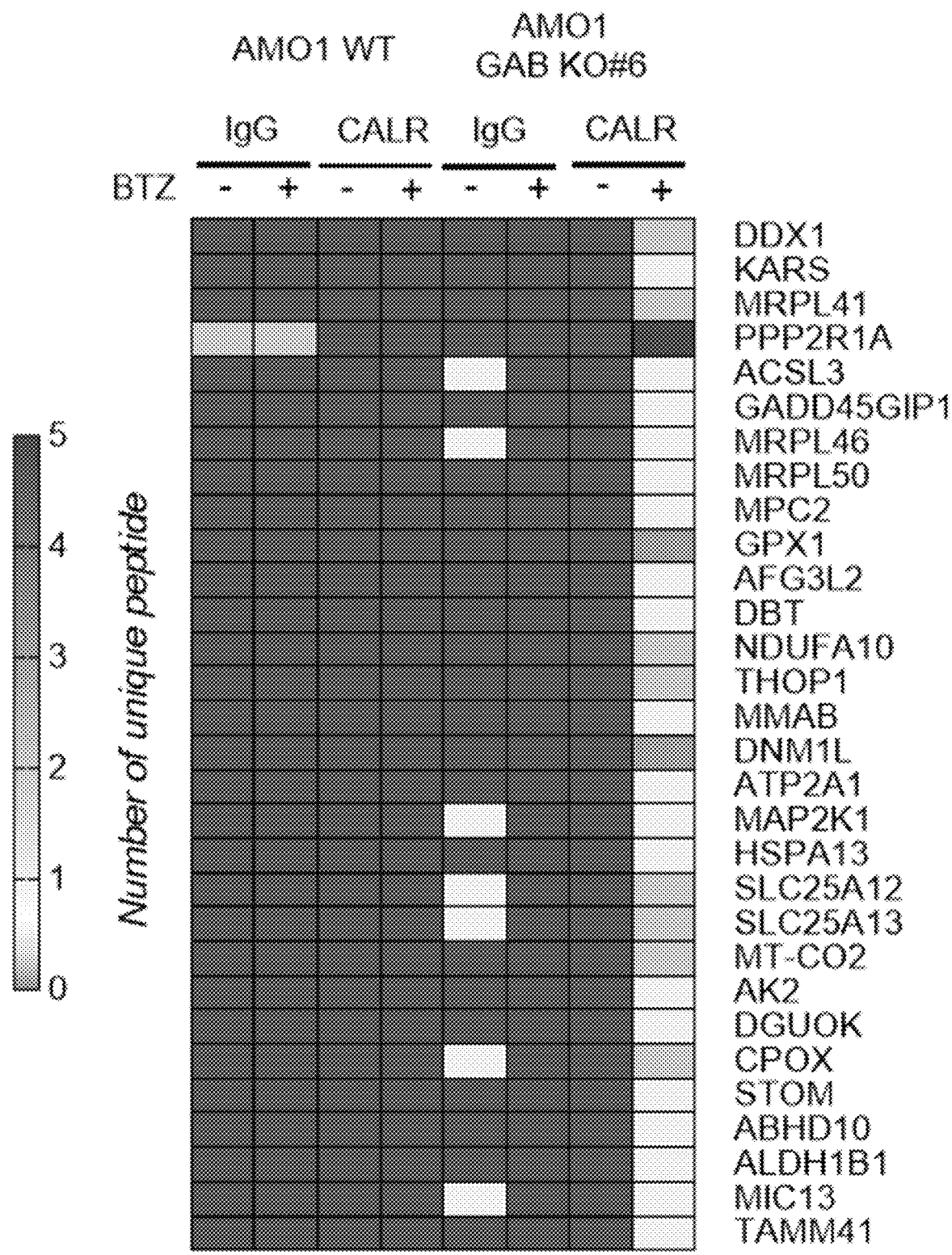
Figure 33A:
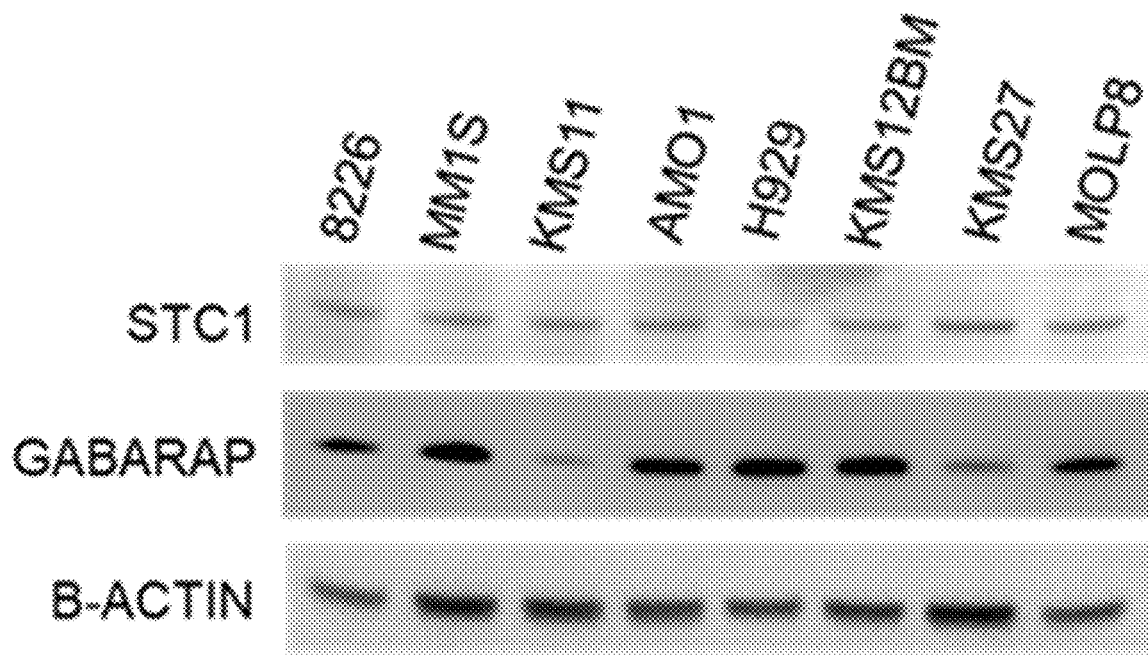
FIG. 33A-FIG. 33D show that GABARAP modulates the binding of STC1 to CALR.
Figure 33B:
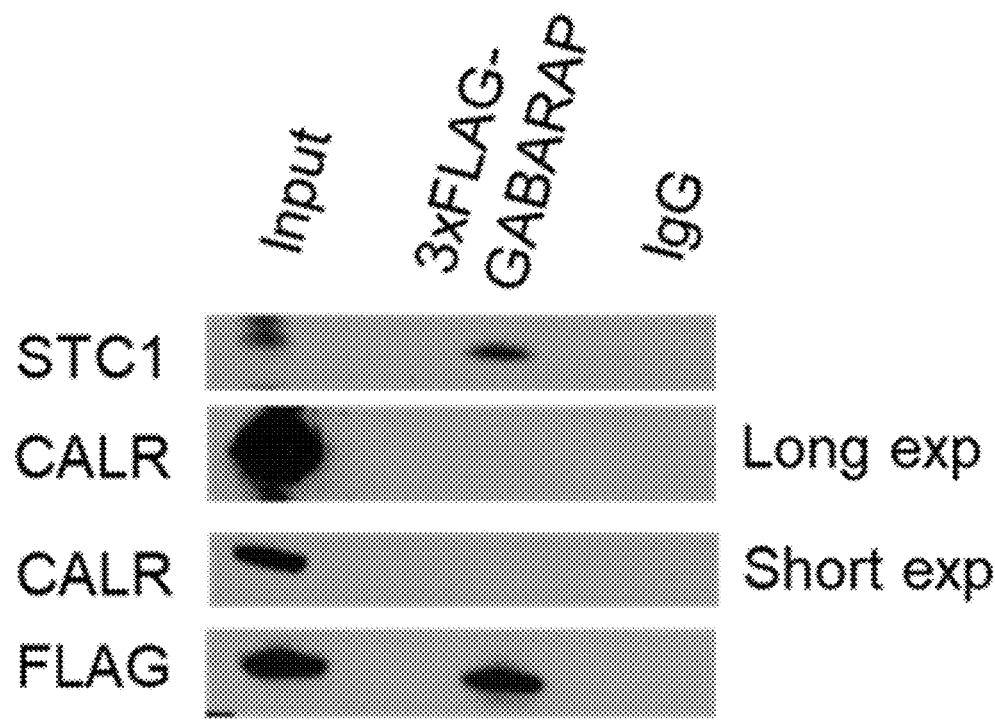
Figure 33C:
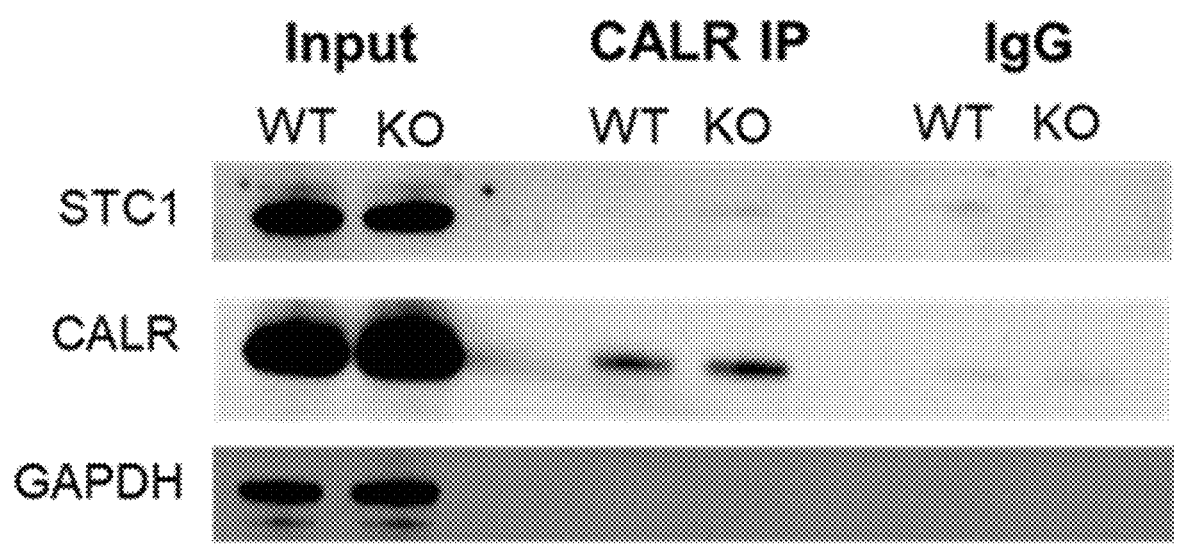
Figure 33D:
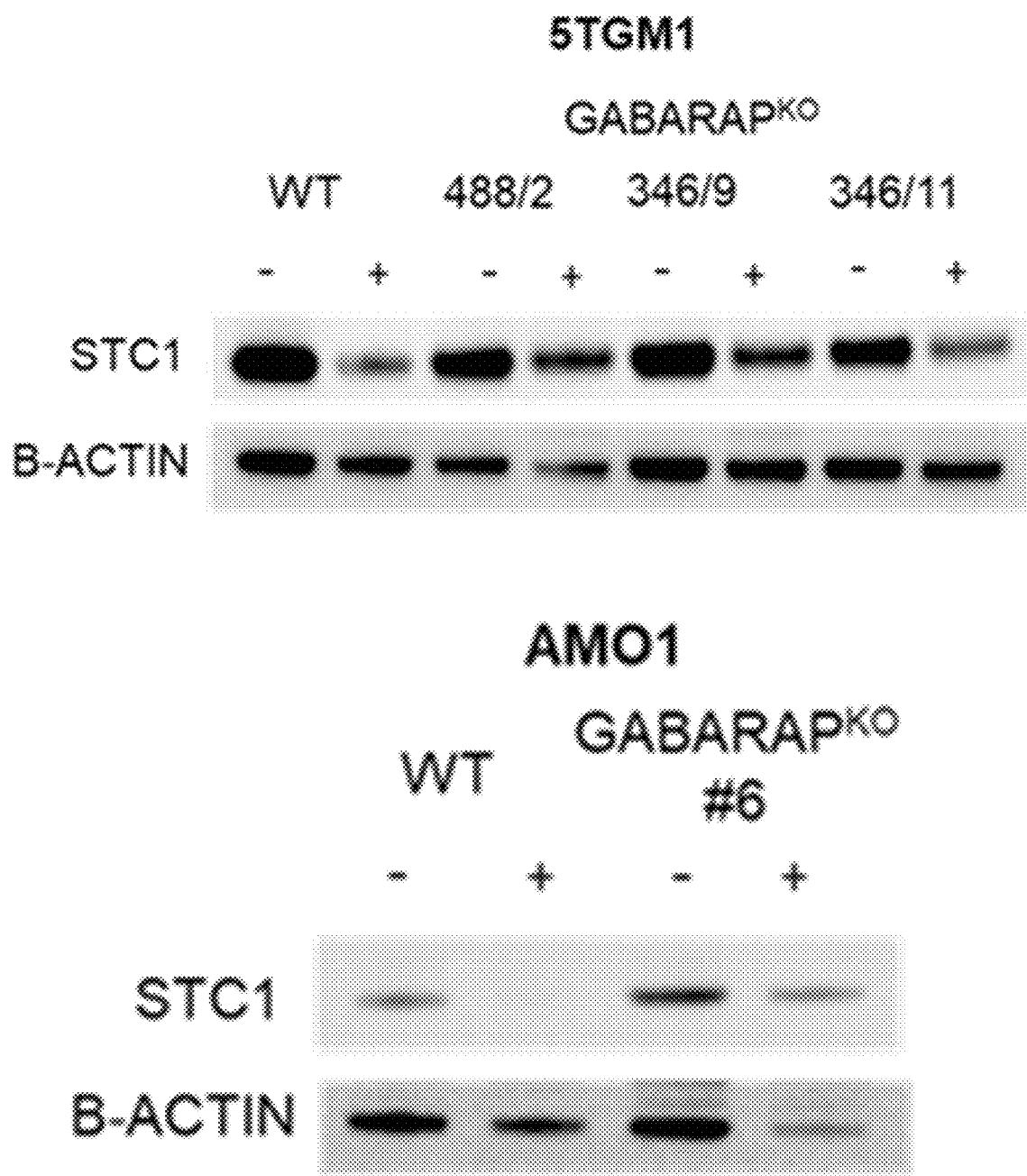
Figure 34:
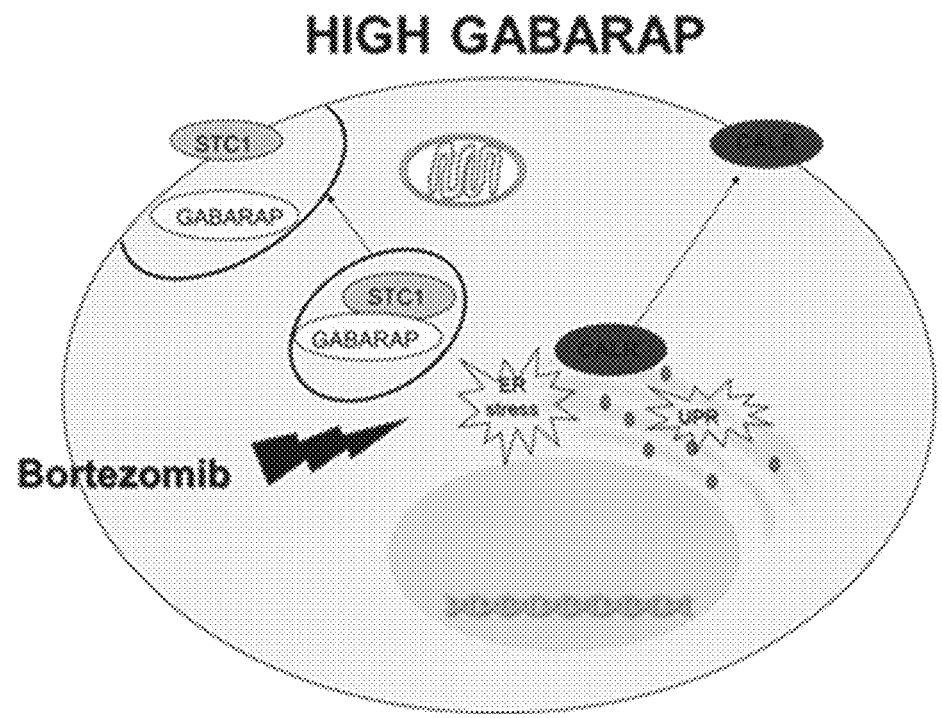
FIG. 34 shows that GABARAP mediates CALR trap into the mitochondria induced by STC1. In tumors expressing STC1, GABARAP prevents STC1-CALR binding and CALR mitochondrial trap; thus eliciting CALR exposure on cell membrane after induction of ICD. In low-GABARAP tumors, STC1 functions as an intracellular "eat-me" signal blocker by trapping calreticulin and impairs DCs phagocytosis and ICD.
Figure 34:
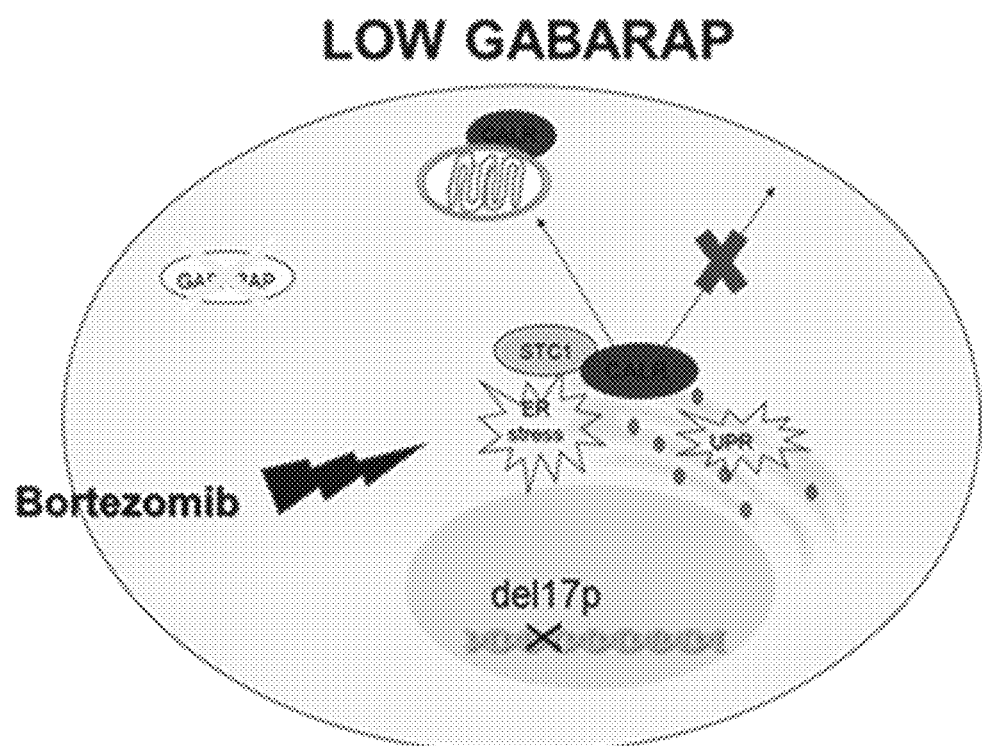

The evidence of CALR loss on cell surface was not associated with an increase of CALR protein degradation in GABARAP$^{KO}$ cells (FIG. 32A), suggesting that GABARAP$^{KO}$ may affect its alternative subcellular localization. To test this hypothesis, the CALR network was explored at the protein level by performing mass spectrometry (MS) after CALR immunoprecipitation (IP) in WT or GABARAP$^{KO}$ AMO1 cells in the presence or absence of BTZ. It was found that an increase of the binding of CALR to mitochondrial proteins only in AMO1 GABARAP$^{KO}$ cells after treatment with BTZ (FIG. 23B), indicating preferential mitochondrial localization of CALR in the GABARAP$^{KO}$ cells upon induction of ICD. CALR trap in the mitochondria has been recently reported in tumors with high stanniocalcin 1 (STC1), a newly recognized phagocytosis checkpoint driving tumor immune resistance (Lin et al. (2021) Cancer Cell. April 12; 39(4):480-493.e6. doi: 10.1016/j.ccell.2020.12.023. Epub 2021 Jan. 28. PMID: 33513345; PMCID: PMC8044011). The data disclosed herein show that that STC1 is ubiquitously expressed in MM cell lines (FIG. 33A). A WB analysis of FLAG-immunoprecipitated proteins in 239T cells expressing FLAG-tagged GABARAP was performed to analyze GABARAP interacting partners. It was found that GABARAP interacts with STC1 (FIG. 33B). To explore how GABARAP-STC1 binding may affect CALR localization, a CALR-IP in WT and GABARAP$^{KO}$ cells was performed, and showed specific binding of CALR with STC1 only in GABARAP$^{KO}$ cells (FIG. 33C). Moreover, it was found that STC1 protein levels decrease in WT cells after BTZ treatment, in contrast to GABARAP$^{KO}$ cells, in which intracellular levels of STC1 are even higher after BTZ treatment (FIG. 33D). These findings identify a molecular mechanism whereby GABARAP prevents STC1 binding to CALR; conversely, in low-GABARAP cells STC1 binding to CALR induces trapping of CALR in the mitochondria (FIG. 34).

These findings highlight a novel mechanism whereby GABARAP controls CALR subcellular localization, and identify STC1 as a novel therapeutic target. The combination of BTZ with STC1 inhibitors in MM HR patients carrying del(17p) will be a successful strategy to restore ICD and anti-tumor immune response.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a compound that induces immunogenic cell death (ICD) of a multiple myeloma cancer cell comprising an increase in an amount of STC1, wherein the STC1 comprises an amino acid sequence of SEQ ID NOs: 14, 16, or 18, the method comprising:
   a) contacting the multiple myeloma cancer cell comprising an increase in the amount of STC1, relative to the amount of STC1 in a non-cancerous cell, with (i) a test compound and (ii) an inducer of ICD; and
   b) determining the level of calreticulin trapped in the mitochondria of the multiple myeloma cancer cell, wherein the decrease in the level of calreticulin trapped in the mitochondria of the multiple myeloma cancer cell in the presence of the test compound as compared to the level of calreticulin trapped in the mitochondria of the multiple myeloma cancer cell in the absence of the test compound indicates that the test compound induces ICD of the multiple myeloma cancer cell comprising the increase in the amount of STC1.

2. The method of claim 1, wherein the multiple myeloma cancer cell is from a relapsed cancer.

3. The method of claim 1, wherein the inducer of ICD is selected from the group consisting of chemotherapeutic agents, radiation therapy, and proteasome inhibitors.

4. The method of claim 3, wherein the chemotherapeutic agent is selected from the group consisting of oxazophorines, platinum-based compounds, anthracyclines, and anthracenediones.

5. The method of claim 1, wherein the inducer of ICD is selected from the group consisting of bortezomib, carfilzomib, cyclophosphamide, idarubicin, doxorubicin, mitoxantrone, epirubicin, and oxaliplatin.

6. A method of identifying a compound that induces immunogenic cell death (ICD) of a multiple myeloma cancer cell comprising an increase in an amount of a nucleic acid encoding STC1, wherein the STC1 comprises an amino acid sequence of SEQ ID NOs: 14, 16, or 18, the method comprising:
   a) contacting the multiple myeloma cancer cell comprising an increase in the amount of the nucleic acid encoding STC1, relative to the amount of nucleic acid encoding STC1 in a non-cancerous cell, with (i) a test compound and (ii) an inducer of ICD; and
   b) determining the level of calreticulin trapped in the mitochondria of the multiple myeloma cancer cell, wherein the decrease in the level of calreticulin trapped in the mitochondria of the multiple myeloma cancer cell in the presence of the test compound as compared to the level of calreticulin trapped in the mitochondria of the multiple myeloma cancer cell in the absence of the test compound indicates that the test compound induces ICD of the multiple myeloma cancer cell comprising the increase in the amount of nucleic acid encoding STC1.

7. The method of claim 6, wherein the multiple myeloma cancer cell is from a relapsed cancer.

8. The method of claim 6, wherein the inducer of ICD is selected from the group consisting of chemotherapeutic agents, radiation therapy, and proteasome inhibitors.

9. The method of claim 8, wherein the chemotherapeutic agent is selected from the group consisting of oxazophorines, platinum-based compounds, anthracyclines, and anthracenediones.

10. The method of claim 6, wherein the inducer of ICD is selected from the group consisting of bortezomib, carfilzomib, cyclophosphamide, idarubicin, doxorubicin, mitoxantrone, epirubicin, and oxaliplatin.

* * * * *